United States Patent
Lee et al.

(10) Patent No.: US 9,809,826 B2
(45) Date of Patent: Nov. 7, 2017

(54) PLANT REGULATORY SEQUENCE

(71) Applicant: Syngenta Participations AG, Basel (CH)

(72) Inventors: Mikyong Lee, Research Triangle Park, NC (US); Michael L. Nuccio, Research Triangle Park, NC (US); Joseph Clarke, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/820,702

(22) Filed: Aug. 7, 2015

(65) Prior Publication Data

US 2015/0337323 A1    Nov. 26, 2015

Related U.S. Application Data

(62) Division of application No. 13/682,982, filed on Nov. 21, 2012, now abandoned, which is a division of application No. 12/172,535, filed on Jul. 14, 2008, now Pat. No. 8,344,209.

(51) Int. Cl.
| | |
|---|---|
| *A01H 5/00* | (2006.01) |
| *C12N 15/00* | (2006.01) |
| *C12N 15/82* | (2006.01) |
| *C07K 14/415* | (2006.01) |
| *A01M 29/00* | (2011.01) |
| *A01H 1/00* | (2006.01) |

(52) U.S. Cl.
CPC ......... *C12N 15/8223* (2013.01); *A01M 29/00* (2013.01); *C07K 14/415* (2013.01); *C12N 15/8222* (2013.01); *C12N 15/8225* (2013.01); *C12N 15/8241* (2013.01); *C12N 15/8273* (2013.01); *C12N 15/8286* (2013.01)

(58) Field of Classification Search
None
See application file for complete search history.

(56) References Cited

U.S. PATENT DOCUMENTS

| | | |
|---|---|---|
| 6,320,100 B1 | 11/2001 | Koziel et al. |
| 2004/0034888 A1 | 2/2004 | Liu et al. |
| 2004/0214272 A1 | 10/2004 | La Rosa et al. |
| 2006/0141495 A1* | 6/2006 | Wu ............ C12Q 1/6895 435/6.11 |
| 2006/0168695 A1 | 7/2006 | Klebsattel et al. |
| 2007/0174935 A1 | 7/2007 | Abbitt et al. |
| 2007/0250959 A1 | 10/2007 | Crane et al. |

OTHER PUBLICATIONS

Lindsey et al., Transgenic Research, 2, 33-47, 1993.
Gaxiola et al., PNAS, vol. 98, No. 20, 11444-11449, Sep. 25, 2001.
Park et al., PNAS, vol. 102, No. 52, 18830-18835, Dec. 27, 2005.
GenBank AC211477 (Jun. 7, 2008). [Retrieved from the Internet Sep. 6, 2009: <http://www.ncbi.nlm.nih.gov/nuccore/166158565>].
Lopez et al., Proc. Natl. Acad. Sci., vol. 93, pp. 7415-7420, Jul. 1996.
Whitelaw et al., EST Database, Direct submission, Accession No. CG295599, Aug. 25, 2003.
Kausch et al., Plant Molecular Biology, Jan. 2001, vol. 41, No. 1, pp. 1-15.
Taniguchi et al., Plant Cell Physiol., Jan. 2000, vol. 41, No. 1, pp. 42-48.
Lu et al., GenEmbl Database, Acc. No. AX540744, WO02053719, Jul. 11, 2002, Seq ID No. 27.

\* cited by examiner

*Primary Examiner* — Phuong Bui
(74) *Attorney, Agent, or Firm* — Christopher Leming

(57) ABSTRACT

The present invention relates to regulatory sequences. In particular, the invention relates to a regulatory nucleic acid molecule, at least part of which has a transcription initiation function directing expression of an operably associated protein encoding polynucleotide of interest to non-tassel tissue in maize, but not or substantially not to tassel.
The invention further relates to chimeric genes and expression cassettes comprising the regulatory nucleic acid molecule and to transgenic plants comprising the chimeric genes and expression cassettes.

7 Claims, No Drawings

PLANT REGULATORY SEQUENCE

This application is a divisional of U.S. application Ser. No. 13/682,982, filed Nov. 21, 2012, now abandoned, which is a divisional of U.S. application Ser. No. 12/172,535, filed Jul. 14, 2008, now U.S. Pat. No. 8,344,209, all of which are incorporated herein by reference in their entirety.

STATEMENT REGARDING ELECTRONIC SUBMISSION OF A SEQUENCE LISTING

A Sequence Listing file in ASCII text format, submitted herewith electronically via EFS web under 37 C.F.R. §1.821, entitled "71760-US-REG-D-NAT-3_Sequence_Listing_ST25" which is 250 kilobytes in size was created Jul. 31, 2015 and is herein incorporated by reference in its entirety.

The present invention is in the field of plant biotechnology and relates to regulatory sequences. In particular, the invention relates to a regulatory nucleotide sequence, at least part of which has a transcription initiation function directing expression of an operably associated protein encoding polynucleotide of interest to basically all plant tissues, but essentially excluding expression in the tissues of the reproductive structures of the plant, particularly in the tissues of the pollen and/or the tassel so that no expression product is present in said tissues to any significant extent. The invention further relates to chimeric genes and expression cassettes comprising said regulatory sequence in association with an expressible protein encoding polynucleotide of interest and to transgenic plants comprising said chimeric genes and expression cassettes, respectively, expressing the protein encoding polynucleotide of interest in basically all plant tissues, but essentially excluding expression in the tissues of the reproductive structures of the plant, particularly in the tissues of the pollen and/or the tassel so that no expression product is present in said tissues to any significant extent.

BACKGROUND OF THE INVENTION

In many agricultural crops such as corn, devastating pests tend to feed on vegetative tissues such as the leaf, stalk and root and also reproductive tissues such as the ear. One technique used to protect plants from pests is the application of chemical compounds. An alternative technique involves genetic recombination, wherein a gene or genes are introduced into the plant to express protein products that are directly or indirectly involved in the control of the pest organisms. Current protein products produced by genetic recombination are expressed constitutively, i.e., throughout the plant at all times and in most tissues and organs. Such protein products are also expressed specifically, either in response to particular stimuli or confined to specific cells or tissues. In contrast, the present invention includes expression of the protein or polynucleotide of interest in basically all plant tissues, but essentially excludes expression in the tissues of the reproductive structures of the plant, particularly in the tissues of the pollen and/or the tassel so that no expression product is present in said tissues to any significant extent.

Several insect control trait genes target the larval stage of development. Under certain circumstances, these proteins also affect unintended insects, which are not corn pests, but do occasionally feed on corn pollen. These insects may be harmed by insecticidal proteins expressed in pollen tissue. This was seen as a problem in early BT-corn events which had high insecticidal protein expression in pollen. This issue was addressed in later BT-corn events through the development of alternative transgene expression systems. These newer events remained effective against target pests and accumulated less insecticidal protein in pollen, but are still viewed as potentially harmful to non-target pests due to the presence of insecticidal protein in pollen.

In some instances, useful insect control trait genes may also compromise the development of reproductive structures of the plant such as, for example, the tassel.

It is, therefore, desirable to provide plants, particularly corn plants that exclude expression of the transgene in the tissues of the reproductive structures of the plant such as the tissues of the pollen and/or the tassel. This could be achieved within the scope of the present invention by providing a regulatory nucleotide sequence, at least part of which has a transcription initiation function directing expression of an operably associated protein encoding a polynucleotide of interest to basically all plant tissues, but essentially excluding expression in the tissues of the male reproductive structures of the plant, particularly in the tissues of the pollen and/or the tassel so that no expression product is present in said tissues to any significant extent. This regulatory nucleotide sequence can then be used to develop expression systems that enable effective accumulation of the polypeptide or protein of interest such as, for example, an insecticidal protein, in tissues that target pests normally feed on, and eliminate or reduce accumulation of the insecticidal protein in non-target tissues or organs and/or in those tissues that may be compromised by the polypeptide or protein of interest.

SUMMARY OF THE INVENTION

In one embodiment, the invention relates to a transgenic plant comprising stably integrated in its genome a chimeric polynucleotide construct, particularly a chimeric construct, comprising a polynucleotide of interest, particularly a polypeptide or protein encoding polynucleotide of interest, associated with and/or under control of a regulatory nucleotide sequence, at least part of which has a transcription initiation function directing expression of said protein encoding polynucleotide of interest to basically all tissues of said plant, particularly the tissues target insects normally feed on, but essentially excluding the tissues of the reproductive plant structures, particularly the tissues of the pollen and/or the tassel so that no expression product is present in said tissues to any significant extent.

In one embodiment, the polynucleotide of interest, particularly a polypeptide or protein encoding polynucleotide of interest, is not transcribed to any significant extent in the tissues of the reproductive plant structures, particularly in pollen and/or tassel tissue of the transgenic plant according to the invention. Therefore, essentially no expression of the polynucleotide of interest, particularly a polypeptide or protein encoding polynucleotide of interest, occurs in the tissues of the male reproductive plant structures, particularly in the tissues of the pollen and/or the tassel, and only residual amounts of the expression product, if any, can be detected in said tissues, which is not sufficient for the expression product to fulfil its envisaged biological function in said tissues, particularly in the tissues of the pollen and/or the tassel, and therefore also does not exhibit any toxic effects on insects feeding on said tissues or on the plant reproductive structures.

In one embodiment of the invention, a transgenic plant is provided as described herein, wherein a chimeric polynucleotide construct, particularly a chimeric DNA construct, comprises a polynucleotide of interest, particularly a polypeptide or protein encoding polynucleotide of interest, operably associated with and/or under operable control of a regulatory nucleotide sequence, at least part of which has a transcription initiation function and is obtainable from a gene encoding an actin depolymerizing factor 3 (ABP3), which polypeptide or protein is highly expressed in most tissues of the plant but essentially excluding the tissues of the pollen so that no expression product is present in said tissues to any significant extent.

In one embodiment, said actin depolymerizing factor 3 (ABP3) gene is obtainable from maize.

In one embodiment of the invention, a transgenic plant is provided as described herein, wherein a chimeric polynucleotide construct, particularly a chimeric DNA construct, comprises a polynucleotide of interest, particularly a polypeptide or protein encoding polynucleotide of interest, operably associated with and/or under operable control of a regulatory nucleotide sequence, at least part of which has a transcription initiation function and is obtainable from a gene represented by a DNA probe, particularly a DNA probe exhibiting a DNA sequence as depicted in SEQ ID NOs: 47 to 56, which DNA probe shows a signal pattern in tissue samples, which is indicative of expression of said gene in all tissues and of no or substantially no expression in pollen.

In one embodiment, a transgenic plant according to the invention and as described herein is provided comprising a regulatory nucleotide sequence or a polynucleotide construct, particularly a chimeric polynucleotide construct, comprising said regulatory sequence as described herein, at least part of which has a transcription initiation function and mediates expression of an operably associated protein encoding polynucleotide of interest in most tissues of the plant but essentially excluding the tissues of the pollen so that no expression product is present in said tissues to any significant extent, which regulatory sequence can be obtained in a PCR reaction from a genomic *Zea mays* DNA template using
  i) a first primer which has at least 90%, particularly at least 91%, particularly at least 92%, 93%, 94%, 95%, 96%, 97%, 98% or 99% sequence identity with a nucleotide sequence as depicted in SEQ ID NO: 1, particularly a first primer of SEQ ID NO: 1; or
  ii) second primer which has at least 90%, particularly at least 91%, particularly at least 92%, 93%, 94%, 95%, 96%, 97%, 98% or 99% sequence identity with a nucleotide sequence as depicted in SEQ ID NO: 2, particularly a second primer of; SEQ ID NO: 2; or
  iii) a first primer as a forward primer which has at least 90%, particularly at least 91%, particularly at least 92%, 93%, 94%, 95%, 96%, 97%, 98% or 99% sequence identity with a nucleotide sequence as depicted in SEQ ID NO: 1 and a second primer as a reverse primer which has at least 90%, particularly at least 91%, particularly at least 92%, 93%, 94%, 95%, 96%, 97%, 98% or 99% sequence identity with a nucleotide sequence as depicted in SEQ ID NO: 2, particularly the forward primer of SEQ ID NO: 1 and the reverse primer of SEQ ID NO: 2.

In one embodiment, the invention relates to a transgenic plant as described herein, wherein the nucleotide sequence providing the transcription initiation function has at least between 80% and 85% sequence identity with a nucleotide sequence depicted in SEQ ID NO: 13, with all integers falling within this range also being comprised herewith, particularly at least between 85% and 90% sequence identity with a nucleotide sequence depicted in SEQ ID NO: 13, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 13, or a fragment thereof, and wherein said regulatory nucleotide sequence or fragment thereof mediates transcription of an operably associated polynucleotide molecule, particularly of an operably associated protein encoding polynucleotide of interest such that said polynucleotide of interest is transcribed in most of the plant tissues but essentially excluding the tissues of the pollen so that no expression product is present in said tissues to any significant extent.

In one embodiment, the invention relates to a transgenic plant as described herein, wherein the complementary strand of the nucleotide sequence providing the transcription initiation function is capable of hybridizing with a nucleotide sequence depicted in SEQ ID NO: 13, particularly under moderate hybridization conditions, more particularly under stringent hybridization conditions, and wherein said regulatory nucleotide sequence mediates transcription of an operably associated polynucleotide molecule, particularly of an operably associated protein encoding polynucleotide of interest such that said polynucleotide of interest is transcribed in most of the plant tissues but essentially excluding the tissues of the pollen so that no expression product is present in said tissues to any significant extent.

In one embodiment, the invention relates to a transgenic plant as described herein, wherein the nucleotide sequence providing the transcription initiation function is the sequence depicted in SEQ ID NO: 13 or a fragment thereof, which still exhibits the full functionality as a transcription initiation sequence.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription termination function obtainable from a gene encoding an actin depolymerizing factor 3 (ABP3), which regulatory sequence mediates transcription of an operably associated polynucleotide molecule, particularly of an operably associated protein encoding polynucleotide molecule of interest such that said polynucleotide of interest is transcribed in most of the plant tissues excluding the tissues of the pollen but essentially excluding the tissues of the pollen so that no expression product is present in said tissues to any significant extent, particularly from a maize actin depolymerizing factor 3 (ABP3) gene, wherein
  i) said regulatory nucleotide sequence comprises a transcription termination sequence which has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 14; or a fragment thereof, which still exhibits the functionality of a termination sequence; or
  ii) the complementary strand of said regulatory nucleotide sequence hybridizes to a nucleotide sequence depicted in SEQ ID NO: 14, particularly under moderate hybridization conditions, more particularly under moderate-stringent hybridization conditions, particularly under stringent hybridization conditions and mediates termination of transcription of an operably associated protein encoding polynucleotide of interest; or.

iii) said regulatory nucleotide sequence has a sequence as depicted in SEQ ID NO: 14, including complements thereof.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a gene encoding an actin depolymerizing factor 3 (ABP3), which is expressed in most plant tissues but essentially excluding the tissues of the pollen so that no expression product is present in said tissues to any significant extent, particularly from a maize actin depolymerizing factor 3 (ABP3) gene, and which regulatory nucleotide sequence comprises a transcription initiation sequence and a transcription termination sequence, respectively, which have at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 13 and SEQ ID NO:14, respectively, or a fragment thereof which still exhibits the full functionality as a transcription initiation and a termination sequence, respectively.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a gene encoding an actin depolymerizing factor 3 (ABP3), which is expressed in most tissues of the plant but essentially excluding the tissues of the pollen so that no expression product is present in said tissues to any significant extent, particularly from a maize actin depolymerizing factor 3 (ABP3) gene, and which regulatory nucleotide sequence comprises a transcription initiation sequence as depicted in SEQ ID NO: 13 and a transcription termination sequence as depicted in SEQ ID NO:14.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a gene represented by a DNA probe, particularly a DNA probe exhibiting a DNA sequence as depicted in SEQ ID NOs: 47 to 56, which DNA probe shows a signal pattern in tissue samples, which is indicative of expression of said gene in all tissues and of no or substantially no expression in pollen.

In one embodiment of the invention, a transgenic plant is provided as described herein, wherein the chimeric polynucleotide construct, particularly the chimeric DNA construct, comprises a polynucleotide of interest, particularly a polypeptide or protein encoding polynucleotide of interest, operably associated with and/or under operable control of a regulatory nucleotide sequence, at least part of which has a transcription initiation function and is obtainable from plant genomic DNA, particularly from maize genomic DNA, which polypeptide or protein is expressed in most tissues of the plant but essentially excluding tissues of the tassel so that no expression product is present in said tissues to any significant extent.

In one embodiment of the invention, a transgenic plant is provided as described herein, wherein the chimeric polynucleotide construct, particularly the chimeric DNA construct, comprises a polynucleotide of interest, particularly a polypeptide or protein encoding polynucleotide of interest, operably associated with and/or under operable control of a regulatory nucleotide sequence, at least part of which has a transcription initiation function and is obtainable from a gene represented by a DNA probe, particularly a DNA probe exhibiting a DNA sequence as depicted in SEQ ID NOs: 57 to 79, which DNA probe shows a signal pattern in tissue samples, which is indicative of expression of said gene in all tissues and of no or substantially no expression in the tissues of the tassel.

In one embodiment, a transgenic plant according to the invention and as described herein is provided comprising a regulatory nucleotide sequence or an expression cassette comprising said regulatory nucleotide sequence or a polynucleotide construct, particularly a chimeric polynucleotide construct, comprising said regulatory sequence as described herein, which regulatory sequence can be obtained in a PCR reaction from a genomic *Zea mays* DNA template using i) a first primer which has at least 90%, particularly at least 91%, particularly at least 92%, 93%, 94%, 95%, 96%, 97%, 98% or 99% sequence identity with a nucleotide sequence as depicted in SEQ ID NO: 19, particularly the primer of SEQ ID NO: 19; or ii) a second primer which has at least 90%, particularly at least 91%, particularly at least 92%, 93%, 94%, 95%, 96%, 97%, 98% or 99% sequence identity with a nucleotide sequence as depicted in SEQ ID NO: 20, particularly the reverse primer of SEQ ID NO: 20; or iii) a first primer as a forward primer which has at least 90%, particularly at least 91%, particularly at least 92%, 93%, 94%, 95%, 96%, 97%, 98% or 99% sequence identity with a nucleotide sequence as depicted in SEQ ID NO: 19 and a second primer as a reverse primer which has at least 90%, particularly at least 91%, particularly at least 92%, 93%, 94%, 95%, 96%, 97%, 98% or 99% sequence identity with a nucleotide sequence as depicted in SEQ ID NO: 20, particularly the forward primer of SEQ ID NO: 19 and the reverse primer of SEQ ID NO: 20.

In one embodiment, the invention relates to a transgenic plant as described herein, wherein the nucleotide sequence providing the transcription initiation function has at least between 80% and 85% sequence identity with a nucleotide sequence depicted in SEQ ID NO: 35, with all integers falling within this range also being comprised herewith, particularly at least between 85% and 90% sequence identity with a nucleotide sequence depicted in SEQ ID NO: 35, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 35, or a fragment thereof, and wherein said regulatory nucleotide sequence or fragment thereof mediates transcription of an operably associated polynucleotide molecule, particularly of an operably associated protein encoding polynucleotide of interest such that said polynucleotide of interest is transcribed in most tissues of the plant but essentially excluding the tissues of the tassel so that no expression product is present in said tissues to any significant extent.

In one embodiment, the invention relates to a transgenic plant as described herein, wherein the complementary strand of the nucleotide sequence providing the transcription initiation function is capable of hybridizing with a nucleotide sequence depicted in SEQ ID NO: 35, particularly under moderate hybridization conditions, more particularly under stringent hybridization conditions and wherein said regulatory nucleotide sequence mediates transcription of an operably associated polynucleotide molecule, particularly of an operably associated protein encoding polynucleotide of interest such that said polynucleotide of interest is transcribed in most tissues of the plant but essentially excluding the tissues of the tassel so that no expression product is present in said tissues to any significant extent.

In one embodiment, the invention relates to a transgenic plant as described herein, wherein the nucleotide sequence providing the transcription initiation function is the sequence depicted in SEQ ID NO: 35 or a fragment thereof, which still exhibits the full functionality as a transcription initiation sequence.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription termination function obtainable from a plant genomic DNA, particularly a maize genomic DNA and mediates transcription of an operably associated polynucleotide molecule, particularly of an operably associated protein encoding polynucleotide of interest such that said polynucleotide of interest is transcribed in most tissues of the plant but essentially excluding the tissues of the tassel so that no expression product is present in said tissues to any significant extent, wherein
  i) said regulatory nucleotide sequence comprises a transcription termination sequence which has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 36; or a fragment thereof which still exhibits the full functionality as a transcription initiation sequence; or
  ii) the complementary strand of said regulatory nucleotide sequence hybridizes to a nucleotide sequence depicted in SEQ ID NO: 36, particularly under moderate hybridization conditions, particularly under moderate-stringent hybridization conditions, particularly under stringent hybridization conditions and mediates termination of transcription of an operably associated protein encoding polynucleotide of interest; or
  iii) said regulatory sequence has a sequence as depicted in SEQ ID NO: 36, or a fragment thereof, which still exhibits the full functionality as a transcription initiation sequence including complements thereof.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a genomic plant DNA, particularly from a genomic maize DNA and is expressed in most tissues of the plant but essentially excluding tissues of the tassel so that no expression product is present in said tissues to any significant extent, which regulatory nucleotide sequence comprises a transcription initiation sequence and a transcription termination sequence, respectively, which sequences have at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 35 and SEQ ID NO:36, respectively, including a fragment thereof, which still exhibits the full functionality as a transcription initiation sequence and a termination sequence, respectively.

In one embodiment the invention relates to a transgenic plant according to the invention and as described herein comprising a regulatory nucleotide sequence or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a genomic plant DNA, particularly a genomic maize DNA and is expressed in most tissues of the plant but essentially excluding tissues of the tassel so that no expression product is present in said tissues to any significant extent, which regulatory nucleotide sequence comprises a transcription initiation sequence as depicted in SEQ ID NO: 35 and a transcription termination sequence as depicted in and SEQ ID NO:36 respectively, including a fragment thereof, which still exhibits the full functionality as a transcription initiation sequence and a termination sequence, respectively.

In one embodiment, a transgenic plant according to the invention and as described herein is provided, wherein the polypeptide or protein encoding polynucleotide of interest encodes a polypeptide product exhibiting an insecticidal activity, particularly an endotoxin of *Bacillus thuringiensis*.

In one embodiment, the concentration of the polypeptide product expressed from the protein encoding polynucleotide of interest in the tissues of the plant reproductive structures, particularly in the tissues of the pollen and/or the tassel is such that no insecticidal activity can be detected in a standard insect feeding assay. In particular, the concentration of the expression product in the tassel is below a basic level of not more than 10 ng/mg soluble protein, particularly of not more than 5 ng/mg soluble protein, more particularly of not more than 3 ng/mg soluble protein, but especially of not more than 2 ng/mg soluble protein or less.

In one embodiment, a transgenic plant according to the invention and as described herein is provided, wherein the polypeptide or protein encoding polynucleotide of interest encodes an endotoxin of *Bacillus thuringiensis* which has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence as depicted in SEQ ID NO:15.

In one embodiment, a transgenic plant according to the invention and as described herein is provided, wherein the polypeptide or protein encoding polynucleotide of interest encodes an endotoxin of *Bacillus thuringiensis* which has the nucleotide sequence as depicted in SEQ ID NO: 15.

In one embodiment, a transgenic plant according to the invention and as described herein is provided, wherein the polypeptide or protein encoding polynucleotide of interest encodes a polypeptide product contributing to the enhancement of drought tolerance, particularly a deregulated form of a $H^+$-pyrophosphatase, wherein said polypeptide or protein is under control of a regulatory sequence according to the invention at least part of which has a transcription initiation function which mediates expression of an operably associated protein encoding polynucleotide of interest in most plant tissues but essentially excluding expression in the tissues of the pollen and/or the tissues of the tassel so that no expression product is present in said tissues to any significant extent.

In one embodiment, the transgenic plant according to the invention and as described herein is a *Zea mays* plant.

In one embodiment, the invention relates to a regulatory nucleotide sequence or an expression cassette comprising said regulatory nucleotide sequence or a polynucleotide construct, particularly a chimeric polynucleotide construct, comprising said regulatory sequence, at least part of which has a transcription initiation function which mediates expression of an operably associated protein encoding a polynucleotide of interest in most plant tissues but essentially excluding expression in the tissues of the male reproductive structures, particularly the tissues of the pollen and/or the tassel so that no expression product is present in said tissues to any significant extent.

In one embodiment of the invention, the regulatory nucleotide sequence is obtainable from a gene represented by a DNA probe, particularly a DNA probe exhibiting a DNA sequence as depicted in SEQ ID NOs: 47 to 56, which DNA probe shows a signal pattern in tissue samples which is indicative of expression of said gene in all tissues and of no or substantially no expression in pollen.

In one embodiment of the invention, the regulatory nucleotide sequence is obtainable from a gene encoding an actin depolymerizing factor 3, which is expressed in most tissues of the plant but essentially excluding the tissues of the pollen so that no expression product is present in said tissues to any significant extent, particularly an actin depolymerizing factor 3 gene from maize.

In one embodiment of the invention, the regulatory nucleotide sequence is obtainable from a gene represented by a DNA probe, particularly a DNA probe exhibiting a DNA sequence as depicted in SEQ ID NOs: 57 to 79, which DNA probe shows a signal pattern in tissue samples, which is indicative of expression of said gene in all tissues and of no or substantially no expression in the tissues of the tassel.

In one embodiment, the invention provides a regulatory nucleotide sequence or an expression cassette comprising said regulatory nucleotide sequence or a polynucleotide construct, particularly a chimeric polynucleotide construct, comprising said regulatory sequence as described herein, which sequence is obtainable from a genomic *Zea mays* DNA template using i) a first primer which has at least 90%, particularly at least 91%, particularly at least 92%, 93%, 94%, 95%, 96%, 97%, 98% or 99% sequence identity with a nucleotide sequence as depicted in SEQ ID NO: 1, particularly a first primer of SEQ ID NO: 1; or
ii) second primer which has at least 90%, particularly at least 91%, particularly at least 92%, 93%, 94%, 95%, 96%, 97%, 98% or 99% sequence identity with a nucleotide sequence as depicted in SEQ ID NO: 2, particularly a second primer of; SEQ ID NO: 2; or
iii) a first primer as a forward primer which has at least 90%, particularly at least 91%, particularly at least 92%, 93%, 94%, 95%, 96%, 97%, 98% or 99% sequence identity with a nucleotide sequence as depicted in SEQ ID NO: 1 and a second primer as a reverse primer which has at least 90%, particularly at least 91%, particularly at least 92%, 93%, 94%, 95%, 96%, 97%, 98% or 99% sequence identity with a nucleotide sequence as depicted in SEQ ID NO: 2, particularly the forward primer of SEQ ID NO: 1 and the reverse primer of SEQ ID NO: 2.

In one embodiment, the regulatory nucleotide sequence according to the invention and as described herein is modified using one or more oligonucleotides selected from the group of oligonucleotides depicted in SEQ ID NO: 3, SEQ ID NO: 4, SEQ ID NO: 5, SEQ ID NO: 6, SEQ ID NO: 7 and SEQ ID NO: 8.

In one embodiment the invention relates to a regulatory nucleotide sequence or an expression cassette comprising said regulatory nucleotide sequence or a polynucleotide construct, particularly a chimeric polynucleotide construct, comprising said regulatory sequence as described herein, which regulatory nucleotide sequence provides a transcription initiation function, wherein the nucleotide sequence providing said function has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 13 and wherein said regulatory nucleotide sequence mediates transcription of an operably associated protein encoding polynucleotide of interest in most tissues of the plant but essentially excluding the tissues of the pollen so that no expression product is present in said tissues to any significant extent.

In one embodiment, the invention relates to a regulatory nucleotide sequence or an expression cassette comprising said regulatory nucleotide sequence or a polynucleotide construct, particularly a chimeric polynucleotide construct, comprising said regulatory sequence as described herein, which regulatory nucleotide sequence provides a transcription initiation function, wherein the complementary strand of the nucleotide sequence providing said function hybridizes to a nucleotide sequence depicted in SEQ ID NO: 13, particularly under moderate hybridization conditions, more particularly under moderately stringent hybridization conditions and wherein said regulatory nucleotide sequence mediates transcription of an operably associated protein encoding polynucleotide of interest in most tissues of the plant but essentially excluding the tissues of the pollen so that no expression product is present in said tissues to any significant extent. In particular, said hybridization occurs under stringent hybridization conditions.

In one embodiment of the invention, the nucleotide sequence providing the transcription initiation function is the sequence depicted in SEQ ID NO: 13, or a fragment thereof which still exhibits full functionality as a transcription initiation sequence, and complements thereof.

In one embodiment, a regulatory nucleotide sequence or an expression cassette comprising said regulatory nucleotide sequence or a polynucleotide construct, particularly a chimeric polynucleotide construct, comprising said regulatory sequence according to the invention and as described herein is provided comprising approximately 1 kb of the nucleotide sequence upstream of the ZmABP3 transcription start site of a ZmABP3 gene, particularly upstream of the ZmABP3 transcription start site of the ZmABP3 gene as depicted in SEQ ID NO: 17.

In one embodiment of the invention, said regulatory nucleotide sequence comprises in addition the ZmABP3 5'-untranslated sequence, the ZmABP3 first exon, the ZmABP3 first intron and a portion of the ZmABP3 second exon, particularly a portion of the ZmABP3 second exon terminating at the translation initiation codon, particularly a portion of the ZmABP3 second exon comprising between about 10 to about 20 nucleotides, particularly between about 12 and about 16 nucleotides, particularly about 14 nucleotides, of the second exon.

In one embodiment, a regulatory nucleotide sequence or an expression cassette comprising said regulatory nucleotide sequence or a polynucleotide construct, particularly a chimeric polynucleotide construct, comprising said regulatory sequence is provided at least part of which has a transcription termination function, which sequence is obtainable in a PCR amplification reaction from a gDNA template, particularly a maize gDNA template, using a forward primer (P3 (5'-tatatagagctcgcatcatgatcatgcatcatggact-3') which has at least 90%, particularly at least 91%, particularly at least 92%, 93%, 94%, 95%, 96%, 97%, 98% or 99% sequence identity with a nucleotide sequence as depicted in SEQ ID NO: 9 and a reverse primer (P4 (5'-atatatactagtggcgcgcca-cactttctgtcgcatgtgatttgca-3') which has at least 90%, particularly at least 91%, particularly at least 92%, 93%, 94%, 95%, 96%, 97%, 98% or 99% sequence identity with a nucleotide sequence as depicted in SEQ ID NO: 10. In particular, said regulatory nucleotide sequence comprises a transcriptional terminator and poly-adenylation signal. In particular, a forward primer (P3 (5'-tatatagagctcgcatcatgatcatgcatcatggact-3')) which has a nucleotide sequence as depicted in SEQ ID NO: 9 and a reverse primer (P4 (5'-atatatactagtggcgcgcca-cactttctgtcgcatgtgatttgca-3') which has a nucleotide sequence as depicted in SEQ ID NO: 10 are used.

In one embodiment of the invention, a regulatory nucleotide sequence or an expression cassette comprising said regulatory nucleotide sequence or a polynucleotide construct, particularly a chimeric polynucleotide construct, comprising said regulatory sequence is provided which comprises a transcription termination sequence obtainable from a gene encoding an actin depolymerizing factor 3 (ABP3), which regulatory sequence mediates transcription of an operably associated polynucleotide molecule, particularly of an operably associated protein encoding polynucleotide molecule of interest such that said polynucleotide of interest is transcribed in most of the plant tissues but not or substantially not in the tissues of the pollen so that no expression product is present in said tissues to any significant extent, particularly from a maize actin depolymerizing factor 3 (ABP3) gene, wherein i) said regulatory nucleotide sequence comprises a transcription termination sequence which regulatory sequence has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 14; or ii) the complementary strand of said regulatory nucleotide sequence hybridizes to a nucleotide sequence depicted in SEQ ID NO: 14, particularly under moderate hybridization conditions, more particularly under moderate-stringent hybridization conditions, particularly under stringent hybridization conditions and mediates termination of transcription of an operably associated protein encoding polynucleotide of interest; or iii) said regulatory nucleotide sequence has a sequence as depicted in SEQ ID NO: 14, or a fragment thereof which still exhibits full functionality as a termination sequence, including complements thereof.

In one embodiment of the invention, a regulatory nucleotide sequence is provided or an expression cassette comprising said regulatory nucleotide sequence or a polynucleotide construct, particularly a chimeric polynucleotide construct, comprising said regulatory sequence at least part of which has a transcription initiation function and a termination function, respectively, which regulatory nucleotide sequence is obtainable from a gene encoding an actin depolymerizing factor 3 (ABP3), which is expressed in most tissues of the plant but not or substantially not in the tissues of the pollen so that no expression product is present in said tissues to any significant extent, particularly from a maize actin depolymerizing factor 3 (ABP3) gene, and which regulatory nucleotide sequence comprises a transcription initiation sequence as depicted in SEQ ID NO: 13 and a transcription termination sequence as depicted in SEQ ID NO:14.

In one embodiment of the invention, the regulatory nucleotide sequence is obtainable from maize genomic DNA, particularly from a putative gene on the maize genome, which is highly expressed in most tissues of the plant but not or substantially not in the tissues of the tassel so that no expression product is present in said tissues to any significant extent.

In one embodiment, a regulatory nucleotide sequence or an expression cassette comprising said regulatory nucleotide sequence or a polynucleotide construct, particularly a chimeric polynucleotide construct, comprising said regulatory sequence according to the invention and as described herein is provided comprising approximately 2.6 kb of the 5'-sequence including approximately 2 kb of 5'-non-transcribed sequence, a 5'-UTR, and exon 1 and part of exon 2 and intron 1, particularly approximately 0.6 kb representing exon 1, intron 1 and about 16 bp of exon 2.

In one embodiment, the invention provides a regulatory nucleotide sequence or an expression cassette comprising said regulatory nucleotide sequence or a polynucleotide construct, particularly a chimeric polynucleotide construct, comprising said regulatory sequence at least part of which has a transcription initiation function as described herein, which regulatory sequence is obtainable from a genomic *Zea mays* DNA template using i) a first primer which has at least 90%, particularly at least 91%, particularly at least 92%, 93%, 94%, 95%, 96%, 97%, 98% or 99% sequence identity with a nucleotide sequence as depicted in SEQ ID NO: 19, particularly the primer of SEQ ID NO: 19; or
ii) a second primer which has at least 90%, particularly at least 91%, particularly at least 92%, 93%, 94%, 95%, 96%, 97%, 98% or 99% sequence identity with a nucleotide sequence as depicted in SEQ ID NO: 20, particularly the reverse primer of SEQ ID NO: 20; or
iii) a first primer as a forward primer which has at least 90%, particularly at least 91%, particularly at least 92%, 93%, 94%, 95%, 96%, 97%, 98% or 99% sequence identity with a nucleotide sequence as depicted in SEQ ID NO: 19 and a second primer as a reverse primer which has at least 90%, particularly at least 91%, particularly at least 92%, 93%, 94%, 95%, 96%, 0.97%, 98% or 99% sequence identity with a nucleotide sequence as depicted in SEQ ID NO: 20, particularly the forward primer of SEQ ID NO: 19 and the reverse primer of SEQ ID NO: 20.

In one embodiment, the regulatory nucleotide sequence according to the invention and as described herein is modified using one or more oligonucleotides selected from the group of oligonucleotides depicted in SEQ ID NO: 21, SEQ ID NO: 22, SEQ ID NO: 23, SEQ ID NO: 24, SEQ ID NO: 25 and SEQ ID NO: 26.

In one embodiment, the invention relates to a regulatory nucleotide sequence or an expression cassette comprising said regulatory nucleotide sequence or a polynucleotide construct, particularly a chimeric polynucleotide construct, comprising said regulatory sequence as described herein, which regulatory nucleotide sequence provides a transcription initiation function, wherein the nucleotide sequence providing said function has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 35 and wherein said regulatory nucleotide sequence mediates transcription of an operably associated protein encoding polynucleotide of interest in most tissues of the plant but essentially excluding the tissues of the tassel so that no expression product is present in said tissues to any significant extent.

In one embodiment, the invention relates to a regulatory nucleotide sequence or an expression cassette comprising said regulatory nucleotide sequence or a polynucleotide construct, particularly a chimeric polynucleotide construct, comprising said regulatory sequence as described herein, which regulatory nucleotide sequence provides a transcription initiation function, wherein the complementary strand of the nucleotide sequence providing said function hybridizes to a nucleotide sequence depicted in SEQ ID NO: 35, particularly under moderate hybridization conditions, more particularly under moderately stringent hybridization conditions and wherein said regulatory nucleotide sequence mediates transcription of an operably associated protein encoding polynucleotide of interest in most tissues of the plant but essentially excluding the tissues of the pollen so that no expression product is present in said tissues to any significant extent. In particular, said hybridization occurs under stringent hybridization conditions.

In one embodiment of the invention, the nucleotide sequence providing the transcription initiation function is the sequence depicted in SEQ ID NO: 35, or a fragment thereof, which still exhibits the full functionality as a transcription initiation sequence and complements thereof.

In one embodiment, a regulatory nucleotide sequence or an expression cassette comprising said regulatory nucleotide sequence or a polynucleotide construct, particularly a chimeric polynucleotide construct, comprising said regulatory sequence is provided at least part of which has a transcription termination function which sequence is obtainable in a PCR amplification reaction from a gDNA template, particularly a maize gDNA template, using a forward primer which has at least 90%, particularly at least 91%, particularly at least 92%, 93%, 94%, 95%, 96%, 97%, 98% or 99% sequence identity with a nucleotide sequence as depicted in SEQ ID NO: 29 and a reverse primer, which has at least 90%, particularly at least 91%, particularly at least 92%, 93%, 94%, 95%, 96%, 97%, 98% or 99% sequence identity with a nucleotide sequence as depicted in SEQ ID NO: 30. In particular, said regulatory nucleotide sequence comprises a transcriptional terminator and poly-adenylation signal. In particular, a forward primer, which has a nucleotide sequence as depicted in SEQ ID NO: 29 and a reverse primer, which has a nucleotide sequence as depicted in SEQ ID NO: 30 are used.

In one embodiment of the invention, a regulatory nucleotide sequence or an expression cassette comprising said regulatory nucleotide sequence or a polynucleotide construct, particularly a chimeric polynucleotide construct, comprising said regulatory sequence is provided wherein
i) said regulatory nucleotide sequence comprises a transcription termination sequence which has at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 36; or
ii) the complementary strand of said regulatory nucleotide sequence hybridizes to a nucleotide sequence depicted in SEQ ID NO: 36, particularly under moderate hybridization conditions, particularly under moderate-stringent hybridization conditions, particularly under stringent hybridization conditions and mediates termination of transcription of an operably associated protein encoding polynucleotide of interest; or
iii) said regulatory sequence has a sequence as depicted in SEQ ID NO: 36, or a fragment thereof, which still exhibits the full functionality as a termination sequence, including complements thereof.

In one embodiment of the invention, a regulatory nucleotide sequence or an expression cassette comprising said regulatory nucleotide sequence or a polynucleotide construct, particularly a chimeric polynucleotide construct, comprising said regulatory sequence, is provided at least part of which has a transcription initiation function and a termination function, respectively, which regulatory nucleotide sequence is obtainable from a maize genomic DNA, which is expressed in most tissues of the plant but not or substantially not in the tissues of the tassel so that no expression product is present in said tissues to any significant extent, and which regulatory nucleotide sequence comprises a transcription initiation sequence and a transcription termination sequence, respectively, which have at least between 80% and 85% sequence identity, with all integers falling within this range also being comprised herewith, particularly at least between 85% and 90% sequence identity, with all integers falling within this range also being comprised herewith, particularly at least 90%, 91%, 92%, 93%, 94%, 95%, 96%, 97%, 98% or 99% sequence identity with a nucleotide sequence depicted in SEQ ID NO: 35 and SEQ ID NO:36, respectively.

In one embodiment of the invention, a regulatory nucleotide sequence or an expression cassette comprising said regulatory nucleotide sequence or a polynucleotide construct, particularly a chimeric polynucleotide construct, comprising said regulatory sequence, is provided at least part of which has a transcription initiation function and a termination function, respectively, which regulatory nucleotide sequence is obtainable from a maize genomic DNA, which is expressed in most tissues of the plant but not or substantially not in the tissues of the tassel so that no expression product is present in said tissues to any significant extent, and which regulatory nucleotide sequence comprises a transcription initiation sequence as depicted in SEQ ID NO: 35 and a transcription termination sequence as depicted in SEQ ID NO: 36.

It is apparent to the skilled artisan that, based on the nucleotide sequences shown in SEQ ID NO: 13, SEQ ID NO 14, SEQ ID NO: 35 and SEQ ID NO: 36, fragments of various length can be obtained from said sequences, for example by using any primer combinations of interest to generate fragments that still exhibit the specific regulatory function according to the invention that is driving expression of an operably associated polynucleotide of interest in most plant tissues but tissues of the pollen and the tassel, respectively. The invention thus includes fragments derived from a full-length transcript promoter and a full-length terminator of the invention and as described herein, respectively that function according to the invention, i.e. are capable of conferring expression and termination of an operably associated nucleotide sequence in most plant tissues but essentially excluding the tissues of the pollen so that no expression product is present in said tissues to any significant extent and/or the tassel.

The function of the promoter and terminator fragments, once obtained, can be easily tested by fusing them to a selectable or screenable marker gene and assaying the fusion constructs for retention of the specific promoter activity. Such assays are within the ordinary skill of the person skilled in the art.

In one embodiment, the invention relates to nucleotide fragments, particularly to nucleotide fragments obtainable from the regulatory sequences of an action depolymerizing factor 3 (ABP3) gene, which nucleotide fragments are of at least about 50 bases, preferably of between about 400 bases and about 650 bases, more preferably of between about 200 bases and about 400 bases and most preferably of about 350 bases in length and still exhibit the specific regulatory function according to the invention that is driving expression of an operably associated polynucleotide of interest in most plant tissues but essentially excluding the tissues of the pollen and/or the tassel so that no expression product is present in said tissues to any significant extent.

In one embodiment, the invention relates to nucleotide fragment comprising a nucleotide sequence comprising a consecutive stretch of at least 50 nt, particularly of between about 400 nt and about 650 nt, particularly of between about 200 nt and about 400 nt, particularly of about 350 nt in length of the nucleotide sequence depicted in SEQ ID NO:13 and SEQ ID NO: 35, respectively, wherein said nucleotide sequences still exhibit the specific regulatory function according to the invention that is driving expression of an operably associated polynucleotide of interest in most plant tissues but essentially excluding the tissues of the pollen and/or the tassel so that no expression product is present in said tissues to any significant extent.

It is also clear to the skilled artisan that variant sequences may be obtained without affecting the specific properties of the regulatory sequences according to the invention by introducing mutations, i.e. insertions, deletions and/or substitutions of one or more nucleotides, into the DNA sequences of SEQ ID NO: 13, SEQ ID NO 14, SEQ ID NO: 35 and SEQ ID NO: 36, respectively, using methods known in the art. In addition, an unmodified or modified nucleotide sequence of the present invention may be further varied by shuffling the sequence of the invention. To test for a function of variant DNA sequences according to the invention, the sequence of interest is operably linked to a selectable or screenable marker gene and expression of the marker gene is tested in transient expression assays with protoplasts or in whole plant tissues or in stably transformed plants. It is known to the skilled artisan that DNA sequences capable of driving expression of an operably associated nucleotide sequence are build in a modular way. Accordingly, expression levels from shorter DNA fragments may be different than the one from the longest fragment and may be different from each other. For example, deletion of a down-regulating upstream element will lead to an increase in the expression levels of the associated nucleotide sequence while deletion of an up-regulating element will decrease the expression levels of the associated nucleotide sequence.

In one embodiment, the invention relates to an expression cassette comprising a regulatory nucleotide sequence or an expression cassette comprising said regulatory nucleotide sequence or a polynucleotide construct, particularly a chimeric polynucleotide construct, comprising said regulatory sequence according to the invention and as described herein.

In one embodiment, the expression cassette according to the invention comprises about 2.3 kb of the 5'-sequence of ZmABP3 which consists of about 1.1 kb of 5'-non-transcribed sequence, about 0.25 kb of 5'-UTR and about 0.98 kb representing ZmABP3-intron 1, about 1.013 kb of the 3'-sequence starting just past the ABP3 translation stop codon including about 0.3 kb of 3'-UTR and about 0.7 kb of non-transcribed sequence, which functions as the transcriptional terminator and poly-adenylation signal.

In one embodiment, an expression cassette according to the invention is provided wherein the natural translation start codon is silenced and moved to the second exon, particularly moved within 15 nucleotides of the 5'-end of ZmABP3 exon 2.

In one embodiment, an expression cassette according to the invention is provided wherein the start codon is preceded by the Kozak sequence 5' . . . CCACC . . . -3'.

In one embodiment, the expression cassette according to the invention comprises a regulatory nucleotide sequence comprising approximately 2.6 kb of the 5'-sequence, which consists of approximately 2 kb of 5'-non-transcribed sequence, and about 12 bp of 5'-UTR, approximately 0.6 kb representing exon 1, intron 1 and about 16 bp of exon 2; and approximately 1 kb of the 3'-sequence that begins just past the translation stop codon and includes approximately 0.6 kb of 3'-UTR and about 0.4 kb of non-transcribed sequence, and functions as the transcriptional terminator and poly-adenylation signal.

In one embodiment, an expression cassette according to the invention is provided wherein the natural translation start codon is silenced and moved to the second exon.

In one embodiment, a polypeptide or protein encoding nucleotide sequence is provided encoding an endotoxin of *Bacillus thuringiensis* which has at least 80% sequence identity, particularly at least 85% sequence identity, particularly at least 90%, 91%, 92%, 93%, 94%, 95%, 96%, 97%, 98% or 99% sequence identity with a nucleotide sequence as depicted in SEQ ID NO:15.

In one embodiment, a polypeptide or protein encoding nucleotide sequence is provided encoding an endotoxin of *Bacillus thuringiensis* which has the nucleotide sequence as depicted in SEQ ID NO: 15.

In one embodiment, the invention relates to a transgenic plant comprising an expression cassette according to the invention and as described herein.

In one embodiment, the invention provides a transgenic plant, particularly a transgenic maize plant comprising a regulatory sequence according to the invention and as described herein.

In one embodiment, the invention provides a transgenic plant, particularly a transgenic maize plant comprising a regulatory sequence according to the invention and as described herein in association with a polynucleotide of interest, particularly a polypeptide or protein encoding polynucleotide of interest.

In one embodiment, the invention provides a transgenic plant, particularly a transgenic maize plant comprising an expression cassette according to the invention and as described herein.

In one embodiment, a transgenic plant according to the invention and as described herein is provided, wherein the polypeptide or protein encoding nucleotide sequence encodes an endotoxin of *Bacillus thuringiensis* which has at least 80% sequence identity, particularly at least 85% sequence identity, particularly at least 90%, 91%, 92%, 93%, 94%, 95%, 96%, 97%, 98% or 99% sequence identity with a nucleotide sequence as depicted in SEQ ID NO:15 and is under the control of a regulatory sequences operable in said plant.

In one embodiment, a transgenic plant according to the invention and as described herein is provided, wherein the polypeptide or protein encoding nucleotide sequence encodes an endotoxin of *Bacillus thuringiensis* which has the nucleotide sequence as depicted in SEQ ID NO: 15 and is under the control of a regulatory sequences operable in said plant.

The invention also provides methods for preparing expression cassettes comprising the regulatory sequence according to the invention comprising linking an expressible polynucleotide encoding a polypeptide or a protein of interest with the regulatory sequence according to the invention and as described herein to obtain an expression construct, wherein the polynucleotide of interest is operably linked or associated with the regulatory sequence such that expression of the polypeptide or a protein of interest is mediated by the regulatory sequence according to the invention and results in the expression of said polypeptide or a protein of interest in essentially all plant tissues, but essentially excludes expression in the tissues of the reproductive structures of the plant, particularly in the tissues of the pollen and/or the tassel so that no expression product is present in said tissues to any significant extent.

In one embodiment, the invention relates to a method of producing a transgenic plant expressing a DNA sequence of interest in non-pollen tissue but not or substantially not in the tissues of the pollen and/or the tassel, comprising
 a. transforming an expression cassette according to the invention and as described herein into a plant cell which comprises a regulatory nucleotide sequence, at least part of which has a transcription initiation function which mediates expression of an operably associated protein encoding polynucleotide of interest in most plant tissues but essentially excluding the tissues of the pollen and/or the tassel so that no expression product is present in said tissues to any significant extent; and
 b. regenerating the plant cell transformed in step a) into a plant.

In one embodiment, the invention relates to a method of controlling insect target-pests feeding on vegetative plant tissues such as the leaf, stalk and root and/or on reproductive tissues such as the ear, but protecting non-target pests feeding on pollen comprising
 a. growing a plant according to the invention and as described herein in an area that is infested with the target pest;
 b. expressing a polypeptide or protein that is capable of controlling said target pest under the control of a regulatory sequence according to the invention and as described herein.

In one embodiment, the invention relates to a method of protecting the reproductive tissues of a plant, particularly the tissues of the pollen and/or the tassel against damage caused by expression in said tissues of a polypeptide or protein of interest comprising
 a. growing a plant according to the invention and as described herein;
 b. expressing in said plant a polypeptide or protein of interest under the control of a regulatory sequence according to the invention and as described herein.

In one embodiment the present invention relates to the use of a regulatory sequence according to the present invention and as disclosed herein for protecting the reproductive tissues of a plant, particularly the tissues of the pollen and/or the tassel against damage caused by expression in said tissues of a polypeptide or protein of interest comprising expressing in said plant said polypeptide or protein of interest under the control of a regulatory sequence according to the invention and as described herein.

BRIEF DESCRIPTION OF THE SEQUENCES

SEQ ID NO: 1 depicts the nucleotide sequence of forward primer P1
SEQ ID NO: 2 depicts the nucleotide sequence of reverse primer P2
SEQ ID NO: 3 depicts the nucleotide sequence of oligonucleotide Patg
SEQ ID NO: 4 depicts the nucleotide sequence of oligonucleotide Pnco
SEQ ID NO: 5 depicts the nucleotide sequence of oligonucleotide ADPc-1
SEQ ID NO: 6 depicts the nucleotide sequence of oligonucleotide ADPc-2
SEQ ID NO: 7 depicts the nucleotide sequence of oligonucleotide ADPc-4
SEQ ID NO: 8 depicts the nucleotide sequence of oligonucleotide adp3-a
SEQ ID NO: 9 depicts the nucleotide sequence of forward primer P3
SEQ ID NO: 10 depicts the nucleotide sequence of reverse primer P4
SEQ ID NO: 11 depicts the nucleotide sequence of forward primer Tnco
SEQ ID NO: 12 depicts the nucleotide sequence of forward primer T2
SEQ ID NO: 13 depicts the nucleotide sequence of modified ZmABP3 regulatory sequence including the transcription initiation sequence SEQ ID NO: 14 depicts the nucleotide sequence of ZmABP3 terminal sequence
SEQ ID NO: 15 depicts the nucleotide sequence of Cry1AbG6
SEQ ID NO: 16 depicts the nucleotide sequence of maize-optimized AtAVP1 D coding sequence
SEQ ID NO: 17 depicts the nucleotide sequence of the ZmABP3 gene
SEQ ID NO: 18 depicts the nucleotide sequence of the pNOV1321 plasmid
SEQ ID NO: 19 depicts the nucleotide sequence of forward primer ABT P1 forw
SEQ ID NO: 20 depicts the nucleotide sequence of reverse primer ABT P2 rev
SEQ ID NO: 21 depicts the nucleotide sequence of oligonucleotide pABT mut1
SEQ ID NO: 22 depicts the nucleotide sequence of oligonucleotide pABT mut2
SEQ ID NO: 23 depicts the nucleotide sequence of oligonucleotide pABT mut3
SEQ ID NO: 24 depicts the nucleotide sequence of oligonucleotide pABT mut4
SEQ ID NO: 25 depicts the nucleotide sequence of oligonucleotide pABT mut5
SEQ ID NO: 26 depicts the nucleotide sequence of oligonucleotide pABT mut6
SEQ ID NO: 27 depicts the nucleotide sequence of forward primer pABT amp1
SEQ ID NO: 28 depicts the nucleotide sequence of reverse primer pABT amp2
SEQ ID NO: 29 depicts the nucleotide sequence of forward primer ABT P4
SEQ ID NO: 30 depicts the nucleotide sequence of reverse primer ABT P5
SEQ ID NO: 31 depicts the nucleotide sequence of oligonucleotide ABTt m1
SEQ ID NO: 32 depicts the nucleotide sequence of oligonucleotide ABTt m2
SEQ ID NO: 33 depicts the nucleotide sequence of ZmABT1 cDNA
SEQ ID NO: 34 depicts the nucleotide sequence of ZmABT2 cDNA
SEQ ID NO: 35 depicts the nucleotide sequence of the ZmABT promoter
SEQ ID NO: 36 depicts the nucleotide sequence of the ZmABT terminal sequence.
SEQ ID NO: 37 depicts the nucleotide sequence of the ZmABP3-Cry1AbG6 Assembly construct.
SEQ ID NO: 38 depicts the nucleotide sequence of the ZmABP3-Cry1AbG6 binary construct.
SEQ ID NO: 39 depicts the nucleotide sequence of the enhanced ZmABP3-Cry1AbG6 binary construct.
SEQ ID NO: 40 depicts the nucleotide sequence of the ZmABP3-AmCyan assembly construct.
SEQ ID NO: 41 depicts the nucleotide sequence of the ZmABP3-AmCyan binary construct.
SEQ ID NO: 42 depicts the nucleotide sequence of the ZmABP3-AtAVP1 D assembly construct.
SEQ ID NO: 43 depicts the nucleotide sequence of the ZmABP3-AtAVP1 D binary construct.
SEQ ID NO: 44 depicts the nucleotide sequence of plasmid 15772 (ZmABT Assembly)
SEQ ID NO: 45 depicts the nucleotide sequence of plasmid 15773
SEQ ID NO: 46 depicts the nucleotide sequence of ZmABT gDNA
SEQ ID NO: 47 depicts the nucleotide sequence of Ctrl_ZMU45855-3_at
SEQ ID NO: 48 depicts the nucleotide sequence of AF032370_at
SEQ ID NO: 49 depicts the nucleotide sequence of Zm001747_s_at
SEQ ID NO: 50 depicts the nucleotide sequence of Zm005803_s_at
SEQ ID NO: 51 depicts the nucleotide sequence of Zm007728_s_at
SEQ ID NO: 52 depicts the nucleotide sequence of Zm009722_s_at
SEQ ID NO: 53 depicts the nucleotide sequence of Zm015335_s_at
SEQ ID NO: 54 depicts the nucleotide sequence of Zm021004_s_at
SEQ ID NO: 55 depicts the nucleotide sequence of Zm058948_s_at
SEQ ID NO: 56 depicts the nucleotide sequence of Zm061393_s_at
SEQ ID NO: 57 depicts the nucleotide sequence of Zm016864_s_at
SEQ ID NO: 58 depicts the nucleotide sequence of Zm018791_at
SEQ ID NO: 59 depicts the nucleotide sequence of ZMMETALL_x_at
SEQ ID NO: 60 depicts the nucleotide sequence of Zm000019_at
SEQ ID NO: 61 depicts the nucleotide sequence of Zm002987_at
SEQ ID NO: 62 depicts the nucleotide sequence of Zm002990_s_at
SEQ ID NO: 63 depicts the nucleotide sequence of Zm002990_x_at
SEQ ID NO: 64 depicts the nucleotide sequence of Zm004433_at
SEQ ID NO: 65 depicts the nucleotide sequence of Zm005761_at
SEQ ID NO: 66 depicts the nucleotide sequence of Zm006285_at
SEQ ID NO: 67 depicts the nucleotide sequence of Zm006481_s_at
SEQ ID NO: 68 depicts the nucleotide sequence of Zm010323_s_at
SEQ ID NO: 69 depicts the nucleotide sequence of Zm011554_at
SEQ ID NO: 70 depicts the nucleotide sequence of Zm011554_x_at
SEQ ID NO: 71 depicts the nucleotide sequence of Zm021403_at
SEQ ID NO: 72 depicts the nucleotide sequence of Zm028405_s_at
SEQ ID NO: 73 depicts the nucleotide sequence of Zm032921_s_at
SEQ ID NO: 74 depicts the nucleotide sequence of Zm033444_s_at
SEQ ID NO: 75 depicts the nucleotide sequence of Zm035082_s_at
SEQ ID NO: 76 depicts the nucleotide sequence of Zm040564_x_at
SEQ ID NO: 77 depicts the nucleotide sequence of Zm054116_s_at
SEQ ID NO: 78 depicts the nucleotide sequence of Zm066342_at
SEQ ID NO: 79 depicts the nucleotide sequence of Zm051284_at SEQ ID NO: 80 depicts the nucleotide sequence of Vector 15289
SEQ ID NO: 81 depicts the nucleotide sequence of ZmABP-948-binary
SEQ ID NO: 82 depicts the nucleotide sequence of ZmABT-990-binary
SEQ ID NO: 83 depicts the nucleotide sequence of 5' Bfr1 primer
SEQ ID NO: 84 depicts the nucleotide sequence of 3' Xba1 primer
SEQ ID NO: 85 depicts the nucleotide sequence of 5'Gfix primer
SEQ ID NO: 86 depicts the nucleotide sequence of 3'Gfix primer
SEQ ID NO: 87 depicts the nucleotide sequence of 5'1Ab5XbaI primer
SEQ ID NO: 88 depicts the nucleotide sequence of 3'1Ab3d6 primer
SEQ ID NO: 89 depicts the nucleotide sequence of cy2'
SEQ ID NO: 90 depicts the nucleotide sequence of cy1
SEQ ID NO: 91 depicts the nucleotide sequence of cy2

DETAILED DESCRIPTION OF THE INVENTION

Definitions

The technical terms and expressions used within the scope of this application are generally to be given the meaning commonly applied to them in the pertinent art of plant molecular biology if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

As used in this specification and the appended claims, the plural form "tissues", includes also the singular form unless the context clearly dictates otherwise. Thus, for example, reference to "tissues of the tassel" includes one or more tissues present in the tassel.

As used in this specification and the appended claims, the phrase "most tissues of the plant" or "essentially all tissues of the plant" is used interchangeably and refers to the majority to the tissues present in the plant with the exception of the tissues of the reproductive structures, particularly the tissues of the pollen and the tassel. In particular, "most tissues" refer to those tissues of the plant where target insects mainly feed on, with the exception of the tissues of the male reproductive structures, such as the tissues of the stalk, the roots, the leaves, the ear, the ear sheath, the silks and the developing kernels.

The term "polynucleotide" is understood herein to refer to polymeric molecule of high molecular weight which can be single-stranded or double-stranded, composed of monomers (nucleotides) containing a sugar, phosphate and a base which is either a purine or pyrimidine. A "polynucleotide fragment" is a fraction of a given polynucleotide molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism, including the genomes of the mitochondria and the plastids. The term "polynucleotide" thus refers to a polymer of DNA or RNA which can be single- or double-stranded, optionally containing synthetic, non-natural or altered nucleotide bases capable of incorporation into DNA or RNA polymers. Unless otherwise indicated, a particular nucleic acid sequence of this invention also implicitly encompasses conservatively modified variants thereof (e.g. degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer, et al., Nucleic Acid Res. 19:5081 (1991); Ohtsuka, et al., J. Biol. Chem. 260:2605-2608 (1985); and Rossolini, et al., Mol. Cell. Probes 8:91-98 (1994)). The term polynucleotide is used interchangeably with nucleic acid, nucleotide sequence and may include genes, cDNAs, and mRNAs encoded by a gene, etc.

A "regulatory nucleotide sequence at least part of which has a transcription initiation function" is understood herein to refer to a nucleotide sequence, which controls the expression of an operably associated coding sequence by providing the recognition for RNA polymerase and other factors required for proper transcription and is located usually upstream (5') to its coding sequence. "Regulatory nucleotide sequences" include 5' regulatory sequences located proximal and more distal elements upstream of the associated coding region, which influence the transcription, RNA processing or stability, or translation of the associated coding sequence. "Regulatory nucleotide sequences" may further include 3' sequences, including 3' non-translated and/or 3' non-transcribed sequences, located downstream of the associated coding region, and can include a transcription termination site. "Regulatory nucleotide sequences" may include enhancers, promoters, untranslated leader sequences, introns, and polyadenylation signal sequences. They include natural and synthetic sequences as well as sequences that may be a combination of synthetic and natural sequences. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term "regulatory nucleotide sequences" includes "transcription initiation" or "promoter" sequences and "promoter regulatory sequences." These terms are used interchangeably herein after.

For purposes of this invention, the definition of the term "3'-nontranscribed sequence" includes modifications to the nucleotide sequence of a 3'-nontranscribed sequence derived from a target gene, provided the modified 3'-nontranscribed sequence does not significantly reduce the activity of its associated 3' regulatory sequence. The 3'-nontranscribed sequence extends approximately 0.5 to 1.5 kb downstream of the transcription termination site.

The polynucleotide of the invention is understood to be provided in isolated form.

The term "isolated" means that the polynucleotide disclosed and claimed herein is not a polynucleotide as it occurs in its natural context, if it indeed has a naturally occurring counterpart. Accordingly, the other compounds of the invention described further below are understood to be isolated. If claimed in the context of a plant genome, the polynucleotide of the invention is distinguished over naturally occurring counterparts by i.e. modifications introduced into the naturally occurring counterpart sequence and/or the insertion side in the genome and the flanking sequences at the insertion side.

"Operably associated" and "operably-linked" are used interchangeably and refer to the association of nucleic acid sequences on a single nucleic acid fragment so that the function of one is affected by the other. For example, a promoter is associated or operably-linked with a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

The term "present to any significant extent" as used within the context of the present invention refers to the fact that only negligible expression occurs in pollen resulting in only minor amounts of the expression product in pollen tissue at concentrations that may be detectable by high-resolution detection methods such as HPLC, ELISA-based assays, Western analysis, insect feeding assays, enzyme activity assays etc., but stay below a certain threshold level that would be needed to effect the envisaged biological function of the expression product. For example, in case of the Cry1AbG6 endotoxin of *Bacillus thuringiensis* the threshold level is in the range of between 5 ng/mg soluble protein and 60 ng/mg soluble protein, particularly in the range of between 20 ng/mg soluble protein and 50 ng/mg soluble protein.

The term "chimeric gene" refers to any gene that contains 1) DNA sequences, including regulatory and coding sequences that are not found together in nature in this specific combination or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

The terms "heterologous DNA sequence," "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling or mutation. These terms also include non-naturally occurring multiple copies of a naturally occurring DNA sequence. Thus, the terms refer to a DNA segment that is foreign or heterologous to the cell, or homologous to the cell but in a position within the host cell genome in which the element is not ordinarily found. Exogenous DNA segments are expressed to yield exogenous polypeptides. A "homologous" DNA sequence is a DNA sequence that is naturally associated with a host cell into which it is introduced.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

"Expression cassette" as used herein means a DNA sequence capable of directing expression of a particular nucleotide sequence in an appropriate host cell, comprising a promoter operably linked to the protein encoding polynucleotide of interest which is operably linked to a terminator. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the protein encoding polynucleotide of interest may be chimeric.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

The terms "protein," "peptide" and "polypeptide" are used interchangeably herein.

A "probe" as used herein refers to a defined nucleic acid (DNA or RNA) fragment of variable length which may be used to detect in a DNA or RNA containing sample nucleotide sequences that are complementary to the sequence represented by the probe molecule.

The probe molecules may be used in a microarray set up, where they are covalently attached to a chemical matrix on an inert surface, such as coated glass slides or silicon based gene chips. Hybridization of the probe molecules to a target nucleic acid in the sample usually occurs under high stringency conditions. Probe-target hybridization is usually detected and quantified by fluorescence-based detection of fluorophore-labeled targets to determine relative transcript abundance of nucleic acid sequences in the target. DNA microarrays may be used in expression profiling experiments to quantify transcript abundance for a target molecule in tissue samples such as the tissues of the pollen and/or the tassel, calculated based on the strength of the signal detected in the respective samples.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridizations experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 0.1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M $Na^+$ ion, typically about 0.01 to 1.0 M $Na^+$ ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. "Plant tissue" includes differentiated and undifferentiated tissues or plants, including but not limited to roots, stems, shoots, leaves, pollen, seeds, tumor tissue and various forms of cells and culture such as single cells, protoplasts, embryos, and callus tissue. The plant tissue may be in plants or in organ, tissue or cell culture.

The use of this term in conjunction with, or in the absence of, any specific type of plant tissue as listed above or otherwise embraced by this definition is not intended to be exclusive of any other type of plant tissue.

The terms "maize", "corn" and "Zea mays" are used herein interchangeably and refer to plants belonging to the genus Zea including, for example, different strains, races or varieties, commercial and non-commercial, of the species Zea mays.

The present invention relates to a transgenic plant comprising stably integrated in its genome a chimeric polynucleotide construct, particularly a chimeric DNA construct, comprising a protein encoding polynucleotide of interest, particularly a polypeptide or protein encoding polynucleotide of interest, under control of a regulatory nucleotide sequence, at least part of which has a transcription initiation function directing expression of said protein encoding polynucleotide of interest to essentially all tissues of the plant with the exception of the tissues of the male reproductive structures, particularly the tissues of the pollen and/or the tassel so that no expression product is present in said tissues to any significant extent.

A regulatory nucleotide sequence according to the present invention at least part of which has a transcription initiation function which mediates expression of an operably associated protein encoding polynucleotide of interest in most plant tissues but the tissues of the male reproductive structures, particularly the tissues of the pollen and/or the tassel, may be obtained in an expression profiling experiment to screen for probes that give strong signals in all samples, but only a weak or no signal in the pollen and/or the tassel sample, which is indicative of expression of the respective polynucleotides represented by said probes in most plant tissues and of no or substantially no expression in the tissues of the pollen and/or the tassel. In particular, maize plant tissues and tissues of the reproductive structures, particularly tissues of the pollen and/or the tassel may be screened to identify and obtain a regulatory sequence according to the present invention.

In particular, samples of all plant tissues, particularly samples of the green tissues and the root of a maize plant, may be directly compared to tissue samples from the male reproductive structures, particularly tissue samples of the pollen and/or the tassel. Probes representing polynucleotides that do not meet the target expression profile are eliminated. Only those probes with the strongest signal across all non-pollen/non-tassel tissues and weak of no signal in pollen and/or the tassel are selected for further analysis that is probes representing polynucleotides that are highly expressed in all tissue samples, but show substantially no expression in pollen and/or the tassel. Said probes may then be aligned with plant cDNA assembly datasets to detect bona fide plant genes, particularly maize genes or putative maize genes.

The DNA sequence representing probes on the maize chip identified as representing genes that are highly expressed in all tissue samples but essentially not expressed in pollen, particularly probes represented by the DNA sequence as given in SEQ ID NOs: 47 to 56 and those representing genes that are highly expressed in all tissue samples and have essentially no or reduced expression in tassel samples, particularly probes represented by the DNA sequence a given in SEQ ID NOs: 57-79, can easily be extended to designed expression cassettes following the steps outlined in the Examples.

Probe candidate sequences from the expression profiling analysis for each expression category may be selected and progressed to a finished binary vector with the designed expression cassette linked to a gene of interest such as, for example, a reported gene, i.e., the GUS reporter gene.

In a first step, each expression cassette is flanked with one or more suitable restriction sites such as, for example, SanDI/RsrII sites and cloned into the vector molecule. The regulatory region including the transcription initiation function typically resides within a fragment of about 1000-1500 bp upstream of the transcription start site and extends into the second exon, or to the natural translation start codon if it is not on the first exon. It typically terminates with the maize optimized Kozak sequence 'gtaaaccatgg'. The engineered translation start codon is then embedded in a suitable restriction site such as the NcoI restriction endonuclease site 'ccatgg'. All translation start codons in the theoretical transcript that are upstream of the engineered restriction site are eliminated. At least one stop codon should be present in each reading frame upstream of the engineered restriction site. The regulatory region including the transcription initiation function is designed to be flanked by suitable restriction sites such as, for example, XhoI/SanDI sites at the 5'-end and a NcoI site at the 3'-end.

The Gene Of Interest (GOI) such as the GUS reporter gene is provided as a suitable restriction fragment, in the example given here as a NcoI/SacI fragment. The terminus extends from just after the translation stop codon for about 1 kb downstream. The terminus is designed to be flanked by suitable restriction sites such as, for example, SacI at the 5'-end and RsrII/XmaI at the 3'-end.

The complete expression cassette is designed to be mobilized as a suitable restriction fragment, such as a SanDI/RsrII fragment, which can be ligated into the corresponding site located on an Agrobacterium binary vector such as the vector given in SEQ ID NO: 80.

All internal restriction sites used in the cloning steps identified above are mutated by single base substitutions to silence them.

Through application of these basic steps a plant expression cassette can be designed that corresponds to the respective probe molecules, particularly probe molecules on the maize chip identified as representing genes that are highly expressed in all tissue samples but essentially not expressed in pollen, particularly probes represented by the DNA sequence as given in SEQ ID NOs: 47 to 56 and those identified as representing genes that are highly expressed in all tissue samples and have essentially no or reduced expression in tassel samples, particularly probes represented by the DNA sequence a given in SEQ ID NOs: 57-79. The former is an expression cassette that should be transcribed in all maize tissues and not in pollen. The latter is an expression cassette that should be transcribed in all maize tissues but not or only moderately transcribed in tassels. This design strategy can be applied to all probes identified in an expression profiling experiment.

In a specific embodiment of the invention, applying the above criteria results in the identification of genes which exhibit the desired expression profile. In particular, a gene is identified which encodes an actin binding protein 3 (ABP3), particularly a actin binding protein 3 of maize (ZmABP3), which is a member of a small gene family that had been previously characterized (Lopez et al., 1996). The gene product has also been called actin depolymerizing factor 3.

It was shown by southern analysis that there are two ABP3 genes in the maize genome (Lopez et al., 1996), designated herein as ZmABP3-A and ZmABP3-B, respectively. The ZmABP3-A and ZmABP3-B cDNAs encode a protein of 139 amino acids that are identical at all residues, except one. The expression profiling data indicate that ZmABP3-B is highly expressed in most tissues of the plant, but essentially excluding the tissues of the pollen so that no expression product is present in said tissues to any significant extent, whereas. ZmABP3-A is not as highly expressed.

A structural analysis of the ZmABP3-B gene reveals that the ZmABP3-B protein coding region is encoded on 3 exons, which are interrupted by two intervening sequences (introns) flanked by the expected GT . . . AG border nucleotides.

The regulatory sequence is located in the 5'-region of the ABP3 gene immediately upstream of the coding sequence. The size of the regulatory region is in a range of between about 2 kb to 3 kb, particularly between about 2.3 kb and 2.5 kb, and comprises a 5'-non-transcribed sequence, particularly a 5'-non-transcribed sequence of between about 0.9 kb and 1.3 kb, but especial of about 1.1 kb, and a 5'-UTR, particularly between about of 0.1 kb and 0.3 kb, but especially 0.25 kb of the 5'-UTR and all or part of a nucleotide sequence representing ZmABP3-intron 1, particularly a nucleotide sequence of between about 0.7 kb and 1.2 kb, but especially of about 0.98 kb.

The regulatory sequence according to the invention further comprises part of 3'-sequence that begins just past the ABP3 translation stop codon including transcribed but not translated sequence (UTR) and non-transcribed sequence that functions as the transcriptional terminator and a polyadenylation signal. In particular, the 3'-sequence is in a range of between about 0.8 kb and about 1.2 kb, particularly between about 0.9 kb and about 1.1 kb, but especially about 1.013 kb. The size of the 3'-UTR is in a range of between about 0.2 kb and about 0.4 kb, but especially about 0.3 kb, and that of the non-transcribed sequence in a range of between about 0.5 kb and about 0.8 kb, but specifically about 0.7 kb.

In a specific embodiment of the invention, the regulatory sequence is modified such that the natural translation start codon is silenced in order to move it to the second exon.

In another embodiment of the invention, candidate probes can be identified on a DNA chip or gene array, particularly a maize DNA chip or gene array such as, for example, the maize Affymetrix™ Chip applying the above criteria, which can be used in the identification of genes or putative genes on the maize genome which exhibit the desired expression profile. Two candidate probes were identified which demonstrate virtually no signal in tassel but a high signal in other tissues. This indicates that the gene represented by said candidate probes is not expressed in tassel, but is highly expressed throughout the rest of the plant. The greatest expression differential, 60-fold higher in non-tassel tissue, was observed in candidate probe Zm033444_S_AT. The other candidate probe (Zm040564_X_AT) showed signal variation depending on the development status of the probed plant material, i.e. a low signal in young tassel that gradually increases to a high or strong signal when the plant becomes older. The signal strength between tassel and non-tassel samples differed by less than 10-fold, but the signal strength in non-tassel samples was nearly 10-fold higher as compared to the other candidate probe. The sequence data indicate that neither probe corresponds to a characterized gene. Both probes identify good candidate genes for development of promoters that deliver high expression in non-tassel tissue and little or no expression in tassels. Given the high signal differential between tassel and non-tassel samples, an expression cassette based on probe Zm033444_S_AT was developed.

Public and proprietary databases can be queried by BLASTN with the candidate probe Zm033444_S_AT sequence to obtain DNA sequence evidence for both transcripts and gDNA corresponding to Zm033444_S_AT. cDNA hits with precise matches to the query sequence fell into two similar contigs. ZmABT1 corresponds to Maize.1482.c47 and Maize.1908.c31, and ZmABT2 corresponds to Maize.1482.c32, Maize.1482.c28, Maize.1482.c53, Maize.1908.c17, Maize.1908.c20, Maize.1908.c37 and AI947567.

The Zm033444_S_AT, ZmABT1 and ZmABT2 sequences can then be used to query maize genomic DNA sequence databases to identify the regulatory sequence(s) that give high expression in non-tassel tissue and little or no expression in tassels. These queries identified three entries, AZM4_12, ZmGSStuc11-12-04.4740.1 and MAGI_88845, that assemble into a single contig. The ZmABT gDNA sequence is shown in SEQ ID NO: 46. It encodes both the ZmABT1 and ZmABT2 transcript, which suggests that they are alternatively spliced variants of the same transcript.

ZmABT1 is encoded on 5 exons, and ZmABT2 is encoded on 6 exons. The additional exon lies between exon 1 and exon 2 of ZmABT1. The largest open reading frame on ZmABT1 and ZmABT2 can be used to define their translation start and stop codons and further to define the location of each translation start and stop codon. By this analysis both cDNAs use the same translation start and stop codon. In one important aspect of the present invention the regulatory sequence according to the invention can be used in the development of robust expression cassettes that express recombinant genes in most tissues of the plant but not or substantially not in the tissues of the male reproductive structures, particularly the tissues of the pollen and/or the tassel so that no expression product is present in said tissues to any significant extent.

In a specific embodiment of the invention a regulatory sequence obtainable from a ABP3 gene, more particularly of regulatory sequence obtainable form a *Zea mays* ABP3 gene, can be used in the development of robust expression cassettes that express recombinant genes in most tissues of the plant but essentially excluding the tissues of the pollen so that no expression product is present in said tissues to any significant extent.

The transcription initiation region of the regulatory sequence according to the invention, particularly of regulatory sequence obtainable from a ABP3 gene, more particularly of regulatory sequence obtainable from a *Zea mays* ABP3 gene can be obtained in a PCR reaction containing a primer pair involving forward primer P1 (5'-atatatgcatgcg-gcgcgccgaaagtagcaaacaacaggttcatgtgcac-3') as depicted in SEQ ID NO: 1 and reverse primer P2 (5'-tatataccatggtgggttt-gcctgcgaccacaagttca-3') as depicted in SEQ ID NO: 2 through amplification from a gDNA template, particularly a maize gDNA template. In a specific embodiment of the invention a thermocycling program is applied involving amplification at about 95° C. for about 15 minutes followed by about 45 cycles at about 94° C. for about 1 minute, at about 64° C. for about 1 minute and at about 72° C. for about 5 minutes. The final extension step is carried out at about 72° C. for about 15 minutes. The reaction product, particularly an about 2.3 kb reaction product, is purified and the DNA extracted using a DNA extraction method known in the art. The DNA is precipitated, recovered and finally cloned into a suitable vector.

The transcription initiation region according to the invention, particularly a transcription initiation region obtainable from an ABP3 gene, more particularly obtainable from a ZmABP3, may be modified in a series of reactions using at least one of the oligonucleotides selected from the group of oligonucleotides depicted in

```
                                          SEQ ID NO: 3
(Patg (5'-cagctcgcccgagttggtaaggccccct-3')), SEQ ID NO: 4
(Pnco (5'-acagattagtccatcgcccacggt-3')), SEQ ID NO: 5
(ADPc-1 (5'-agccctgtccatgacggcccaagcaac-3')), SEQ ID NO: 6
(ADPc-2 (5'-agtagcaattcggtaggcacaggcac-3')), SEQ ID NO: 7
(ADPc-4 (5'-tctatggtctgcgaggtgcggtggc-3')),
and SEQ ID NO: 8
(adp3-a (5'-gtcccttcttcgccgcgccagctcgc-3')).
```

The terminus of the regulatory sequence according to the invention, particularly a terminal sequence obtainable from an ABP3 gene, more particularly a terminal sequence obtainable from a ZmABP3, can be amplified from a gDNA template, particularly a maize gDNA template, in a DNA polymerase reaction using a forward primer (P3 (5'-tatata-gagctcgcatcatgatcatgcatcatggact-3')) as depicted in SEQ ID NO: 9 and a reverse primer (P4 (5'-atatatactagtggcgcgcca-cactttctgtcgcatgtgatttgca-3')) as depicted in SEQ ID NO: 10. A thermocycling program may be applied comprising a first cycle of about 95° C. for about 5 minutes followed by about 45 cycles of about 94° C. for about 30 seconds, about 50° C. for about 1 minute and about 72° C. for about 4 minutes. The final extension step may be carried out at about 72° C. for about 15 minutes. The about 1 kb reaction product is then purified and the DNA extracted using standard extraction methods. The DNA is precipitated, recovered and cloned into a suitable vector.

The terminus of the regulatory sequence according to the invention, particularly a terminal sequence obtainable from a ABP3 gene, more particularly a terminal sequence obtainable from a ZmABP3, may be modified to remove an internal restriction site, particularly a NcoI restriction site using a suitable primer pair, particularly primer pair Tnco (5'-Pgtaaaaaaaggtcccttggctcccagaaga-3')/T2 (5'-Pcaatgtgtta-gactgacgtg-3') as depicted in SEQ ID NO: 11 and SEQ ID NO: 12, respectively, in a DNA polymerase reaction. The thermocycling program employed may comprise a first cycle at about 95° C. for about 5 minutes followed by about 30 cycles of about 95° C. for about 1 minute, about 50° C. for about 1 minute and about 65° C. for about 15 minutes. The product may then be processed and sequenced. The present invention is also directed to expression cassettes that incorporate the regulatory mechanisms of a target gene of interest that shows the desired expression profile, that is high expression in most plant tissues but no expression in pollen tissue, particularly an ABP target gene, more particularly of a ZmABP3 target gene, to control in plants the expression of products of nucleic acid molecules of interest in a manner that mimics the expression profile of the original target gene. The present invention further includes expression cassettes that incorporate regulatory sequences obtainable from the 5'-region of the target gene, particularly an ABP target gene, more particularly of a ZmABP3 target gene, to express the products of nucleic acid hb molecules of interest in plant tissues but not or substantially not in pollen tissue, The present invention is also directed to expression cassettes incorporating both regulatory sequences obtainable from the 5'-region and the 3'-region of the target gene, particularly an ABP3 target gene, more particularly of a ZmABP3 target gene.

In another specific embodiment of the invention a regulatory sequence obtainable from maize genomic DNA can be used in the development of robust expression cassettes that transcribe polynucleotides in most tissues of the plant but essentially excluding the tissues of the tassel so that no expression product is present in said tissues to any significant extent.

An inclusive gene structure-based design strategy may be used to construct such an expression cassette. To incorporate the known alternative splicing of the putative maize gene identified in a method as described above into the expression cassette, the design strategy can be based on the structure of ZmABT1 transcript as shown in SEQ ID NO: 33.

The transcription initiation region of the regulatory sequence according to the invention, particularly of the ZmABT promoter region can be amplified from a maize gDNA template in a DNA polymerase reaction containing gDNA and a primer pair involving forward primer ABT P1 forw (5'-CGACCAGCGCGACATGCATGGCA-3') as depicted in SEQ ID NO: 19 and ABT P2 rev (5'-ACCCCA-GGGCGTACGACAAG-GCC-3') as depicted in SEQ ID NO: 20. In a specific embodiment of the invention a thermocycling program is applied involving amplification at about 95° C. for about 5 minutes followed by about 40 cycles of 94° C. for about 30 seconds, about 67° C. for about 30 seconds and about 72° C. for about 2.5 minutes. The final extension step was done at about 72° C. for about 10 minutes.

This amplification reaction leads to an amplification product of about 2.6 kb, which can be purified and the DNA extracted using a standard DNA extraction method. The DNA can than be cloned into a suitable vector such as, for example, the pCR-BluntII-TOPO vector.

The ZmABT promoter can be modified in a series of mutagenesis reactions to silence the endogenous translation start codon, silence a SanDI restriction site and correct point mutations created during amplification. This can be done in a series of reactions using at least one of the oligonucleotides selected from the group of oligonucleotides depicted in

```
pABT mutt
                                         SEQ ID NO: 21
(5'-GATGGCCGGATTGGGCTCCCGGGGTGGAG-3')

pABT mut2
                                         SEQ ID NO: 22
(5'-CTGGGAGGCGCGCAAGGGGCAGTTCCTCG-3')

pABT mut3
                                         SEQ ID NO: 23
(5'-CCCACCGCCGGAGCACCGAAAGGCCCCGCG-3')

pABT mut4
                                         SEQ ID NO: 24
(5'-GTCACCCGGGAGCACTTCCCGGCGCCG-3')
```

```
pABT mut5
                               SEQ ID NO: 25
(5'-CATTGGGCCGAGCACGGCTTCTTCCGC-3')

pABT mut6
                               SEQ ID NO: 26
(5'-GGGGTACGGTGTTCTTGAGTCGTGAAGCGAC-3')
```

The modified ZmABT promoter can the be amplified in another PCR reaction using primers pABT amp1 (5'-GCGTCTAGAGGGACCCCGACCAGCGCGACATG-CATGGCA-3') as depicted in SEQ ID NO: 27 and pABT amp2 (5'-ACCCCAGGGCGTACGACAAGGCCCCAC-CATGGGCGC-3') as depicted in SEQ ID NO: 28. The PCR product can then be purified and the DNA extracted using standard a DNA extraction method. The DNA can be cloned into a suitable vector such as, for example, the pCR-BluntII-TOPO vector, transformed and sequenced. The ZmABT promoter can then be excised, particularly as an XbaI/NcoI fragment and ligated to a suitable expression vector such as, for example, pNOV6901.

In one embodiment of the invention, an expression cassette is provided comprising a termination sequence which can be obtained form the ZmABT gene identified and described herein above. The ZmABT terminus can be amplified from maize gDNA template in a DNA polymerase reaction containing gDNA and a primer pair involving forward primer ABT P4 (5'-TATATAGAGCTCGAATC-GAAGAAGCCACACTGTAAATCTGCCGGG-3') as depicted in SEQ ID NO: 29 and reverse primer ABT P5 (5'-AGCAAGGCATATGCAGCAGCTGCTGGTCGGAC-CGGGCCCTATATA-3') as depicted in SEQ ID NO: 30 resulting in an amplification product of about 1 kb.

This reaction product can be purified and the DNA extracted using a standard DNA extraction method. The purified DNA can then be cloned into a suitable vector such as, for example, the pCR4-TOPO-Blunt vector.

In one embodiment of the invention, the ZmABP3 terminus is modified to remove internal NcoI and XhoI restriction sites. This can be done in a series of reactions using at least one of the oligonucleotides selected from the group of oligonucleotides depicted in.

```
ABTt m1
                               SEQ ID NO: 31
(5'-GTCATGCATGGGCATGTGAAGGAGGAGCC-3')

ABTt m2
                               SEQ ID NO: 32
(5'-GTTGCATGCATGCTGCATGGCGTCGAGAT-3')
```

The amplification product can then be processed and sequenced to result in a terminator sequence as shown in SEQ ID NO: 36.

In one embodiment of the invention, an expression cassette is provided that express recombinant genes in most tissues of the plant but essentially excluding the tissues of the tassel so that no expression product is present in said tissues to any significant extent, comprising both a regulatory sequence at least part of which has a transcription initiation function and a regulatory sequence at least part of which has a termination function, which regulatory sequences can be obtained form the ZmABT gene identified and described herein above.

In one embodiment of the invention such an expression cassette can be obtained by excising the ZmABT terminus excised and ligating it into a suitable vector already comprising a regulatory sequence at least part of which has a transcription initiation function, particularly the sequence of the ZmABT promoter such as, for example, the pNOV6901-prABT vector as described above.

In one embodiment, the expression cassette according to the invention comprises a regulatory nucleotide sequence comprising approximately 2.6 kb of the 5'-sequence, which consists of approximately 2 kb of 5'-non-transcribed sequence, and about 12 bp of 5'-UTR, approximately 0.6 kb representing exon 1, intron 1 and about 16 bp of exon 2; and approximately 1 kb of the 3'-sequence that begins just past the translation stop codon and includes approximately 0.6 kb of 3'-UTR and about 0.4 kb of non-transcribed sequence, and functions as the transcriptional terminator and polyadenylation signal.

In one embodiment, an expression cassette according to the invention is provided wherein the natural translation start codon is silenced and moved to the second exon The complete expression cassette can then be mobilized into a suitable vector for plant transformation and expression such as, for example, an *Agrobacterium* binary vector, particularly *Agrobacterium* binary vector 15289.

The nucleic acid segment of interest can, for example, code for a ribosomal RNA, an antisense RNA or any other type of RNA that is not translated into protein. In another preferred embodiment of the invention, the nucleic acid segment of interest is translated into a protein product. The nucleotide sequence which directs transcription and/or the nucleic acid segment may be of homologous or heterologous origin with respect to the plant to be transformed. A recombinant DNA molecule useful for introduction into plant cells includes that which has been derived or isolated from any source that may be subsequently characterized as to structure size and/or function, chemically altered, and later introduced into plants. Therefore a useful nucleotide sequence, segment or fragment of interest includes completely synthetic DNA, semi-synthetic DNA, DNA isolated from biological sources, etc. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that is involved in carbohydrate metabolism or any other gene of interest as provided in the SEQ ID NOs of the sequence listing.

The introduced recombinant DNA molecule includes but is not limited to, DNA from plant genes, and non-plant genes such as those from bacteria, yeasts, animals or viruses. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA, In one embodiment, the regulatory sequences may be operably associated with an expressible polynucleotide of interest. The expressible polynucleotide may encode a polypeptide or protein of interest.

Such a polypeptide or protein of interest may be one exhibiting a certain biological activity such as, for example, an insecticidal, herbicidal or fungicidal activity or may contribute of an improved performance of a crop plant of agronomic interest in form of improved yield, quality, lodging, biotic and abiotic stress resistance, flowering control, etc.

In one embodiment, the concentration of the polypeptide product expressed from the protein encoding polynucleotide of interest in the tissues of the reproductive structures, particularly in the tissues of the pollen and/or the tassel, is such that no insecticidal activity can be detected in a standard insect feeding assay. In particular, the concentration of the expression product in the tissues of the male reproductive structures, particularly in the tissues of the pollen and/or the tassel, is below a basic level of about 10 ng/mg soluble protein, particularly of about 5 ng/mg soluble protein, more particularly of about 3 ng/mg soluble protein, but especially of about 2 ng/mg soluble protein or below.

In one specific embodiment of the invention, the polypeptide or protein of interest is an insecticidally active protein or polypeptide, particularly an insecticidally active protein or polypeptide obtainable from *Bacillus thuringiensis*, more particularly a *Bacillus thuringiensis* endotoxin such as, for example, cryIA(b) endotoxin. Other endotoxins known to occur in *Bacillus thuringiensis* may likewise be used in association with the regulatory sequence according to the invention to obtain toxin expression in most plant tissues except pollen and/or the tassel so that no expression product is present in said tissues to any significant extent.

In one embodiment, a transgenic plant according to the invention and as described herein is provided, wherein the polypeptide or protein encoding polynucleotide of interest encodes an endotoxin of *Bacillus thuringiensis* which has at least 80% sequence identity, particularly at least 85% sequence identity, particularly at least 90%, 91%, 92%, 93%, 94%, 95%, 96%, 97%, 98% or 99% sequence identity with a nucleotide sequence as depicted in SEQ ID NO:15.

In one embodiment, a transgenic plant according to the invention and as described herein is provided, wherein the polypeptide or protein encoding polynucleotide of interest encodes an endotoxin of *Bacillus thuringiensis* which has the nucleotide sequence as depicted in SEQ ID NO: 15.

Once completed, the expression cassette may be mobilized into a suitable vector for plant transformation, such as, for example, a binary vector, which may then be mobilized to maize via *Agrobacterium*-mediated transformation.

Transgenic plants (or plant cells, or plant explants, or plant tissues) incorporating the polynucleotides of the invention and/or expressing a polypeptide of interest such as, for example, a toxin protein of *B. thuringiensis*, can be produced by a variety of well established techniques. Following construction of an expression cassette and a vector incorporating the regulatory polynucleotide sequence according to the invention and as described herein, standard techniques can be used to introduce the polynucleotide into a plant, a plant cell, a plant explant or a plant tissue of interest. Optionally, the plant cell, explant or tissue can be regenerated to produce a transgenic plant. The plant can be any higher plant, including gymnosperms, monocotyledonous and dicotyledonous plants. Suitable protocols are available for Leguminosae (alfalfa, soybean, clover, etc.), Umbelliferae (carrot, celery, parsnip), Cruciferae (cabbage, radish, rapeseed, broccoli, etc.), Curcurbitaceae (melons and cucumber), Gramineae (wheat, corn, rice, barley, millet, etc.), Solanaceae (potato, tomato, tobacco, peppers, etc.), and various other crops. See protocols described in Ammirato et al., eds., (1984) Handbook of Plant Cell Culture—Crop Species, Macmillan Publ. Co., New York, N.Y.; Shimamoto et al. (1989) Nature 338:274 276; Fromm et al. (1990) Bio/Technol. 8:833 839; and Vasil et al. (1990) Bio/Technol. 8: 429 434. Transformation and regeneration of both monocotyledonous and dicotyledonous plant cells is now routine, and the selection of the most appropriate transformation technique will be determined by the practitioner. The choice of method will vary with the type of plant to be transformed; those skilled in the art will recognize the suitability of particular methods for given plant types. Suitable methods can include, but are not limited to: electroporation of plant protoplasts; liposome-mediated transformation; polyethylene glycol (PEG) mediated transformation; transformation using viruses; micro-injection of plant cells; microprojectile bombardment of plant cells; vacuum infiltration; and *Agrobacterium tumefaciens* mediated transformation.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing *A. tumefaciens* or *A. rhizogenes* as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and *Agrobacterium* and *Agrobacterium*-mediated gene transfer, can be found in Gruber et al. (1993).

Expression vectors containing the regulatory polynucleotide sequence according to the invention can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues, (Lindsey et al., 1993; Auch & Reth et al.).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., 1985: Byrne et al., 1987; Sukhapinda et al., 1987; Lorz et al., 1985; Potrykus, 1985; Park et al., 1985: Hiei et al., 1994). The use of T-DNA to transform plant cells has received extensive study and is amply described (EP 120516; Hoekema, 1985; Knauf, et al., 1983; and An et al., 1985). For introduction into plants, the chimeric genes of the invention can be inserted into binary vectors as described in the examples.

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway et al., 1986), electroporation (Riggs et al., 1986), *Agrobacterium*-mediated transformation (Hinchee et al., 1988), direct gene transfer (Paszkowski et al., 1984), and ballistic particle acceleration using devices available from Agracetus, Inc., Madison, Wis. and BioRad, Hercules, Calif. (see, for example, Sanford et al., U.S. Pat. No. 4,945,050; and McCabe et al., 1988). Also see, Weissinger et al., 1988; Sanford et al., 1987 (onion); Christou et al., 1988 (soybean); McCabe et al., 1988 (soybean); Datta et al., 1990 (rice); Klein et al., 1988 (maize); Klein et al., 1988 (maize); Klein et al., 1988 (maize); Fromm et al., 1990 (maize); and Gordon-Kamm et al., 1990 (maize); Svab et al., 1990 (tobacco chloroplast); Koziel et al., 1993 (maize); Shimamoto et al., 1989 (rice); Christou et al., 1991 (rice); European Patent Application EP 0 332 581 (orchardgrass and other Pooideae); Vasil et al., 1993 (wheat); Weeks et al., 1993 (wheat). In one embodiment, the protoplast transformation method for maize is employed (European Patent Application EP 0 292 435, U.S. Pat. No. 5,350,689).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. Following transformation, plants are preferably selected using a dominant selectable marker incorporated into the transformation vector. Typically, such a marker will confer antibiotic or herbicide resistance on the transformed plants and selection of transformants can be accomplished by exposing the plants to appropriate concentrations of the antibiotic or herbicide.

After transformed plant cells or plants are selected and grown to maturity, those plants showing the trait of interest are identified. The trait can be any of those traits described above. Additionally, to confirm that the trait of interest is due to the expression of the introduced polynucleotide of interest under control of the regulatory nucleotide according to the invention, expression levels or activity of the polypeptide or polynucleotide of interest can be determined by analyzing mRNA expression using Northern blots, RT-PCR or microarrays, or protein expression using immunoblots or Western blots or enzyme activity assays.

The invention thus relates to plant cells and tissues, to plants derived from such cells and tissues, respectively, to plant material, to the progeny and to seeds derived from such plants, and to agricultural products including processed plant products with improved properties obtainable by, for example, any one of the transformation methods described below.

Once an expression cassette according the present invention and as described herein comprising a regulatory sequence according to the invention in association with a polynucleotide of interest has been transformed into a particular plant species, it may be propagated in that species or moved into other varieties of the same species, particularly including commercial varieties, using traditional breeding techniques. Preferred plants of the invention include gymnosperms, monocots, and dicots, especially agronomically important crop plants, such as rice, wheat, barley, rye, rape, corn, potato, carrot, sweet potato, sugar beet, bean, pea, chicory, lettuce, cabbage, cauliflower, broccoli, turnip, radish, spinach, asparagus, onion, garlic, eggplant, pepper, celery, carrot, squash, pumpkin, zucchini, cucumber, apple, pear, quince, melon, plum, cherry, peach, nectarine, apricot, strawberry, grape, raspberry, blackberry, pineapple, avocado, papaya, mango, banana, soybean, tobacco, tomato, sorghum and sugarcane.

The genetic properties engineered into the transgenic plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. Use of the advantageous genetic properties of the transgenic plants according to the invention can further be made in plant breeding that aims at the development of plants with improved properties such as tolerance to pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

In one embodiment of the invention, the plant has been transformed with and expresses a polypeptide or protein encoding nucleotide sequence encoding a polypeptide product exhibiting an insecticidal activity, particularly an endotoxin of *Bacillus thuringiensis* in most tissues of the plant but essentially excluding the tissues of the pollen and/or the tassel so that no expression product is present in said tissues to any significant extent, where the nucleotide sequence is not transcribed to any significant extent. Therefore, essentially no expression occurs in the pollen and/or the tassel tissue and only residual amounts of the expression product, if any, can be detected in said tissues, which is not sufficient for the expression product to fulfil its envisaged biological function in said tissues or to exhibit any toxic effects either towards insects feeding on these tissues or the plant itself.

In particular, the concentration of the polypeptide product expressed from the protein encoding polynucleotide of interest in the tissues of the pollen and/or the tassel is such that no insecticidal activity can be detected in a standard insect feeding assay. In one embodiment of the invention, the concentration of the expression product in pollen is below a basic level of about 10 ng/mg soluble protein, particularly of about 5 ng/mg soluble protein, more particularly of about 3 ng/mg soluble protein, but especially of about 2 ng/mg soluble protein or below.

The invention also provides methods for preparing expression cassettes comprising the regulatory sequence according to the invention comprising linking an expressible polynucleotide encoding a polypeptide or a protein of interest with the regulatory sequence according to the invention and as described herein to obtain an expression construct, wherein the polynucleotide of interest is operably linked or associated with the regulatory sequence such that expression of the polypeptide or a protein of interest is mediated by the regulatory sequence according to the invention and results in the expression of said polypeptide or a protein of interest in essentially all plant tissues, but essentially excludes expression in the tissues of the reproductive structures of the plant, particularly in the tissues of the pollen and/or the tassel so that no expression product is present in said tissues to any significant extent.

In one embodiment, the invention relates to a method of producing a transgenic plant expressing a DNA sequence of interest in non-pollen tissue but not or substantially not in the tissues of the pollen and/or the tassel, comprising
  a) transforming an expression cassette according to the invention and as described herein into a plant cell which comprises a regulatory nucleotide sequence, at least part of which has a transcription initiation function which mediates expression of an operably associated protein encoding polynucleotide of interest in most plant tissues but essentially excluding the tissues of the pollen and/or the tassel so that no expression product is present in said tissues to any significant extent; and
  b) regenerating the plant cell transformed in step a) into a plant.

In one embodiment, the invention relates to a method of controlling insect target-pests feeding on vegetative plant tissues such as the leaf, stalk and root and/or on reproductive tissues such as the ear, but protecting non-target pests feeding on pollen comprising
  a) growing a plant according to the invention and as described herein in an area that is infested with the target pest;
  b) expressing a polypeptide or protein that is capable of controlling said target pest under the control of a regulatory sequence according to the invention and as described herein.

In one embodiment, the invention relates to a method of protecting the reproductive tissues of a plant, particularly the tissues of the pollen and/or the tassel against damage caused by expression in said tissues of a polypeptide or protein of interest comprising
  a) growing a plant according to the invention and as described herein;
  b) expressing a polypeptide or protein of interest under the control of a regulatory sequence according to the invention and as described herein.

In one embodiment the present invention relates to the use of a regulatory sequence according to the present invention and as disclosed herein for controlling insect target-pests feeding on vegetative plant tissues such as the leaf, stalk and root and/or on reproductive tissues such as the ear, but protecting non-target pests feeding on pollen comprising
  a) growing a plant according to the invention and as described herein in an area that is infested with the target pest;
  b) expressing a polypeptide or protein that is capable of controlling said target pest under the control of a regulatory sequence according to the invention and as described herein.

In one embodiment the present invention relates to the use of a regulatory sequence according to the present invention and as disclosed herein for protecting the reproductive tissues of a plant, particularly the tissues of the pollen and/or the tassel against damage caused by expression in said tissues of a polypeptide or protein of interest comprising expressing said polypeptide or protein of interest under the control of a regulatory sequence according to the invention and as described herein.

EXAMPLE

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

All manipulations and techniques necessary to construct and propagate strains described in this invention are known to those skilled in the art. Technical details are described e.g. in Ausubel et al 1995; Sambrook, J, 2001 and Miller, J. H. 1992 and in relevant publications cited within this invention.

Example 1: Non-Pollen Expression

Example 1.1 Identification of ZmABP3

In an expression profiling experiment a maize developmental series was queried on a *Zea mays* (Zm80K) Affymetrix chip for probes that gave strong signals in all samples, but not or substantially not in the pollen sample. All the green tissue and root samples were directly compared to pollen, and probes representing polynucleotides that did not meet the target expression profile were eliminated. The analysis produced two sets of results. The first set contains 36 probes representing polynucleotides that were highly expressed in all the tissue samples, but very low in pollen. The second set contains 10 probes represented polynucleotides that are highly expressed in all tissue samples, but gave no signal in pollen. Alignment of probe sequence with maize cDNA assembly datasets showed that all 46 probes represent bona fide maize genes. The top 10 probes are those with the strongest signal across all non-pollen tissues and no signal in pollen (see Table A).

Applying further criteria including determination of the availability of genomic DNA (gDNA) and cDNA sequence for each lead produced Zm07728_s_at as the top candidate that met all promoter development requirements. Literature analysis revealed that this probe represents the gene encoding actin binding protein 3 (ZmABP3) which is a member of a small gene family that had been previously characterized (Lopez et al., 1996). The gene product has also been called actin depolymerizing factor 3. Lopez et al (1996) confirms in FIG. 3 that ZmABP3 is highly expressed in most tissues of the plant examined, except pollen samples. Lopez et al (1996) also show by southern analysis that there are two ABP3 genes in the maize genome. The ZmABP3 cDNA they report is GenBank Accession X97726, and it corresponds to the TIGR Accession TC248585. This gene was designated ZmABP3-A. Both ZmABP3 genes are represented on the maize (Zm80K) Affymetrix Chip: ZmABP3-A corresponds to probe Zm007595_at and ZmABP3-B corresponds to Zm07728_s_at. The 'Zm07728_s_at' sequence was used to identify the TC248588 in the TIGR database, and MAIZE.974.CB1 in a maize cDNA assembly database. It also identified the MAGI_93606, MAGI_93607, AZM4_39177, ZmGSStuc11-12-04.2725.1, ZmGSStuc11-12-04.2725.2 and CC463190 gDNA sequences. The ZmABP3-A and ZmABP3-B cDNAs encode proteins that are identical at all residues, except one. The expression profiling data indicate that ZmABP3-B is highly expressed in most tissues of the plant, but essentially excluding the tissues of the pollen so that no expression product is present in said tissues to any significant extent. ZmABP3-A is not as highly expressed.

SEQ ID NO: 16 show that the ZmABP3-B mRNA is encoded on 3 exons. The two intervening sequences (introns) are bracketed by the expected GT . . . AG border nucleotides.

More specifically, SEQ ID NO: 16 discloses the design of the ZmABP3 expression cassette. The ZmABP3 regulatory components to be included in the construct are 2.3 kb of 5'-sequence (prZmABP3-01) which contains 1.1 kb of 5'-non-transcribed sequence, 0.25 kb of 5'-UTR and 0.98 kb representing ZmABP3-B-intron 1; and 1.013 kb of 3'-sequence (tZmZBP3-01) that begins just past the ABP3-B translation stop codon. This includes about 0.3 kb of 3'-UTR and 0.7 kb of non-transcribed sequence.

Table A shows a summary of the top 10 candidate probes representing polynucleotides with a high expression level in all maize tissues and no expression signal in pollen gan) was gel purified and ligated to pTrcHisB expression vector (In vitrogen life technologies, Cat# V36020), which was cut with BamHI/SacI. This construct was named as Michigan-pTrcHisB. The Geiser sequence (81 bp) was deleted from Michigan-pTrcHisB by overlapping PCR with the following primers:

```
5' Bfr1
                                        (SEQ ID NO: 83)
(5'-cctggtggagtgcttaagcgacgagttctgcctgg-3'), 3' Xba1
                                        (SEQ ID NO: 84)
(5'-gggcttctcctccaggaactctagattgcccaggcg-3'), 5'Gfix
                                        (SEQ ID NO: 85)
(5'-catcggcaagtgccaccacagccaccacttcagcctg-3')
and 3'Gfix
                                        (SEQ ID NO: 86)
(5'-gctgtggtggcacttgccgatggggctggg-3').
```

PCR product A was made using high-fidelity PCR with Michigan-pTrcHisB as a template, and the 5' Bfr1 and 3' Gfix primers. PCR product B was made using high-fidelity PCR with Michigan-pTrcHisB as a template, and the 5'Gfix and 3'Xba1 primers. The final PCR used products A and B as templates, and the 5'Bfr1 and 3'Xba1 primers. The final PCR band was digested with AflII/XbaI and gel-purified.

| Probe Name | Description of Reference Gene | Pollen Expression | Average Expression (all tissues) | Zea mays TIGR Hit |
|---|---|---|---|---|
| AF032370_at | "Zea mays profilin (PRO4) mRNA, complete cds." | absent | 4208 | TC269677 |
| Ctrl_ZmU45855-3_at | From 808 to 1307 of glyceraldehyde-3-phosphate dehydrogenase GAPC2 (gpc2) mRNA, complete cds. | absent | 4275 | TC269361 |
| Zm001747_s_at | Similar to CAA63903.1 Pennisetum glaucum; heat shock protein 17.9; P. glaucum mRNA for heat shock protein, HSP 17.9 | absent | 4945 | TC268849 |
| Zm005803_s_at | "Similar to AAB99745.1 Triticum aestivum; HSP70; Triticum aestivum 70 kDa heat shock protein (TaHSP70d) mRNA, complete cds; 70 kDa heat shock protein, molecular chaperone" | absent | 4091 | TC247918 |
| Zm007728_s_at | Similar to SW:ADF3_MAIZE Q41764 zea mays (maize), actin-depolymerizing factor 3 (adf 3) (zmabp3) (zmadf3). | absent | 4805 | TC248588 |
| Zm009722_s_at | "Similar to BAC22420.1 Oryza sativa (japonica cultivar-group);; Oryza sativa (japonica cultivar-group) genomic DNA, chromosome 7, PAC clone:P0453E03; contains ESTs C96778(C10671), D22278(C10671) unknown | absent | 3306 | TC248975 |
| Zm015335_s_at | Similar to SW:RS5A_ARATH Q9zut9 arabidopsis thaliana (mouse-ear cress). 40s ribosomal protein s5-1. February 2003 | absent | 3598 | TC269022 |
| Zm021004_s_at | "Similar to AAD39835.1 Arabidopsis thaliana; Ran-binding protein siRanBP; Arabidopsis thaliana Ran-binding protein (siRanBP) mRNA, complete cds; atranbp1a homolog" | absent | 3092 | TC259986 |
| Zm058948_s_at | No Description | absent | 4337 | TC270333 |
| Zm061393_s_a | No Description = sucrose synthase | absent | 6509 | TC258905 |

Example 1.2 Cry1AbG6 Construction

Cry1AbG6 (2814 bp) is a modified version of the full-length Cry1Ab (pNOV1321, 3546 bp) gene. The Geiser sequence (81 bp from 4398-4478 in pNOV1321) and the 3'-end (651 bp from 4908-5558 in pNOV1321) were deleted.

The Cry1AbG6 sequence was constructed from pNOV1321 (source vector for the Cry1Ab full-length gene) as follows: pNOV1321 plasmid DNA was cut with BamHI/SacI. The Cry1Ab full-length gene (3546 bp, named Michi- This fragment was ligated to Michigan-pTrcHisB that had also been digested with XbaI/AflII. The correct recombinant DNA product was identified by AflII/XbaI digestion analysis. This construct was named as Cry1Ab-G.

A second PCR product was made by high-fidelity PCR using pNOV1321 as a template, the 5'1Ab5XbaI (5'-gcccgc-ctgggcaatctagagttcctggaggag-3') primer depicted in SEQ ID NO: 87, and the 3'1Ab3d6 (5'-gcgagctcctagatgcggccctcgagt-tcctcgaaga-3') primer depicted in SEQ ID NO: 88. The PCR product was digested with XbaI/SacI then ligated to Cry1Ab-G that was also digested with XbaI/SacI. The correct recombinant DNA product was identified using BamHI/SacI restriction analysis. This construct was named as Cry1AbG6.

The Cry1AbG6 sequence was subjected to QuikChange mutagenesis to remove an internal NcoI site. The 25 μL reaction contained
1 μL Cry1AbG6 template,
2.5 μL 10× QuikChange buffer,
1 μL QuikChange dNTP mix,

```
1 μL of 20 μM cy2'
(5'-Pccctgtacggcacgatgggcaacgctgca-3';
SEQ ID NO: 89),
```

0.75 μL Quik solution and
1 μL QuikChange DNA polymerase.

The thermocycling program was 95° C. for 5 minutes followed by 30 cycles of 95° C. for 1 minute, 55° C. for 1 minute and 65° C. for 20 minutes. The product was processed as described by the manufacturer (Stratagene) and completely sequenced.

The Cry1AbG6 coding sequence was amplified from the mutagenized plasmid template, above, in a 50 μL Pfu turbo (Stratagene) DNA polymerase reaction containing
5 μL template,
5 μL 10× Pfu buffer,
1 μL 10 mM dNTP mix,

```
1 μL of 20 μM cy1
(5'-atatatccaccatggacaacaaccccaaca-3';
SEQ ID NO: 90),

1 μL of 20 μM cy2
(5'-tatatagagctcctagatgcggccctcgagt-3';
SEQ ID NO: 91)
``` and
1 μL Pfu turbo DNA polymerase.

The thermocycling program was 95° C. for 2 minutes followed by 40 cycles of 95° C. for 1 minute, 50° C. for 1 minute and 72° C. for 7 minutes. The final extension step was 72° C. for 15 minutes. The 2.8 kb reaction product was gel-purified on 1% TAE agarose, and the DNA was extracted using Qiaprep DNA extraction method. The recovered DNA was digested with NcoI/SacI, then ligated to pNOV6901 vector that was also digested with NcoI/SacI. This operation replaced the GUS coding sequence in pNOV6901 with Cry1AbG6. The Cry1AbG6 sequence is given in SEQ ID NO: 15.

Example 1.3 Construction of the ZmABP3 Expression Cassette

An inclusive design strategy was used to develop the ZmABP3 expression cassette. The cassette contains 2.3 kb of 5'-sequence which consists of 1.1 kb of 5'-non-transcribed sequence, 0.25 kb of 5'-UTR and 0.98 kb representing ZmABP3-intron 1. The natural translation start codon was silenced in order to move it to the second exon. The expression cassette also contains 1.013 kb of 3'-sequence that begins just past the ABP3 translation stop codon. This includes about 0.3 kb of 3'-UTR and 0.7 kb of non-transcribed sequence, and functions as the transcriptional terminator and poly-adenylation signal.

The ZmABP3 terminus was amplified from maize gDNA template in a 50 μL Proofstart (Qiagen) DNA polymerase reaction containing
10 μg gDNA,
5 μL 10× Proofstart buffer,
1.5 μL 10 mM dNTP mix,

```
2.5 μL of 20 μM P3
(5'-tatatagagctcgcatcatgatcatgcatcatggact-3';
SEQ ID NO: 9), 2.5 μL of 20 μM P4
(5'-atatatactagtggcgcgccacactttctgtcgcatgtgatt
tgca-3'; SEQ ID NO: 10),
```

10 μL Q solution and
2 μL Proofstart DNA polymerase.

The thermocycling program was 95° C. for 5 minutes followed by 45 cycles of 94° C. for 30 seconds, 50° C. for 1 minute and 72° C. for 4 minutes. The final extension step was 72° C. for 15 minutes. The 1 kb reaction product was gel-purified on 1% TAE agarose, and the DNA was extracted using Qiaprep DNA extraction method. The DNA was ethanol precipitated and recovered in 4 μL ddH$_2$O, then cloned into the pCR4-TOPO-Blunt vector.

The ZmABP3 terminus was modified to remove an internal NcoI restriction site using the Stratagene QuikChange Multi-site mutagenesis kit. The 25 μL reaction contained
1 μL pCR4-TOPO-ZmABP3-terminus,
2.5 μL 10× QuikChange buffer,
1 μL QuikChange dNTP mix,

```
1 μL of 20 μM Tnco
(5'-Pgtaaaaaaaggtcccttggctcccagaaga-3';
SEQ ID NO: 11),

1 μL of 20 μM T2
(5'-Pcaatgtgttagactgacgtg-3'; SEQ ID NO: 12),
```

0.75 μL Quik solution and
1 μL QuikChange DNA polymerase.

The thermocycling program was 95° C. for 5 minutes followed by 30 cycles of 95° C. for 1 minute, 50° C. for 1 minute and 65° C. for 15 minutes. The product was processed as described by the manufacturer (Stratagene) and completely sequenced. The ZmABP3-terminus sequence is shown in SEQ ID NO: 14.

The ZmABP3 promoter was amplified from maize gDNA template in a 50 μL Hotstart (Qiagen) DNA polymerase reaction containing
10 μg gDNA,
25 μL 2× Hotstart Master Mix,

```
1.25 μL of 20 μM P1
(5'-atatatgcatgcggcgcgccgaaagtagcaaacaacaggttc
atgtgcac-3'; SEQ ID NO: 1), 1.25 μL of 20 μM P2
(5'-tatataccatggtgggtttgcctgcgaccacaagttca-3';
SEQ ID NO: 2),
```

10.5 μL Q solution and
2 μL 25 mM MgCl$_2$.

The thermocycling program was 95° C. for 15 minutes followed by 45 cycles of 94° C. for 1 minute, 64° C. for 1 minute and 72° C. for 5 minutes. The final extension step was 72° C. for 15 minutes. The 2.3 kb reaction product was gel-purified on 1% TAE agarose, and the DNA was extracted using Qiaprep DNA extraction method. The DNA was ethanol precipitated and recovered in 4 μL ddH$_2$O, then cloned into the pCR4-TOPO vector.

The ZmABP3 promoter was modified in a series of QuikChange reactions as outlined above using the following oligonucleotides:

```
Patg
(5'-cagctcgcccgagttggtaaggcccct-3'; SEQ ID NO: 3),

Pnco
(5'-acagattagtccatcgcccacggt-3'; SEQ ID NO: 4),

ADPc-1
(5'-agccctgtccatgacggcccaagcaac-3'; SEQ ID NO: 5),

ADPc-2
(5'-agtagcaattcggtaggcacaggcac-3'; SEQ ID NO: 6),

ADPc-4
(5'-tctatggtctgcgaggtgcggtggc-3'; SEQ ID NO: 7),
and adp3-a
(5'-gtccccttcttcgccgcgccagctcgc-3'; SEQ ID NO: 8).
```

The ZmABP3 promoter sequence is shown in SEQ ID NO: 13.

The ZmABP3 terminus was ligated to the pNOV6901-Cry1AbG6 vector (from Example 2) as a SacI/SpeI fragment. The ZmABP3 Promoter was subsequently ligated to the vector as a SphI/NcoI fragment. This produced ZmABP3-Cry1AbG6-assembly, shown in SEQ ID NO: 37. The complete ZmABP3-Cry1AbG6 expression cassette was mobilized into a binary vector, pNOV6900, as an AscI fragment. These constructs, ZmABP3-Cry1AbG6-6900 and enhanced ZmABP3-Cry1AbG6-binary, are shown in SEQ ID NOS: 38 and 39, respectively. The only difference between these vectors is the presence of the CaMV-FMV dual enhancer in enhanced ZmABP3-Cry1AbG6-binary. Both were mobilized to maize via *Agrobacterium*-mediated transformation.

Example 1.4 Construction of ZmABP3-AmCyan

The Cry1AbG6 coding sequence was excised from ZmABP3-Cry1AbG6-assembly as an NcoI/SacI fragment. It was replaced with the AmCyan reporter gene coding sequence that was excised from plasmid 13718 as an NcoI/SacI fragment. This produced the ZmABP3-AmCyan-assembly construct shown in SEQ ID NO: 40. The ZmABP3-AmCyan expression cassette was mobilized into a binary vector, pNOV6900, as an AscI fragment. This construct, ZmABP3-AmCyan-binary, is shown in SEQ ID NO: 41. It was mobilized to maize via *Agrobacterium*-mediated transformation.

Example 1.5 Expression from ZmABP3-AmCyan in Transgenic Maize

Several transgenic maize events containing the ZmABP3-AmCyan expression cassette were produced. Those containing a single-copy of the transgene and no un-intended vector sequence were analyzed. All transgenic events accumulated AmCyan transcript in leaf tissue (data not shown). Several tissues from a representative event were examined for AmCyan transcript accumulation. Total RNA was prepared using the Plant RNAeasy total RNA isolation system (Qiagen). Pollen total RNA was prepared using the method described by Shirzadegan et al (1991). Preparation quality was assessed by UV spectrophotometry, and 10 µg of total RNA per sample was resolved on a 1% formaldehyde gel then transferred to Nytran SuPerCharge membrane following the recommended protocol (Schleicher & Schuell). The blot was hybridized to a random-primed $^{32}$P-labeled AmCyan DNA probe using high stringency conditions. The results clearly show that ZmABP3 promotes transcription in tassel, leaf, silk, ear and root tissue, but does not promote transcription in pollen.

Example 1.6 Expression from ZmABP3-Cry1AbG6 in Transgenic Maize

Several transgenic maize events containing the ZmABP3-Cry1AbG6 expression cassette were produced. Those containing a single-copy of the transgene and no un-intended vector sequence were analyzed. The T0 events were tested for insecticidal activity against corn earworm twice during the course of development. The first samples were taken at V2-V4, and the second samples were taken at V7-V9. Leaf discs from lower leaf tips were excised and placed on water-moistened Whatman paper in 47×10 mm petri dishes. Ten-to-twenty L1 corn earworm or European corn borer larvae were added to each dish, and they were incubated for 48 hours at 28° C. Leaf discs were then scored for insect damage. Samples with no visible leaf damage and absolute mortality were scored as positive, and those with visible damage were negative. The data obtained show that several transgenic events with activity against both insects were identified.

Cry1AbG6 protein accumulation was also measured in T0 plants using the enzyme-linked immunosorbent assay (ELISA) with a fully-truncated Cry1Ab standard. The first assay was done on seedling leaf tissue, sampled 1-2 weeks after transfer to soil. The second assay was done on leaf tissue from maturing plants, sampled just prior to the transition to reproductive development. The data in TABLE B show the range of Cry1AbG6 protein accumulated in plants with insecticidal activity. The data indicate that plants require nearly 50 ng (or more) Cry1AbG6 protein/mg extractable protein to have insecticidal activity.

TABLE B shows the insect control characteristics of greenhouse grown plants.

| Event Number | Cassette Description | Cry1AbG6 (ng/mg extractable protein) | | Corn Earworm Activity | | ECB Activity |
| --- | --- | --- | --- | --- | --- | --- |
| | | seedling | adult | V2-V4 | V7-V9 | V7-V9 |
| 1 | ABP3-Cry1Abg6 | 63 | 79 | + | + | + |
| 2 | ABP3-Cry1Abg6 | 54 | 56 | + | + | + |
| 3 | ABP3-Cry1Abg6 | 85 | 108 | + | + | + |
| 4 | ABP3-Cry1Abg6 | 67 | 94 | + | + | + |
| 5 | ABP3-Cry1Abg6 | 45 | 83 | + | +/− | +/− |
| 6 | ABP3-Cry1Abg6 | 68 | 120 | + | + | + |
| 7 | ABP3-Cry1Abg6 | 133 | 159 | + | + | + |

-continued

| Event Number | Cassette Description | Cry1AbG6 (ng/mg extractable protein) | | Corn Earworm Activity | | ECB Activity |
| --- | --- | --- | --- | --- | --- | --- |
| | | seedling | adult | V2-V4 | V7-V9 | V7-V9 |
| 8 | ABP3-Cry1Abg6 | 96 | 46 | + | + | + |
| 9 | ABP3-Cry1Abg6 | 138 | 101 | + | + | + |
| 10 | ABP3-Cry1Abg6 | 131 | 100 | + | + | + |
| 11 | ABP3-Cry1Abg6 | 94 | 65 | + | + | + |
| 12 | ABP3-Cry1Abg6 | 111 | 59 | + | + | + |
| 13 | ABP3-Cry1Abg6 | 139 | 60 | + | + | + |
| 14 | ABP3-Cry1Abg6 | 121 | 81 | | | |
| 15 | ABP3-Cry1Abg6 | 66 | 55 | + | + | + |
| 16 | ABP3-Cry1Abg6 | 130 | 95 | + | + | + |

Leaf tissue from T0 plants was assayed for Cry1AbG6 protein by ELISA using truncated Cry1Ab protein as standard, Corn Earworm activity and European Corn Borer (ECB) activity. The plant developmental stage when sampled is indicated at the top of each column. The older (lower) leaf tissue was sampled. For insect assays a (+) indicates no visible leaf damage and complete and absolute insect mortality. Visible leaf damage produced a (−) score.

Example 1.7 European Cornborer Efficacy of ZmABP3-Cry1AbG6 Events in the Field The ECB (European corn borer) field efficacy studies were conducted in Stanton, Minn. (SMN) and Bloomington, Ill. (BIL) during the 2006 growing season. Near-isogenic hybrids, comprising the ABP3-Cry1AbG6 events listed in TABLE C, Bt11, and a nontransgenic control hybrid were tested. The experimental design was randomized complete block with three replications in each location. A plot consisted of one 5.31 m long row containing 25 plants, with 0.76 m spacing between rows.

TABLE C shows the performance of ZmABP3-Cry1AbG6 maize in field studies.

| Trial Location Trial Type | | MG371 BIL ECB | | | | MG331 SMN ECB | | | |
| --- | --- | --- | --- | --- | --- | --- | --- | --- | --- |
| Event Number | Cassette Description | ECBLR Leaf Feeding Rating | CEBSN Shank (cm) | ECBKN Ear Feeding (cm) | ECBSN Stalk Feeding (cm) | ECBLR Leaf Feeding Rating | CEBSN Shank (cm) | ECBKN Ear Feeding (cm) | ECBSN Stalk Feeding (cm) |
| 1 | ABP3-Cry1Abg6 | 1.0 | 0.00 | 1.42 | 0.00 | 1.1 | 0.00 | 0.00 | 0.30 |
| 2 | ABP3-Cry1Abg6 | 1.0 | 0.00 | 1.42 | 0.08 | 1.0 | 0.00 | 0.15 | 0.10 |
| 3 | ABP3-Cry1Abg6 | 1.0 | 0.00 | 1.25 | 0.08 | 1.0 | 0.00 | 0.00 | 0.80 |
| 4 | ABP3-Cry1Abg6 | 1.0 | 0.00 | 1.57 | 0.00 | 1.0 | 0.10 | 0.51 | 1.10 |
| 5 | ABP3-Cry1Abg6 | 1.0 | 0.00 | 1.25 | 0.04 | 1.0 | 0.00 | 0.07 | 0.20 |
| 6 | ABP3-Cry1Abg6 | 1.0 | 0.00 | 1.08 | 0.00 | | | | |
| 7 | ABP3-Cry1Abg6 | 1.0 | 0.00 | 1.31 | 0.00 | 1.1 | 0.10 | 0.45 | 0.80 |
| 8 | ABP3-Cry1Abg6 | 1.0 | 0.04 | 2.00 | 0.08 | 1.1 | 0.00 | 0.00 | 0.30 |
| 9 | ABP3-Cry1Abg6 | 1.0 | 0.00 | 0.92 | 0.00 | 1.3 | 0.00 | 0.00 | 0.10 |
| 10 | ABP3-Cry1Abg6 | 1.0 | 0.00 | 1.42 | 0.04 | 1.2 | 0.00 | 0.00 | 0.40 |
| 11 | ABP3-Cry1Abg6 | 1.0 | 0.13 | 1.17 | 0.00 | 1.0 | 0.00 | 0.00 | 0.10 |
| 12 | ABP3-Cry1Abg6 | 1.0 | 0.00 | 1.62 | 0.08 | 1.1 | 0.00 | 0.17 | 0.30 |
| 13 | ABP3-Cry1Abg6 | 1.0 | 0.00 | 1.29 | 0.00 | 1.2 | 0.00 | 0.00 | 0.20 |
| 14 | ABP3-Cry1Abg6 | 1.0 | 0.00 | 1.10 | 0.13 | 1.0 | 0.00 | 0.07 | 0.10 |
| 15 | ABP3-Cry1Abg6 | 1.0 | 0.08 | 1.33 | 0.04 | 1.1 | 0.00 | 0.24 | 0.20 |
| 16 | ABP3-Cry1Abg6 | 1.0 | 0.00 | 1.33 | 0.21 | 1.0 | 0.00 | 0.00 | 0.10 |
| | Bt11 | 1.0 | 0.00 | 2.75 | 0.00 | 1.3 | 0.00 | 0.00 | 0.00 |
| | Negative Check | 7.0 | 0.21 | 3.00 | 4.67 | 4.3 | 0.40 | 5.80 | 13.50 |
| | Rep with data | 3 | 3 | 3 | 3 | 3 | 3 | 3 | 3 |
| | Loc with data | 1 | 1 | 1 | 1 | 1 | 1 | 1 | 1 |
| | Design Used | RCB | RCB | RCB | RCB | RCB | RCB | RCB | RCB |
| | LSD (5%) General EE | | 0.149 | 0.923 | 0.257 | 0.399 | 0.200 | 1.988 | 0.650 |
| | LSD (5%) Excluded Negatives | | 0.158 | 0.936 | 0.255 | 0.397 | 0.181 | 0.505 | 1.391 |
| | CV % | | 242.21 | 38.47 | 72.14 | 20.10 | 292.75 | 138.76 | 120.87 |
| | Probablitiy % | | 0.90 | 0.09 | 0.00 | 0.00 | 4.10 | 0.00 | 0.00 |

Two studies were undertaken in Bloomington, Ill. (BIL) and Stanton, Minn. (SMN) in 2006. Several ZmABP3-Cry1AG6 events were compared to positive and negative benchmarks represented by Bt11 and Negative Check, respectively.

First-instar ECB larvae were produced from a laboratory colony following procedures outlined in Guthrie (1989) at the Syngenta Seeds, Inc. entomology laboratory in Slater, Iowa. Eggs were incubated at about 28° C. and approximately 80% relative humidity, and neonates were collected from hatching containers approximately 6 hours after hatch. Larvae were healthy and vigorous when placed on the plants as indicated by movement.

Two ECB application types were performed: ECB1, applied at approximately leaf stage V6-V8 and ECB2, applied at pollen shed. The applications were made with the BioServe Davis Inoculator using 1 ml corn cob grits per application. For ECB1 (first-generation ECB infestation) a total of about 150 larvae were placed into the whorl of each plant, in corn cob grits. Two to four applications were made, with one to six days between each application. The first plant in the row was not treated, and then up to 10 consecutive plants were infested.

For ECB2 (second-generation ECB infestation) a total of about 200 larvae were applied per plant, placed into the ear leaf axil and leaf axils directly above or below the ear, in corn cob grits. Four applications were made, with one to six days between each application. Up to ten consecutive plants on the opposite end of the row from the ECB1 treatment were infested. The last plant in the row was not treated.

The following observations were recorded. For ECB1, up to eight consecutive infested plants in the row were evaluated for foliar ECB damage (ECBLR in TABLE C) at least 14 days after the first infestation. The Guthrie scale of 1-9 (Guthrie et al. (1960) was used and one rating, the average for the evaluated plants, was recorded for each plot. For ECB2, approximately 45 days after the plants were infested, up to eight consecutively infested plants on the opposite end of the row from the ECB1 evaluations were dissected to assess ear shank, ear kernel, and stalk feeding, by measuring feeding tunnel lengths (cm).

ECB2 data were subjected to analyses of variance appropriate for a randomized complete block design. Replications were considered random while all other effects were considered fixed. Mean separation was done using the least significant difference (LSD) procedure, but only if the F-test for entries was significant at the customary 5% significance level. Because there was no variability among the events in the ECB1 data, an analysis of variance was not done for this trait. The data and analysis are summarized in TABLE D. In general, the data show that ZmABP3-Cry1ABG6 affords protection against ECB similar to that observed in Bt11 material.

TABLE D shows the amount of Cry1AbG6 protein in transgenic maize tissue. The youngest developing leaf was tested for Cry1AbG6 by ELISA at 5 developmental stages (V5-V6, V8, V10, R1, R3-R4) for each plant. Cry1AbG6 was also measured in pollen. Events 5, 12, 15 and 16 express the ABP3-Cry1AbG6 construct, and Events A-D express the enhanced ABP3-Cry1Ab construct. Data shown are the mean±SD (n=8-10).

Example 1.8 Use of ZmABP3 Expression Cassette to Improve Drought Tolerance in Maize A deregulated form of an *Arabidopsis* $H^+$-pyrophosphatase (AtAVP1 D) has been shown to improve drought tolerance when over-expressed in several plants (Gaxiola et al., 2001; Park et al., 2005). The improved performance is enabled by high expression throughout the plant. To demonstrate the utility of AtAVP1 D to improve drought tolerance in maize, a maize-optimized coding sequence was synthesized. The sequence of the AtAVP1D synthetic gene is shown in SEQ ID NO: 16. It was ligated to the ZmABP3 expression cassette as an NcoI/SacI fragment. The vector map shown in SEQ ID: 42 illustrates the ZmABP3-AtAVP1D expression cassette. The complete ZmABP3-AVP1 D expression cassette was excised from the Assembly vector as a SanDI/RsrII fragment and ligated to the RsrII site of the *Agrobacterium* binary vector, 15289. A map of the construct is shown in SEQ ID NO: 43.

Example 1.9 Measurement of Cry1AbG6 in Maize Tissue

Hybrid T1 seed (in the ID5829/AX5707 background) for several ZmABP3-Cry1ABG6 events were produced at a Syngenta field station in Bloomington, Ill. Several seed were germinated in 2 inch pots. Seedlings were tested for transgene zygosity, and only hemizygotes were retained. A minimum of 8 plants per event were transplanted to 3 gallon pots and grown in a temperature controlled greenhouse. Leaf tissue from each plant was sampled and assayed for Cry1AbG6 protein at 5 stages of development, V5-V6, V8, V10, R1, and R3-R4 (Ritchie et al., 1997). Pollen was also collected and assayed for Cry1AbG6 protein.

At each stage, leaf tissue (minus the collar, midrib and sheath) was sampled from the youngest expanding leaf. Duplicate samples were pulverized in 96-well blocks. The powder was suspended in 500 μL-1 mL extraction buffer (0.1 M Sodium Borate, 0.5% Tween 20, 0.2% Polyvinylpyrrolidone, 0.05% Sodium Azide, and 1× protease inhibitor cocktail tablets (Roche)). The mixture was clarified by centrifugation and soluble protein quantified using the BCA assay. Fresh pollen was collected in 1.5 mL Eppendorf tubes. Three 3 mm glass beads were added to each tube and the samples were frozen at −80° C. Samples were then pulverized in a horizontal oscillator at 600 rpm. Protein was extracted by adding 500 μL-1 mL extraction buffer and incubating at 4° C. for 30 minutes. The samples were clarified by centrifugation at 4° C., and the soluble protein in each sample was quantified by BCA Assay.

|  | Developmental Stage | | | | | |
| --- | --- | --- | --- | --- | --- | --- |
|  | V5-V6 | V8 | V10 | R1 | R3-R4 | Pollen |
| Event 5 | 39(3.8) | 38(2.7) | 61(8.2) | 75(5.3) | 60(3.5) | 1.5(0.14) |
| Event 12 | 61(5.2) | 32(1.9) | 50(6.1) | 44(5.1) | 49(4.4) | 1.4(0.39) |
| Event 15 | 45(4.5) | 45(4.8) | 46(4.8) | 38(7.4) | 55(5.4) | 1.0(0.14) |
| Event 16 | 58(5.4) | 30(2.9) | 47(5.3) | 53(7.2) | 44(4.6) | 1.2(0.17) |
| Event A | 260(24) | 190(22) | 250(18) | 200(21) | 150(14) | 1.3(0.19) |
| Event B | 260(22) | 227(29) | 240(30) | 200(23) | 150(76) | 1.6(0.30) |
| Event C | 310(31) | 210(26) | 270(26) | 150(15) | 160(16) | 1.9(0.31) |
| Event D | 310(30) | 180(23) | 240(15) | 170(26) | 150(18) | 1.4(0.19) |

Samples were normalized for protein content and Cry1AbG6 was quantified by ELISA using fully-truncated Cry1Ab as a standard. Each data point is the mean of duplicate measurements, taken at a different dilution of total protein. Data for each event are reported as the mean±SD for all siblings.

Results in TABLE D show that the ZmABP3-Cry1AbG6 cassette produces steady Cry1AbG6 protein in leaf tissue throughout development. Some reduction in CryAbG6 protein is evident as the vegetative tissue begins to senesce (R3-R4). Also evident is the 3-5 fold increase in Cry1AbG6 accumulation in events that also have the CaMV-FMV dual-enhancer complex. Finally, the data show virtually no detectable Cry1AbG6 protein in pollen. In all events CryAbG6, on average, accumulates to less than 1.5 ng/mg total soluble protein. Furthermore, the dual-enhancer complex does not influence Cry1AbG6 accumulation in pollen; it is identical between all events. This is consistent with our data showing that ZmABP3 is not transcribed in pollen (Example 1.5). We conclude that detectable Cry1AbG6 in pollen was likely produced in the microspore mother cells or their progenitors, and carried to pollen through cell division.

Example 2: Non-Tassel Expression

Example 2.1 Identification of ZmABT 2.1.1 Expression Profiling Experiment

A maize developmental series on the Zm80K Affymetrix chip, was queried for probes that gave strong signals in all samples, and a low or no signal in the tassel samples. Twenty-three (23) probes were identified representing polynucleotides that met the expression criteria. To better represent the differential expression signal between the tassel samples and other tissue samples, the ratio of mean signal for other samples and tassel was calculated for each probe. This indicates the expression differential between tassel and other samples. Any signal below 50 is in the experimental noise, which means the gene may not be transcribed or is transcribed at a very low level. To understand the expression level of each gene represented by candidate probes, a second expression profiling study was queried. In this experiment tissues from two maize genotypes were hybridized to the Zm80K Affymetrix chip. In general signals over 1000 indicate high expression and signals over 10,000 indicate very high expression.

2.1.2 Identification of Candidate Probes

Two top candidate probes were identified. Probe Zm033444_S_AT demonstrates virtually no signal in tassel and a high signal in other tissues. This indicates that the gene represented by Zm033444_S_AT is not expressed in tassel and is highly expressed throughout the rest of the plant. It also demonstrates the greatest expression differential, 60-fold higher in non-tassel tissue. Probe Zm040564_X_AT has a low signal in young tassel that gradually increases to a high or strong signal. The signal strength between tassel and non-tassel samples differs by less than 10-fold. However the signal strength in non-tassel samples is nearly 10-fold higher than Zm033444_S_AT. The sequence data indicate that neither probe corresponds to a characterized gene. Both probes identify good candidate genes for development of promoters that deliver high expression in non-tassel tissue and little or no expression in tassels. Given the high signal differential between tassel and non-tassel samples, an expression cassette based on probe Zm033444_S_AT was developed.

Table E: shows a summary of the top candidate probes representing polynucleotides with a high expression level in all maize tissues and low expression signal in tassel

| Probe | P-Value | BH Q-Value | Mean induction in non-tassel samples | V9 tassel | V12 tassel | V15 tassel |
|---|---|---|---|---|---|---|
| Zm033444_s_at | 0.00 | 0.00 | 60 | 16.2 | 10.2 | 132 |
| Zm002990_s_at | 0.00 | 0.00 | 45 | 32.8 | 68.7 | 47.8 |
| Zm006285_at | 0.00 | 0.00 | 20 | 37.9 | 44.1 | 35.8 |
| Zm000019_at | 0.00 | 0.00 | 16 | 117 | 200 | 242 |
| Zm006481_s_at | 0.00 | 0.00 | 14 | 26.9 | 32.1 | 31.5 |
| Zm002987_at | 0.00 | 0.00 | 14 | 83.7 | 80.8 | 119 |
| Zm004433_at | 0.00 | 0.00 | 12 | 53.8 | 35.3 | 127 |
| Zm010323_s_at | 0.00 | 0.00 | 11 | 45.4 | 63 | 71.5 |
| Zm016864_s_at | 0.01 | 0.01 | 11 | 89.5 | 55.6 | 1280 |
| Zm018791_at | 0.01 | 0.01 | 11 | 41.4 | 34.7 | 252 |
| Zm028405_s_at | 0.00 | 0.00 | 10 | 69 | 65.1 | 89 |
| Zm021403_at | 0.00 | 0.00 | 10 | 42.2 | 41.4 | 71 |
| Zm054116_s_at | 0.00 | 0.00 | 10 | 93.3 | 62.4 | 219 |
| Zm002990_x_at | 0.00 | 0.00 | 10 | 13.6 | 29.5 | 29.2 |
| Zm005761_at | 0.00 | 0.00 | 9.6 | 33.2 | 40 | 46.7 |
| Zm035082_s_at | 0.00 | 0.00 | 8.5 | 83 | 84 | 143 |
| Zm066342_at | 0.00 | 0.00 | 8.2 | 52.9 | 59.2 | 199 |
| Zm032921_s_at | 0.00 | 0.00 | 8.1 | 57.5 | 29.8 | 90.5 |
| Zm040564_x_at | 0.01 | 0.01 | 7.5 | 277 | 143 | 3710 |
| Zm051284_at | 0.01 | 0.01 | 6.5 | 53.2 | 40 | 194 |
| Zm011554_at | 0.03 | 0.04 | 5.4 | 72.5 | 64.2 | 895 |
| Zmmetall_x_at | 0.01 | 0.01 | 5.3 | 325 | 199 | 2330 |
| Zm011554_x_at | 0.04 | 0.04 | 4.9 | 63.5 | 62.6 | 664 |

Example 2.2 Development of an Expression Cassette

DNA sequence evidence to identify cDNAs corresponding to Zm033444_S_AT was collected. Public and proprietary databases were queried by BLASTN with Zm033444_S_AT sequence. cDNA hits with precise matches to the query sequence fell into two similar contigs. ZmABT1 corresponds to Maize.1482.c47 and Maize.1908.c31, and ZmABT2 corresponds to Maize.1482.c32, Maize.1482.c28, Maize.1482.c53, Maize.1908.c17, Maize.1908.c20, Maize.1908.c37 and AI947567. The Zm033444_S_AT, ZmABT1 and ZmABT2 sequences were used to query maize genomic DNA sequence databases to identify the regulatory sequence(s) that give high expression in non-tassel tissue and little or no expression in tassels. The queries identified three entries, AZM4_12, ZmGSStuc11-12-04.4740.1 and MAGI_88845, that assemble into a single contig. The ZmABT gDNA sequence is shown in SEQ ID NO: 46. It encodes both ZmABT1 and ZmABT2 (SEQ ID NO: 33 and 34, respectively). They are alternatively spliced variants of the same transcript.

ZmABT1 is encoded on 5 exons, and ZmABT2 is encoded on 6 exons. The additional exon lies between exon 1 and exon 2 of ZmABT1. The largest open reading frame on ZmABT1 and ZmABT2 was used to define their translation start and stop codons. Both cDNAs used the same translation start and stop codon. This information enabled the design of a ZmABT-based expression cassette.

Example 3: Construction of a ZmABT-GUS Expression Cassette

An inclusive, gene structure-based design strategy was used to construct the ZmABT expression cassette. To incorporate the known alternative splicing of this gene into the expression cassette, the design strategy was based on the structure of ZmABT1. The cassette contains 2.615 kb of 5'-sequence, which consists of 2.020 kb of 5'-non-transcribed sequence, 12 bp of 5'-UTR and 0.58 kb representing exon 1, intron 1 and 16 bp of exon 2. The natural translation start codon was silenced in order to move it to the second exon. The expression cassette also contains 1.039 kb of 3'-sequence that begins just past the translation stop codon. This includes 0.603 kb of 3'-UTR and 0.436 kb of non-transcribed sequence, and functions as the transcriptional terminator and poly-adenylation signal.

The ZmABT promoter was amplified from maize gDNA template in a 50 µL Proofstart (Qiagen) DNA polymerase reaction containing 10 µg gDNA, 5 µL 10× Proofstart Buffer, 1.0 µL 10 mM dNTP mix, 1.0 µL of 20 µM ABT P1 forw (5'-CGACCAGCGCGACATGCATGGCA-3'; SEQ ID NO: 19), 1.0 µL of 20 µM ABT P2 rev (5'-ACCCCAGGGCG-TACGACAAGGCC-3'; SEQ ID NO: 20), and 10.0 µL 5×Q solution. The thermocycling program was 95° C. for 5 minutes followed by 40 cycles of 94° C. for 30 seconds, 67° C. for 30 seconds and 72° C. for 2.5 minutes. The final extension step was 72° C. for 10 minutes. The 2.6 kb reaction product was gel-purified on 1% TBE agarose and the DNA was extracted using Qiaprep DNA extraction method. The DNA was cloned into the pCR-BluntII-TOPO vector.

The ZmABT promoter was modified in a series of mutagenesis reactions to silence the endogenous START codon, silence a SanDI restriction site and correct point mutations created during amplification. This was done using the Stratagene QuikChange Multi-site mutagenesis kit. The 25 µL reaction contained 1 µL pCR4-TOPO-ZmABT-promoter, 2.5 µL 10× QuikChange buffer, 1 µL QuikChange dNTP mix, 0.75 µL Quik solution, 1 µL QuikChange DNA polymerase and 1 µL of 20 µM of at least one of the following oligonucleotides:

pABT mut1
(SEQ ID NO: 21)
(5'-GATGGCCGGATTGGGCTCCCGGGGTGGAG-3')

pABT mut2
(SEQ ID NO: 22)
(5'-CTGGGAGGCGCGCAAGGGGCAGTTCCTCG-3')

pABT mut3
(SEQ ID NO: 23)
(5'-CCCACCGCCGGAGCACCGAAAGGCCCCGCG-3')

pABT mut4
(SEQ ID NO: 24)
(5'-GTCACCCGGGAGCACTTCCCGGCGCCG-3')

pABT mut5
(SEQ ID NO: 25)
(5'-CATTGGGCCGAGCACGGCTTCTTCCGC-3')

pABT mut6
(SEQ ID NO: 26)
(5'-GGGGTACGGTGTTCTTGAGTCGTGAAGCGAC-3')

The thermocycling program was 95° C. for 1 minute followed by 35 cycles of 95° C. for 1 minute, 50° C. for 1 minute and 65° C. for 12 minutes. The product was processed as described by the manufacturer (Stratagene) and completely sequenced. The ZmABT promoter sequence is shown in SEQ ID NO: 35.

The corrected ZmABT promoter was PCR amplified from the TOPO vector in a 50 µL Proofstart (Qiagen) DNA polymerase reaction as above using primers pABT amp1 (5'-GCGTCTAGAGGGACCCCGACCAGCGCGACATG-CATGGCA-3'), depicted in SEQ ID NO: 27 and pABT amp2 (5'-ACCCCAGGGCGTACGACAAGGCCCCAC-CATGGGCGC-3'), depicted in SEQ ID NO: 28. The PCR product was gel-purified on 1% TBE agarose and the DNA was extracted using Qiaprep DNA extraction method. The DNA was cloned into the pCR-BluntII-TOPO vector, transformed and sequenced. The ZmABT promoter was excised as an XbaI/NcoI fragment and ligated to pNOV6901.

The ZmABT terminus was amplified from maize gDNA template in a 50 µL Extensor (ABgene) DNA polymerase reaction containing 10 µg gDNA, 5 µL 10× Extensor buffer #1, 2.0 µL 10 mM dNTP mix, 2.0 µL of 20 µM ABT P4 (5'-TATATAGAGCTCGAATCGAAGAAGCCACACTG-TAAATCTGCCGGG-3'; SEQ ID NO: 29), 2.0 µL of 20 µM ABT P5 (5'-AGCAAGGCATATGCAGCAGCTGCTG-GTCGGACCGGGCCCTATATA-3'; SEQ ID NO: 30), 10 µL 5× Q solution, 0.5 µL Extensor DNA polymerase and 0.5 µL Amplitaq DNA polymerase. The reactions were overlaid with mineral oil and the thermocycling program was 95° C. for 2 minutes followed by 40 cycles of 98° C. for 2 seconds, 63° C. for 1 minute and 68° C. for 4 minutes. The final extension step was 68° C. for 7 minutes. The 1 kb reaction product was gel-purified on 1% TAE agarose, and the DNA was extracted using Qiaprep DNA extraction method. The DNA was ethanol precipitated and recovered in 4 µL ddH$_2$O, then cloned into the pCR4-TOPO-Blunt vector.

The ZmABT terminus was modified to remove internal NcoI and XhoI restriction sites using the Stratagene QuikChange Multi-site mutagenesis kit, as above. The 25 µL reaction contained 1 µL pCR4-TOPO-ZmABT-promoter, 2.5 µL 10× QuikChange buffer, 1 µL QuikChange dNTP mix, 0.75 µL Quik solution, 1 µL QuikChange DNA polymerase and 1 µL of 20 µM of at least one of the following oligonucleotides:

ABTt m1
(SEQ ID NO: 31)
(5'-GTCATGCATGGGCATGTGAAGGAGGAGCC-3')

ABTt m2
(SEQ ID NO: 32)
(5'-GTTGCATGCATGCTGCATGGCGTCGAGAT-3')

The thermocycling program was 95° C. for 1 minute followed by 35 cycles of 95° C. for 1 minute, 50° C. for 1 minute and 65° C. for 13 minutes. The product was processed as described by the manufacturer (Stratagene) and completely sequenced. The ZmABT terminator sequence is shown in SEQ ID NO: 36.

The ZmABT terminus was excised as a SacI/ApaI fragment and ligated to pNOV6901-prABT vector (above). This produced plasmid 15772 (ZmABT Assembly), and a plasmid map is shown in SEQ ID NO: 44. The complete ZmABT expression cassette was mobilized as a SanDI/RsrII fragment into the RsrII site of the *Agrobacterium* binary vector 15289. A plasmid map of this construct, 15773, is shown in SEQ ID NO: 45.

Example 4: Extension of DNA Probe Sequences to Designed Expression Cassettes

DNA sequence representing probes on the maize chip can easily be extended to designed expression cassettes following the steps outlined above. The DNA sequence for probes identified as representing genes that are highly expressed in all tissue samples and not expressed in pollen (Table A) and those that are highly expressed in all tissue samples and have reduced expression in tassel samples (Table E) is reported as SEQ ID NOs: 47-79.

An additional probe candidate from the expression profiling analysis for each expression category was selected to demonstrate progression from this DNA sequence to a finished binary vector with the designed expression cassette linked to the GUS reporter gene. The method used is identical to that for ZmABP3 and ZmABT. In summary the process steps to be applied are as follows:
1. Flank each expression cassette with SanDI/RsrII sites and report as cloned into the RsrII site of 15289 (SEQ ID NO: 80).
2. Promoter consists of 1000-1500 bp of sequence upstream of the transcription start site and extends 10 bases into the second exon, or to the natural translation start codon if it is not on the first exon. It terminates with the maize optimized Kozak sequence 'gtaaaccatgg'. The engineered translation start codon is now embedded in the NcoI restriction endonuclease site 'ccatgg'. Mutate all translation start codons in the theoretical transcript that are upstream of the engineered NcoI site. Ensure at least one stop codon is in each reading frame upstream of the engineered NcoI site. The promoter is designed to be flanked by XhoI/SanDI at the 5'-end and NcoI at the 3'-end.
3. The Gene Of Interest (GOI) is represented by the GUS reporter gene as an NcoI/SacI fragment.
4. The terminus extends from just after the translation stop codon for 1 kb downstream. The terminus is designed to be flanked by SacI at the 5'-end and RsrII/XmaI at the 3'-end.
5. The complete expression cassette is designed to be mobilized as a SanDI/RsrII fragment, which can be ligated into an RsrII site located on an *Agrobacterium* binary vector such as 15289 (SEQ ID NO: 80).
6. Mutate all internal SanDI, RsrII, NcoI, SacI, XhoI and XmaI sites by single base substitution to silence them.

Through application of these basic steps a plant expression cassette (SEQ ID NO: 81) can be designed that corresponds to probe Zm058948_s_at (SEQ ID NO: 55) and a plant expression cassette (SEQ ID NO: 82) that corresponds to probe Zm002990_s_at (SEQ ID NO: 62). The former is an expression cassette that should be transcribed in all maize tissues and not in pollen. The latter is an expression cassette that should be transcribed in all maize tissues and have reduced transcription in tassels. This design strategy applies to all probes identified in Tables A and E.

Further details of how to make such expression cassettes are described in US2005235311, which is incorporated herein by reference in its entirety.

REFERENCES

Ammirato et al., eds., (1984) Handbook of Plant Cell Culture—Crop Species, Macmillan Publ. Co., New York, N.Y.
An et al., (1985) EMBO J. 4, 277 287
Auch & Reth et al.
Batzer, et al., Nucleic Acid Res. 19:5081 (1991)
Byrne, M. C., McDonnell, R. E., Wright, M. S. and Carnes, M. G., 1987. "Strain and Cultivar Specificity in the *Agrobacterium*-soybean Interaction." Plant Cell Tissue and Organ Culture 8:3-15
Christou et al., *Plant Physiol.* 87:671-674 (1988)
Christou et al., *Biotechnology* 9: 957-962 (1991)
Crossway et al., *BioTechniques* 4:320-334 (1986)
Datta et al., *Bio/Technology* 8:736-740 (1990)
Fromm et al., *Bio/Technology* 8:833-839 (1990)
Gaxiola, R. A., Li, J., Undurraga, S., Dang, L. M., Allen, G. J. Alper, S. L., Fink, G. R. (2001). Drought- and salt-tolerant plants result from over-expression of the AVP1 H+-pump. Proc. Natl. Acad. Sci. USA 98: 11444-11449.
Gordon-Kamm et al., *Plant Cell* 2:603-618 (1990)
Gruber, et al., "Vectors for Plant Transformation, in Methods in Plant Molecular Biology & Biotechnology" in Glich, et al., (Eds. pp. 89-119, CRC Press, 1993).
Guthrie, W. D., F. F. Dicke, and C. R. Neiswander (1960) Leaf and sheath feeding resistance to the Eur. corn borer in eight inbred lines of dent corn. Ohio Agric. Exp. Stn. Res. Bull. 860.
Guthrie, W. D. (1989) Advances in Rearing the European Corn Borer on a Meridic Diet, In: *Toward Insect Resistant Maize for the Third World; Proceedings of the International Symposium on Methodologies for Developing Host Plant Resistance to Maize Insects.* Mexico, D. F.:CIMMYT
Hiei et al., (1994) Plant J. 6, 271-282
Hinchee et al., *Biotechnology* 6:915-921 (1988)
Hoekema (1985) The Binary Plant Vector System, Offsetdrukkerij Kanters B. V., Alblasserdam, Chap. V
Klein et al., *Proc. Natl. Acad. Sci. USA,* 85:4305-4309 (1988)
Klein et al., *Bio/Technology* 6:559-563 (1988)(maize); Klein et al., *Plant Physiol.* 91:440-444 (1988)
Knauf, et al., 1983
Koziel et al., *Biotechnology* 11: 194-200 (1993)
Lindsey K, Wei W, Clarke M C, McArdle H F, Rooke L M, Topping J F. Tagging genomic sequences that direct transgene expression by activation of a promoter trap in plants. Transgenic Res. 1993 January; 2(1):33-47.
Lopez, I, Anthony, R. G., Maciver, S. K., Jiang, C.-J., Khan, S., Weeds, A. G., Hussey, P. J. (1996) Pollen specific expression of maize genes encoding actin depolymerizing factor-like proteins. Proc. Natl. Acad. Sci. USA. 93: 7415-7420.
Lörz et al. (Mol. Gen. Genet. 199, 178, (1985))
McBride, et al. (1994) Proc. Natl. Acad. Sci. USA 91:7301-7305
McCabe et al., *Biotechnology* 6:923-926 (1988)
Ohtsuka, et al., J. Biol. Chem. 260:2605-2608 (1985)
Pacciotti et al. (1985) Bio/Technology 3:241
Park et al., 1985

Park, S., Li, J., Pittman, J. K., Berkowitz, G. A., Yang, H., Undurrago, S., Morris, J., Hirschi, K. D., Gaxiola, R. A. (2005). Up-regulation of a H$^+$-pyrophosphatase (H$^+$-PPase) as a strategy to engineer drought-resistant crop plants. Proc. Natl. Acad. Sci. USA 102: 18830-18835.
Paszkowski et al., *EMBO J.* 3:2717-2722 (1984)
Pearson, W. R. (1990), Methods in Enzymology 183, 63-98
Potrykus, I., Paszkowski, J. P., Saul, M. W., Petruska, P. and Shillito, R. D. 1985. Molecular and general genetics of a hybrid foreign gene introduced into tobacco by direct gene transfer. *Mol. Gen. Genet.* 199:169-177.
Ritchie, S. W., Hanway, J. J., Benson, G. O. (1997). How a corn plant develops: Special Report No. 48. Iowa State University of Science and Technology Cooperative Extension service: Ames, Iowa.
Riggs et al., *Proc. Natl. Acad. Sci. USA* 83:5602-5606 (1986)
Rossolini, et al., Mol. Cell. Probes 8:91-98 (1994)
Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980)
Sanford et al., *Particulate Science and Technology* 5:27-37 (1987)
Shimamoto et al., *Nature* 338:274-277 (1989)
Shirzadegan, M., Christie, P., Seemann, J. (1991) An efficient method for isolation of RNA from tissue-cultured plant cells. Nucleic Acids Res. 19(21): 6055.
Smith and Waterman, Advances in Applied Mathematics 2 (1981), 482-489
Sukhapinda et al., Plant Mol. Biol., vol. 8:209-216, 1987
Svab et al., *Proc. Natl. Acad. Sci. USA* 87: 8526-8530 (1990)
Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York.,
Vasil et al., *Biotechnology* 11: 1553-1558 (1993)
Weeks et al., *Plant Physiol.* 102: 1077-1084 (1993)
Weissinger et al., *Annual Rev. Genet.* 22:421-477 (1988)

PATENT LITERATURE

EP 0 332 581
EP 0 292 435
EP 0 295959
EP 0 138341
EP 0 120516
U.S. Pat. No. 5,451,513
U.S. Pat. No. 5,545,817
U.S. Pat. No. 5,545,818
U.S. Pat. No. 5,350,689
U.S. Pat. No. 5,451,513,
U.S. Pat. No. 4,945,050
WO 95/16783

The invention claimed is:

1. An isolated polynucleotide comprising SEQ ID NO:35 operably linked to a heterologous nucleotide sequence of interest in maize, wherein the heterologous nucleotide sequence is transcribed in maize leaf tissue and not in tassel.

2. An expression cassette comprising the isolated polynucleotide of claim 1.

3. A vector molecule comprising the expression cassette according to claim 2.

4. A transgenic plant comprising the expression cassette of claim 2.

5. A transgenic plant comprising the vector of claim 3.

6. The transgenic plant of claim 5 wherein the plant is Zea mays.

7. A seed of the transgenic plant of claim 6, wherein the seed comprises an isolated polynucleotide comprising SEQ ID NO: 35 operably linked to a heterologous nucleotide sequence of interest in maize.

* * * * *

SEQUENCE LISTING

```
<160> NUMBER OF SEQ ID NOS: 91

<210> SEQ ID NO 1
<211> LENGTH: 50
<212> TYPE: DNA
<213> ORGANISM: Artificial Sequence
<220> FEATURE:
<223> OTHER INFORMATION: forward primer P1

<400> SEQUENCE: 1
atatatgcat gcggcgcgcc gaaagtagca acaacaggt tcatgtgcac            50

<210> SEQ ID NO 2
<211> LENGTH: 38
<212> TYPE: DNA
<213> ORGANISM: Artificial Sequence
<220> FEATURE:
<223> OTHER INFORMATION: reverse primer P2

<400> SEQUENCE: 2 tataccat ggtgggtttg cctgcgacca caagttca                         38

<210> SEQ ID NO 3
<211> LENGTH: 28
<212> TYPE: DNA
<213> ORGANISM: Artificial Sequence
<220> FEATURE:
<223> OTHER INFORMATION: oligonucleotide Patg

<400> SEQUENCE: 3
cagctcgccc gagttggtaa ggccccct                                  28

<210> SEQ ID NO 4
<211> LENGTH: 24
<212> TYPE: DNA
<213> ORGANISM: Artificial Sequence
```

```
<220> FEATURE:
<223> OTHER INFORMATION: oligonucleotide Pnco

<400> SEQUENCE: 4
acagattagt ccatcgccca cggt                                          24

<210> SEQ ID NO 5
<211> LENGTH: 27
<212> TYPE: DNA
<213> ORGANISM: Artificial Sequence
<220> FEATURE:
<223> OTHER INFORMATION: oligonucleotide ADPc-1

<400> SEQUENCE: 5
agccctgtcc atgacggccc aagcaac                                       27

<210> SEQ ID NO 6
<211> LENGTH: 26
<212> TYPE: DNA
<213> ORGANISM: Artificial Sequence
<220> FEATURE:
<223> OTHER INFORMATION: oligonucleotide ADPc-2

<400> SEQUENCE: 6
agtagcaatt cggtaggcac aggcac                                        26

<210> SEQ ID NO 7
<211> LENGTH: 25
<212> TYPE: DNA
<213> ORGANISM: Artificial Sequence
<220> FEATURE:
<223> OTHER INFORMATION: oligonucleotide ADPc-4

<400> SEQUENCE: 7
tctatggtct gcgaggtgcg gtggc                                         25

<210> SEQ ID NO 8
<211> LENGTH: 27
<212> TYPE: DNA
<213> ORGANISM: Artificial Sequence
<220> FEATURE:
<223> OTHER INFORMATION: oligonucleotide adp3-a

<400> SEQUENCE: 8
gtccccttct tcgccgcgcc agctcgc                                       27

<210> SEQ ID NO 9
<211> LENGTH: 37
<212> TYPE: DNA
<213> ORGANISM: Artificial Sequence
<220> FEATURE:
<223> OTHER INFORMATION: forward primer P3

<400> SEQUENCE: 9
tatatagagc tcgcatcatg atcatgcatc atggact                            37

<210> SEQ ID NO 10
<211> LENGTH: 46
<212> TYPE: DNA
<213> ORGANISM: Artificial Sequence
<220> FEATURE:
<223> OTHER INFORMATION: reverse primer P4

<400> SEQUENCE: 10
atatatacta gtggcgcgcc acactttctg tcgcatgtga tttgca                  46
```

<210> SEQ ID NO 11
<211> LENGTH: 30
<212> TYPE: DNA
<213> ORGANISM: Artificial Sequence
<220> FEATURE:
<223> OTHER INFORMATION: forward primer Tnco

<400> SEQUENCE: 11
gtaaaaaaag gtcccttggc tcccagaaga                              30

<210> SEQ ID NO 12
<211> LENGTH: 20
<212> TYPE: DNA
<213> ORGANISM: Artificial Sequence
<220> FEATURE:
<223> OTHER INFORMATION: forward primer T2

<400> SEQUENCE: 12
caatgtgtta gactgacgtg                                         20

<210> SEQ ID NO 13
<211> LENGTH: 2333
<212> TYPE: DNA
<213> ORGANISM: Zea mays

<400> SEQUENCE: 13
gcatgcggcg cgccgaaagt agcaaacaac aggttcatgt gcactataaa aagacaaaat    60
tctcgagttt catcttttat tccacataag ccttatattt tccattttca tatgattttt   120
agtttaagtt tgtgtcttaa cttttttcgtt aatacgtaat tctatgcatt atggatgcgt   180
gaagtatttt tgtttaaaaa aatgaaatgt caaaatacgt tttgtgatct atttccatgt   240
tttcacctaa caggtggttt ttactatata ttctgccata actctagcct tagatgtaaa   300
tcgaaaaaaa atgagagatg agctggagat agccttagat gaagcgtctg aaatataaaa   360
gaaagagtaa tgttgaacgc agtaggtgta gcagctgtag ttccatctct aggaaaggga   420
actgcaatcc gggctccggg cctcgcgcaa tctggcctgt cgtgtagatg cagccctgtc   480
catgacggcc caagcaacgc ccgcggctct cgatccacca cggaacccac tccgacacac   540
actgacacac acatgctgga tgtggatgtg ctgtccaatt attagtagca attcggtagg   600
cacaggcacg tactggccgg tgttttagct gtaagtaccg aaccaatcac ggttaagaac   660
cgattaatcc gtgcccagcc gccgagtgcg ttcgtacgtg catcggatgc actgcatgaa   720
ttgagagcat catcatatca tacgcaggag tagtacgacg ccgctgctgt cttgtccggc   780
taatgctttg ctcacagatt agtccatcgc ccacggtcgg tgtggtgtgg atcgctgatg   840
ccactgcttt ttgtttggtt tttattcccc tgataatcct ccgcgtccct gaatgtatct   900
atttattttc attccgaaat ccctttcacg aaaaagaaaa cgaataaaaa gagagttacg   960
aatacgcttc cggcggccca catcaccttc cagcgaacat cgcgccgcgc tgacgtgtcg  1020
cccatcgcgg ccgtccatat cgccatccga cgaccgtgga agctggcagc ggccgctccg  1080
ttccgtcgaa ggggcaggtc agtcaggtca cccacacggc cacacccgcg cgggggatac  1140
gcggtggaaa acccggcgac cacatcaaaa cacgaggcgt ctcccgcagg actggtcact  1200
cggcacgcag gcagaggcag cacagcagca gccagctcca tccatcctct ttccccctcct  1260 cgcttcgctt cctcggcgga ttcctcctcc ctcggccgtc ccgtcccct tcttcgccgc  1320 gccagctcgc ccgagttggt aaggccccct ccacccctcc gcttcccctc ccccgggcgc  1380
gctctggctt cctccccgga tcggcgcggg gcgtgctggc tccgcgcctg atttcgggcc  1440

| | | | | |
|---|---|---|---|---|
| ttttgtttcc | ttctcgcgga | gcgctcgtgt | aacgcttcgg | atctagctgg attcaggcgg | 1500 |
| gatcgcggcc | gctcggcttc | ctcgtggcct | gattcgtggt | tttcctcggg gagggaatcc | 1560 |
| tgatcggatc | atcgggattc | ctcgtgcggc | cgggacacgc | ttgcgagcca gaaacatagt | 1620 |
| ctgcgtggcc | gggattccac | gatctgtgat | ctagacgtcg | ggcgcttcgt ctatgtgctc | 1680 |
| gctgcaggct | gtggcgtact | ggcgtggtgc | gcggccgcta | tggatccgtg cttgtttgtt | 1740 |
| cgccctgtag | cgtgtgaaat | cgagctgtgt | agatctatgg | tctgcgaggt gcggtggcgg | 1800 |
| tggaatctcg | gttgatcttt | acctcagcgg | cgccagtgta | gctcgtgtgg ctgcagttca | 1860 |
| tctgcgaatt | tggctctcgg | cggcttaggt | cgcggagctt | ggattatgga gcaccagctg | 1920 |
| cagcgtgacc | ctgttggttc | tcatgtggat | ctgttggctg | aggttgcaga cttcaagtgc | 1980 |
| cactgccatt | gaccggagct | gctgcacgat | atactggaa | tatctagcgg tagtatactc | 2040 |
| tgctagtact | caatacgggt | ctcctgacaa | atgtctttcg | tgtttaggga cctagcactc | 2100 |
| tagtgtcaag | actatttgct | ggaatatcta | atattagcag | tttctgtagt ggctcagttg | 2160 |
| cagcctggtt | tagaatgatg | gggacagttg | gctgtgccat | gcaaaataaa gtgtgtgaaa | 2220 |
| gcaactgcct | cttaaactat | gggtggtgca | agcaggttat | ttgaagggac tctccacact | 2280 |
| gtatctccag | ttaactatga | ctgaacttgt | ggtcgcaggc | aaacccacca tgg | 2333 |

<210> SEQ ID NO 14
<211> LENGTH: 1031
<212> TYPE: DNA
<213> ORGANISM: Zea mays

<400> SEQUENCE: 14

| | | | | |
|---|---|---|---|---|
| gagctcgcat | catgatcatg | catcatggac | tcggcctact | actgtggatt tgtatgccat | 60 |
| tatagacttg | gtgctgtgaa | agactgcttg | atgatttgcg | ggtttgttgc tgtgtaaaaa | 120 |
| aaggtcccctt | ggctcccaga | agaccatgaa | ggttcggatc | tatcatgtaa ttccttgtta | 180 |
| tctgccaatt | atgtatggac | tatggacatg | tgttgcgctg | ttcaacttac tactacaaat | 240 |
| aagtaatcga | tatgttccct | tcccatgtct | cggtgacaat | tgtctggaga agcttagggg | 300 |
| tcgtttgttt | gggattatgt | ctggagaaac | ttatttttaaa | ctaagtgtga gttcaagtta | 360 |
| agttagatta | tataatctag | gcagattata | attccaagcg | aacaggtcct tagtgttttt | 420 |
| ggaaaatcct | aggtgttctt | ttggctacat | tgttgtgtgt | gcagatccct tgttggtctg | 480 |
| taagcgtggg | gaagtaagaa | tcgtccgttt | ctactgaaga | cctgctcgag ttaggcaccg | 540 |
| aggatgccgg | taaccaaaca | gagcaatagt | gtctctgtgg | gcacagtgga gtgtgaatct | 600 |
| gtgtgatgca | aatccgtcat | ttgtttagca | aaatttccag | cgttgcatga tgcagtttct | 660 |
| ttaacacgga | cttaagggaa | gggaaaaaaa | tgttgagcca | ggagatcctt caatgtgtta | 720 |
| gactgacgtg | atagccaact | aaaccacgac | gcaatgttgt | cgttaatgac aaaaaaacta | 780 |
| tttgttccta | aatccttggc | gacattgcat | ggctgtctca | tgagataatg gtctcatctc | 840 |
| ttatttatct | cttatttata | gccggaagtg | gtagtgaccc | ctgcttgatt gctcgtatgc | 900 |
| catctcaagt | tctcaaccgt | gtcgagcagc | catttttccca | tctcaagcgc atcatcgttt | 960 |
| cgtttgacct | catctgctat | cctgctccta | gtgcaaatca | catgcgacag aaagtgtggc | 1020 |
| gcgccactag | t | | | | 1031 |

<210> SEQ ID NO 15
<211> LENGTH: 1031
<212> TYPE: DNA

<213> ORGANISM: Zea mays

<400> SEQUENCE: 15

```
gagctcgcat catgatcatg catcatggac tcggcctact actgtggatt tgtatgccat    60
tatagacttg gtgctgtgaa agactgcttg atgatttgcg ggtttgttgc tgtgtaaaaa   120
aaggtccctt ggctcccaga agaccatgaa ggttcggatc tatcatgtaa ttccttgtta   180
tctgccaatt atgtatggac tatggacatg tgttgcgctg ttcaacttac tactacaaat   240
aagtaatcga tatgttccct tcccatgtct cggtgacaat tgtctggaga agcttagggg   300
tcgtttgttt gggattatgt ctggagaaac ttattttaaa ctaagtgtga gttcaagtta   360
agttagatta tataatctag gcagattata attccaagcg aacaggtcct tagtgttttt   420
ggaaaatcct aggtgttctt ttggctacat tgttgtgtgt gcagatccct tgttggtctg   480
taagcgtggg gaagtaagaa tcgtccgttt ctactgaaga cctgctcgag ttaggcaccg   540
aggatgccgg taaccaaaca gagcaatagt gtctctgtgg gcacagtgga gtgtgaatct   600
gtgtgatgca aatccgtcat ttgtttagca aaatttccag cgttgcatga tgcagtttct   660
ttaacacgga cttaagggaa gggaaaaaaa tgttgagcca ggagatcctt caatgtgtta   720
gactgacgtg atagccaact aaaccacgac gcaatgttgt cgttaatgac aaaaaaacta   780
tttgttccta aatccttggc gacattgcat ggctgtctca tgagataatg gtctcatctc   840
ttatttatct cttatttata gccggaagtg gtagtgaccc ctgcttgatt gctcgtatgc   900
catctcaagt tctcaaccgt gtcgagcagc catttttccca tctcaagcgc atcatcgttt   960
cgtttgacct catctgctat cctgctccta gtgcaaatca catgcgacag aaagtgtggc  1020
gcgccactag t                                                      1031
```

<210> SEQ ID NO 16
<211> LENGTH: 1031
<212> TYPE: DNA
<213> ORGANISM: Zea mays

<400> SEQUENCE: 16

```
gagctcgcat catgatcatg catcatggac tcggcctact actgtggatt tgtatgccat    60
tatagacttg gtgctgtgaa agactgcttg atgatttgcg ggtttgttgc tgtgtaaaaa   120
aaggtccctt ggctcccaga agaccatgaa ggttcggatc tatcatgtaa ttccttgtta   180
tctgccaatt atgtatggac tatggacatg tgttgcgctg ttcaacttac tactacaaat   240
aagtaatcga tatgttccct tcccatgtct cggtgacaat tgtctggaga agcttagggg   300
tcgtttgttt gggattatgt ctggagaaac ttattttaaa ctaagtgtga gttcaagtta   360
agttagatta tataatctag gcagattata attccaagcg aacaggtcct tagtgttttt   420
ggaaaatcct aggtgttctt ttggctacat tgttgtgtgt gcagatccct tgttggtctg   480
taagcgtggg gaagtaagaa tcgtccgttt ctactgaaga cctgctcgag ttaggcaccg   540
aggatgccgg taaccaaaca gagcaatagt gtctctgtgg gcacagtgga gtgtgaatct   600
gtgtgatgca aatccgtcat ttgtttagca aaatttccag cgttgcatga tgcagtttct   660
ttaacacgga cttaagggaa gggaaaaaaa tgttgagcca ggagatcctt caatgtgtta   720
gactgacgtg atagccaact aaaccacgac gcaatgttgt cgttaatgac aaaaaaacta   780
tttgttccta aatccttggc gacattgcat ggctgtctca tgagataatg gtctcatctc   840
ttatttatct cttatttata gccggaagtg gtagtgaccc ctgcttgatt gctcgtatgc   900
catctcaagt tctcaaccgt gtcgagcagc catttttccca tctcaagcgc atcatcgttt   960
```

```
cgtttgacct catctgctat cctgctccta gtgcaaatca catgcgacag aaagtgtggc    1020
gcgccactag t                                                         1031

<210> SEQ ID NO 17
<211> LENGTH: 1031
<212> TYPE: DNA
<213> ORGANISM: Zea mays

<400> SEQUENCE: 17
gagctcgcat catgatcatg catcatggac tcggcctact actgtggatt tgtatgccat      60
tatagacttg gtgctgtgaa agactgcttg atgatttgcg ggtttgttgc tgtgtaaaaa     120
aaggtccctt ggctcccaga agaccatgaa ggttcggatc tatcatgtaa ttccttgtta    180
tctgccaatt atgtatggac tatggacatg tgttgcgctg ttcaacttac tactacaaat    240
aagtaatcga tatgttccct tcccatgtct cggtgacaat tgtctggaga agcttagggg    300
tcgtttgttt gggattatgt ctggagaaac ttattttaaa ctaagtgtga gttcaagtta    360
agttagatta tataatctag gcagattata attccaagcg aacaggtcct tagtgttttt    420
ggaaaatcct aggtgttctt ttggctacat tgttgtgtgt gcagatccct tgttggtctg    480
taagcgtggg gaagtaagaa tcgtccgttt ctactgaaga cctgctcgag ttaggcaccg    540
aggatgccgg taaccaaaca gagcaatagt gtctctgtgg gcacagtgga gtgtgaatct    600
gtgtgatgca aatccgtcat ttgtttagca aaatttccag cgttgcatga tgcagtttct    660
ttaacacgga cttaagggaa gggaaaaaaa tgttgagcca ggagatcctt caatgtgtta    720
gactgacgtg atagccaact aaaccacgac gcaatgttgt cgttaatgac aaaaaaacta    780
tttgttccta aatccttggc gacattgcat ggctgtctca tgagataatg gtctcatctc    840
ttatttatct cttatttata gccggaagtg gtagtgaccc ctgcttgatt gctcgtatgc    900
catctcaagt tctcaaccgt gtcgagcagc catttcccca tctcaagcgc atcatcgttt    960
cgtttgacct catctgctat cctgctccta gtgcaaatca catgcgacag aaagtgtggc    1020
gcgccactag t                                                         1031

<210> SEQ ID NO 18
<211> LENGTH: 8546
<212> TYPE: DNA
<213> ORGANISM: Artificial sequence
<220> FEATURE:
<223> OTHER INFORMATION: plasmid pNOV1321

<400> SEQUENCE: 18
cttgcatgcc tgcagtgcag cgtgacccgg tcgtgcccct ctctagagat aatgagcatt      60
gcatgtctaa gttataaaaa attaccacat attttttttg tcacacttgt ttgaagtgca    120
gtttatctat ctttatacat atatttaaac tttactctac gaataatata atctatagta    180
ctacaataat atcagtgttt tagagaatca tataaatgaa cagttagaca tggtctaaag    240
gacaattgag tattttgaca acaggactct acagttttat cttttttagtg tgcatgtgtt    300 ctcctttttt tttgcaaata gcttcaccta tataatactt catccatttt attagtacat    360
ccatttaggg tttagggtta atggtttttta tagactaatt tttttagtac atctatttta    420
ttctatttta gcctctaaat taagaaaact aaaactctat tttagttttt tatttaata    480 atttagatat aaaatagaat aaaataaagt gactaaaaat taaacaaata ccctttaaga    540
aattaaaaaa actaaggaaa cattttttctt gtttcgagta gataatgcca gcctgttaaa    600
```

```
cgccgtcgac gagtctaacg gacaccaacc agcgaaccag cagcgtcgcg tcgggccaag    660
cgaagcagac ggcacggcat ctctgtcgct gcctctggac ccctctcgag agttccgctc    720
caccgttgga cttgctccgc tgtcggcatc cagaaattgc gtggcggagc ggcagacgtg    780
agccggcacg gcaggcggcc tcctcctcct ctcacggcac cggcagctac gggggattcc    840
tttcccaccg ctccttcgct ttcccttcct cgcccgccgt aataaataga cacccccctcc    900 acacctctt tccccaacct cgtgttgttc ggagcgcaca cacacacaac cagatctccc    960
ccaaatccac ccgtcggcac ctccgcttca aggtacgccg ctcgtcctcc cccccccccc   1020
ctctctacct tctctagatc ggcgttccgg tccatggtta gggcccggta gttctacttc   1080
tgttcatgtt tgtgttagat ccgtgtttgt gttagatccg tgctgctagc gttcgtacac   1140
ggatgcgacc tgtacgtcag acacgttctg attgctaact tgccagtgtt tctctttggg   1200
gaatcctggg atggctctag ccgttccgca gacgggatcg atttcatgat tttttttgtt   1260
tcgttgcata gggtttggtt tgcccttttc ctttatttca atatatgccg tgcacttgtt   1320
tgtcgggtca tcttttcatg cttttttttg tcttggttgt gatgatgtgg tctggttggg   1380
cggtcgttct agatcggagt agaattctgt ttcaaactac ctggtggatt tattaatttt   1440
ggatctgtat gtgtgtgcca tacatattca tagttacgaa ttgaagatga tggatggaaa   1500
tatcgatcta ggataggtat acatgttgat gcgggtttta ctgatgcata tacagagatg   1560 cttttttgttc gcttggttgt gatgatgtgg tgtggttggg cggtcgttca ttcgttctag   1620
atcggagtag aatactgttt caaactacct ggtgtattta ttaattttgg aactgtatgt   1680
gtgtgtcata catcttcata gttacgagtt taagatggat ggaaatatcg atctaggata   1740
ggtatacatg ttgatgtggg ttttactgat gcatatacat gatggcatat gcagcatcta   1800
ttcatatgct ctaaccttga gtacctatct attataataa acaagtatgt tttataatta   1860
ttttgatctt gatatacttg gatgatggca tatgcagcag ctatatgtgg attttttttag   1920 ccctgccttc atacgctatt tatttgcttg gtactgtttc ttttgtcgat gctcaccctg   1980
ttgtttggtg ttacttctgc agggatccaa caatggacaa caaccccaac atcaacgagt   2040
gcatccccta caactgcctg agcaacccccg aggtggaggt gctgggcggc gagcgcatcg   2100
agaccggcta caccccatc gacatcagcc tgagcctgac ccagttcctg ctgagcgagt   2160
tcgtgcccgg cgccggcttc gtgctgggcc tggtggacat catctggggc atcttcggcc   2220
ccagccagtg ggacgccttc ctggtgcaga tcgagcagtt gataaaccaa cgcatagagg   2280
aattcgcccg caaccaggcc atcagccgcc tggagggcct gagcaacctg taccaaatct   2340
acgccgagag cttccgcgag tgggaggccg accccaccaa ccccgccctg cgcgaggaga   2400
tgcgcatcca gttcaacgac atgaacagcc cctgaccac cgccatcccc ctgttcgccg   2460
tgcagaacta ccaggtgccc ctgctgagcg tgtacgtgca ggccgccaac ctgcacctga   2520
gcgtgctgcg cgacgtcagc gtgttcggcc agcgctgggg cttcgacgcc gccaccatca   2580
acagccgcta caacgacctg accgcctga tcggcaacta caccgaccac gccgtgcgct   2640
ggtacaacac cggcctggag cgcgtgtggg gtcccgacag ccgcgactgg atcaggtaca   2700
accagttccg ccgcgagctg acctgaccg tgctggacat cgtgagcctg ttccccaact   2760
acgacagccg cacctacccc atccgcaccg tgagccagct gacccgcgag atttacacca   2820
accccgtgct ggagaacttc gacggcagct tccgcggcag cgccagggc atcgagggca   2880 gcatccgcag cccccacctg atggacatcc tgaacagcat caccatctac accgacgccc   2940
accgcggcga gtactactgg agcggccacc agatcatggc cagccccgtc ggcttcagcg   3000
```

```
gccccgagtt caccttcccc ctgtacggca ccatgggcaa cgctgcacct cagcagcgca   3060
tcgtggcaca gctgggccag ggagtgtacc gcaccctgag cagcaccctg taccgtcgac   3120
ctttcaacat cggcatcaac aaccagcagc tgagcgtgct ggacggcacc gagttcgcct   3180
acggcaccag cagcaacctg cccagcgccg tgtaccgcaa gagcggcacc gtggacagcc   3240
tggacgagat cccccctcag aacaacaacg tgccacctcg acagggcttc agccaccgtc   3300
tgagccacgt gagcatgttc cgcagtggct tcagcaacag cagcgtgagc atcatccgtg   3360
cacctatgtt cagctggatt caccgcagtg ccgagttcaa caacatcatc cccagcagcc   3420
agatcaccca gatcccccctg accaagagca ccaacctggg cagcggcacc agcgtggtga   3480
agggcccccgg cttcaccggc ggcgacatcc tgcgccgcac cagccccggc cagatcagca   3540
ccctgcgcgt gaacatcacc gcccccctga gccagcgcta ccgcgtccgc atccgctacg   3600
ccagcaccac caacctgcag ttccacacca gcatcgacgg ccgccccatc aaccagggca   3660
acttcagcgc caccatgagc agcggcagca acctgcagag cggcagcttc cgcaccgtgg   3720
gcttcaccac cccccttcaac ttcagcaacg gcagcagcgt gttcaccctg agcgcccacg   3780
tgttcaacag cggcaacgag gtgtacatcg accgcatcga gttcgtgccc gccgaggtga   3840
ccttcgaggc cgagtacgac ctggagaggg ctcagaaggc cgtgaacgag ctgttcacca   3900
gcagcaacca gatcggcctg aagaccgacg tgaccgacta ccacatcgac caggtgagca   3960
acctggtgga gtgcttaagc gacgagttct gcctggacga gaagaaggag ctgagcgaga   4020
aggtgaagca cgccaagcgc ctgagcgacg agcgcaacct gctgcaggac cccaacttcc   4080
gcggcatcaa ccgccagctg gaccgcggct ggcgaggcag caccgatatc accatccagg   4140
gcggcgacga cgtgttcaag gagaactacg tgaccctgct gggccacctt gacgagtgct   4200
acccccaccta cctgtaccag aagatcgacg agagcaagct gaaggcctac acccgctacc   4260
agctgcgcgg ctacatcgag gacagccagg acctggaaat ctacctgatc cgctacaacg   4320
cgaagcacga gaccgtgaac gtgcccggca ccggcagcct gtggccctg agcgccccca   4380
gccccatcgg caagtgcggg gagccgaatc gatgcgctcc gcacctggag tggaacccgg   4440
acctagactg cagctgcagg gacggggaga agtgcgccca ccacagccac cacttcagcc   4500
tggacatcga cgtgggctgc accgacctga acgaggacct gggcgtgtgg gtgatcttca   4560
agatcaagac ccaggacggc cacgcccgcc tgggcaatct agagttcctg gaggagaagc   4620
ccctggtggg cgaggccctg gccccgcgtga agcgtgctga agaagtgg cgcgacaagc   4680
gcgagaagct ggagtgggag accaacatcg tgtacaagga ggccaaggag agcgtggacg   4740
ccctgttcgt gaacagccag tacgaccgcc tgcaggccga caccaacatc gccatgatcc   4800
acgccgccga caagcgcgtg cacagcattc gcgaggccta cctgcccgag ctgagcgtga   4860
tccccggtgt gaacgccgcc atcttcgagg aactcgaggg ccgcatcttc accgccttca   4920
gcctgtacga cgccccgcaac gtgatcaaga acggcgactt caacaacggc ctgagctgct   4980
ggaacgtgaa gggccacgtg gacgtggagg agcagaacaa ccaccgcagc gtgctggtgg   5040
tgcccgagtg ggaggccgag gtgagccagg aggtgcgcgt gtgcccccggc cgcggctaca   5100
tcctgcgcgt gaccgcctac aaggagggct acggcgaggg ctgcgtgacc atccacgaga   5160
tcgagaacaa caccgacgaa ctcaagttca gcaactgcgt ggaggaggag gtttaccccca   5220
acaacaccgt gacctgcaac gactacaccg cgacccagga ggagtacgaa ggcacctaca   5280
cctctcgcaa caggggttac gacggcgcct acgagtccaa cagctccgtg ccagctgact   5340
```

```
acgccagcgc ctacgaggag aaagcctaca ccgacggtag acgcgacaac ccatgtgaga    5400
gcaacagagg ctacggcgac tacacccccc tgcccgctgg atacgtgacc aaggagctgg    5460
agtacttccc cgagaccgac aaggtgtgga tcgagattgg cgagaccgag ggcaccttca    5520
tcgtggacag cgtggagctg ctgctgatgg aggagtagta gatccatctg cagatgagct    5580
ctagatcccc gaatttcccc gatcgttcaa acatttggca ataaagtttc ttaagattga    5640
atcctgttgc cggtcttgcg atgattatca tataatttct gttgaattac gttaagcatg    5700
taataattaa catgtaatgc atgacgttat ttatgagatg ggttttatg attagagtcc     5760 cgcaattata catttaatac gcatagaaa acaaaatata gcgcgcaaac taggataaat     5820
tatcgcgcgc ggtgtcatct atgttactag atcgggaatt gggtaccgaa ttcactggcc    5880
gtcgttttac aacgtcgtga ctgggaaaac cctggcgtta cccaacttaa tcgccttgca    5940
gcacatcccc ctttcgccag ctggcgtaat agcgaagagg cccgcaccga tcgcccttcc    6000
caacagttgc gcagcctgaa tggcgaatgg cgcctgatgc ggtattttct ccttacgcat    6060
ctgtgcggta tttcacaccg catatggtgc actctcagta caatctgctc tgatgccgca    6120
tagttaagcc agccccgaca cccgccaaca cccgctgacg cgccctgacg gcttgtctg     6180 ctcccggcat ccgcttacag acaagctgtg accgtctccg ggagctgcat gtgtcagagg    6240
ttttcaccgt catcaccgaa acgcgcgaga cgaaagggcc tcgtgatacg cctattttta    6300
taggttaatg tcatgataat aatggtttct tagacgtcag gtggcacttt tcggggaaat    6360
gtgcgcggaa cccctatttg tttatttttc taaatacatt caaatatgta tccgctcatg    6420
agacaataac cctgataaat gcttcaatgg cgcgccgcgg ccgcttaaga atattgaaaa    6480
aggaagagta tgagtattca acatttccgt gtcgccctta ttcccttttt tgcggcattt    6540
tgccttcctg ttttgctca cccagaaacg ctggtgaaag taaaagatgc tgaagatcag    6600
ttgggtgcac gagtgggtta catcgaactg gatctcaaca gcggtaagat ccttgagagt    6660
tttcgccccg aagaacgttt tccaatgatg agcacttta aagttctgct atgtggcgcg    6720
gtattatccc gtattgacgc cgggcaagag caactcggtc gccgcataca ctattctcag    6780
aatgacttgg ttgagtactc accagtcaca gaaaagcatc ttacggatgg catgacagta    6840
agagaattat gcagtgctgc cataaccatg agtgataaca ctgcggccaa cttacttctg    6900
acaacgatcg aggaccgaa ggagctaacc gcttttttgc acaacatggg ggatcatgta     6960
actcgccttg atcgttggga accggagctg aatgaagcca taccaaacga cgagcgtgac    7020
accacgatgc ctgtagcaat ggcaacaacg ttgcgcaaac tattaactgg cgaactactt    7080
actctagctt cccggcaaca attaatagac tggatggagg cggataaagt tgcaggacca    7140
cttctgcgct cggcccttcc ggctggctgg tttattgctg ataaatctgg agccggtgag    7200
cgtgggtctc gcggtatcat tgcagcactg gggccagatg gtaagccctc ccgtatcgta    7260
gttatctaca cgacggggag tcaggcaact atggatgaac gaaatagaca gatcgctgag    7320
ataggtgcct cactgattaa gcattggtaa ctgtcagacc aagtttactc atatatactt    7380
tagattgatt taaaacttca ttttaatttt aaaaggatct aggtgaagat cctttttgat    7440
aatctcatga ccaaaatccc ttaacgtgag ttttcgttcc actgagcgtc agaccccgta    7500
gaaaagatca aaggatcttc ttgagatcct ttttttctgc gcgtaatctg ctgcttgcaa    7560
acaaaaaaac caccgctacc agcggtggtt tgtttgccgg atcaagagct accaactctt    7620
tttccgaagg taactggctt cagcagagcg cagataccaa atactgtcct tctagtgtag    7680
ccgtagttag gccaccactt caagaactct gtagcaccgc ctacatacct cgctctgcta    7740
```

```
atcctgttac cagtggctgc tgccagtggc gataagtcgt gtcttaccgg gttggactca   7800
agacgatagt taccggataa ggcgcagcgg tcgggctgaa cgggggttc gtgcacacag    7860 cccagcttgg agcgaacgac ctacaccgaa ctgagatacc tacagcgtga gctatgagaa   7920
agcgccacgc ttcccgaagg gagaaaggcg acaggtatc cggtaagcgg cagggtcgga    7980
acaggagagc gcacgaggga gcttccaggg ggaaacgcct ggtatcttta tagtcctgtc   8040
gggtttcgcc acctctgact tgagcgtcga ttttgtgat gctcgtcagg ggggcggagc    8100
ctatggaaaa acgccagcaa cgcggccttt ttacggttcc tggccttttg ctggcctttt   8160
gctcacatgt tctttcctgc gttatcccct gattctgtgg ataaccgtat taccgccttt   8220
gagtgagctg ataccgctcg ccgcagccga acgaccgagc gcagcgagtc agtgagcgag   8280
gaagcggaag agcttaagcg gccgcggcgc gccgcccaat acgcaaaccg cctctccccg   8340
cgcgttggcc gattcattaa tgcagctggc acgacaggtt tcccgactgg aaagcgggca   8400
gtgagcgcaa cgcaattaat gtgagttagc tcactcatta ggcacccag gctttacact    8460 ttatgcttcc ggctcgtatg ttgtgtggaa ttgtgagcgg ataacaattt cacacaggaa   8520
acagctatga ccatgattac gccaag                                        8546

<210> SEQ ID NO 19
<211> LENGTH: 23
<212> TYPE: DNA
<213> ORGANISM: Artificial sequence
<220> FEATURE:
<223> OTHER INFORMATION: forward primer ABT P1 forw

<400> SEQUENCE: 19
cgaccagcgc gacatgcatg gca                                            23

<210> SEQ ID NO 20
<211> LENGTH: 23
<212> TYPE: DNA
<213> ORGANISM: Artificial sequence
<220> FEATURE:
<223> OTHER INFORMATION: reverse primer ABT P2 rev

<400> SEQUENCE: 20
accccagggc gtacgacaag gcc                                            23

<210> SEQ ID NO 21
<211> LENGTH: 29
<212> TYPE: DNA
<213> ORGANISM: Artificial sequence
<220> FEATURE:
<223> OTHER INFORMATION: oligonucleotide pABT mut1

<400> SEQUENCE: 21
gatggccgga ttgggctccc ggggtggag                                      29

<210> SEQ ID NO 22
<211> LENGTH: 29
<212> TYPE: DNA
<213> ORGANISM: Artificial sequence
<220> FEATURE:
<223> OTHER INFORMATION: oligonucleotide pABT mut2

<400> SEQUENCE: 22
ctgggaggcg cgcaaggggc agttcctcg                                      29

<210> SEQ ID NO 23
```

```
<211> LENGTH: 30
<212> TYPE: DNA
<213> ORGANISM: Artificial sequence
<220> FEATURE:
<223> OTHER INFORMATION: oligonucleotide pABT mut3

<400> SEQUENCE: 23
cccaccgccg agcaccgaa aggccccgcg                              30

<210> SEQ ID NO 24
<211> LENGTH: 27
<212> TYPE: DNA
<213> ORGANISM: Artificial sequence
<220> FEATURE:
<223> OTHER INFORMATION: oligonucleotide pABT mut4

<400> SEQUENCE: 24
gtcacccggg agcacttccc ggcgccg                                27

<210> SEQ ID NO 25
<211> LENGTH: 27
<212> TYPE: DNA
<213> ORGANISM: Artificial sequence
<220> FEATURE:
<223> OTHER INFORMATION: oligonucleotide pABT mut5

<400> SEQUENCE: 25
cattgggccg agcacggctt cttccgc                                27

<210> SEQ ID NO 26
<211> LENGTH: 31
<212> TYPE: DNA
<213> ORGANISM: Artificial sequence
<220> FEATURE:
<223> OTHER INFORMATION: oligonucleotide pABT mut6

<400> SEQUENCE: 26
ggggtacggt gttcttgagt cgtgaagcga c                           31

<210> SEQ ID NO 27
<211> LENGTH: 39
<212> TYPE: DNA
<213> ORGANISM: Artificial sequence
<220> FEATURE:
<223> OTHER INFORMATION: forward primer pABT amp1

<400> SEQUENCE: 27
gcgtctagag ggaccccgac cagcgcgaca tgcatggca                   39

<210> SEQ ID NO 28
<211> LENGTH: 36
<212> TYPE: DNA
<213> ORGANISM: Artificial sequence
<220> FEATURE:
<223> OTHER INFORMATION: reverse primer pABT amp2

<400> SEQUENCE: 28
accccagggc gtacgacaag gccccaccat gggcgc                      36

<210> SEQ ID NO 29
<211> LENGTH: 45
<212> TYPE: DNA
<213> ORGANISM: Artificial sequence
<220> FEATURE:
<223> OTHER INFORMATION: forward primer ABT P4

<400> SEQUENCE: 29
```

```
tatatagagc tcgaatcgaa gaagccacac tgtaaatctg ccggg            45
```

<210> SEQ ID NO 30
<211> LENGTH: 45
<212> TYPE: DNA
<213> ORGANISM: Artificial sequence
<220> FEATURE:
<223> OTHER INFORMATION: reverse primer ABT P5

<400> SEQUENCE: 30

```
agcaaggcat atgcagcagc tgctggtcgg accgggccct atata            45
```

<210> SEQ ID NO 31
<211> LENGTH: 29
<212> TYPE: DNA
<213> ORGANISM: Artificial sequence
<220> FEATURE:
<223> OTHER INFORMATION: oligonucleotide ABTt m1

<400> SEQUENCE: 31

```
gtcatgcatg ggcatgtgaa ggaggagcc                              29
```

<210> SEQ ID NO 32
<211> LENGTH: 29
<212> TYPE: DNA
<213> ORGANISM: Artificial sequence
<220> FEATURE:
<223> OTHER INFORMATION: oligonucleotide ABTt m2

<400> SEQUENCE: 32

```
gttgcatgca tgctgcatgg cgtcgagat                              29
```

<210> SEQ ID NO 33
<211> LENGTH: 873
<212> TYPE: DNA
<213> ORGANISM: Zea mays

<400> SEQUENCE: 33

```
tgggaggcgc gcatggggca gttcctcggc aagaaggcgt acgacaaggc cgcgatcaaa    60
tgcaacggta gagaggccgt gacgaacttc gagcccagca cgtacgacgg ggagctgctg   120
ctgactgctg aagctagcgc agaagttgct gacgacgttg atctgaactt gagcatctcg   180
caaccggcat cgtcccagag ccccaaaaga gacaagaact gccttggtcc gcagctccac   240
caccaccatg ggcggccgtt tgacggctcc gccgttctga agaaaaccaa gatcgatgct   300
ccgtctgagc tgtcgtcggc gggccgccct caccggtcgt cctccctca tctcgtggct   360
gccgagcatc taccgcctcg gtctcacccc ttcttcatca cacaccatga gagtgatgca   420
tcaagaagag atcccagctg ggcagcagca gcagcatgga aggtgaccgc agctgcacct   480
cctcctccta ccaccaccct gttgccgttg ccgctgccgt cgacgtcgtc cgctgcagca   540
tcatcaggat tctccaatac cgccacgaca gctgccgccg ccccatcggc cgcctcctcc   600
cgccggttcg acccgccgcc accgtcgtcg tcctcctcct cgagccatca ccaccaccac   660
caccgccgct gagaatcgaa gaagccacac tgtaaatctg ccgggaagcg gctggtggca   720
tccggcccgc tcctccctcc gggcgccgca acttttttcg atcggttttg cgccgccgg    780
gacgggttgt agttgatcga ttggattctt cataactgta tttgcgtact gcttacacta   840
cccaagtgaa atcgaaaatg gcgccttctc tcg                                873
```

<210> SEQ ID NO 34

```
<211> LENGTH: 921
<212> TYPE: DNA
<213> ORGANISM: Zea mays

<400> SEQUENCE: 34
gaggcgcgca tggggcagtt cctcggcaag aagtacatat atcttgggct attcgacagc      60
gaagtagagg ctgcaagggc gtacgacaag gccgcgatca aatgcaacgg tagagaggcc     120
gtgacgaact tcgagcccag cacgtacgac ggggagctgc tgctgactgc tgaagctagc     180
gcagaagttg ctgacgacgt tgatctgaac ttgagcatct cgcaaccggc atcgtcccag     240
agccccaaaa gagacaagaa ctgccttggt ccgcagctcc accaccacca tgggcggccg     300
tttgacggct ccgccgttct gaagaaaacc aagatcgatg ctccgtctga gctgtcgtcg     360
gcgggccgcc ctcaccggtc gttcctccct catctcgtgg ctgccgagca tctaccgcct     420
cggtctcacc ccttcttcat cacacaccat gagagtgatg catcaagaag agatcccagc     480
tgggcagcag cagcagcatg aaggtgaccg cagctgcac ctcctcctcc taccaccacc      540
ctgttgccgt tgccgctgcc gtcgacgtcg tccgctgcag catcatcagg attctccaat     600
accgccacga cagctgccgc cgccccatcg gccgcctcct cccgccggtt cgacccgccg     660
ccaccgtcgt cgtcctcctc ctcgagccat caccaccacc accaccgccg ctgagaatcg     720
aagaagccac actgtaaatc tgccgggaag cggctggtgg catccggccc gctcctccct     780
ccgggcgccg caactttttt cgatcggttt tgcgccgccc gggacgggtt gtagttgatc     840
gattggattc ttcataactg tatttgcgta ctgcttacac tacccaagtg aaatcgaaaa     900
tggcgccttc tctcgttgaa t                                              921

<210> SEQ ID NO 35
<211> LENGTH: 2644
<212> TYPE: DNA
<213> ORGANISM: Zea mays

<400> SEQUENCE: 35
gcgtctagag ggaccccgac cagcgcgaca tgcatggcat ggcaaactat atatcgtcat      60
catcattatt atcatctgac cctctttttt tttcactctc actcccatgt ttttattccc     120
gggcggggcc gtgtgggtgt gggttgggat ggccggattg ggctcccggg gtggagaaat     180
gacaaatcca ggcccgcagg cggccaccca ccaaatcgga cgacgcaggg tgcccaaatc     240
aggaaggatt ttaaggttaa ccggccaccg gcggtgaccg acgccccacc ccactctcct     300
tctcctattc tatctatata tcacccgcct cttttttctc cctcactccg ccacaccttc     360
cctcttcttc ctcagctccg tcgcccaccg ccggagcacc gaaaggcccc gcgcccgccg     420
cctttcctgt aaaaaaccca acctttagct agctaaccgc tcctcttctc ccctactcc      480
ccttgcccaa atcagagaag atatttaacg gaggagggga aggagaggat atttagctga     540
ttgttgattg gtggtccggg gtacggtgtt cttgagtcgt gaagcgaccg tacagtggct     600
agggccgtct ccgggttgcg tgcaggatgg tcgtcagaga tcgggagtga ggaggcagct     660
cgtggtcgtg gaggctaaat gtaccgcaag aacgactcgg cactctcctg tttctacctc     720
ttcctcctct ggttcttctt cttgaaatag accagcgcca gccaccaggt agctacctac     780
tagctagcag cccagttgcg actggggacg ggctgctgct tgcaagttgg aatcttggag     840
caggagcaga ggagcgggag atggagctgg atctgaacgt ggccgaggtg gcgccggaga     900
agccatcggc ggcgctggag gcgagcgact cggggtcctc gggctcgtcg gtgctgaacg     960
cggaggcggc atcggcgggc ggcggggggc ccgcgccggg ggaggagggg tcaagctcga    1020
```

```
cgccggccgt gctcgagttc agcatcctca ggagcgacag cgacgcggcc ggcgcggacg    1080
ccgacgacgg cgacgccacg ccgtcgccac ctcgccacca ccagcagcag ctcgtcaccc    1140
gggagcactt cccggcgccg cagcattggg ccgagcacgg cttcttccgc gccggcccgc    1200
agcagcagcc ggacatcagg gtcctgccgc acccgcaccc gtaccgcccc cgccgccgc     1260 ccgcgcagcc gcagcaggcc aagaagagcc gccgcggccc gcgctcccgc agctcgcagt    1320
accgcggcgt caccttctac cgccgcaccg gccgctggga gtcccacatc tggtcagtag    1380
cactgcaagc tcaccatgcg ccctttcacc taccgaccaa taatcgcttg tgattctgac    1440
acccaaatgt ttcgtcttcc tgtgctgtcc tgttcctcgg aaatggcagg gattgcggga    1500
agcaggtgta cttaggtgag cagcaataag cagatcgatc tgcagcataa atttcccgtt    1560
attaactagt tcgtgatctc gatcgaatgg cctaattaac cgattcggtg atctggccga    1620
tggccaatct acgcaggtgg attcgacact gctcatgccg ctgcaaggta acgatcaatc    1680
catccatcca cccttgtcta gctacccac cgaccggccg gattaatgga ccgctagctc     1740
tcgggacggg cttgctgcag ggcgtacgac cgagcggcga tcaagttccg cggcgtcgac    1800
gccgacataa acttcaacct cagcgactac gacgacgata tgaagcaggt acatacacga    1860
gtgttcttgc agctagcacc gactgaaaca tctgctgaac gtacacgcat ggccctgtgc    1920
accagatgaa gagcctgtcc aaggaggagt tcgttcacgc cctgcggcgg cagagcaccg    1980
gcttctcccg cggcagctcc aagtacaggg gcgtcaccct gcacaagtgc ggccgctggg    2040
aggcgcgcaa ggggcagttc ctcggcaaga agtaagaaac aacacttcgt ttgcaggcgc    2100
tgtactttgc tgcagattat ttcatttcat ccttgcatgt gcctttcctt tccatccact    2160
cacttgatgg ctgtagtctc gatagagttc gttcgttcgt acttcgcacc agatgaactc    2220
ccacgcacat gatttagtac tagttttacc atgcattgtt cagtaaaagt atatgcttgc    2280
ttgatcagtg gttgtttcaa tcagaagatt aaaaaaacgg aatattaata taaaaaaaag    2340
gggaagtggc tagggaattc ctcagtccta gctagctagc tcaccggtgg gaacgccatg    2400
cttggcttgg gtgcaggtac atatatcttg ggctattcga cagcgaagta gaggctgcaa    2460
ggttgttcac ctcggacgat tctgccattt gttcatatac accatgcctt ttgatttctc    2520
tcttgcaatt tctcttcttt tatcatggct tttgattccc aaagggttga gtaccgactc    2580
gatattcgat tctccctgcc gtttcgtgac cccagggcgt acgacaaggc cccaccatgg    2640
gcgc                                                                2644

<210> SEQ ID NO 36
<211> LENGTH: 1069
<212> TYPE: DNA
<213> ORGANISM: Zea mays

<400> SEQUENCE: 36
tatatagagc tcgaatcgaa gaagccacac tgtaaatctg ccgggaagcg gctggtggca      60
tccggcccgc tcctccctcc gggcgccgca actttttttcg atcggttttg cgccgcccgg    120
gacgggttgt agttgatcga ttggattctt cataactgta tttgcgtact gcttacacta    180
cccaagtgaa atcgaaaatg gcgccttctc tcgttgaata aattgcacgt acgctactcg    240
atccgctgcg gctcttgctg gagtggccgc cgccgctata gatagaagga tcaagccaag    300
gaatctgtca tgcatgggca tgtgaaggag gagcctcctg caatgtttag tcttttttgg    360
tcgacgccca ccagagatat acgcactaga tttcatatag ctgagctaga tcgattccgt    420
```

| | |
|---|---|
| tgcatgcatg ctgcatggcg tcgagattcg agctagcacc gcctgttcat catcgaccga | 480 |
| tccattctga tcgattcccc tctcgagctt tcacgaactg aacctaccta gtgagggtga | 540 |
| cgcctaacgc ctagtgcgcg cgcgtgggtc tccgatgtca gtggccgcac gcgcgcgcgc | 600 |
| gttctcgaga tcgcatgtgg tcatagcgca gcaggtttgc cctcagaacc tacagcaact | 660 |
| cgaccaccgg tttggatttc ttcttttttc aaggatatga tcggagagag agagctacct | 720 |
| aggcgtcgtc cttgttttct tgtatcgcat gtggtgtggg tctctctcct cctttcgtac | 780 |
| gcacgcatga ttccattctt accccccctc gagatcgaga ggaaatatat tgctatttta | 840 |
| tacacacacg gcgcccccag ctatacgtca ctgcttacgt taattccccc accggatagt | 900 |
| agttgtttaa tggcccaaac aaaccttgtt gttgcatgca tcatggacca aacaaaatac | 960 |
| atagttagtt aaatattact gttatatata caactaataa taattatatt attagttaaa | 1020 |
| acaaagcaag gcatatgcag cagctgctgg tcggaccggg ccctatata | 1069 |

<210> SEQ ID NO 37
<211> LENGTH: 8599
<212> TYPE: DNA
<213> ORGANISM: Artificial sequence
<220> FEATURE:
<223> OTHER INFORMATION: ZmABP3-Cry1AbG6 Assembly construct

<400> SEQUENCE: 37

| | |
|---|---|
| cggcgcgccg aaagtagcaa acaacaggtt catgtgcact ataaaagac aaaattctcg | 60 |
| agtttcatct tttattccac ataagcctta tattttccat tttcatatga ttttttagttt | 120 |
| aagtttgtgt cttaactttt tcgttaatac gtaattctat gcattatgga tgcgtgaagt | 180 |
| attttttgttt aaaaaaatga aatgtcaaaa tacgttttgt gatctatttc catgttttca | 240 |
| cctaacaggt ggttttttact atatattctg ccataactct agccttagat gtaaatcgaa | 300 |
| aaaaaatgag agatgagctg gagatagcct tagatgaagc gtctgaaata taaaagaaag | 360 |
| agtaatgttg aacgcagtag gtgtagcagc tgtagttcca tctctaggaa agggaactgc | 420 |
| aatccgggct ccgggcctcg cgcaatctgg cctgtcgtgt agatgcagcc ctgtccatga | 480 |
| cggcccaagc aacgcccgcg gctctcgatc caccacggaa cccactccga cacacactga | 540 |
| cacacacatg ctggatgtgg atgtgctgtc caattattag tagcaattcg gtaggcacag | 600 |
| gcacgtactg gccggtgttt tagctgtaag taccgaacca atcacggtta agaaccgatt | 660 |
| aatccgtgcc cagccgccga gtgcgttcgt acgtgcatcg gatgcactgc atgaattgag | 720 |
| agcatcatca tatcatacgc aggagtagta cgacgccgct gctgtcttgt ccggctaatg | 780 |
| cttttgctcac agattagtcc atcgcccacg gtcggtgtgg tgtggatcgc tgatgccact | 840 |
| gcttttttgtt tggttttttat tcccctgata atcctccgcg tccctgaatg tatctatta | 900 |
| ttttcattcc gaaatccctt tcacgaaaaa gaaaacgaat aaaagagag ttacgaatac | 960 |
| gcttccggcg gcccacatca ccttccagcg aacatcgcgc cgcgctgacg tgtcgcccat | 1020 |
| cgcggccgtc catatcgcca tccgacgacc gtggaagctg gcagcggccg ctccgttccg | 1080 |
| tcgaaggggc aggtcagtca ggtcacccac acggccacac ccgcgcgggg gatacgcggt | 1140 |
| ggaaaacccg gcgaccacat caaaacgacga ggcgtctccc gcaggactgg tcactcggca | 1200 |
| cgcaggcaga ggcagcacag cagcagccag ctccatccat cctctttccc ctcctcgctt | 1260 |
| cgcttcctcg gcggattcct cctccctcgg ccgtccccgt ccccttcttc gccgcgccag | 1320 |
| ctcgcccgag ttggtaaggc cccctccacc cctccgcttc cctccccccg ggcgcgctct | 1380 |
| ggcttcctcc ccggatcggc gcggggcgtg ctggctccgc gcctgatttc gggccttttg | 1440 |

```
tttccttctc gcggagcgct cgtgtaacgc ttcggatcta gctggattca ggcgggatcg    1500
cggccgctcg gcttcctcgt ggcctgattc gtggttttcc tcggggaggg aatcctgatc    1560
ggatcatcgg gattcctcgt gcggccggga cacgcttgcg agccagaaac atagtctgcg    1620
tggccgggat tccacgatct gtgatctaga cgtcgggcgc ttcgtctatg tgctcgctgc    1680
aggctgtggc gtactggcgt ggtgcgcggc cgctatggat ccgtgcttgt tgttcgccc    1740
tgtagcgtgt gaaatcgagc tgtgtagatc tatggtctgc gaggtgcggt ggcggtggaa    1800
tctcggttga tctttacctc agcggcgcca gtgtagctcg tgtggctgca gttcatctgc    1860
gaatttggct ctcggcggct taggtcgcgg agcttggatt atggagcacc agctgcagcg    1920
tgaccctgtt ggttctcatg tggatctgtt ggctgaggtt gcagacttca agtgccactg    1980
ccattgaccg gagctgctgc acgattatac tggaatatct agcggtagta tactctgcta    2040
gtactcaata cgggtctcct gacaaatgtc tttcgtgttt agggacctag cactctagtg    2100
tcaagactat ttgctggaat atctaatatt agcagtttct gtagtggctc agttgcagcc    2160
tggtttagaa tgatggggac agttggctgt gccatgcaaa ataaagtgtg tgaaagcaac    2220
tgcctcttaa actatgggtg gtgcaagcag gttatttgaa gggactctcc acactgtatc    2280
tccagttaac tatgactgaa cttgtggtcg caggcaaacc caccatggac aacaacccca    2340
acatcaacga gtgcatcccc tacaactgcc tgagcaaccc cgaggtggag gtgctgggcg    2400
gcgagcgcat cgagaccggc tacaccccca tcgacatcag cctgagcctg acccagttcc    2460
tgctgagcga gttcgtgccc ggcgccggct cgtgctggg cctggtggac atcatctggg    2520
gcatcttcgg ccccagccag tgggacgcct tcctggtgca gatcgagcag ttgataaacc    2580
aacgcataga ggaattcgcc cgcaaccagg ccatcagccg cctggagggc ctgagcaacc    2640
tgtaccaaat ctacgccgag agcttccgcg agtgggaggc cgaccccacc aacccccgccc   2700
tgcgcgagga gatgcgcatc cagttcaacg acatgaacag cgccctgacc accgccatcc    2760
ccctgttcgc cgtgcagaac taccaggtgc ccctgctgag cgtgtacgtg caggccgcca    2820
acctgcacct gagcgtgctg cgcgacgtca gcgtgttcgg ccagcgctgg ggcttcgacg    2880
ccgccaccat caacagccgc tacaacgacc tgacccgcct gatcggcaac tacaccgacc    2940
acgccgtgcg ctggtacaac accggcctgg agcgcgtgtg gggtcccgac agccgcgact    3000
ggatcaggta caaccagttc cgccgcgagc tgaccctgac cgtgctggac atcgtgagcc    3060
tgttccccaa ctacgacagc cgcacctacc ccatccgcac cgtgagccag ctgacccgcg    3120
agatttacac caacccccgtg ctggagaact tcgacgcag cttccgcggc agcgcccagg    3180
gcatcgaggg cagcatccgc agcccccacc tgatggacat cctgaacagc atcaccatct    3240
acaccgacgc ccaccgcggc gagtactact ggagcggcca ccagatcatg gccagccccg    3300
tcggcttcag cggccccgag ttcaccttcc ccctgtacgg cacgatgggc aacgctgcac    3360
ctcagcagcg catcgtggca cagctgggcc agggagtgta ccgcaccctg agcagcaccc    3420
tgtaccgtcg acctttcaac atcggcatca acaaccagca gctgagcgtg ctggacggca    3480
ccgagttcgc ctacggcacc agcagcaacc tgcccagcgc cgtgtaccgc aagagcggca    3540
ccgtggacag cctggacgag atccccctc agaacaacaa cgtgccacct cgacagggct    3600
tcagccaccg tctgagccac gtgagcatgt tccgcagtgg cttcagcaac agcagcgtga    3660
gcatcatccg tgcacctatg ttcagctgga ttcaccgcag tgccgagttc aacaacatca    3720
tccccagcag ccagatcacc cagatccccc tgaccaagag caccaacctg ggcagcggca    3780
```

-continued

```
ccagcgtggt gaagggcccc ggcttcaccg gcggcgacat cctgcgccgc accagccccg    3840
gccagatcag caccctgcgc gtgaacatca ccgccccct gagccagcgc taccgcgtcc     3900
gcatccgcta cgccagcacc accaacctgc agttccacac cagcatcgac ggccgcccca    3960
tcaaccaggg caacttcagc gccaccatga gcagcggcag caacctgcag agcggcagct    4020
tccgcaccgt gggcttcacc accccttca acttcagcaa cggcagcagc gtgttcaccc     4080
tgagcgccca cgtgttcaac agcggcaacg aggtgtacat cgaccgcatc gagttcgtgc    4140
ccgccgaggt gaccttcgag gccgagtacg acctggagag ggctcagaag gccgtgaacg    4200
agctgttcac cagcagcaac cagatcggcc tgaagaccga cgtgaccgac taccacatcg    4260
accaggtgag caacctggtg gagtgcttaa gcgacgagtt ctgcctggac gagaagaagg    4320
agctgagcga gaaggtgaag cacgccaagc gcctgagcga cgagcgcaac ctgctgcagg    4380
accccaactt ccgcggcatc aaccgccagc tggaccgcgg ctggcgaggc agcaccgata    4440
tcaccatcca gggcggcgac gacgtgttca aggagaacta cgtgaccctg ctgggcacct    4500
tcgacgagtg ctaccccacc tacctgtacc agaagatcga cgagagcaag ctgaaggcct    4560
acacccgcta ccagctgcgc ggctacatcg aggacagcca ggacctggaa atctacctga    4620
tccgctacaa cgcgaagcac gagaccgtga acgtgcccgg caccggcagc ctgtggcccc    4680
tgagcgcccc cagccccatc ggcaagtgcc accacagcca ccacttcagc ctggacatcg    4740
acgtgggctg caccgacctg aacgaggacc tgggcgtgtg ggtgatcttc aagatcaaga    4800
cccaggacgg ccacgcccgc ctgggcaatc tagagttcct ggaggagaag cccctggtgg    4860
gcgaggccct ggcccgcgtg aagcgtgctg agaagaagtg gcgcgacaag cgcgagaagc    4920
tggagtggga gaccaacatc gtgtacaagg aggccaagga gagcgtggac gccctgttcg    4980
tgaacagcca gtacgaccgc ctgcaggccg acaccaacat cgccatgatc cacgccgccg    5040
acaagcgcgt gcacagcatt cgcgaggcct acctgcccga gctgagcgtg atccccggtg    5100
tgaacgccgc catcttcgag gaactcgagg gccgcatcta ggagctcgca tcatgatcat    5160
gcatcatgga ctcggcctac tactgtggat ttgtatgcca ttatagactt ggtgctgtga    5220
aagactgctt gatgatttgc gggtttgttg ctgtgtaaaa aaaggtccct tggctcccag    5280
aagaccatga aggttcggat ctatcatgta attccttgtt atctgccaat tatgtatgga    5340
ctatggacat gtgttgcgct gttcaactta ctactacaaa taagtaatcg atatgttccc    5400
ttcccatgtc tcggtgacaa ttgtctggag aagcttaggg gtcgtttgtt tgggattatg    5460
tctggagaaa cttattttaa actaagtgtg agttcaagtt aagttagatt atataatcta    5520
ggcagattat aattccaagc gaacaggtcc ttagtgtttt tggaaaatcc taggtgttct    5580
tttggctaca ttgttgtgtg tgcagatccc ttgttggtct gtaagcgtgg ggaagtaaga    5640
atcgtccgtt tctactgaag acctgctcga gttaggcacc gaggatgccg gtaaccaaac    5700
agagcaatag tgtctctgtg ggcacagtgg agtgtgaatc tgtgtgatgc aaatccgtca    5760
tttgtttagc aaaatttcca gcgttgcatg atgcagtttc tttaacacgg acttaaggga    5820
agggaaaaaa atgttgagcc aggagatcct tcaatgtgtt agactgacgt gatagccaac    5880
taaaccacga cgcaatgttg tcgttaatga caaaaaaact atttgttcct aaatccttgg    5940
cgacattgca tggctgtctc atgagataat ggtctcatct cttatttatc tcttatttat    6000
agccggaagt ggtagtgacc cctgcttgat tgctcgtatg ccatctcaag ttctcaaccg    6060
tgtcgagcag ccattttccc atctcaagcg catcatcgtt tcgtttgacc tcatctgcta    6120
tcctgctcct agtgcaaatc acatgcgaca gaaagtgtgg cgcgccacta gtcccgggcc    6180
```

```
catcgatgat atcagatctg gttctatagt gtcacctaaa tcgtatgtgt atgatacata    6240
aggttatgta ttaattgtag ccgcgttcta acgacaatat gtccatatgg tgcactctca    6300
gtacaatctg ctctgatgcc gcatagttaa gccagccccg acaccgcca acacccgctg     6360 acgcgccctg acgggcttgt ctgctcccgg catccgctta cagacaagct gtgaccgtct    6420
ccgggagctg catgtgtcag aggttttcac cgtcatcacc gaaacgcgcg agacgaaagg    6480
gcctcgtgat acgcctattt ttataggtta atgtcatgat aataatggtt tcttagacgt    6540
caggtggcac ttttcgggga atgtgcgcg gaaccctat tgtttattt ttctaaatac       6600 attcaaatat gtatccgctc atgagacaat aaccctgata aatgcttcaa taatattgaa    6660
aaaggaagag tatgagtatt caacatttcc gtgtcgccct tattccctt tttgcggcat     6720 tttgccttcc tgttttgct cacccagaaa cgctggtgaa agtaaaagat gctgaagatc     6780
agttgggtgc acgagtgggt tacatcgaac tggatctcaa cagcggtaag atccttgaga    6840
gttttcgccc cgaagaacgt tttccaatga tgagcacttt taaagttctg ctatgtggcg    6900
cggtattatc ccgtattgac gccgggcaag agcaactcgg tcgccgcata cactattctc    6960
agaatgactt ggttgagtac tcaccagtca cagaaaagca tcttacggat ggcatgacag    7020
taagagaatt atgcagtgct gccataacca tgagtgataa cactgcggcc aacttacttc    7080
tgacaacgat cggaggaccg aaggagctaa ccgcttttt gcacaacatg ggggatcatg     7140
taactcgcct tgatcgttgg gaaccggagc tgaatgaagc cataccaaac gacgagcgtg    7200
acaccacgat gcctgtagca atggcaacaa cgttgcgcaa actattaact ggcgaactac    7260
ttactctagc ttcccggcaa caattaatag actggatgga ggcggataaa gttgcaggac    7320
cacttctgcg ctcggccctt ccggctggct ggtttattgc tgataaatct ggagccggtg    7380
agcgtgggtc tcgcggtatc attgcagcac tggggccaga tggtaagccc tcccgtatcg    7440
tagttatcta cacgacgggg agtcaggcaa ctatggatga acgaaataga cagatcgctg    7500
agataggtgc ctcactgatt aagcattggt aactgtcaga ccaagtttac tcatatatac    7560
tttagattga tttaaaactt catttttaat ttaaaaggat ctaggtgaag atcctttttg    7620
ataatctcat gaccaaaatc ccttaacgtg agttttcgtt ccactgagcg tcagaccccg    7680
tagaaaagat caaaggatct tcttgagatc ctttttttct gcgcgtaatc tgctgcttgc    7740
aaacaaaaaa accaccgcta ccagcggtgg tttgtttgcc ggatcaagag ctaccaactc    7800
tttttccgaa ggtaactggc ttcagcagag cgcagatacc aaatactgtt cttctagtgt    7860
agccgtagtt aggccaccac ttcaagaact ctgtagcacc gcctacatac ctcgctctgc    7920
taatcctgtt accagtggct gctgccagtg gcgataagtc gtgtcttacc gggttggact    7980
caagacgata gttaccggat aaggcgcagc ggtcgggctg aacggggggt tcgtgcacac    8040
agcccagctt ggagcgaacg acctacaccg aactgagata cctacagcgt gagctatgag    8100
aaagcgccac gcttcccgaa gggagaaagg cggacaggta tccggtaagc ggcagggtcg    8160
gaacaggaga gcgcacgagg gagcttccag ggggaaacgc ctggtatctt tatagtcctg    8220
tcgggtttcg ccacctctga cttgagcgtc gatttttgtg atgctcgtca ggggggcgga    8280
gcctatggaa aaacgccagc aacgcggcct ttttacggtt cctggccttt tgctggcctt    8340
ttgctcacat gttctttcct gcgttatccc ctgattctgt ggataaccgt attaccgcct    8400
ttgagtgagc tgataccgct cgccgcagcc gaacgaccga gcgcagcgag tcagtgagcg    8460
aggaagcgga agagcgccca atacgcaaac cgcctctccc cgcgcgttgg ccgattcatt    8520
```

| | |
|---|---:|
| aatgcaggtt aacctggctt atcgaaatta atacgactca ctatagggag accggcctcg | 8580 |
| agcagctgaa gcttgcatg | 8599 |

<210> SEQ ID NO 38
<211> LENGTH: 15162
<212> TYPE: DNA
<213> ORGANISM: Artificial sequence
<220> FEATURE:
<223> OTHER INFORMATION: ZmABP3-Cry1AbG6 binary construct

<400> SEQUENCE: 38

| | |
|---|---:|
| taattcctgt ggttggcatg cacatacaaa tggacgaacg gataaacctt ttcacgccct | 60 |
| tttaaatatc cgattattct aataaacgct cttttctctt aggtttaccc gccaatatat | 120 |
| cctgtcaaac actgatagtt taaactgaag gcgggaaacg acaatctgat catgagcgga | 180 |
| gaattaaggg agtcacgtta tgaccccgc cgatgacgcg ggacaagccg ttttacgttt | 240 |
| ggaactgaca gaaccgcaac gctgcaggaa ttggccgcag cggccattta aatcaattgg | 300 |
| gcgcgccaca ctttctgtcg catgtgattt gcactaggag caggatagca gatgaggtca | 360 |
| aacgaaacga tgatgcgctt gagatgggaa aatggctgct cgacacggtt gagaacttga | 420 |
| gatggcatac gagcaatcaa gcaggggtca ctaccacttc cggctataaa taagagataa | 480 |
| ataagagatg agaccattat ctcatgagac agccatgcaa tgtcgccaag gatttaggaa | 540 |
| caaatagttt ttttgtcatt aacgacaaca ttgcgtcgtg gtttagttgg ctatcacgtc | 600 |
| agtctaacac attgaaggat ctcctggctc aacatttttt tcccttccct taagtccgtg | 660 |
| ttaaagaaac tgcatcatgc aacgctggaa attttgctaa acaaatgacg gatttgcatc | 720 |
| acacagattc acactccact gtgcccacag agacactatt gctctgtttg gttaccggca | 780 |
| tcctcggtgc ctaactcgag caggtcttca gtagaaacgg acgattctta cttccccacg | 840 |
| cttacagacc aacaagggat ctgcacacac aacaatgtag ccaaaagaac acctaggatt | 900 |
| ttccaaaaac actaaggacc tgttcgcttg gaattataat ctgcctagat tatataatct | 960 |
| aacttaactt gaactcacac ttagtttaaa ataagtttct ccagacataa tcccaaacaa | 1020 |
| acgaccccta agcttctcca gacaattgtc accgagacat gggaagggaa catatcgatt | 1080 |
| acttatttgt agtagtaagt tgaacagcgc aacacatgtc catagtccat acataattgg | 1140 |
| cagataacaa ggaattacat gatagatccg aaccttcatg gtcttctggg agccaaggga | 1200 |
| cctttttta cacagcaaca aacccgcaaa tcatcaagca gtctttcaca gcaccaagtc | 1260 |
| tataatggca tacaaatcca cagtagtagg ccgagtccat gatgcatgat catgatgcga | 1320 |
| gctcctagat gcggccctcg agttcctcga agatggcggc gttcacaccg gggatcacgc | 1380 |
| tcagctcggg caggtaggcc tcgcgaatgc tgtgcacgcg cttgtcggcg cgtggatca | 1440 |
| tggcgatgtt ggtgtcggcc tgcaggcggt cgtactggct gttcacgaac agggcgtcca | 1500 |
| cgctctcctt ggcctccttg tacacgatgt tggtctccca ctccagcttc tcgcgcttgt | 1560 |
| cgcgccactt cttctcagca cgcttcacgc gggccagggc ctcgcccacc aggggcttct | 1620 |
| cctccaggaa ctctagattg cccaggcggg cgtggccgtc ctgggtcttg atcttgaaga | 1680 |
| tcacccacac gccaggtcc tcgttcaggt cggtgcagcc cacgtcgatg tccaggctga | 1740 |
| agtggtggct gtggtggcac ttgccgatgg ggctggggc gctcaggggc acaggctgc | 1800 |
| cggtgccggg cacgttcacg gtcgtcgtgct tcgcgttgta gcggatcagg tagatttcca | 1860 |
| ggtcctggct gtcctcgatg tagccgcgca gctggtagcg ggtgtaggcc ttcagcttgc | 1920 |
| tctcgtcgat cttctggtac aggtaggtgg ggtagcactc gtcgaaggtg cccagcaggg | 1980 |

```
tcacgtagtt ctccttgaac acgtcgtcgc cgccctggat ggtgatatcg gtgctgcctc   2040
gccagccgcg gtccagctgg cggttgatgc cgcggaagtt ggggtcctgc agcaggttgc   2100
gctcgtcgct caggcgcttg gcgtgcttca ccttctcgct cagctccttc ttctcgtcca   2160
ggcagaactc gtcgcttaag cactccacca ggttgctcac ctggtcgatg tggtagtcgg   2220
tcacgtcggt cttcaggccg atctggttgc tgctggtgaa cagctcgttc acggccttct   2280
gagccctctc caggtcgtac tcggcctcga aggtcacctc ggcgggcacg aactcgatgc   2340
ggtcgatgta cacctcgttg ccgctgttga acacgtgggc gctcagggtg aacacgctgc   2400
tgccgttgct gaagttgaag ggggtggtga agcccacggt gcggaagctg ccgctctgca   2460
ggttgctgcc gctgctcatg gtggcgctga agttgccctg gttgatgggg cggccgtcga   2520
tgctggtgtg gaactgcagg ttggtggtgc tggcgtagcg gatgcggacg cggtagcgct   2580
ggctcagggg ggcggtgatg ttcacgcgca gggtgctgat ctggccgggg ctggtgcggc   2640
gcaggatgtc gccgccggtg aagccggggc ccttcaccac gctggtgccg ctgcccaggt   2700
tggtgctctt ggtcaggggg atctgggtga tctggctgct ggggatgatg ttgttgaact   2760
cggcactgcg gtgaatccag ctgaacatag gtgcacggat gatgctcacg ctgctgttgc   2820
tgaagccact gcggaacatg ctcacgtggc tcagacggtg gctgaagccc tgtcgaggtg   2880
gcacgttgtt gttctgaggg gggatctcgt ccaggctgtc cacggtgccg ctcttgcggt   2940
acacggcgct gggcaggttg ctgctggtgc cgtaggcgaa ctcggtgccg tccagcacgc   3000
tcagctgctg gttgttgatg ccgatgttga aggtcgacg gtacagggtg ctgctcaggg   3060
tgcggtacac tccctggccc agctgtgcca cgatgcgctg ctgaggtgca gcgttgccca   3120
tcgtgccgta caggggggaag gtgaactcgg ggccgctgaa gccgacgggg ctggccatga   3180
tctggtggcc gctccagtag tactcgccgc ggtgggcgtc ggtgtagatg gtgatgctgt   3240
tcaggatgtc catcaggtgg gggctgcgga tgctgccctc gatgccctgg gcgctgccgc   3300
ggaagctgcc gtcgaagttc tccagcacgg ggttggtgta atctcgcgg gtcagctggc   3360
tcacggtgcg gatggggtag gtgcggctgt cgtagttggg gaacaggctc acgatgtcca   3420
gcacggtcag ggtcagctcg cggcggaact ggttgtacct gatccagtcg cggctgtcgg   3480
gaccccacac gcgctccagg ccggtgttgt accagcgcac ggcgtggtcg gtgtagttgc   3540
cgatcaggcg ggtcaggtcg ttgtagcggc tgttgatggt ggcggcgtcg aagcccagc   3600
gctggccgaa cacgctgacg tcgcgcagca cgctcaggtg caggttggcg gcctgcacgt   3660
acacgctcag caggggcacc tggtagttct gcacggcgaa caggggatg gcggtggtca   3720
gggcgctgtt catgtcgttg aactggatgc gcatctcctc gcgcagggcg gggttggtgg   3780
ggtcggcctc ccactcgcgg aagctctcgg cgtagatttg gtacaggttg ctcaggccct   3840
ccaggcggct gatggcctgg ttgcgggcga attcctctat gcgttggttt atcaactgct   3900
cgatctgcac caggaaggcg tcccactggc tggggccgaa gatgccccag atgatgtcca   3960
ccaggcccag cacgaagccg gcgccgggca cgaactcgct cagcaggaac tgggtcaggc   4020
tcaggctgat gtcgatgggg gtgtagccgg tctcgatgcg ctcgccgccc agcacctcca   4080
cctcggggtt gctcaggcag ttgtagggga tgcactcgtt gatgttgggg ttgttgtcca   4140
tggtgggttt gcctgcgacc acaagttcag tcatagttaa ctggagatac agtgtggaga   4200
gtcccttcaa ataacctgct tgcaccaccc atagtttaag aggcagttgc tttcacacac   4260
tttattttgc atggcacagc caactgtccc catcattcta aaccaggctg caactgagcc   4320
```

```
actacagaaa ctgctaatat tagatattcc agcaaatagt cttgacacta gagtgctagg    4380
tccctaaaca cgaaagacat ttgtcaggag acccgtattg agtactagca gagtatacta    4440
ccgctagata ttccagtata atcgtgcagc agctccggtc aatggcagtg cacttgaag     4500 tctgcaacct cagccaacag atccacatga gaaccaacag ggtcacgctg cagctggtgc    4560
tccataatcc aagctccgcg acctaagccg ccgagagcca aattcgcaga tgaactgcag    4620
ccacacgagc tacactggcg ccgctgaggt aaagatcaac cgagattcca ccgccaccgc    4680
acctcgcaga ccatagatct acacagctcg atttcacacg ctacagggcg aacaaacaag    4740
cacggatcca tagcggccgc gcaccacgcc agtacgccac agcctgcagc gagcacatag    4800
acgaagcgcc cgacgtctag atcacagatc gtggaatccc ggccacgcag actatgtttc    4860
tggctcgcaa gcgtgtcccg gccgcacgag gaatcccgat gatccgatca ggattccctc    4920
cccgaggaaa accacgaatc aggccacgag gaagccgagc ggccgcgatc ccgcctgaat    4980
ccagctagat ccgaagcgtt acacgagcgc tccgcgagaa ggaaacaaaa ggcccgaaat    5040
caggcgcgga gccagcacgc cccgcgccga tccgggagg aagccagagc gcgcccgggg    5100
gaggggaagc ggagggtgg agggggcctt accaactcgg gcgagctggc gcggcgaaga    5160
aggggacggg gacggccgag ggaggaggaa tccgccgagg aagcgaagcg aggaggggaa    5220
agaggatgga tggagctggc tgctgctgtg ctgcctctgc ctgcgtgccg agtgaccagt    5280
cctgcgggag acgcctcgtg ttttgatgtg gtcgccgggt tttccaccgc gtatcccccg    5340
cgcgggtgtg gccgtgtggg tgacctgact gacctgcccc ttcgacggaa cggagcggcc    5400
gctgccagct tccacggtcg tcggatggcg atatggacgg ccgcgatggg cgacacgtca    5460
gcgcggcgcg atgttcgctg gaaggtgatg tgggccgccg gaagcgtatt cgtaactctc    5520
tttttattcg ttttcttttt cgtgaaaggg atttcggaat gaaataaat agatacattc     5580 agggacgcgg aggattatca ggggaataaa aaccaaacaa aaagcagtgg catcagcgat    5640
ccacaccaca ccgaccgtgg gcgatggact aatctgtgag caaagcatta gccggacaag    5700
acagcagcgg cgtcgtacta ctcctgcgta tgatatgatg atgctctcaa ttcatgcagt    5760
gcatccgatg cacgtacgaa cgcactcggc ggctgggcac ggattaatcg gttcttaacc    5820
gtgattggtt cggtacttac agctaaaaca ccggccagta cgtgcctgtg cctaccgaat    5880
tgctactaat aattggacag cacatccaca tccagcatgt gtgtgtcagt gtgtgtcgga    5940
gtgggttccg tggtggatcg agagccgcgg gcgttgcttg ggccgtcatg gacagggctg    6000
catctacacg acaggccaga ttgcgcgagg cccggagccc ggattgcagt tccctttcct    6060
agagatggaa ctacagctgc tacacctact gcgttcaaca ttactctttc ttttatattt    6120
cagacgcttc atctaaggct atctccagct catctctcat ttttttttcga tttacatcta   6180 aggctagagt tatggcagaa tatatagtaa aaaccacctg ttaggtgaaa acatggaaat    6240
agatcacaaa acgtattttg acatttcatt tttttaaaca aaaatacttc acgcatccat    6300
aatgcataga attacgtatt aacgaaaaag ttaagacaca aacttaaact aaaaatcata    6360
tgaaaatgga aaatataagg cttatgtgga ataaaagatg aaactcgaga attttgtctt    6420
tttatagtgc acatgaacct gttgtttgct actttcggcg cgccagctgc ttgtggggac    6480
cagacaaaaa aggaatggtg cagaattgtt aggcgcacct accaaaagca tctttgcctt    6540
tattgcaaag ataaagcaga ttcctctagt acaagtgggg aacaaataa cgtggaaaag    6600 agctgtcctg acagcccact cactaatgcg tatgacgaac gcagtgacga ccacaaaact    6660
cgagactttt caacaaaggg taatatccgg aaacctcctc ggattccatt gcccagctat    6720
```

```
ctgtcacttt attgtgaaga tagtggaaaa ggaaggtggc tcctacaaat gccatcattg    6780
cgataaagga aaggctatcg ttgaagatgc ctctgccgac agtggtccca agatggacc    6840 cccacccacg aggagcatcg tggaaaaaga agacgttcca accacgtctt caaagcaagt    6900
ggattgatgt gatatctcca ctgacgtaag ggatgacgaa caatcccact atccttcggt    6960
accggaccgc gatcgcttaa ttaagcttgc atgcctgcag tgcagcgtga cccggtcgtg    7020
cccctctcta gagataatga gcattgcatg tctaagttat aaaaaattac cacatatttt    7080
ttttgtcaca cttgtttgaa gtgcagttta tctatcttta tacatatatt taaactttac    7140
tctacgaata atataatcta tagtactaca ataaatcag tgttttagag aatcatataa    7200
atgaacagtt agacatggtc taaaggacaa ttgagtattt tgacaacagg actctacagt    7260
tttatctttt tagtgtgcat gtgttctcct ttttttttgc aaatagcttc acctatataa    7320
tacttcatcc atttattag tacatccatt tagggtttag ggttaatggt ttttatagac    7380 taatttttt agtacatcta ttttattcta ttttagcctc taaattaaga aaactaaaac    7440
tctattttag tttttttatt taataattta gatataaaat agaataaaat aaagtgacta    7500
aaaattaaac aaatacccctt taagaaatta aaaaaactaa ggaaacattt ttcttgtttc    7560
gagtagataa tgccagcctg ttaaacgccg ccgacgagtc taacggacac caaccagcga    7620
accagcagcg tcgcgtcggg ccaagcgaag cagacggcac ggcatctctg tcgctgcctc    7680
tggacccctc tcgagagttc cgctccaccg ttggacttgc tccgctgtcg gcatccagaa    7740
attgcgtggc ggagcggcag acgtgagccg gcacggcagg cggcctcctc ctcctctcac    7800
ggcaccggca gctacggggg attcctttcc caccgctcct tcgctttccc ttcctcgccc    7860
gccgtaataa atagacaccc cctccacacc ctctttcccc aacctcgtgt tgttcggagc    7920
gcacacacac acaaccagat ctcccccaaa tccacccgtc ggcacctccg cttcaaggta    7980
cgccgctcgt cctccccccc ccccctctc taccttctct agatcggcgt tccggtccat    8040
agttagggcc cggtagttct acttctgttc atgtttgtgt tagatccgtg tttgtgttag    8100
atccgtgctg ttagcgttcg tacacggatg cgacctgtac gtcagacacg ttctgattgc    8160
taacttgcca gtgtttctct ttggggaatc ctggatggc tctagccgtt ccgcagacgg    8220
gatcgatttc atgattttt ttgtttcgtt gcataggggtt tggtttgccc ttttcctta    8280 tttcaatata tgccgtgcac ttgttgtcg ggtcatcttt tcatgctttt ttttgtcttg    8340
gttgtgatga tgtggtctgg ttgggcggtc gttctagatc ggagtagaat tctgtttcaa    8400
actacctggt ggatttatta attttggatc tgtatgtgtg tgccatacat attcatagtt    8460
acgaattgaa gatgatggat ggaaatatcg atctaggata ggtatacatg ttgatgcggg    8520
ttttactgat gcatatacag agatgctttt tgttcgcttg gttgtgatga tgtggtgtgg    8580
ttgggcggtc gttcattcgt tctagatcgg agtagaatac tgtttcaaac tacctggtgt    8640
atttattaat tttggaactg tatgtgtgtg tcatacatct tcatagttac gagtttaaga    8700
tggatggaaa tatcgatcta ggataggtat acatgttgat gtgggtttta ctgatgcata    8760
tacatgatgg catatgcagc atctattcat atgctctaac cttgagtacc tatctattat    8820
aataaacaag tatgttttat aattattttg atcttgatat acttggatga tggcatatgc    8880
agcagctata tgtggatttt tttagccctg ccttcatacg ctatttattt gcttggtact    8940
gtttcttttg tcgatgctca ccctgttgtt tggtgttact tctgcaggga tccactagtc    9000
caccatgtct ccggagagga gaccagttga gattaggcca gctacagcag ctgatatggc    9060
```

```
cgcggtttgt gatatcgtta accattacat tgagacgtct acagtgaact ttaggacaga    9120
gccacaaaca ccacaagagt ggattgatga tctagagagg ttgcaagata gatacccttg    9180
gttggttgct gaggttgagg gtgttgtggc tggtattgct tacgctgggc cctggaaggc    9240
taggaacgct tacgattgga cagttgagag tactgtttac gtgtcacata ggcatcaaag    9300
gttgggccta ggatccacat tgtacacaca tttgcttaag tctatggagg cgcaaggttt    9360
taagtctgtg gttgctgtta taggccttcc aaacgatcca tctgttaggt tgcatgaggc    9420
tttgggatac acagcccggg gtacattgcg cgcagctgga tacaagcatg gtggatggca    9480
tgatgttggt ttttggcaaa gggatttttga gttgccagct cctccaaggc cagttaggcc    9540
agttacccag atctgaacta gtgatatcgg cgccatgggt cgacctgcag atcgttcaaa    9600
catttggcaa taaagtttct taagattgaa tcctgttgcc ggtcttgcga tgattatcat    9660
ataatttctg ttgaattacg ttaagcatgt aataattaac atgtaatgca tgacgttatt    9720
tatgagatgg gttttatga ttagagtccc gcaattatac atttaatacg cgatagaaaa    9780
caaaatatag cgcgcaaact aggataaatt atcgcgcgcg gtgtcatcta tgttactaga    9840
tctgctagcc ctgcaggaaa tttaccggtg cccgggcggc cagcatggcc gtatccgcaa    9900
tgtgttatta agttgtctaa gcgtcaattt gtttacacca caatatatcc tgccaccagc    9960
cagccaacag ctcccccgacc ggcagctcgg cacaaaatca ccactcgata caggcagccc   10020
atcagaatta attctcatgt ttgacagctt atcatcgact gcacggtgca ccaatgcttc   10080
tggcgtcagg cagccatcgg aagctgtggt atggctgtgc aggtcgtaaa tcactgcata   10140
attcgtgtcg ctcaaggcgc actcccgttc tggataatgt ttttgcgcc gacatcataa   10200 cggttctggc aaatattctg aaatgagctg ttgcaatta atcatccggc tcgtataatg   10260
tgtggaattg tgagcggata caatttcac acaggaaaca gaccatgagg gaagcgttga    10320
tcgccgaagt atcgactcaa ctatcagagg tagttggcgt catcgagcgc catctcgaac   10380
cgacgttgct ggccgtacat ttgtacggct ccgcagtgga tggcggcctg aagccacaca   10440
gtgatattga tttgctggtt acggtgaccg taaggcttga tgaaacaacg cggcgagctt   10500
tgatcaacga ccttttggaa acttcggctt cccctggaga gagcgagatt ctccgcgctg   10560
tagaagtcac cattgttgtg cacgacgaca tcattccgtg gcgttatcca gctaagcgcg   10620
aactgcaatt tggagaatgg cagcgcaatg acattcttgc aggtatcttc gagccagcca   10680
cgatcgacat tgatctggct atcttgctga caaaagcaag agaacatagc gttgccttgg   10740
taggtccagc ggcggaggaa ctctttgatc cggttcctga acaggatcta tttgaggcgc   10800
taaatgaaac cttaacgcta tggaactcgc cgcccgactg ggctggcgat gagcgaaatg   10860
tagtgcttac gttgtcccgc atttggtaca gcgcagtaac cggcaaaatc gcgccgaagg   10920
atgtcgctgc cgactgggca atggagcgcc tgccggccca gtatcagccc gtcatacttg   10980
aagctaggca ggcttatctt ggacaagaag atcgcttggc ctcgcgcgca gatcagttgg   11040
aagaatttgt tcactacgtg aaaggcgaga tcaccaaagt agtcggcaaa taaagctcta   11100
gtggatctcc gtacccaggg atctggctcg cggcggacgc acgacgccgg ggcgagacca   11160
taggcgatcc cctaaatcaa tagtagctgt aacctcgaag cgtttcactt gtaacaacga   11220
ttgagaattt ttgtcataaa attgaaatac ttggttcgca ttttttgtcat ccgcggtcag   11280 ccgcaattct gacgaactgc ccatttagct ggagatgatt gtacatcctt cacgtgaaaa   11340
tttctcaagc gctgtgaaca agggttcaga ttttagattg aaaggtgagc cgttgaaaca   11400
cgttcttctt gtcgatgacg acgtcgctat gcggcatctt attattgaat accttacgat   11460
```

```
ccacgccttc aaagtgaccg cggtagccga cagcacccag ttcacaagag tactctcttc   11520
cgcgacggtc gatgtcgtgg ttgttgatct agatttaggt cgtgaagatg ggctcgagat   11580
cgttcgtaat ctggcggcaa agtctgatat tccaatcata attatcagtg gcgaccgcct   11640
tgaggagacg gataaagttg ttgcactcga gctaggagca agtgatttta tcgctaagcc   11700
gttcagtatc agagagtttc tagcacgcat tcgggttgcc ttgcgcgtgc gccccaacgt   11760
tgtccgctcc aaagaccgac ggtcttttg ttttactgac tggacactta atctcaggca   11820
acgtcgcttg atgtccgaag ctggcggtga ggtgaaactt acggcaggtg agttcaatct   11880
tctcctcgcg tttttagaga acccccgcga cgttctatcg cgcgagcaac ttctcattgc   11940
cagtcgagta cgcgacgagg aggtttatga caggagtata gatgttctca ttttgaggct   12000
gcgccgcaaa cttgaggcag atccgtcaag ccctcaactg ataaaaacag caagaggtgc   12060
cggttatttc tttgacgcgg acgtgcaggt ttcgcacggg gggacgatgg cagcctgagc   12120
caattcccag atccccgagg aatcggcgtg agcggtcgca aaccatccgg cccggtacaa   12180
atcggcgcgg cgctgggtga tgacctggtg agaagttga aggccgcgca ggccgcccag   12240
cggcaacgca tcgaggcaga agcacgcccc ggtgaatcgt ggcaagcggc cgctgatcga   12300
atccgcaaag aatcccggca accgccggca gccggtgcgc cgtcgattag gaagccgccc   12360
aagggcgacg agcaaccaga tttttcgtt ccgatgctct atgacgtggg cacccgcgat   12420
agtcgcagca tcatggacgt ggccgttttc cgtctgtcga agcgtgaccg acgagctggc   12480
gaggtgatcc gctacgagct tccagacggg cacgtagagg tttccgcagg gccggccggc   12540
atggccagtg tgtgggatta cgacctggta ctgatggcgg tttcccatct aaccgaatcc   12600
atgaaccgat accggaagg gaagggagac aagcccggcc gcgtgttccg tccacacgtt   12660
gcggacgtac tcaagttctg ccggcgagcc gatggcggaa agcagaaaga cgacctggta   12720
gaaacctgca ttcggttaaa caccacgcac gttgccatgc agcgtacgaa gaaggccaag   12780
aacggccgcc tggtgacggt atccgagggt gaagccttga ttagccgcta caagatcgta   12840
aagagcgaaa ccgggcggcc ggagtacatc gagatcgagc tggctgattg gatgtaccgc   12900
gagatcacag aaggcaagaa cccggacgtg ctgacggttc accccgatta cttttttgatc   12960
gatcccggca tcggccgttt tctctaccgc ctggcacgcc cgccgcagg caaggcagaa   13020
gccagatggt tgttcaagac gatctacgaa cgcagtggca gcgccggaga gttcaagaag   13080
ttctgtttca ccgtgcgcaa gctgatcggg tcaaatgacc tgccggagta cgatttgaag   13140
gaggaggcgg ggcaggctgg cccgatccta gtcatgcgct accgcaacct gatcgagggc   13200
gaagcatccg ccggttccta atgtacggag cagatgctag ggcaaattgc cctagcaggg   13260
gaaaaaggtc gaaaggtct cttccctgtg gatagcacgt acattgggaa cccaaagccg   13320
tacattggga accggaaccc gtacattggg aacccaaagc cgtacattgg gaaccggtca   13380
cacatgtaag tgactgatat aaaagagaaa aaggcgatt tttccgccta aaactcttta   13440
aaacttatta aaactcttaa aacccgcctg gcctgtgcat aactgtctgg ccagcgcaca   13500
gccgaagagc tgcaaaaagc gcctacccttcggtcgctgc gctccctacg ccccgccgct   13560
tcgcgtcggc ctatcgcggc cgctggccgc tcaaaaatgg ctggcctacg gccaggcaat   13620
ctaccagggc gcggacaagc cgcgccgtcg ccactcgacc gccggcgctg aggtctgcct   13680
cgtgaagaag gtgttgctga ctcataccag gcctgaatcg ccccatcatc cagccagaaa   13740
gtgagggagc cacggttgat gagagctttg ttgtaggtgg accagttggt gattttgaac   13800
```

```
ttttgctttg ccacggaacg gtctgcgttg tcgggaagat gcgtgatctg atccttcaac   13860
tcagcaaaag ttcgatttat tcaacaaagc cgccgtcccg tcaagtcagc gtaatgctct   13920
gccagtgtta caaccaatta accaattctg attagaaaaa ctcatcgagc atcaaatgaa   13980
actgcaattt attcatatca ggattatcaa taccatattt ttgaaaaagc cgtttctgta   14040
atgaaggaga aaactcaccg aggcagttcc ataggatggc aagatcctgg tatcggtctg   14100
cgattccgac tcgtccaaca tcaatacaac ctattaattt cccctcgtca aaaataaggt   14160
tatcaagtga gaaatcacca tgagtgacga ctgaatccgg tgagaatggc aaaagctctg   14220
cattaatgaa tcggccaacg cgcggggaga ggcggtttgc gtattgggcg ctcttccgct   14280
tcctcgctca ctgactcgct gcgctcggtc gttcggctgc ggcgagcggt atcagctcac   14340
tcaaaggcgg taatacggtt atccacagaa tcaggggata acgcaggaaa gaacatgtga   14400
gcaaaaggcc agcaaaaggc caggaaccgt aaaaaggccg cgttgctggc gtttttccat   14460
aggctccgcc cccctgacga gcatcacaaa aatcgacgct caagtcagag gtggcgaaac   14520
ccgacaggac tataaagata ccaggcgttt ccccctggaa gctccctcgt gcgctctcct   14580
gttccgaccc tgccgcttac cggatacctg tccgcctttc tcccttcggg aagcgtggcg   14640
ctttctcata gctcacgctg taggtatctc agttcggtgt aggtcgttcg ctccaagctg   14700
ggctgtgtgc acgaaccccc cgttcagccc gaccgctgcg ccttatccgg taactatcgt   14760
cttgagtcca acccggtaag acacgactta tcgccactgg cagcagccac tggtaacagg   14820
attagcagag cgaggtatgt aggcggtgct acagagttct tgaagtggtg gcctaactac   14880
ggctacacta gaagaacagt atttggtatc tgcgctctgc tgaagccagt taccttcgga   14940
aaaagagttg gtagctcttg atccggcaaa caaaccaccg ctggtagcgg tggttttttt   15000
gtttgcaagc agcagattac gcgcagaaaa aaaggatctc aagaagatcc tttgatcttt   15060
tctacggggt ctgacgctca gtggaacgaa aactcacgtt aagggatttt ggtcatgaga   15120
ttatcaaaaa ggatcttcac ctagatcctt ttgatccgga at                     15162
```

<210> SEQ ID NO 39
<211> LENGTH: 15162
<212> TYPE: DNA
<213> ORGANISM: Artificial sequence
<220> FEATURE:
<223> OTHER INFORMATION: enhanced ZmABP3-Cry1AbG6 binary construct

<400> SEQUENCE: 39

```
taattcctgt ggttggcatg cacatacaaa tggacgaacg gataaacctt ttcacgccct     60
tttaaatatc cgattattct aataaacgct cttttctctt aggtttaccc gccaatatat    120
cctgtcaaac actgatagtt taaactgaag gcgggaaacg acaatctgat catgagcgga    180
gaattaaggg agtcacgtta tgacccccgc cgatgacgcg ggacaagccg ttttacgttt    240
ggaactgaca gaaccgcaac gctgcaggaa ttggccgcag cggccattta aatcaattgg    300
gcgcgccaca ctttctgtcg catgtgattt gcactaggag caggatagca gatgaggtca    360
aacgaaacga tgatgcgctt gagatgggaa aatggctgct cgacacggtt gagaacttga    420
gatggcatac gagcaatcaa gcaggggtca ctaccacttc cggctataaa taagagataa    480
ataagagatg agaccattat ctcatgagac agccatgcaa tgtcgccaag gatttaggaa    540
caaatagttt ttttgtcatt aacgacaaca ttgcgtcgtg gtttagttgg ctatcacgtc    600
agtctaacac attgaaggat ctcctggctc aacatttttt tccctccct taagtccgtg    660
ttaaagaaac tgcatcatgc aacgctggaa attttgctaa acaaatgacg gatttgcatc    720
```

```
acacagattc acactccact gtgcccacag agacactatt gctctgtttg gttaccggca      780
tcctcggtgc ctaactcgag caggtcttca gtagaaacgg acgattctta cttccccacg      840
cttacagacc aacaagggat ctgcacacac aacaatgtag ccaaaagaac acctaggatt      900
ttccaaaaac actaaggacc tgttcgcttg gaattataat ctgcctagat tatataatct      960
aacttaactt gaactcacac ttagtttaaa ataagtttct ccagacataa tcccaaacaa     1020 acgacccccta agcttctcca gacaattgtc accgagacat gggaagggaa catatcgatt    1080
acttatttgt agtagtaagt tgaacagcgc aacacatgtc catagtccat acataattgg     1140
cagataacaa ggaattacat gatagatccg aaccttcatg gtcttctggg agccaaggga    1200 cctttttta cacagcaaca aacccgcaaa tcatcaagca gtctttcaca gcaccaagtc      1260
tataatggca tacaaatcca cagtagtagg ccgagtccat gatgcatgat catgatgcga    1320
gctcctagat gcggccctcg agttcctcga agatggcggc gttcacaccg ggatcacgc     1380 tcagctcggg caggtaggcc tcgcgaatgc tgtgcacgcg cttgtcggcg cgtggatca     1440 tggcgatgtt ggtgtcggcc tgcaggcggt cgtactggct gttcacgaac agggcgtcca    1500
cgctctcctt ggcctccttg tacacgatgt tggtctccca ctccagcttc tcgcgcttgt    1560
cgcgccactt cttctcagca cgcttcacgc gggccagggc ctcgcccacc aggggcttct    1620
cctccaggaa ctctagattg cccaggcggg cgtggccgtc ctgggtcttg atcttgaaga    1680
tcacccacac gcccaggtcc tcgttcaggt cggtgcagcc cacgtcgatg tccaggctga    1740
agtggtggct gtggtggcac ttgccgatgg ggctggggc gctcagggc cacaggctgc      1800 cggtgccggg cacgttcacg gtctcgtgct tcgcgttgta gcggatcagg tagatttcca    1860
ggtcctggct gtcctcgatg tagccgcgca gctggtagcg ggtgtaggcc ttcagcttgc    1920
tctcgtcgat cttctggtac aggtaggtgg ggtagcactc gtcgaaggtg cccagcaggg    1980
tcacgtagtt ctccttgaac acgtcgtcgc cgccctggat ggtgatatcg gtgctgcctc    2040
gccagccgcg gtccagctgg cggttgatgc cgcggaagtt ggggtcctgc agcaggttgc    2100
gctcgtcgct caggcgcttg gcgtgcttca ccttctcgct cagctccttc ttctcgtcca    2160
ggcagaactc gtcgcttaag cactccacca ggttgctcac ctggtcgatg tggtagtcgg    2220
tcacgtcggt cttcaggccg atctggttgc tgctggtgaa cagctcgttc acggccttct    2280
gagccctctc caggtcgtac tcggcctcga aggtcacctc ggcgggcacg aactcgatgc    2340
ggtcgatgta cacctcgttg ccgctgttga acacgtgggc gctcagggtg aacacgctgc    2400
tgccgttgct gaagttgaag ggggtggtga agcccacggt gcggaagctg ccgctctgca    2460
ggttgctgcc gctgctcatg gtggcgctga agttgccctg gttgatgggg cggccgtcga    2520
tgctggtgtg gaactgcagg ttggtggtgc tggcgtagcg gatgcggacg cggtagcgct    2580
ggctcagggg ggcggtgatg ttcacgcgca gggtgctgat ctggccgggg ctggtgcggc    2640
gcaggatgtc gccgccggtg aagccgggcc ccttcaccac gctggtgccg ctgcccaggt    2700
tggtgctctt ggtcaggggg atctgggtga tctggctgct ggggatgatg ttgttgaact    2760
cggcactgcg gtgaatccag ctgaacatag gtgcacggat gatgctcacg ctgctgttgc    2820
tgaagccact gcggaacatg ctcacgtggc tcagacggtg gctgaagccc tgtcgaggtg    2880
gcacgttgtt gttctgaggg gggatctcgt ccaggctgtc cacggtgccg ctcttgcggt    2940
acacggcgct gggcaggttg ctgctggtgc cgtaggcgaa ctcggtgccg tccagcacgc    3000
tcagctgctg gttgttgatg ccgatgttga aaggtcgacg gtacagggtg ctgctcaggg    3060
```

```
tgcggtacac tccctggccc agctgtgcca cgatgcgctg ctgaggtgca gcgttgccca    3120
tcgtgccgta caggggggaag gtgaactcgg ggccgctgaa gccgacgggg ctggccatga    3180
tctggtggcc gctccagtag tactcgccgc ggtgggcgtc ggtgtagatg gtgatgctgt    3240
tcaggatgtc catcaggtgg gggctgcgga tgctgccctc gatgccctgg gcgctgccgc    3300
ggaagctgcc gtcgaagttc tccagcacgg ggttggtgta atctcgcgg gtcagctggc    3360 tcacggtgcg gatggggtag gtgcggctgt cgtagttggg gaacaggctc acgatgtcca    3420
gcacggtcag ggtcagctcg cggcggaact ggttgtacct gatccagtcg cggctgtcgg    3480 gacccacac gcgctccagg ccggtgttgt accagcgcac ggcgtggtcg gtgtagttgc    3540
cgatcaggcg ggtcaggtcg ttgtagcggc tgttgatggt ggcggcgtcg aagccccagc    3600
gctggccgaa cacgctgacg tcgcgcagca cgctcaggtg caggttggcg gcctgcacgt    3660
acacgctcag caggggcacc tggtagttct gcacggcgaa caggggatg gcggtggtca    3720 gggcgctgtt catgtcgttg aactggatgc gcatctcctc gcgcagggcg gggttggtgg    3780
ggtcggcctc ccactcgcgg aagctctcgg cgtagatttg gtacaggttg ctcaggccct    3840
ccaggcggct gatggcctgg ttgcgggcga attcctctat gcgttggttt atcaactgct    3900
cgatctgcac caggaaggcg tcccactggc tggggccgaa gatgccccag atgatgtcca    3960
ccaggcccag cacgaagccg gcgccgggca cgaactcgct cagcaggaac tgggtcaggc    4020
tcaggctgat gtcgatgggg gtgtagccgg tctcgatgcg ctcgccgccc agcacctcca    4080
cctcggggtt gctcaggcag ttgtagggga tgcactcgtt gatgttgggg ttgttgtcca    4140
tggtgggttt gcctgcgacc acaagttcag tcatagttaa ctggagatac agtgtggaga    4200
gtcccttcaa ataacctgct tgcaccaccc atagtttaag aggcagttgc tttcacacac    4260
tttattttgc atggcacagc caactgtccc catcattcta aaccaggctg caactgagcc    4320
actacagaaa ctgctaatat tagatattcc agcaaatagt cttgacacta gagtgctagg    4380
tccctaaaca cgaaagacat ttgtcaggag accgtattg agtactagca gagtatacta    4440
ccgctagata ttccagtata atcgtgcagc agctccggtc aatggcagtg cacttgaag    4500 tctgcaacct cagccaacag atccacatga gaaccaacag ggtcacgctg cagctggtgc    4560
tccataatcc aagctccgcg acctaagccg ccgagagcca aattcgcaga tgaactgcag    4620
ccacacgagc tacactggcg ccgctgaggt aaagatcaac cgagattcca ccgccaccgc    4680
acctcgcaga ccatagatct acacagctcg atttcacacg ctacagggcg aacaaacaag    4740
cacggatcca tagcggccgc gcaccacgcc agtacgccac agcctgcagc gagcacatag    4800
acgaagcgcc cgacgtctag atcacagatc gtggaatccc ggccacgcag actatgtttc    4860
tggctcgcaa gcgtgtcccg gccgcacgag gaatcccgat gatccgatca ggattccctc    4920
cccgaggaaa accacgaatc aggccacgag gaagccgagc ggccgcgatc ccgcctgaat    4980
ccagctagat ccgaagcgtt acacgagcgc tccgcgagaa ggaaacaaaa ggcccgaaat    5040
caggcgcgga gccagcacgc cccgcgccga tccggggagg aagccagagc gcgcccgggg    5100
gaggggaagc ggagggggtgg aggggggcctt accaactcgg gcgagctggc gcggcgaaga    5160
aggggacggg gacggccgag ggaggaggaa tccgccgagg aagcgaagcg aggaggggaa    5220
agaggatgga tggagctggc tgctgctgtg ctgcctctgc ctgcgtgccg agtgaccagt    5280
cctgcgggag acgcctcgtg tttgatgtg gtcgccgggt tttccaccgc gtatcccccg    5340
cgcgggtgtg gccgtgtggg tgacctgact gacctgcccc ttcgacggaa cggagcggcc    5400
gctgccagct tccacggtcg tcggatggcg atatggacgg ccgcgatggg cgacacgtca    5460
```

```
gcgcggcgcg atgttcgctg aaggtgatg tgggccgccg gaagcgtatt cgtaactctc   5520
tttttattcg ttttcttttt cgtgaaaggg atttcggaat gaaataaat agatacattc   5580 agggacgcgg aggattatca ggggaataaa aaccaaacaa aaagcagtgg catcagcgat   5640
ccacaccaca ccgaccgtgg gcgatggact aatctgtgag caaagcatta gccggacaag   5700
acagcagcgg cgtcgtacta ctcctgcgta tgatatgatg atgctctcaa ttcatgcagt   5760
gcatccgatg cacgtacgaa cgcactcggc ggctgggcac ggattaatcg gttcttaacc   5820
gtgattggtt cggtacttac agctaaaaca ccggccagta cgtgcctgtg cctaccgaat   5880
tgctactaat aattggacag cacatccaca tccagcatgt gtgtgtcagt gtgtgtcgga   5940
gtgggttccg tggtggatcg agagccgcgg gcgttgcttg ggccgtcatg gacagggctg   6000
catctacacg acaggccaga ttgcgcgagg cccggagccc ggattgcagt tccctttcct   6060
agagatggaa ctacagctgc tacacctact gcgttcaaca ttactctttc ttttatattt   6120
cagacgcttc atctaaggct atctccagct catctctcat tttttttcga tttacatcta   6180
aggctagagt tatggcagaa tatatagtaa aaaccacctg ttaggtgaaa acatggaaat   6240
agatcacaaa acgtattttg acatttcatt tttttaaaca aaaatacttc acgcatccat   6300
aatgcataga attacgtatt aacgaaaaag ttaagacaca aacttaaact aaaaatcata   6360
tgaaaatgga aaatataagg cttatgtgga ataaaagatg aaactcgaga attttgtctt   6420
tttatagtgc acatgaacct gttgtttgct actttcggcg cgccagctgc ttgtggggac   6480
cagacaaaaa aggaatggtg cagaattgtt aggcgcacct accaaaagca tctttgcctt   6540
tattgcaaag ataaagcaga ttcctctagt acaagtgggg aacaaaataa cgtggaaaag   6600
agctgtcctg acagcccact cactaatgcg tatgacgaac gcagtgacga ccacaaaact   6660
cgagactttt caacaaaggg taatatccgg aaacctcctc ggattccatt gcccagctat   6720
ctgtcacttt attgtgaaga tagtggaaaa ggaaggtggc tcctacaaat gccatcattg   6780
cgataaagga aaggctatcg ttgaagatgc ctctgccgac agtggtccca aagatggacc   6840
cccacccacg aggagcatcg tggaaaaaga agacgttcca accacgtctt caaagcaagt   6900
ggattgatgt gatatctcca ctgacgtaag ggatgacgaa caatcccact atccttcggt   6960
accggaccgc gatcgcttaa ttaagcttgc atgcctgcag tgcagcgtga cccggtcgtg   7020
cccctctcta gagataatga gcattgcatg tctaagttat aaaaaattac cacatatttt   7080
ttttgtcaca cttgtttgaa gtgcagttta tctatcttta tacatatatt taaactttac   7140
tctacgaata atataatcta tagtactaca ataatatcag tgttttagag aatcatataa   7200
atgaacagtt agacatggtc taaaggacaa ttgagtattt tgacaacagg actctacagt   7260
tttatctttt tagtgtgcat gtgttctcct ttttttttgc aaatagcttc acctatataa   7320
tacttcatcc atttttattag tacatccatt tagggtttag ggttaatggt tttttatagac   7380 taatttttt agtacatcta ttttattcta ttttagcctc taaattaaga aaactaaaac   7440
tctattttag tttttttatt taataattta gatataaaat agaataaaat aaagtgacta   7500
aaaattaaac aaataccctt taagaaatta aaaaaactaa ggaaacattt ttcttgtttc   7560
gagtagataa tgccagcctg ttaaacgccg ccgacgagtc taacggacac caaccagcga   7620
accagcagcg tcgcgtcggg ccaagcgaag cagacggcac ggcatctctg tcgctgcctc   7680 tggaccctc tcgagagttc cgctccaccg ttggacttgc tccgctgtcg gcatccagaa   7740
attgcgtggc ggagcggcag acgtgagccg gcacggcagg cggcctcctc ctcctctcac   7800
```

```
ggcaccggca gctacggggg attcctttcc caccgctcct tcgctttccc ttcctcgccc   7860
gccgtaataa atagacaccc cctccacacc ctctttcccc aacctcgtgt tgttcggagc   7920
gcacacacac acaaccagat ctcccccaaa tccacccgtc ggcacctccg cttcaaggta   7980
cgccgctcgt cctccccccc cccccctctc taccttctct agatcggcgt tccggtccat   8040
agttagggcc cggtagttct acttctgttc atgtttgtgt tagatccgtg tttgtgttag   8100
atccgtgctg ttagcgttcg tacacggatg cgacctgtac gtcagacacg ttctgattgc   8160
taacttgcca gtgtttctct ttggggaatc ctgggatggc tctagccgtt ccgcagacgg   8220
gatcgatttc atgattttt ttgtttcgtt gcatagggtt tggtttgccc ttttcctta   8280 tttcaatata tgccgtgcac ttgtttgtcg ggtcatcttt tcatgctttt ttttgtcttg   8340
gttgtgatga tgtggtctgg ttgggcggtc gttctagatc ggagtagaat tctgtttcaa   8400
actacctggt ggatttatta attttggatc tgtatgtgtg tgccatacat attcatagtt   8460
acgaattgaa gatgatggat ggaaatatcg atctaggata ggtatacatg ttgatgcggg   8520
ttttactgat gcatatacag agatgctttt tgttcgcttg gttgtgatga tgtggtgtgg   8580
ttgggcggtc gttcattcgt tctagatcgg agtagaatac tgtttcaaac tacctggtgt   8640
atttattaat tttggaactg tatgtgtgtg tcatacatct tcatagttac gagtttaaga   8700
tggatggaaa tatcgatcta ggataggtat acatgttgat gtgggtttta ctgatgcata   8760
tacatgatgg catatgcagc atctattcat atgctctaac cttgagtacc tatctattat   8820
aataaacaag tatgttttat aattattttg atcttgatat acttggatga tggcatatgc   8880
agcagctata tgtggatttt tttagccctg ccttcatacg ctatttattt gcttggtact   8940
gtttcttttg tcgatgctca ccctgttgtt tggtgttact tctgcaggga tccactagtc   9000
caccatgtct ccggagagga gaccagttga gattaggcca gctacagcag ctgatatggc   9060
cgcggtttgt gatatcgtta accattacat tgagacgtct acagtgaact ttaggacaga   9120
gccacaaaca ccacaagagt ggattgatga tctagagagg ttgcaagata gatacccttg   9180
gttggttgct gaggttgagg gtgttgtggc tggtattgct tacgctgggc cctggaaggc   9240
taggaacgct tacgattgga cagttgagag tactgtttac gtgtcacata ggcatcaaag   9300
gttgggccta ggatccacat tgtacacaca tttgcttaag tctatggagg cgcaaggttt   9360
taagtctgtg gttgctgtta taggccttcc aaacgatcca tctgttaggt tgcatgaggc   9420
tttgggatac acagcccggg gtacattgcg cgcagctgga tacaagcatg gtggatggca   9480
tgatgttggt ttttggcaaa gggattttga gttgccagct cctccaaggc cagttaggcc   9540
agttacccag atctgaacta gtgatatcgg cgccatgggt cgacctgcag atcgttcaaa   9600
catttggcaa taaagtttct taagattgaa tcctgttgcc ggtcttgcga tgattatcat   9660
ataatttctg ttgaattacg ttaagcatgt aataattaac atgtaatgca tgacgttatt   9720
tatgagatgg gttttatga ttagagtccc gcaattatac atttaatacg cgatagaaaa   9780
caaaatatag cgcgcaaact aggataaatt atcgcgcgcg gtgtcatcta tgttactaga   9840
tctgctagcc ctgcaggaaa tttaccggtg cccgggcggc cagcatggcc gtatccgcaa   9900
tgtgttatta agttgtctaa gcgtcaattt gtttacacca caatatatcc tgccaccagc   9960
cagccaacag ctccccgacc ggcagctcgg cacaaaatca ccactcgata caggcagccc  10020
atcagaatta attctcatgt ttgacagctt atcatcgact gcacggtgca ccaatgcttc  10080
tggcgtcagg cagccatcgg aagctgtggt atggctgtgc aggtcgtaaa tcactgcata  10140
attcgtgtcg ctcaaggcgc actcccgttc tggataatgt ttttgcgcc gacatcataa  10200
```

```
cggttctggc aaatattctg aaatgagctg ttgacaatta atcatccggc tcgtataatg   10260
tgtggaattg tgagcggata acaatttcac acaggaaaca gaccatgagg gaagcgttga   10320
tcgccgaagt atcgactcaa ctatcagagg tagttggcgt catcgagcgc catctcgaac   10380
cgacgttgct ggccgtacat ttgtacggct ccgcagtgga tggcggcctg aagccacaca   10440
gtgatattga tttgctggtt acggtgaccg taaggcttga tgaaacaacg cggcgagctt   10500
tgatcaacga ccttttggaa acttcggctt ccctggaga gagcgagatt ctccgcgctg    10560
tagaagtcac cattgttgtg cacgacgaca tcattccgtg gcgttatcca gctaagcgcg   10620
aactgcaatt tggagaatgg cagcgcaatg acattcttgc aggtatcttc gagccagcca   10680
cgatcgacat tgatctggct atcttgctga caaaagcaag agaacatagc gttgccttgg   10740
taggtccagc ggcggaggaa ctctttgatc cggttcctga acaggatcta tttgaggcgc   10800
taaatgaaac cttaacgcta tggaactcgc cgcccgactg ggctggcgat gagcgaaatg   10860
tagtgcttac gttgtcccgc atttggtaca gcgcagtaac cggcaaaatc gcgccgaagg   10920
atgtcgctgc cgactgggca atggagcgcc tgccggccca gtatcagccc gtcatacttg   10980
aagctaggca ggcttatctt ggacaagaag atcgcttggc ctcgcgcgca gatcagttgg   11040
aagaatttgt tcactacgtg aaaggcgaga tcaccaaagt agtcggcaaa taaagctcta   11100
gtggatctcc gtacccaggg atctggctcg gcggacgc acgacgccgg ggcgagacca    11160
taggcgatct cctaaatcaa tagtagctgt aacctcgaag cgtttcactt gtaacaacga   11220
ttgagaattt tgtcataaa attgaaatac ttggttcgca tttttgtcat ccgcggtcag    11280
ccgcaattct gacgaactgc ccatttagct ggagatgatt gtacatcctt cacgtgaaaa   11340
tttctcaagc gctgtgaaca agggttcaga ttttagattg aaaggtgagc cgttgaaaca   11400
cgttcttctt gtcgatgacg acgtcgctat gcggcatctt attattgaat accttacgat   11460
ccacgccttc aaagtgaccg cggtagccga cagcacccag ttcacaagag tactctcttc   11520
cgcgacggtc gatgtcgtgg ttgttgatct agatttaggt cgtgaagatg ggctcgagat   11580
cgttcgtaat ctggcggcaa agtctgatat tccaatcata attatcagtg gcgaccgcct   11640
tgaggagacg gataaagttg ttgcactcga gctaggagca agtgattta tcgctaagcc     11700 gttcagtatc agagagtttc tagcacgcat tcgggttgcc ttgcgcgtgc gccccaacgt   11760
tgtccgctcc aaagaccgac ggtcttttg ttttactgac tggacactta atctcaggca     11820
acgtcgcttg atgtccgaag ctggcggtga ggtgaaactt acggcaggtg agttcaatct   11880
tctcctcgcg ttttagaga aaccccgcga cgttctatcg cgcgagcaac ttctcattgc     11940
cagtcgagta cgcgacgagg aggtttatga caggagtata gatgttctca ttttgaggct   12000
gcgccgcaaa cttgaggcag atccgtcaag ccctcaactg ataaaaacag caagaggtgc   12060
cggttatttc tttgacgcgg acgtgcaggt ttcgcacggg gggacgatgg cagcctgagc   12120
caattcccag atccccgagg aatcggcgtg agcggtcgca aaccatccgg cccggtacaa   12180
atcggcgcgg cgctgggtga tgacctggtg gagaagttga aggccgcgca ggccgcccag   12240
cggcaacgca tcgaggcaga agcacgcccc ggtgaatcgt ggcaagcggc cgctgatcga   12300
atccgcaaag aatcccggca accgccggca gccggtgcgc cgtcgattag gaagccgccc   12360
aagggcgacg agcaaccaga ttttttcgtt ccgatgctct atgacgtggg cacccgcgat   12420
agtcgcagca tcatggacgt ggccgttttc cgtctgtcga agcgtgaccg acagctggc    12480 gaggtgatcc gctacgagct tccagacggg cacgtagagg tttccgcagg gccggccggc   12540
```

```
atggccagtg tgtgggatta cgacctggta ctgatggcgg tttcccatct aaccgaatcc   12600
atgaaccgat accgggaagg gaagggagac aagcccggcc gcgtgttccg tccacacgtt   12660
gcggacgtac tcaagttctg ccggcgagcc gatggcggaa agcagaaaga cgacctggta   12720
gaaacctgca ttcggttaaa caccacgcac gttgccatgc agcgtacgaa gaaggccaag   12780
aacggccgcc tggtgacggt atccgagggt gaagccttga ttagccgcta caagatcgta   12840
aagagcgaaa ccgggcggcc ggagtacatc gagatcgagc tggctgattg gatgtaccgc   12900
gagatcacag aaggcaagaa cccggacgtg ctgacggttc accccgatta cttttttgatc  12960 gatcccggca tcggccgttt tctctaccgc ctggcacgcc gcgccgcagg caaggcagaa   13020
gccagatggt tgttcaagac gatctacgaa cgcagtggca gcgccggaga gttcaagaag   13080
ttctgtttca ccgtgcgcaa gctgatcggg tcaaatgacc tgccggagta cgatttgaag   13140
gaggaggcgg ggcaggctgg cccgatccta gtcatgcgct accgcaacct gatcgagggc   13200
gaagcatccg ccggttccta atgtacggag cagatgctag gcaaattgc  cctagcaggg    13260 gaaaaaggtc gaaaaggtct cttttcctgtg gatagcacgt acattgggaa cccaaagccg   13320
tacattggga accggaaccc gtacattggg aacccaaagc cgtacattgg gaaccggtca   13380
cacatgtaag tgactgatat aaaagagaaa aaaggcgatt tttccgccta aaactcttta   13440
aaacttatta aaactcttaa aacccgcctg gcctgtgcat aactgtctgg ccagcgcaca   13500
gccgaagagc tgcaaaaagc gcctacccttc ggtcgctgc gctccctacg ccccgccgct    13560
tcgcgtcggc ctatcgcggc cgctggccgc tcaaaaatgg ctggcctacg gccaggcaat   13620
ctaccagggc gcggacaagc cgcgccgtcg ccactcgacc gccggcgctg aggtctgcct   13680
cgtgaagaag gtgttgctga ctcataccag gcctgaatcg ccccatcatc cagccagaaa   13740
gtgagggagc cacggttgat gagagctttg ttgtaggtgg accagttggt gattttgaac   13800
ttttgctttg ccacggaacg gtctgcgttg tcgggaagat gcgtgatctg atccttcaac   13860
tcagcaaaag ttcgatttat tcaacaaagc cgccgtcccg tcaagtcagc gtaatgctct   13920
gccagtgtta caaccaatta accaattctg attagaaaaa ctcatcgagc atcaaatgaa   13980
actgcaattt attcatatca ggattatcaa taccatattt ttgaaaaagc cgtttctgta   14040
atgaaggaga aaactcaccg aggcagttcc ataggatggc aagatcctgg tatcggtctg   14100
cgattccgac tcgtccaaca tcaatacaac ctattaattt cccctcgtca aaataaggt    14160 tatcaagtga gaaatcacca tgagtgacga ctgaatccgg tgagaatggc aaaagctctg   14220
cattaatgaa tcgccaacg cgcggggaga ggcggtttgc gtattgggcg ctcttccgct     14280
tcctcgctca ctgactcgct gcgctcggtc gttcggctgc ggcgagcggt atcagctcac   14340
tcaaaggcgg taatacggtt atccacagaa tcagggggata acgcaggaaa gaacatgtga   14400
gcaaaaggcc agcaaaaggc caggaaccgt aaaaaggccg cgttgctggc gttttttccat   14460 aggctccgcc cccctgacga gcatcacaaa aatcgacgct caagtcagag gtggcgaaac   14520
ccgacaggac tataaagata ccaggcgttt ccccctggaa gctccctcgt gcgctctcct   14580
gttccgaccc tgccgcttac cggatacctg tccgcctttc tcccttcggg aagcgtggcg   14640
ctttctcata gctcacgctg taggtatctc agttcggtgt aggtcgttcg ctccaagctg   14700
ggctgtgtgc acgaaccccc cgttcagccc gaccgctgcg ccttatccgg taactatcgt   14760
cttgagtcca acccggtaag acacgactta tcgccactgg cagcagccac tggtaacagg   14820
attagcagag cgaggtatgt aggcggtgct acagagttct tgaagtggtg gcctaactac   14880
ggctacacta gaagaacagt atttggtatc tgcgctctgc tgaagccagt taccttcgga   14940
```

```
aaaagagttg gtagctcttg atccggcaaa caaaccaccg ctggtagcgg tggttttttt    15000
gtttgcaagc agcagattac gcgcagaaaa aaaggatctc aagaagatcc tttgatcttt    15060
tctacggggt ctgacgctca gtggaacgaa aactcacgtt aagggatttt ggtcatgaga    15120
ttatcaaaaa ggatcttcac ctagatcctt ttgatccgga at                      15162

<210> SEQ ID NO 40
<211> LENGTH: 6472
<212> TYPE: DNA
<213> ORGANISM: Artificial sequence
<220> FEATURE:
<223> OTHER INFORMATION: ZmABP3-AmCyan assembly construct

<400> SEQUENCE: 40
taatacgact cactataggg agaccggcct cgagcagctg aagcttgcat gcggcgcgcc      60
gaaagtagca acaacaggt tcatgtgcac tataaaaaga caaaattctc gagtttcatc     120
ttttattcca cataagcctt atattttcca ttttcatatg attttttagtt taagtttgtg    180 tcttaacttt ttcgttaata cgtaattcta tgcattatgg atgcgtgaag tatttttgtt    240
taaaaaaatg aaatgtcaaa atacgttttg tgatctattt ccatgttttc acctaacagg    300 tggttttttac tatatattct gccataactc tagccttaga tgtaaatcga aaaaaaatga    360
gagatgagct ggagatagcc ttagatgaag cgtctgaaat ataaaagaaa gagtaatgtt    420
gaacgcagta ggtgtagcag ctgtagttcc atctctagga aagggaactg caatccgggc    480
tccgggcctc gcgcaatctg gcctgtcgtg tagatgcagc cctgtccatg acggcccaag    540
caacgcccgc ggctctcgat ccaccacgga acccactccg acacacactg acacacacat    600
gctggatgtg gatgtgctgt ccaattatta gtagcaattc ggtaggcaca ggcacgtact    660
ggccggtgtt ttagctgtaa gtaccgaacc aatcacggtt aagaaccgat taatccgtgc    720
ccagccgccg agtgcgttcg tacgtgcatc ggatgcactg catgaattga gagcatcatc    780
atatcatacg caggagtagt acgacgccgc tgctgtcttg tccggctaat gctttgctca    840
cagattagtc catcgcccac ggtcggtgtg gtgtggatcg ctgatgccac tgcttttttgt    900 ttggttttta ttccctgat aatcctccgc gtccctgaat gtatctattt attttcattc     960
cgaaatccct ttcacgaaaa agaaaacgaa taaaagaga gttacgaata cgcttccggc    1020
ggcccacatc accttccagc gaacatcgcg ccgcgctgac gtgtcgccca tcgcggccgt    1080
ccatatcgcc atccgacgac cgtggaagct ggcagcggcc gctccgttcc gtcgaagggg    1140
caggtcagtc aggtcaccca cacggccaca cccgcgcggg ggatacgcgg tggaaaaccc    1200
ggcgaccaca tcaaaacacg aggcgtctcc cgcaggactg gtcactcggc acgcaggcag    1260
aggcagcaca gcagcagcca gctccatcca tcctcttttcc cctcctcgct tcgcttcctc    1320
ggcggattcc tcctccctcg gccgtccccg tcccctttctt cgccgcgcca gctcgcccga    1380
gttggtaagg ccccctccac ccctccgctt ccctccccc gggcgcgctc tggcttcctc    1440
cccggatcgg cgcggggcgt gctggctccg cgcctgattt cgggccttttt gtttccttct    1500 cgcggagcgc tcgtgtaacg cttcggatct agctggattc aggcgggatc gcggccgctc    1560
ggcttcctcg tggcctgatt cgtggttttc ctcggggagg gaatcctgat cggatcatcg    1620
ggattcctcg tgcggccggg acacgcttgc gagccagaaa catagtctgc gtggccggga    1680
ttccacgatc tgtgatctag acgtcggggcg cttcgtctat gtgctcgctg caggctgtgg    1740
cgtactggcg tggtgcgcgg ccgctatgga tccgtgcttg tttgttcgcc ctgtagcgtg    1800
```

```
tgaaatcgag ctgtgtagat ctatggtctg cgaggtgcgg tggcggtgga atctcggttg    1860
atctttacct cagcggcgcc agtgtagctc gtgtggctgc agttcatctg cgaatttggc    1920
tctcggcggc ttaggtcgcg gagcttggat tatggagcac cagctgcagc gtgaccctgt    1980
tggttctcat gtggatctgt tggctgaggt tgcagacttc aagtgccact gccattgacc    2040
ggagctgctg cacgattata ctggaatatc tagcggtagt atactctgct agtactcaat    2100
acgggtctcc tgacaaatgt ctttcgtgtt tagggaccta gcactctagt gtcaagacta    2160
tttgctggaa tatctaatat tagcagtttc tgtagtggct cagttgcagc ctggtttaga    2220
atgatgggga cagttggctg tgccatgcaa aataaagtgt gtgaaagcaa ctgcctctta    2280
aactatgggt ggtgcaagca ggttatttga agggactctc cacactgtat ctccagttaa    2340
ctatgactga acttgtggtc gcaggcaaac ccaccatggc cctgtccaac aagttcatcg    2400
gcgacgacat gaagatgacc taccacatgg acggctgcgt gaacggccac tacttcaccg    2460
tgaagggcga gggcagcggc aagccctacg agggcaccca gacctccacc ttcaaggtga    2520
cgatggccaa cggcggcccc ctggccttct ccttcgacat cctgtccacc gtgttcatgt    2580
acggcaaccg ctgcttcacc gcctacccca ccagcatgcc cgactacttc aagcaggcct    2640
tccccgacgg catgtcctac gagagaacct tcacctacga ggacggcggc gtggccaccg    2700
ccagctggga gatcagcctg aagggcaact gcttcgagca caagtccacc ttccacggcg    2760
tgaacttccc cgccgacggc cccgtgatgg ccaagaagac caccggctgg gacccctcct    2820
tcgagaagat accgtgtgc gacggcatct gaagggcga cgtgaccgcc ttcctgatgc    2880
tgcagggcgg cggcaactac agatgccagt ccacacctc ctacaagacc aagaagcccg    2940
tgaccatgcc ccccaaccac gtggtggagc accgcatcgc cagaaccgac ctggacaagg    3000
gcggcaacag cgtgcagctg accgagcacg ccgtggccca catcacctcc gtggtgccct    3060
tctgagagct cgcatcatga tcatgcatca tggactcggc ctactactgt ggatttgtat    3120
gccattatag acttggtgct gtgaaagact gcttgatgat ttgcgggttt gttgctgtgt    3180
aaaaaaaggt cccttggctc ccagaagacc atgaaggttc ggatctatca tgtaattcct    3240
tgttatctgc caattatgta tggactatgg acatgtgttg cgctgttcaa cttactacta    3300
caaataagta atcgatatgt tcccttccca tgtctcggtg acaattgtct ggagaagctt    3360
aggggtcgtt tgtttgggat tatgtctgga gaaacttatt ttaaactaag tgtgagttca    3420
agttaagtta gattatataa tctaggcaga ttataattcc aagcgaacag gtccttagtg    3480
tttttggaaa atcctaggtg ttcttttggc tacattgttg tgtgtgcaga tcccttgttg    3540
gtctgtaagc gtggggaagt aagaatcgtc cgtttctact gaagacctgc tcgagttagg    3600
caccgaggat gccggtaacc aaacagagca atagtgtctc tgtgggcaca gtggagtgtg    3660
aatctgtgtg atgcaaatcc gtcatttgtt tagcaaaatt tccagcgttg catgatgcag    3720
tttctttaac acggacttaa gggaagggaa aaaaatgttg agccaggaga tccttcaatg    3780
tgttagactg acgtgatagc caactaaacc acgacgcaat gttgtcgtta atgacaaaaa    3840
aactatttgt tcctaaatcc ttggcgacat tgcatggctg tctcatgaga taatggtctc    3900
atctcttatt tatctcttat ttatagccgg aagtggtagt gaccctgct tgattgctcg    3960 tatgccatct caagttctca accgtgtcga gcagccattt tcccatctca agcgcatcat    4020
cgtttcgttt gacctcatct gctatcctgc tcctagtgca aatcacatgc gacagaaagt    4080
gtggcgcgcc actagtcccg ggcccatcga tgatatcaga tctggttcta tagtgtcacc    4140
taaatcgtat gtgtatgata cataaggtta tgtattaatt gtagccgcgt tctaacgaca    4200
```

```
atatgtccat atggtgcact ctcagtacaa tctgctctga tgccgcatag ttaagccagc    4260
cccgacaccc gccaacaccc gctgacgcgc cctgacgggc ttgtctgctc ccggcatccg    4320
cttacagaca agctgtgacc gtctccggga gctgcatgtg tcagaggttt tcaccgtcat    4380
caccgaaacg cgcgagacga aagggcctcg tgatacgcct attttatag gttaatgtca     4440 tgataataat ggtttcttag acgtcaggtg gcacttttcg gggaaatgtg cgcggaaccc    4500
ctatttgttt atttttctaa atacattcaa atatgtatcc gctcatgaga caataaccct    4560
gataaatgct tcaataatat tgaaaaagga agagtatgag tattcaacat ttccgtgtcg    4620
cccttattcc cttttttgcg gcattttgcc ttcctgtttt tgctcaccca gaaacgctgg    4680
tgaaagtaaa agatgctgaa gatcagttgg gtgcacgagt gggttacatc gaactggatc    4740
tcaacagcgg taagatcctt gagagttttc gccccgaaga acgttttcca atgatgagca    4800
cttttaaagt tctgctatgt ggcgcggtat tatcccgtat tgacgccggg caagagcaac    4860
tcggtcgccg catacactat tctcagaatg acttggttga gtactcacca gtcacagaaa    4920
agcatcttac ggatggcatg acagtaagag aattatgcag tgctgccata accatgagtg    4980
ataacactgc ggccaactta cttctgacaa cgatcgagg accgaaggag ctaaccgctt     5040
ttttgcacaa catgggggat catgtaactc gccttgatcg ttgggaaccg gagctgaatg    5100
aagccatacc aaacgacgag cgtgacacca cgatgcctgt agcaatggca acaacgttgc    5160
gcaaactatt aactggcgaa ctacttactc tagcttcccg gcaacaatta atagactgga    5220
tggaggcgga taaagttgca ggaccacttc tgcgctcggc ccttccggct ggctggttta    5280
ttgctgataa atctggagcc ggtgagcgtg ggtctcgcgg tatcattgca gcactggggc    5340
cagatggtaa gccctcccgt atcgtagtta tctacacgac ggggagtcag gcaactatgg    5400
atgaacgaaa tagacagatc gctgagatag gtgcctcact gattaagcat tggtaactgt    5460
cagaccaagt ttactcatat atactttaga ttgatttaaa acttcatttt taatttaaaa    5520
ggatctaggt gaagatcctt tttgataatc tcatgaccaa aatcccttaa cgtgagtttt    5580
cgttccactg agcgtcagac cccgtagaaa agatcaaagg atcttcttga gatccttttt    5640
ttctgcgcgt aatctgctgc ttgcaaacaa aaaaaccacc gctaccagcg gtggtttgtt    5700
tgccggatca agagctacca actctttttc cgaaggtaac tggcttcagc agagcgcaga    5760
taccaaatac tgttcttcta gtgtagccgt agttaggcca ccacttcaag aactctgtag    5820
caccgcctac atacctcgct ctgctaatcc tgttaccagt ggctgctgcc agtggcgata    5880
agtcgtgtct taccgggttg gactcaagac gatagttacc ggataaggcg cagcggtcgg    5940
gctgaacggg gggttcgtgc acacagccca gcttggagcg aacgacctac accgaactga    6000
gatacctaca gcgtgagcta tgagaaagcg ccacgcttcc cgaagggaga aaggcggaca    6060
ggtatccggt aagcggcagg gtcggaacag gagagcgcac gagggagctt ccaggggaa     6120 acgcctggta tctttatagt cctgtcgggt ttcgccacct ctgacttgag cgtcgatttt    6180
tgtgatgctc gtcagggggg cggagcctat ggaaaaacgc cagcaacgcg gccttttac     6240 ggttcctggc cttttgctgg ccttttgctc acatgttctt tcctgcgtta tcccctgatt    6300
ctgtggataa ccgtattacc gcctttgagt gagctgatac cgctcgccgc agccgaacga    6360
ccgagcgcag cgagtcagtg agcgaggaag cggaagagcg cccaatacgc aaaccgcctc    6420
tccccgcgcg ttggccgatt cattaatgca ggttaacctg gcttatcgaa at           6472
```

<210> SEQ ID NO 41

<211> LENGTH: 13200
<212> TYPE: DNA
<213> ORGANISM: Artificial sequence
<220> FEATURE:
<223> OTHER INFORMATION: ZmABP3-AmCyan binary construct

<400> SEQUENCE: 41

```
aattaattcc tgtggttggc atgcacatac aaatggacga acggataaac cttttcacgc      60
ccttttaaat atccgattat tctaataaac gctcttttct cttaggttta cccgccaata     120
tatcctgtca aacactgata gtttaaactg aaggcgggaa acgacaatct gatcatgagc     180
ggagaattaa gggagtcacg ttatgacccc cgccgatgac gcgggacaag ccgttttacg     240
tttggaactg acagaaccgc aacgctgcag gaattggccg cagcggccat ttaaatcaat     300
tgggcgcgcc gaaagtagca aacaacaggt tcatgtgcac tataaaaaga caaaattctc     360
gagtttcatc ttttattcca cataagcctt atattttcca ttttcatatg attttttagtt    420
taagtttgtg tcttaacttt ttcgttaata cgtaattcta tgcattatgg atgcgtgaag     480
tatttttgtt taaaaaaatg aaatgtcaaa atacgttttg tgatctattt ccatgttttc     540
acctaacagg tggtttttac tatatattct gccataactc tagccttaga tgtaaatcga     600
aaaaaaatga gagatgagct ggagatagcc ttagatgaag cgtctgaaat ataaaagaaa     660
gagtaatgtt gaacgcagta ggtgtagcag ctgtagttcc atctctagga aagggaactg     720
caatccgggc tccgggcctc gcgcaatctg gcctgtcgtg tagatgcagc cctgtccatg     780
acggcccaag caacgcccgc ggctctcgat ccaccacgga acccactccg acacacactg     840
acacacacat gctggatgtg gatgtgctgt ccaattatta gtagcaattc ggtaggcaca     900
ggcacgtact ggccggtgtt ttagctgtaa gtaccgaacc aatcacggtt aagaaccgat     960
taatccgtgc ccagccgccg agtgcgttcg tacgtgcatc ggatgcactg catgaattga    1020
gagcatcatc atatcatacg caggagtagt acgacgccgc tgctgtcttg tccggctaat    1080
gctttgctca cagattagtc catcgcccac ggtcggtgtg gtgtggatcg ctgatgccac    1140
tgctttttgt ttggttttta ttcccctgat aatcctccgc gtccctgaat gtatctattt    1200
attttcattc cgaaatccct ttcacgaaaa agaaaacgaa taaaaagaga gttacgaata    1260
cgcttccggc ggcccacatc accttccagc gaacatcgcg ccgcgctgac gtgtcgccca    1320
tcgcggccgt ccatatcgcc atccgacgac cgtggaagct ggcagcggcc gctccgttcc    1380
gtcgaagggg caggtcagtc aggtcaccca cacggccaca cccgcgcggg ggatacgcgg    1440
tggaaaaccc ggcgaccaca tcaaaacacg aggcgtctcc cgcaggactg gtcactcggc    1500
acgcaggcag aggcagcaca gcagcagcca gctccatcca tcctctttcc cctcctcgct    1560
tcgcttcctc ggcggattcc tcctcccctcg gccgtccccg tccccttctt cgccgcgcca    1620
gctcgcccga gttggtaagg ccccctccac ccctccgctt cccctccccc gggcgcgctc    1680
tggcttcctc cccggatcgg cgcggggcgt gctggctccg cgcctgattt cgggccttt     1740
gtttccttct cgcggagcgc tcgtgtaacg cttcggatct agctgattc aggcgggatc     1800
gcggccgctc ggcttcctcg tggcctgatt cgtggttttc ctcggggagg gaatcctgat    1860
cggatcatcg ggattcctcg tgcggccggg acacgcttgc gagccagaaa catagtctgc    1920
gtggccggga ttccacgatc tgtgatctag acgtcgggcg cttcgtctat gtgctcgctg    1980
caggctgtgg cgtactggcg tggtgcgcgg ccgctatgga tccgtgcttg tttgttcgcc    2040
ctgtagcgtg tgaaatcgag ctgtgtagat ctatggtctg cgaggtgcgg tggcggtgga    2100
atctcggttg atctttacct cagcggcgcc agtgtagctc gtgtggctgc agttcatctg    2160
```

```
cgaatttggc tctcggcggc ttaggtcgcg gagcttggat tatggagcac cagctgcagc   2220
gtgaccctgt tggttctcat gtggatctgt tggctgaggt tgcagacttc aagtgccact   2280
gccattgacc ggagctgctg cacgattata ctggaatatc tagcggtagt atactctgct   2340
agtactcaat acgggtctcc tgacaaatgt ctttcgtgtt tagggaccta gcactctagt   2400
gtcaagacta tttgctggaa tatctaatat tagcagtttc tgtagtggct cagttgcagc   2460
ctggtttaga atgatgggga cagttggctg tgccatgcaa aataaagtgt gtgaaagcaa   2520
ctgcctctta aactatgggt ggtgcaagca ggttatttga agggactctc cacactgtat   2580
ctccagttaa ctatgactga acttgtggtc gcaggcaaac ccaccatggc cctgtccaac   2640
aagttcatcg gcgacgacat gaagatgacc taccacatgg acggctgcgt gaacggccac   2700
tacttcaccg tgaagggcga gggcagcggc aagcccacg agggcaccca gacctccacc   2760
ttcaaggtga cgatggccaa cggcggcccc ctggccttct ccttcgacat cctgtccacc   2820
gtgttcatgt acggcaaccg ctgcttcacc gcctacccca ccagcatgcc cgactacttc   2880
aagcaggcct cccccgacgg catgtcctac gagagaacct tcacctacga ggacggcggc   2940
gtggccaccg ccagctggga gatcagcctg aagggcaact gcttcgagca caagtccacc   3000
ttccacggcg tgaacttccc cgccgacggc cccgtgatgg ccaagaagac caccggctgg   3060
gacccctcct tcgagaagat gaccgtgtgc gacggcatct tgaagggcga cgtgaccgcc   3120
ttcctgatgc tgcagggcgg cggcaactac agatgccagt tccacacctc ctacaagacc   3180
aagaagcccg tgaccatgcc ccccaaccac gtggtggagc accgcatcgc cagaaccgac   3240
ctggacaagg cggcaacag cgtgcagctg accgagcacg ccgtggccca catcacctcc   3300
gtggtgccct tctgagagct cgcatcatga tcatgcatca tggactcggc ctactactgt   3360
ggatttgtat gccattatag acttggtgct gtgaaagact gcttgatgat ttgcgggttt   3420
gttgctgtgt aaaaaaaggt cccttggctc ccagaagacc atgaaggttc ggatctatca   3480
tgtaattcct tgttatctgc caattatgta tggactatgg acatgtgttg cgctgttcaa   3540
cttactacta caaataagta atcgatatgt tccctttccca tgtctcggtg acaattgtct   3600
ggagaagctt aggggtcgtt tgtttgggat tatgtctgga gaaacttatt ttaaactaag   3660
tgtgagttca agttaagtta gattatataa tctaggcaga ttataattcc aagcgaacag   3720
gtccttagtg tttttggaaa atcctaggtg ttcttttggc tacattgttg tgtgtgcaga   3780
tcccttgttg gtctgtaagc gtggggaagt aagaatcgtc cgtttctact gaagacctgc   3840
tcgagttagg caccgaggat gccggtaacc aaacagagca atagtgtctc tgtgggcaca   3900
gtggagtgtg aatctgtgtg atgcaaatcc gtcatttgtt tagcaaaatt ccagcgttg   3960 catgatgcag tttctttaac acggacttaa gggaagggaa aaaaatgttg agccaggaga   4020
tccttcaatg tgttagactg acgtgatagc caactaaacc acgacgcaat gttgtcgtta   4080
atgacaaaaa aactatttgt tcctaaatcc ttggcgacat tgcatggctg tctcatgaga   4140
taatggtctc atctcttatt tatctcttat ttatagccgg aagtggtagt gaccctgct   4200 tgattgctcg tatgccatct caagttctca accgtgtcga gcagccattt tcccatctca   4260
agcgcatcat cgtttcgttt gacctcatct gctatcctgc tcctagtgca aatcacatgc   4320
gacagaaagt gtggcgcgcc gaattcgagc tcggtaccgg accgcgatcg cttaattaag   4380
cttgcatgcc tgcagtgcag cgtgacccgg tcgtgccct ctctagagat aatgagcatt   4440
gcatgtctaa gttataaaaa attaccacat atttttttg tcacacttgt ttgaagtgca   4500
```

```
gtttatctat ctttatacat atatttaaac tttactctac gaataatata atctatagta    4560
ctacaataat atcagtgttt tagagaatca tataaatgaa cagttagaca tggtctaaag    4620
gacaattgag tattttgaca acaggactct acagttttat cttttagtg tgcatgtgtt     4680
ctccttttt tttgcaaata gcttcaccta tataatactt catccatttt attagtacat     4740
ccatttaggg tttagggtta atggttttta tagactaatt tttttagtac atctatttta    4800
ttctatttta gcctctaaat taagaaaact aaaactctat tttagttttt ttatttaata    4860
atttagatat aaaatagaat aaaataaagt gactaaaaat taaacaaata ccctttaaga    4920
aattaaaaaa actaaggaaa catttttctt gtttcgagta gataatgcca gcctgttaaa    4980
cgccgtcgac gagtctaacg gacaccaacc agcgaaccag cagcgtcgcg tcgggccaag    5040
cgaagcagac ggcacggcat ctctgtcgct gcctctggac ccctctcgag agttccgctc    5100
caccgttgga cttgctccgc tgtcggcatc cagaaattgc gtggcggagc ggcagacgtg    5160
agccggcacg gcaggcggcc tcctcctcct ctcacggcac cggcagctac gggggattcc    5220
tttcccaccg ctccttcgct ttcccttcct cgcccgccgt aataaataga cacccccctcc   5280
acacctctt tccccaacct cgtgttgttc ggagcgcaca cacacacaac cagatctccc     5340
ccaaatccac ccgtcggcac ctccgcttca aggtacgccg ctcgtcctcc ccccccccc     5400
ctctctacct tctctagatc ggcgttccgg tccatggtta gggcccggta gttctacttc    5460
tgttcatgtt tgtgttagat ccgtgtttgt gttagatccg tgctgctagc gttcgtacac    5520
ggatgcgacc tgtacgtcag acacgttctg attgctaact tgccagtgtt tctctttggg    5580
gaatcctggg atggctctag ccgttccgca gacgggatcg atttcatgat tttttttgtt    5640
tcgttgcata gggtttggtt tgccccttttc ctttatttca atatatgccg tgcacttgtt    5700
tgtcgggtca tcttttcatg ctttttttg tcttggttgt gatgatgtgg tctggttggg     5760
cggtcgttct agatcggagt agaattctgt ttcaaactac ctggtggatt tattaatttt    5820
ggatctgtat gtgtgtgcca tacatattca tagttacgaa ttgaagatga tggatggaaa    5880
tatcgatcta ggataggtat acatgttgat gcgggttta ctgatgcata tacagagatg     5940
cttttttgttc gcttggttgt gatgatgtgg tgtggttggg cggtcgttca ttcgttctag   6000
atcggagtag aatactgttt caaactacct ggtgtattta ttaattttgg aactgtatgt    6060
gtgtgtcata catcttcata gttacgagtt taagatggat ggaaatatcg atctaggata    6120
ggtatacatg ttgatgtggg ttttactgat gcatatacat gatggcatat gcagcatcta    6180
ttcatatgct ctaaccttga gtacctatct attataataa acaagtatgt tttataatta    6240
ttttgatctt gatatacttg gatgatggca tatgcagcag ctatatgtgg attttttag     6300
ccctgccttc atacgctatt tatttgcttg gtactgtttc ttttgtcgat gctcaccctg    6360
ttgtttggtg ttacttctgc agggatcccc gatcatgcaa aaactcatta actcagtgca    6420
aaactatgcc tggggcagca aaacggcgtt gactgaactt tatggtatgg aaaatccgtc    6480
cagccagccg atgccgagc tgtggatggg cgcacatccg aaaagcagtt cacgagtgca     6540
gaatgccgcc ggagatatcg tttcactgcg tgatgtgatt gagagtgata atcgactct     6600
gctcggagag gccgttgcca aacgctttgg cgaactgcct tcctgttca aagtattatg     6660
cgcagcacag ccactctcca ttcaggttca tccaaacaaa cacaattctg aaatcggttt    6720
tgccaaagaa aatgccgcag gtatcccgat ggatgccgcc gagcgtaact ataaagatcc    6780
taaccacaag ccggagctgg ttttgcgct gacgcctttc cttgcgatga acgcgtttcg     6840
tgaattttcc gagattgtct ccctactcca gccggtcgca ggtgcacatc cggcgattgc    6900
```

```
tcactttttta caacagcctg atgccgaacg tttaagcgaa ctgttcgcca gcctgttgaa    6960
tatgcagggt gaagaaaaat cccgcgcgct ggcgatttta aaatcggccc tcgatagcca    7020
gcagggtgaa ccgtggcaaa cgattcgttt aatttctgaa ttttaccccgg aagacagcgg    7080 tctgttctcc ccgctattgc tgaatgtggt gaaattgaac cctggcgaag cgatgttcct    7140
gttcgctgaa acaccgcacg cttacctgca aggcgtggcg ctggaagtga tggcaaactc    7200
cgataacgtg ctgcgtgcgg gtctgacgcc taaatacatt gatattccgg aactggttgc    7260
caatgtgaaa ttcgaagcca accggctaa ccagttgttg acccagccgg tgaaacaagg    7320
tgcagaactg gacttcccga ttccagtgga tgattttgcc ttctcgctgc atgaccttag    7380
tgataaagaa accaccatta gccagcagag tgccgccatt ttgttctgcg tcgaaggcga    7440
tgcaacgttg tggaaaggtt ctcagcagtt acagcttaaa ccgggtgaat cagcgtttat    7500
tgccgccaac gaatcaccgg tgactgtcaa aggccacggc cgtttagcgc gtgtttacaa    7560
caagctgtaa gagcttactg aaaaaattaa catctcttgc taagctggga gctcgatccg    7620
tcgacctgca gatcgttcaa acatttggca ataaagtttc ttaagattga atcctgttgc    7680
cggtcttgcg atgattatca tataatttct gttgaattac gttaagcatg taataattaa    7740
catgtaatgc atgacgttat ttatgagatg gttttttatg attagagtcc cgcaattata    7800
catttaatac gcgatagaaa acaaaatata gcgcgcaaac taggataaat tatcgcgcgc    7860
ggtgtcatct atgttactag atctgctagc cctgcaggaa atttaccggt gcccgggcgg    7920
ccagcatggc cgtatccgca atgtgttatt aagttgtcta agcgtcaatt tgtttacacc    7980
acaatatatc ctgccaccag ccagccaaca gctccccgac cggcagctcg gcacaaaatc    8040
accactcgat acaggcagcc catcagaatt aattctcatg tttgacagct tatcatcgac    8100
tgcacggtgc accaatgctt ctggcgtcag gcagccatcg gaagctgtgg tatggctgtg    8160
caggtcgtaa atcactgcat aattcgtgtc gctcaaggcg cactcccgtt ctggataatg    8220
ttttttgcgc cgacatcata acggttctgg caaatattct gaaatgagct gttgacaatt    8280
aatcatccgg ctcgtataat gtgtggaatt gtgagcggat aacaatttca cacaggaaac    8340
agaccatgag ggaagcgttg atcgccgaag tatcgactca actatcagag gtagttggcg    8400
tcatcgagcg ccatctcgaa ccgacgttgc tggccgtaca tttgtacggc tccgcagtgg    8460
atggcggcct gaagccacac agtgatattg atttgctggt tacggtgacc gtaaggcttg    8520
atgaaacaac gcggcgagct ttgatcaacg acctttttgga aacttcggct tcccctggag    8580
agagcgagat tctccgcgct gtagaagtca ccattgttgt gcacgacgac atcattccgt    8640
ggcgttatcc agctaagcgc gaactgcaat ttggagaatg gcagcgcaat gacattcttg    8700
caggtatctt cgagccagcc acgatcgaca ttgatctggc tatcttgctg acaaaagcaa    8760
gagaacatag cgttgccttg gtaggtccag cggcggagga actctttgat ccggttcctg    8820
aacaggatct atttgaggcg ctaaatgaaa ccttaacgct atggaactcg ccgcccgact    8880
gggctggcga tgagcgaaat gtagtgctta cgttgtcccg catttggtac agcgcagtaa    8940
ccggcaaaat cgcgccgaag gatgtcgctg ccgactgggc aatggagcgc ctgccggccc    9000
agtatcagcc cgtcatactt gaagctaggc aggcttatct tggacaagaa gatcgcttgg    9060
cctcgcgcgc agatcagttg gaagaatttg ttcactacgt gaaaggcgag atcaccaaag    9120
tagtcggcaa ataagctct agtggatctc cgtacccggg gatctggctc gcggcggacg    9180
cacgacgccg gggcgagacc ataggcgatc tcctaaatca atagtagctg taacctcgaa    9240
```

```
gcgtttcact tgtaacaacg attgagaatt tttgtcataa aattgaaata cttggttcgc   9300
atttttgtca tccgcggtca gccgcaattc tgacgaactg cccatttagc tggagatgat   9360
tgtacatcct tcacgtgaaa atttctcaag cgctgtgaac aagggttcag attttagatt   9420
gaaaggtgag ccgttgaaac acgttcttct tgtcgatgac gacgtcgcta tgcggcatct   9480
tattattgaa taccttacga tccacgcctt caaagtgacc gcggtagccg acagcaccca   9540
gttcacaaga gtactctctt ccgcgacggt cgatgtcgtg gttgttgatc tagatttagg   9600
tcgtgaagat gggctcgaga tcgttcgtaa tctggcggca aagtctgata ttccaatcat   9660
aattatcagt ggcgaccgcc ttgaggagac ggataaagtt gttgcactcg agctaggagc   9720
aagtgatttt atcgctaagc cgttcagtat cagagagttt ctagcacgca ttcgggttgc   9780
cttgcgcgtg cgccccaacg ttgtccgctc caaagaccga cggtcttttt gttttactga   9840
ctggacactt aatctcaggc aacgtcgctt gatgtccgaa gctggcggtg aggtgaaact   9900
tacggcaggt gagttcaatc ttctcctcgc gttttagag aaaccccgcg acgttctatc   9960
gcgcgagcaa cttctcattg ccagtcgagt acgcgacgag gaggtttatg acaggagtat  10020
agatgttctc attttgaggc tgcgccgcaa acttgaggca gatccgtcaa gccctcaact  10080
gataaaaaca gcaagaggtg ccggttattt ctttgacgcg gacgtgcagg tttcgcacgg  10140
ggggacgatg gcagcctgag ccaattccca gatccccgag gaatcggcgt gagcggtcgc  10200
aaaccatccg gcccggtaca aatcggcgcg gcgctgggtg atgacctggt ggagaagttg  10260
aaggccgcgc aggccgccca gcggcaacgc atcgaggcag aagcacgccc cggtgaatcg  10320
tggcaagcgg ccgctgatcg aatccgcaaa gaatcccggc aaccgccggc agccggtgcg  10380
ccgtcgatta ggaagccgcc caagggcgac gagcaaccag atttttttcgt tccgatgctc  10440 tatgacgtgg gcacccgcga tagtcgcagc atcatggacg tggccgtttt ccgtctgtcg  10500
aagcgtgacc gacgagctgg cgaggtgatc cgctacgagc ttccagacgg gcacgtagag  10560
gtttccgcag ggccggccgg catggccagt gtgtgggatt acgacctggt actgatggcg  10620
gtttcccatc taaccgaatc catgaaccga taccgggaag ggaagggaga caagcccggc  10680
cgcgtgttcc gtccacacgt tgcggacgta ctcaagttct gccggcgagc cgatggcgga  10740
aagcagaaag acgacctggt agaaacctgc attcggttaa acaccacgca cgttgccatg  10800
cagcgtacga agaaggccaa gaacggccgc ctggtgacgg tatccgaggg tgaagccttg  10860
attagccgct acaagatcgt aaagagcgaa accgggcggc cggagtacat cgagatcgag  10920
ctagctgatt ggatgtaccg cgagatcaca gaaggcaaga acccgacgt gctgacggtt  10980 cacccccgatt acttttttgat cgatcccggc atcggccgtt ttctctaccg cctggcacgc  11040
cgcgccgcag gcaaggcaga agccagatgg ttgttcaaga cgatctacga acgcagtggc  11100
agcgccggag agttcaagaa gttctgtttc accgtgcgca agctgatcgg gtcaaatgac  11160
ctgccggagt acgatttgaa ggaggaggcg gggcaggctg gcccgatcct agtcatgcgc  11220
taccgcaacc tgatcgaggg cgaagcatcc gccggttcct aatgtacgga gcagatgcta  11280
gggcaaattg ccctagcagg ggaaaaaggt cgaaaaggtc tctttcctgt ggatagcacg  11340
tacattggga acccaaagcc gtacattggg aaccggaacc cgtacattgg gaacccaaag  11400
ccgtacattg ggaaccggtc acacatgtaa gtgactgata taaagagaaa aaaaggcgat  11460
ttttccgcct aaaactcttt aaaacttatt aaaactctta aaacccgcct ggcctgtgca  11520
taactgtctg gccagcgcac agccgaagag ctgcaaaaag cgcctaccct tcggtcgctg  11580
cgctccctac gccccgccgc ttcgcgtcgg cctatcgcgg ccgctggccg ctcaaaaatg  11640
```

```
gctggcctac ggccaggcaa tctaccaggg cgcggacaag ccgcgccgtc gccactcgac   11700
cgccggcgct gaggtctgcc tcgtgaagaa ggtgttgctg actcatacca ggcctgaatc   11760
gccccatcat ccagccagaa agtgaggag ccacggttga tgagagcttt gttgtaggtg   11820
gaccagttgg tgattttgaa cttttgcttt gccacggaac ggtctgcgtt gtcgggaaga   11880
tgcgtgatct gatccttcaa ctcagcaaaa gttcgattta ttcaacaaag ccgccgtccc   11940
gtcaagtcag cgtaatgctc tgccagtgtt acaaccaatt aaccaattct gattagaaaa   12000
actcatcgag catcaaatga aactgcaatt tattcatatc aggattatca ataccatatt   12060
tttgaaaaag ccgtttctgt aatgaaggag aaaactcacc gaggcagttc cataggatgg   12120
caagatcctg gtatcggtct gcgattccga ctcgtccaac atcaatacaa cctattaatt   12180
tcccctcgtc aaaataagg ttatcaagtg agaaatcacc atgagtgacg actgaatccg   12240
gtgagaatgg caaaagctct gcattaatga atcggccaac gcgcggggag aggcggtttg   12300
cgtattgggc gctcttccgc ttcctcgctc actgactcgc tgcgctcggt cgttcggctg   12360
cggcgagcgg tatcagctca ctcaaaggcg gtaatacggt tatccacaga atcaggggat   12420
aacgcaggaa agaacatgtg agcaaaaggc cagcaaaagg ccaggaaccg taaaaaggcc   12480
gcgttgctgg cgtttttcca taggctccgc ccccctgacg agcatcacaa aaatcgacgc   12540
tcaagtcaga ggtggcgaaa cccgacagga ctataaagat accaggcgtt tcccctgga   12600 agctccctcg tgcgctctcc tgttccgacc ctgccgctta ccggatacct gtccgccttt   12660
ctcccttcgg gaagcgtggc gctttctcat agctcacgct gtaggtatct cagttcggtg   12720
taggtcgttc gctccaagct gggctgtgtg cacgaacccc ccgttcagcc cgaccgctgc   12780
gccttatccg gtaactatcg tcttgagtcc aacccggtaa gacacgactt atcgccactg   12840
gcagcagcca ctggtaacag gattagcaga gcgaggtatg taggcggtgc tacagagttc   12900
ttgaagtggt ggcctaacta cggctacact agaagaacag tatttggtat ctgcgctctg   12960
ctgaagccag ttaccttcgg aaaaagagtt ggtagctctt gatccggcaa acaaaccacc   13020
gctggtagcg gtggtttttt tgtttgcaag cagcagatta cgcgcagaaa aaaggatct   13080 caagaagatc ctttgatctt ttctacgggg tctgacgctc agtggaacga aaactcacgt   13140
taagggattt tggtcatgag attatcaaaa aggatcttca cctagatcct tttgatccgg   13200
```

<210> SEQ ID NO 42
<211> LENGTH: 8961
<212> TYPE: DNA
<213> ORGANISM: Artificial sequence
<220> FEATURE:
<223> OTHER INFORMATION: ZmABP3-AtAVP1D assembly construct

<400> SEQUENCE: 42

```
gggacccaaa gtagcaaaca acaggttcat gtgcactata aaagacaaa attctcgagt     60 ttcatctttt attccacata agccttatat tttccatttt catatgattt ttagtttaag    120
tttgtgtctt aacttttcg ttaatacgta attctatgca ttatggatgc gtgaagtatt    180
tttgtttaaa aaaatgaaat gtcaaaatac gttttgtgat ctatttccat gttttcacct    240
aacaggtggt ttttactata tattctgcca taactctagc cttagatgta aatcgaaaaa    300
aaatgagaga tgagctggag atagccttag atgaagcgtc tgaaatataa agaaagagt    360 aatgttgaac gcagtaggtg tagcagctgt agttccatct ctaggaaagg gaactgcaat    420
ccgggctccg ggcctcgcgc aatctggcct gtcgtgtaga tgcagccctg tccatgacgg    480
```

```
cccaagcaac gcccgcggct ctcgatccac cacggaaccc actccgacac acactgacac    540
acacatgctg gatgtggatg tgctgtccaa ttattagtag caattcggta ggcacaggca    600
cgtactggcc ggtgttttag ctgtaagtac cgaaccaatc acggttaaga accgattaat    660
ccgtgcccag ccgccgagtg cgttcgtacg tgcatcggat gcactgcatg aattgagagc    720
atcatcatat catacgcagg agtagtacga cgccgctgct gtcttgtccg gctaatgctt    780
tgctcacaga ttagtccatc gcccacggtc ggtgtggtgt ggatcgctga tgccactgct    840
ttttgtttgg ttttttattcc cctgataatc ctccgcgtcc ctgaatgtat ctatttattt    900
tcattccgaa atcccttttca cgaaaaagaa aacgaataaa aagagagtta cgaatacgct    960
tccggcggcc cacatcacct tccagcgaac atcgcgccgc gctgacgtgt cgcccatcgc   1020
ggccgtccat atcgccatcc gacgaccgtg gaagctggca gcggccgctc cgttccgtcg   1080
aaggggcagg tcagtcaggt cacccacacg gccacacccg cgcggggat acgcggtgga    1140 aaacccggcg accacatcaa aacacgaggc gtctcccgca ggactggtca ctcggcacgc   1200
aggcagaggc agcacagcag cagccagctc catccatcct ctttcccctc ctcgcttcgc   1260
ttcctcggcg gattcctcct ccctcggccg tcccgtccc cttcttcgcc gcgccagctc   1320
gcccgagttg gtaaggcccc ctccacccct ccgcttcccc tcccccgggc gcgctctggc   1380
ttcctccccg gatcggcgcg gggcgtgctg gctccgcgcc tgatttcggg cctttttgttt  1440 ccttctcgcg gagcgctcgt gtaacgcttc ggatctagct ggattcaggc gggatcgcgg   1500
ccgctcggct tcctcgtggc ctgattcgtg gttttcctcg gggagggaat cctgatcgga   1560
tcatcgggat tcctcgtgcg gccgggacac gcttgcgagc cagaaacata gtctgcgtgg   1620
ccgggattcc acgatctgtg atctagacgt cgggcgcttc gtctatgtgc tcgctgcagg   1680
ctgtggcgta ctggcgtggt gcgcggccgc tatggatccg tgcttgtttg ttcgccctgt   1740
agcgtgtgaa atcgagctgt gtagatctat ggtctgcgag gtgcggtggc ggtggaatct   1800
cggttgatct ttacctcagc ggcgccagtg tagctcgtgt ggctgcagtt catctgcgaa   1860
tttggctctc ggcggcttag gtcgcggagc ttggattatg gagcaccagc tgcagcgtga   1920
ccctgttggt tctcatgtgg atctgttggc tgaggttgca gacttcaagt gccactgcca   1980
ttgaccggag ctgctgcacg attatactgg aatatctagc ggtagtatac tctgctagta   2040
ctcaatacgg gtctcctgac aaatgtcttt cgtgtttagg gacctagcac tctagtgtca   2100
agactatttg ctggaatatc taatattagc agtttctgta gtggctcagt tgcagcctgg   2160
tttagaatga tggggacagt tggctgtgcc atgcaaaata aagtgtgtga aagcaactgc   2220
ctcttaaact atgggtggtg caagcaggtt atttgaaggg actctccaca ctgtatctcc   2280
agttaacttt gactgaactt gtggtcgcag gcaaacccac catggttgca ccagcattgc   2340
ttccggaact gtggacggag atactggtcc caatctgcgc tgtgatcggc atagccttca   2400
gcctgttcca gtggtacgtc gtgtcaaggg tgaagctcac gagcgacttg ggagccagta   2460
gtagcggagg ggcgaacaac gggaagaacg gctatggcga ctatctgatc gaggaggaag   2520
agggtgtgaa cgaccaatca gtggtggcga agtgtgcgga gattcagacc gccattagcg   2580
agggagctac gagcttcctg tttacggagt acaagtacgt gggcgtcttc atgatcttct   2640
tcgctgccgt catcttcgtg ttcctgggtt ctgtcgaagg cttctccacc gacaacaagc   2700
cgtgcactta cgacaccacc agaacctgca aacctgcact ggccactgct gcgttctcca   2760
ccatagcgtt cgtgcttggt gctgtgacaa gcgtcctgag tggcttcttg gggatgaaga   2820
tcgctaccta cgccaatgcc agaaccacac tggaggcaag gaaaggtgtc gggaaagcct   2880
```

```
tcatcgtggc ctttcggagt ggtgctgtca tgggcttcct gcttgctgcc agtggattgc   2940
tcgtgctcta catcaccatc aacgtgttca agatctacta cggcgacgat tgggaagggc   3000
tcttcgacgc aatcactggc tatgggttgg gtggctcttc aatggcgctc ttcggaagag   3060
tgggaggtgg catctacacg aaagcggctg atgtgggagc tgacctggtc gggaagatcg   3120
agcgcaacat cccggaagat gacccaagga acccagcagt gatcgccgac aatgtcggcg   3180
acaatgtcgg tgacatagcg ggtatgggaa gcgacctctt tggctcatac gccgaagcca   3240
gctgcgcagc gcttgttgtc gcctccatct ccagcttcgg gatcaaccac gacttcacag   3300
ccatgtgcta tcccctcctg atcagcagca tgggcatact ggtgtgcctc atcaccacgc   3360
tgtttgcgac cgacttcttc gagatcaagc tggtgaagga gatcgaacct gcgctgaaga   3420
accagctgat catctcgacc gtgatcatga ccgttgggat cgccatcgtc tcatgggtgg   3480
gtcttcctac ctcgttcacc atcttcaact ttggcactca gaaggtggtg aagaactggc   3540
agctcttcct ctgcgtttgc gtcggacttt gggctgggct gatcatcggc tttgtcacgg   3600
agtactacac ctccaacgcc tacagtcctg tgcaggatgt ggccgattct tgccgtactg   3660
gtgctgcaac gaacgtcatc ttcggtcttg cactgggcta caagtcggtc atcatcccca   3720
tcttcgccat tgccatctcc atcttcgtga gcttctcgtt cgcagccatg tacggtgttg   3780
ccgttgctgc attgggcatg ctctccacca tcgctactgg cctcgctatt gacgcgtatg   3840
gtccgatttc ggacaatgct ggagggattg ccgagatggc tgggatgtcg cacaggatca   3900
gagagcgtac ggatgcactg gatgctgcag ggaacactac cgctgccatt ggcaagggct   3960
ttgccatagg gtctgctgca ctcgttagcc tggccttgtt tggcgctttc gtgtcgagag   4020
ctggcatcca cacagtggac gttctgactc ccaaggtgat catcggactt ctggtgggag   4080
ctatgctccc gtactggttc tctgcgatga cgatgaagtc ggtcggatca gcagcgctga   4140
agatggtcga ggaggttagg aggcagttca acacgatccc cggattgatg gagggcacag   4200
ctaagccgga ctatgctacc tgcgtgaaga tctccacaga cgcctccatc aaggagatga   4260
tccctccagg gtgcctggtg atgcttactc cgctgattgt gggcttcttc ttcggcgtgg   4320
agacactttc cggcgtgttg gcaggaagcc tcgtgagtgg agtgcagatc gcgatcagtg   4380
ccagcaatac tggagggggca tgggacaacg cgaagaagta catcgaagcc ggcgtctcag   4440
aacacgcgaa gtctctgggt ccgaaagggt cagaacccca taaggccgct gtgatcggcg   4500
atacgattgg cgatcccttg aaggacactt ctggcccatc cctcaacatc ctgatcaagc   4560
tcatggcagt ggagagcctc gttttcgcgc ctttcttcgc gactcatggt ggcatcctgt   4620
tcaagtactt ctagagctcg catcatgatc atgcatcatg gactcggcct actactgtgg   4680
atttgtatgc cattatagac ttggtgctgt gaaagactgc ttgatgattt gcgggtttgt   4740
tgctgtgtaa aaaaggtcc cttggctccc agaagaccat gaaggttcgg atctatcatg   4800
taattccttg ttatctgcca attatgtatg gactatggac atgtgttgcg ctgttcaact   4860
tactactaca aataagtaat cgatatgttc ccttcccatg tctcggtgac aattgtctgg   4920
agaagcttag gggtcgtttg tttgggatta tgtctggaga aacttatttt aaactaagtg   4980
tgagttcaag ttaagttaga ttatataatc taggcagatt ataattccaa gcgaacaggt   5040
ccttagtgtt tttggaaaat cctaggtgtt cttttggcta cattgttgtg tgtgcagatc   5100
ccttgttggc ctgtaagcgt ggggaagtaa gaatcgtccg tttctactga agacctgctc   5160
gagttaggca ccgaggatgc cggtaaccaa acagagcaat agtgtctctg tgggcacagt   5220
```

```
ggagtgtgaa tctgtgtgat gcaaatccgt catttgttta gcaaaatttc cagcgttgca    5280
tgatgcagtt tctttaacac ggacttaagg gaagggaaaa aaatgttgag ccaggagatc    5340
cttcaatgtg ttagactgac gtgatagcca actaaaccac gacgcaatgt tgtcgttaat    5400
gacaaaaaaa ctatttgttc ctaaatcctt ggcgacattg catggctgtc tcatgagata    5460
atggtctcat ctcttattta tctcttattt atagccggaa gtggtagtga cccctgcttg    5520
attgctcgta tgccatctca agttctcaac cgtgtcgagc agccattttc ccatctcaag    5580
cgcatcatcg tttcgtttga cctcatctgc tatcctgctc ctagtgcaaa tcacatgcga    5640
cagaaagtgt cggaccgcag ctccagcttt tgttcccttt agtgagggtt aattgcgcgc    5700
ttggcgtaat catggtcata gctgtttcct gtgtgaaatt gttatccgct cacaattcca    5760
cacaacatac gagccggaag cataaagtgt aaagcctggg gtgcctaatg agtgagctaa    5820
ctcacattaa ttgcgttgcg ctcactgccc gctttccagt cgggaaacct gtcgtgccag    5880
ctgcattaat gaatcggcca acgcgcgggg agaggcggtt tgcgtattgg gcgctcttcc    5940
gcttcctcgc tcactgactc gctgcgctcg gtcgttcggc tgcggcgagc ggtatcagct    6000
cactcaaagg cggtaatacg gttatccaca gaatcagggg ataacgcagg aaagaacatg    6060
tgagcaaaag gccagcaaaa ggccaggaac cgtaaaaagg ccgcgttgct ggcgtttttc    6120
cataggctcc gcccccctga cgagcatcac aaaaatcgac gctcaagtca gaggtggcga    6180
aacccgacag gactataaag ataccaggcg tttccccctg gaagctccct cgtgcgctct    6240
cctgttccga cctgccgct taccggatac ctgtccgcct ttctcccttc gggaagcgtg    6300
gcgctttctc atagctcacg ctgtaggtat ctcagttcgg tgtaggtcgt tcgctccaag    6360
ctgggctgtg tgcacgaacc ccccgttcag cccgaccgct gcgccttatc cggtaactat    6420
cgtcttgagt ccaacccggt aagacacgac ttatcgccac tggcagcagc cactggtaac    6480
aggattagca gagcgaggta tgtaggcggt gctacagagt tcttgaagtg gtggcctaac    6540
tacggctaca ctagaaggac agtatttggt atctgcgctc tgctgaagcc agttaccttc    6600
ggaaaaagag ttggtagctc ttgatccggc aaacaaacca ccgctggtag cggtggtttt    6660
tttgtttgca agcagcagat tacgcgcaga aaaaaaggat ctcaagaaga tcctttgatc    6720
ttttctacgg ggtctgacgc tcagtggaac gaaaactcac gttaagggat tttggtcatg    6780
agattatcaa aaaggatctt cacctagatc cttttcgacc gaataaatac ctgtgacgga    6840
agatcacttc gcagaataaa taaatcctgg tgtccctgtt gataccggga agccctgggc    6900
caacttttgg cgaaaatgag acgttgatcg gcacgtaaga ggttccaact tcaccataa    6960 tgaaataaga tcactaccgg gcgtattttt tgagttgtcg agattttcag gagctaagga    7020
agctaaaatg gagaaaaaaa tcactggata taccaccgtt gatatatccc aatggcatcg    7080
taaagaacat tttgaggcat ttcagtcagt tgctcaatgt acctataacc agaccgttca    7140
gctggatatt acggccttt taagaccgt aaagaaaaat aagcacaagt tttatccggc    7200
ctttattcac attcttgccc gcctgatgaa tgctcatccg gaattacgta tggcaatgaa    7260
agacggtgag ctggtgatat gggatagtgt tcacccttgt tacaccgttt tccatgagca    7320
aactgaaacg ttttcatcgc tctggagtga ataccacgac gatttccggc agtttctaca    7380
catatattcg caagatgtgg cgtgttacgg tgaaaacctg gcctatttcc ctaaagggtt    7440
tattgagaat atgttttttcg tctcagccaa tccctgggtg agtttcacca gttttgattt    7500
aaacgtggcc aatatggaca acttcttcgc ccccgttttc actatgggca aatattatac    7560
gcaaggcgac aaggtgctga tgccgctggc gattcaggtt catcatgccg tttgtgatgg    7620
```

-continued

```
cttccatgtc ggcagaatgc ttaatgaatt acaacagtac tgcgatgagt ggcagggcgg      7680
ggcgtaattt ttttaaggca gttattggtg cccttaaacg cctggttgct acgcctgaat      7740
aagtgataat aagcggatga atggcagaaa ttcgaaagca aattcgaccc ggtcgtcggt      7800
tcagggcagg gtcgttaaat agccgcttat gtctattgct ggtttaccgg tttattgact      7860
accggaagca gtgtgaccgt gtgcttctca aatgcctgag gccagtttgc tcaggctctc      7920
cccgtggagg taataattga cgatatgatc cttttttttct gatcaaaagt gctcatcatt      7980
ggaaaacgtt cttcggggcg aaaactctca aggatcttac cgctgttgag atccagttcg      8040
atgtaaccca ctcgtgcacc caactgatct tcagcatctt ttactttcac cagcgtttct      8100
gggtgagcaa aaacaggaag gcaaaatgcc gcaaaaaagg gaataagggc gacacggaaa      8160
tgttgaatac tcatactctt cctttttcaa tattattgaa gcatttatca agggttattg      8220
tctcatgagc ggatacatat ttgaatgtat ttagaaaaat aaacaaatag gggttccgcg      8280
cacatttccc cgaaaagtgc cacctaaatt gtaagcgtta atattttgtt aaaattcgcg      8340 ttaaatttt gttaaatcag ctcatttttt aaccaatagg ccgaaatcgg caaaatccct      8400
tataaatcaa agaatagac cgagataggg ttgagtgttg ttccagtttg gaacaagagt      8460
ccactattaa agaacgtgga ctccaacgtc aaagggcgaa aaccgtcta tcagggcgat      8520 ggcccactac gtgaaccatc accctaatca agtttttgg ggtcgaggtg ccgtaaagca      8580
ctaaatcgga accctaaagg gagcccccga tttagagctt gacggggaaa gccggcgaac      8640
gtggcgagaa aggaagggaa gaaagcgaaa ggagcgggcg ctagggcgct ggcaagtgta      8700
gcggtcacgc tgcgcgtaac caccacaccc gccgcgctta atgcgccgct acagggcgcg      8760
tcccattcgc cattcaggct gcgcaactgt tgggaagggc gatcggtgcg ggcctcttcg      8820
ctattacgcc agctggcgaa aggggatgt gctgcaaggc gattaagttg ggtaacgcca      8880
gggttttccc agtcacgacg ttgtaaaacg acggccagtg agcgcgcgta atacgactca      8940
ctatagggcg aattgggtac g                                              8961
```

<210> SEQ ID NO 43
<211> LENGTH: 15301
<212> TYPE: DNA
<213> ORGANISM: Artificial sequence
<220> FEATURE:
<223> OTHER INFORMATION: ZmABP3-AtAVP1D binary construct

<400> SEQUENCE: 43

```
aattcctgtg gttggcatgc acatacaaat ggacgaacgg ataaaccttt tcacgccctt       60
ttaaatatcc gattattcta ataaacgctc ttttctctta ggtttacccg ccaatatatc      120
ctgtcaaaca ctgatagttt aaactgaagg cgggaaacga caatctgatc atgagcggag      180
aattaaggga gtcacgttat daccccccgcc gatgacgcgg gacaagccgt tttacgtttg      240
gaactgacag aaccgcaacg ctgcaggaat tggccgcagc ggccatttaa atcaattggg      300
cgcgccagct gcttgtgggg accagacaaa aaaggaatgg tgcagaattg ttaggcgcac      360
ctaccaaaag catctttgcc tttattgcaa agataaagca gattcctcta gtacaagtgg      420
ggaacaaaat aacgtggaaa agagctgtcc tgacagccca ctcactaatg cgtatgacga      480
acgcagtgac gaccacaaaa ctcgagactt tcaacaaag gtaatatcc ggaaacctcc      540 tcggattcca ttgcccagct atctgtcact ttattgtgaa gatagtggaa aaggaaggtg      600
gctcctacaa atgccatcat tgcgataaag gaaaggctat cgttgaagat gcctctgccg      660
```

```
acagtggtcc caaagatgga cccccaccca cgaggagcat cgtggaaaaa gaagacgttc      720
caaccacgtc ttcaaagcaa gtggattgat gtgatatctc cactgacgta agggatgacg      780
aacaatccca ctatccttcg gtaccggacc caaagtagca acaacaggt tcatgtgcac       840 tataaaaaga caaattctc gagtttcatc ttttattcca cataagcctt atattttcca       900
ttttcatatg atttttagtt taagtttgtg tcttaacttt ttcgttaata cgtaattcta     960
tgcattatgg atgcgtgaag tattttttgtt taaaaaaatg aaatgtcaaa atacgttttg     1020
tgatctattt ccatgttttc acctaacagg tggttttac tatatattct gccataactc      1080
tagccttaga tgtaaatcga aaaaaaatga gagatgagct ggagatagcc ttagatgaag      1140
cgtctgaaat ataaaagaaa gagtaatgtt gaacgcagta ggtgtagcag ctgtagttcc      1200
atctctagga aagggaactg caatccgggc tccgggcctc gcgcaatctg gcctgtcgtg      1260
tagatgcagc cctgtccatg acggcccaag caacgcccgc ggctctcgat ccaccacgga      1320
acccactccg acacacactg acacacacat gctggatgtg gatgtgctgt ccaattatta     1380
gtagcaattc ggtaggcaca ggcacgtact ggccggtgtt ttagctgtaa gtaccgaacc     1440
aatcacggtt aagaaccgat taatccgtgc ccagccgccg agtgcgttcg tacgtgcatc     1500
ggatgcactg catgaattga gagcatcatc atatcatacg caggagtagt acgacgccgc     1560
tgctgtcttg tccggctaat gctttgctca cagattagtc catcgcccac ggtcggtgtg     1620
gtgtggatcg ctgatgccac tgcttttttgt ttggttttta ttcccctgat aatcctccgc    1680
gtccctgaat gtatctattt attttcattc cgaaatccct ttcacgaaaa agaaaacgaa      1740
taaaaagaga gttacgaata cgcttccggc ggcccacatc accttccagc gaacatcgcg      1800
ccgcgctgac gtgtcgccca tcgcggccgt ccatatcgcc atccgacgac cgtggaagct     1860
ggcagcggcc gctccgttcc gtcgaagggg caggtcagtc aggtcaccca cacggccaca     1920
cccgcgcggg ggatacgcgg tggaaaaccc ggcgaccaca tcaaaacacg aggcgtctcc     1980
cgcaggactg gtcactcggc acgcaggcag aggcagcaca gcagcagcca gctccatcca     2040
tcctctttcc cctcctcgct tcgcttcctc ggcggattcc tcctccctcg gccgtccccg      2100
tccccttctt cgccgcgcca gctcgcccga gttggtaagg ccccctccac ccctccgctt    2160
cccctccccc gggcgcgctc tggcttcctc cccggatcgg cgcggggcgt gctggctccg     2220
cgcctgattt cgggccttttt gtttccttct cgccgagcgc tcgtgtaacg cttcggatct     2280
agctggattc aggcgggatc gcggccgctc ggcttcctcg tggcctgatt cgtggttttc     2340
ctcggggagg gaatcctgat cggatcatcg ggattcctcg tgcggccggg acacgcttgc     2400
gagccagaaa catagtctgc gtggccggga ttccacgatc tgtgatctag acgtcgggcg     2460
cttcgtctat gtgctcgctg caggctgtgg cgtactggcg tggtgcgcgg ccgctatgga     2520
tccgtgcttg tttgttcgcc ctgtagcgtg tgaaatcgag ctgtgtagat ctatggtctg     2580
cgaggtgcgg tggcggtgga atctcggttg atctttacct cagcggcgcc agtgtagctc     2640
gtgtggctgc agttcatctg cgaatttggc tctcggcggc ttaggtcgcg gagcttggat     2700
tatggagcac cagctgcagc gtgaccctgt tggttctcat gtggatctgt ggctgaggt      2760 tgcagacttc aagtgccact gccattgacc ggagctgctg cacgattata ctggaatatc     2820
tagcggtagt atactctgct agtactcaat acgggtctcc tgacaaatgt ctttcgtgtt     2880
tagggaccta gcactctagt gtcaagacta tttgctggaa tatctaatat tagcagtttc     2940
tgtagtggct cagttgcagc ctggtttaga atgatgggga cagttggctg tgccatgcaa     3000
aataaagtgt gtgaaagcaa ctgcctctta aactatgggt ggtgcaagca ggttatttga     3060
```

-continued

```
agggactctc cacactgtat ctccagttaa ctttgactga acttgtggtc gcaggcaaac    3120
ccaccatggt tgcaccagca ttgcttccgg aactgtggac ggagatactg gtcccaatct    3180
gcgctgtgat cggcatagcc ttcagcctgt ccagtggta cgtcgtgtca agggtgaagc    3240
tcacgagcga cttgggagcc agtagtagcg agggggcgaa caacgggaag aacggctatg    3300
gcgactatct gatcgaggag gaagagggtg tgaacgacca atcagtggtg gcgaagtgtg    3360
cggagattca gaccgccatt agcgagggag ctacgagctt cctgtttacg gagtacaagt    3420
acgtgggcgt cttcatgatc ttcttcgctg ccgtcatctt cgtgttcctg ggttctgtcg    3480
aaggcttctc caccgacaac aagccgtgca cttacgacac caccagaacc tgcaaacctg    3540
cactggccac tgctgcgttc tccaccatag cgttcgtgct tggtgctgtg acaagcgtcc    3600
tgagtggctt cttggggatg aagatcgcta cctacgccaa tgccagaacc acactggagg    3660
caaggaaagg tgtcgggaaa gccttcatcg tggcctttcg gagtggtgct gtcatgggct    3720
tcctgcttgc tgccagtgga ttgctcgtgc tctacatcac catcaacgtg ttcaagatct    3780
actacggcga cgattgggaa gggctcttcg acgcaatcac tggctatggg ttgggtggct    3840
cttcaatggc gctcttcgga agagtgggag gtggcatcta cacgaaagcg gctgatgtgg    3900
gagctgacct ggtcgggaag atcgagcgca acatcccgga agatgaccca aggaacccag    3960
cagtgatcgc cgacaatgtc ggcgacaatg tcggtgacat agcgggtatg ggaagcgacc    4020
tctttggctc atacgccgaa gccagctgcg cagcgcttgt tgtcgcctcc atctccagct    4080
tcggatcaa ccacgacttc acagccatgt gctatcccct cctgatcagc agcatgggca    4140
tactggtgtg cctcatcacc acgctgtttg cgaccgactt cttcgagatc aagctggtga    4200
aggagatcga acctgcgctg aagaaccagc tgatcatctc gaccgtgatc atgaccgttg    4260
ggatcgccat cgtctcatgg gtgggtcttc ctacctcgtt caccatcttc aactttggca    4320
ctcagaaggt ggtgaagaac tggcagctct cctctgcgt ttgcgtcgga ctttgggctg    4380
ggctgatcat cggctttgtc acggagtact acacctccaa cgcctacagt cctgtgcagg    4440
atgtggccga ttcttgccgt actggtgctg caacgaacgt catcttcggt cttgcactgg    4500
gctacaagtc ggtcatcatc cccatcttcg ccattgccat ctccatcttc gtgagcttct    4560
cgttcgcagc catgtacggt gttgccgttg ctgcattggg catgctctcc accatcgcta    4620
ctggcctcgc tattgacgcg tatggtccga tttcggacaa tgctggaggg attgccgaga    4680
tggctgggat gtcgcacagg atcagagagc gtacggatgc actggatgct gcagggaaca    4740
ctaccgctgc cattggcaag ggctttgcca tagggtctgc tgcactcgtt agcctggcct    4800
tgtttggcgc tttcgtgtcg agagctggca tccacacagt ggacgttctg actcccaagg    4860
tgatcatcga acttctggtg ggagctatgc tcccgtactg gttctctgcg atgacgatga    4920
agtcggtcgg atcagcagcg ctgaagatgg tcgaggaggt taggaggcag ttcaacacga    4980
tccccggatt gatggagggc acagctaagc cggactatgc tacctgcgtg aagatctcca    5040
cagacgcctc catcaaggag atgatcctc cagggtgcct ggtgatgctt actccgctga    5100
ttgtgggctt cttcttcggc gtggagacac tttccggcgt gttggcagga agcctcgtga    5160
gtggagtgca gatcgcgatc agtgccagca atactggagg ggcatgggac aacgcgaaga    5220
agtacatcga agccggcgtc tcagaacacg cgaagtctct gggtccgaaa gggtcagaac    5280
cccataaggc cgctgtgatc ggcgatacga ttggcgatcc cttgaaggac acttctggcc    5340
catccctcaa catcctgatc aagctcatgg cagtggagag cctcgttttc gcgcctttct    5400
```

```
tcgcgactca tggtggcatc ctgttcaagt acttctagag ctcgcatcat gatcatgcat    5460
catggactcg gcctactact gtggatttgt atgccattat agacttggtg ctgtgaaaga    5520
ctgcttgatg atttgcgggt tgttgctgt gtaaaaaaag gtcccttggc tcccagaaga    5580
ccatgaaggt tcggatctat catgtaattc cttgttatct gccaattatg tatggactat    5640
ggacatgtgt tgcgctgttc aacttactac tacaaataag taatcgatat gttcccttcc    5700
catgtctcgg tgacaattgt ctggagaagc ttagggtcg tttgtttggg attatgtctg     5760
gagaaactta ttttaaacta agtgtgagtt caagttaagt tagattatat aatctaggca    5820
gattataatt ccaagcgaac aggtccttag tgttttttgga aaatcctagg tgttcttttg   5880
gctacattgt tgtgtgtgca gatcccttgt tggtctgtaa gcgtggggaa gtaagaatcg    5940
tccgtttcta ctgaagacct gctcgagtta ggcaccgagg atgccggtaa ccaaacagag    6000
caatagtgtc tatgtgggca cagtggagtg tgaatctgtg tgatgcaaat ccgtcatttg    6060
tttagcaaaa tttccagcgt tgcatgatgc agtttcttta acacggactt aagggaaggg    6120
aaaaaaatgt tgagccagga gatccttcaa tgtgttagac tgacgtgata gccaactaaa    6180
ccacgacgca atgttgtcgt taatgacaaa aaaactatt gttcctaaat ccttggcgac     6240
attgcatggc tgtctcatga gataatggtc tcatctctta tttatctctt atttatagcc    6300
ggaagtggta gtgaccctg cttgattgct cgtatgccat ctcaagttct caaccgtgtc     6360
gagcagccat tttcccatct caagcgcatc atcgtttcgt tgacctcat ctgctatcct     6420 gctcctagtg caaatcacat gcgacagaaa gtgtcggacc gcgatcgctt aattaagctt    6480
gcatgcctgc agtgcagcgt gacccggtcg tgcccctctc tagagataat gagcattgca    6540
tgtctaagtt ataaaaaatt accacatatt ttttttgtca cacttgtttg aagtgcagtt    6600
tatctatctt tatacatata tttaaacttt actctacgaa taatataatc tatagtacta    6660
caataatatc agtgttttag agaatcatat aaatgaacag ttagacatgg tctaaaggac    6720
aattgagtat tttgacaaca ggactctaca gttttatctt tttagtgtgc atgtgttctc    6780 ctttttttt gcaaatagct tcacctatat aatacttcat ccatttatt agtacatcca      6840 tttagggttt agggttaatg gttttttatag actaattttt ttagtacatc tattttattc   6900
tattttagcc tctaaattaa gaaaactaaa actctatttt agttttttta tttaataatt    6960
tagatataaa atagaataaa ataaagtgac taaaaattaa acaaataccc tttaagaaat    7020
taaaaaaact aaggaaacat ttttcttgtt tcgagtagat aatgccagcc tgttaaacgc    7080
cgtcgacgag tctaacggac accaaccagc gaaccagcag cgtcgcgtcg gccaagcga    7140 agcagacggc acggcatctc tgtcgctgcc tctggacccc tctcgagagt tccgctccac    7200
cgttggactt gctccgctgt cggcatccag aaattgcgtg gcggagcggc agacgtgagc    7260
cggcacggca ggcggcctcc tcctcctctc acggcaccgg cagctacggg ggattccttt    7320
cccaccgctc cttcgctttc ccttcctcgc ccgccgtaat aaatagacac ccctccaca    7380 ccctctttcc ccaacctcgt gttgttcgga gcgcacacac acacaaccag atctccccca    7440
aatccacccg tcggcacctc cgcttcaagg tacgccgctc gtcctccccc cccccccctc    7500
tctaccttct ctagatcggc gttccggtcc atggttaggg cccggtagtt ctacttctgt    7560
tcatgtttgt gttagatccg tgtttgtgtt agatccgtgc tgctagcgtt cgtacacgga    7620
tgcgacctgt acgtcagaca cgttctgatt gctaacttgc cagtgtttct ctttggggaa    7680
tcctgggatg gctctagccg ttccgcagac gggatcgatt tcatgatttt ttttgtttcg    7740
ttgcataggg tttggtttgc ccttttcctt tatttcaata tatgccgtgc acttgtttgt    7800
```

```
cgggtcatct tttcatgctt ttttttgtct tggttgtgat gatgtggtct ggttgggcgg    7860
tcgttctaga tcggagtaga attctgtttc aaactacctg gtggatttat taattttgga    7920
tctgtatgtg tgtgccatac atattcatag ttacgaattg aagatgatgg atggaaatat    7980
cgatctagga taggtataca tgttgatgcg ggttttactg atgcatatac agagatgctt    8040
tttgttcgct tggttgtgat gatgtggtgt ggttgggcgg tcgttcattc gttctagatc    8100
ggagtagaat actgtttcaa actacctggt gtatttatta attttggaac tgtatgtgtg    8160
tgtcatacat cttcatagtt acgagtttaa gatggatgga aatatcgatc taggataggt    8220
atacatgttg atgtgggttt tactgatgca tatacatgat ggcatatgca gcatctattc    8280
atatgctcta accttgagta cctatctatt ataataaaca agtatgtttt ataattattt    8340
tgatcttgat atacttggat gatggcatat gcagcagcta tatgtggatt tttttagccc    8400
tgccttcata cgctatttat ttgcttggta ctgtttcttt tgtcgatgct caccctgttg    8460
tttggtgtta cttctgcagg gatccccgat catgcaaaaa ctcattaact cagtgcaaaa    8520
ctatgcctgg ggcagcaaaa cggcgttgac tgaactttat ggtatggaaa atccgtccag    8580
ccagccgatg gccgagctgt ggatgggcgc acatccgaaa agcagttcac gagtgcagaa    8640
tgccgccgga gatatcgttt cactgcgtga tgtgattgag agtgataaat cgactctgct    8700
cggagaggcc gttgccaaac gctttggcga actgcctttc ctgttcaaag tattatgcgc    8760
agcacagcca ctctccattc aggttcatcc aaacaaacac aattctgaaa tcggttttgc    8820
caaagaaaat gccgcaggta tcccgatgga tgccgccgag cgtaactata aagatcctaa    8880
ccacaagccg gagctggttt tgcgctgac gcctttcctt gcgatgaacg cgtttcgtga    8940
attttccgag attgtctccc tactccagcc ggtcgcaggt gcacatccgg cgattgctca    9000
cttttttacaa cagcctgatg ccgaacgttt aagcgaactg ttcgccagcc tgttgaatat    9060
gcagggtgaa gaaaaatccc gcgcgctggc gattttaaaa tcggccctcg atagccagca    9120
gggtgaaccg tggcaaacga ttcgtttaat ttctgaattt tacccggaag acagcggtct    9180
gttctccccg ctattgctga atgtggtgaa attgaaccct ggcgaagcga tgttcctgtt    9240
cgctgaaaca ccgcacgctt acctgcaagg cgtggcgctg gaagtgatgg caaactccga    9300
taacgtgctg cgtgcgggtc tgacgcctaa atacattgat attccggaac tggttgccaa    9360
tgtgaaattc gaagccaaac cggctaacca gttgttgacc cagccggtga acaaggtgc     9420
agaactggac ttcccgattc cagtggatga ttttgccttc tcgctgcatg accttagtga    9480
taaagaaacc accattagcc agcagagtgc cgccattttg ttctgcgtcg aaggcgatgc    9540
aacgttgtgg aaaggttctc agcagttaca gcttaaaccg ggtgaatcag cgtttattgc    9600
cgccaacgaa tcaccggtga ctgtcaaagg ccacggccgt ttagcgcgtg tttacaacaa    9660
gctgtaagag cttactgaaa aaattaacat ctcttgctaa gctgggagct cgatccgtcg    9720
acctgcagat cgttcaaaca tttggcaata agtttctta agattgaatc ctgttgccgg    9780
tcttgcgatg attatcatat aatttctgtt gaattacgtt aagcatgtaa taattaacat    9840
gtaatgcatg acgttattta tgagatgggt ttttatgatt agagtcccgc aattatacat    9900
ttaatacgcg atagaaaaca aaatatagcg cgcaaactag gataaattat cgcgcgcggt    9960
gtcatctatg ttactagatc tgctagccct gcaggaaatt taccggtgcc cgggcggcca   10020
gcatggccgt atccgcaatg tgttattaag ttgtctaagc gtcaatttgt ttacaccaca   10080
atatatcctg ccaccagcca gccaacagct ccccgaccgg cagctcggca caaaatcacc   10140
```

```
actcgataca ggcagcccat cagaattaat tctcatgttt gacagcttat catcgactgc   10200
acggtgcacc aatgcttctg gcgtcaggca gccatcggaa gctgtggtat ggctgtgcag   10260
gtcgtaaatc actgcataat tcgtgtcgct caaggcgcac tcccgttctg gataatgttt   10320
tttgcgccga catcataacg gttctggcaa atattctgaa atgagctgtt gacaattaat   10380
catccggctc gtataatgtg tggaattgtg agcggataac aatttcacac aggaaacaga   10440
ccatgaggga agcgttgatc gccgaagtat cgactcaact atcagaggta gttggcgtca   10500
tcgagcgcca tctcgaaccg acgttgctgg ccgtacattt gtacggctcc gcagtggatg   10560
gcggcctgaa gccacacagt gatattgatt tgctggttac ggtgaccgta aggcttgatg   10620
aaacaacgcg gcgagctttg atcaacgacc ttttggaaac ttcggcttcc cctggagaga   10680
gcgagattct ccgcgctgta gaagtcacca ttgttgtgca cgacgacatc attccgtggc   10740
gttatccagc taagcgcgaa ctgcaatttg gagaatggca gcgcaatgac attcttgcag   10800
gtatcttcga gccagccacg atcgacattg atctggctat cttgctgaca aaagcaagag   10860
aacatagcgt tgccttggta ggtccagcgg cggaggaact ctttgatccg gttcctgaac   10920
aggatctatt tgaggcgcta aatgaaacct taacgctatg gaactcgccg cccgactggg   10980
ctggcgatga gcgaaatgta gtgcttacgt tgtcccgcat ttggtacagc gcagtaaccg   11040
gcaaaatcgc gccgaaggat gtcgctgccg actgggcaat ggagcgcctg ccggcccagt   11100
atcagcccgt catacttgaa gctaggcagg cttatcttgg acaagaagat cgcttggcct   11160
cgcgcgcaga tcagttggaa gaatttgttc actacgtgaa aggcgagatc accaaagtag   11220
tcggcaaata aagctctagt ggatctccgt acccggggat ctggctcgcg gcggacgcac   11280
gacgccgggg cgagaccata ggcgatctcc taaatcaata gtagctgtaa cctcgaagcg   11340
tttcacttgt aacaacgatt gagaattttt gtcataaaat tgaaatactt ggttcgcatt   11400
tttgtcatcc gcggtcagcc gcaattctga cgaactgccc atttagctgg agatgattgt   11460
acatccttca cgtgaaaatt tctcaagcgc tgtgaacaag ggttcagatt ttagattgaa   11520
aggtgagccg ttgaaacacg ttcttcttgt cgatgacgac gtcgctatgc ggcatcttat   11580
tattgaatac cttacgatcc acgccttcaa agtgaccgcg gtagccgaca gcacccagtt   11640
cacaagagta ctctcttccg cgacggtcga tgtcgtggtt gttgatctag atttaggtcg   11700
tgaagatggg ctcgagatcg ttcgtaatct ggcggcaaag tctgatattc caatcataat   11760
tatcagtggc gaccgccttg aggagacgga taaagttgtt gcactcgagc taggagcaag   11820
tgattttatc gctaagccgt tcagtatcag agagtttcta gcacgcattc gggttgcctt   11880
gcgcgtgcgc cccaacgttg tccgctccaa agaccgacgg tcttttttgtt ttactgactg   11940
gacacttaat ctcaggcaac gtcgcttgat gtccgaagct ggcggtgagg tgaaacttac   12000
ggcaggtgag ttcaatcttc tcctcgcgtt tttagagaaa ccccgcgacg ttctatcgcg   12060
cgagcaactt ctcattgcca gtcgagtacg cgacgaggag gtttatgaca ggagtataga   12120
tgttctcatt ttgaggctgc gccgcaaact tgaggcagat ccgtcaagcc ctcaactgat   12180
aaaaacagca agaggtgccg gttatttctt tgacgcggac gtgcaggttt cgcacggggg   12240
gacgatggca gcctgagcca attcccagat ccccgaggaa tcgcgtgag cggtcgcaaa   12300
ccatccggcc cggtacaaat cggcgcggcg ctgggtgatg acctggtgga gaagttgaag   12360
gccgcgcagg ccgcccagcg gcaacgcatc gaggcagaag cacgcccgg tgaatcgtgg   12420
caagcggccg ctgatcgaat ccgcaaagaa tcccggcaac cgccgcagc cggtgcgccc   12480
tcgattagga agccgcccaa gggcgacgag caaccagatt ttttcgttcc gatgctctat   12540
```

```
gacgtgggca cccgcgatag tcgcagcatc atggacgtgg ccgttttccg tctgtcgaag   12600
cgtgaccgac gagctggcga ggtgatccgc tacgagcttc cagacgggca cgtagaggtt   12660
tccgcagggc cggccggcat ggccagtgtg tgggattacg acctggtact gatggcggtt   12720
tcccatctaa ccgaatccat gaaccgatac cgggaaggga agggagacaa gcccggccgc   12780
gtgttccgtc cacacgttgc ggacgtactc aagttctgcc ggcgagccga tggcggaaag   12840
cagaaagacg acctggtaga aacctgcatt cggttaaaca ccacgcacgt tgccatgcag   12900
cgtacgaaga aggccaagaa cggccgcctg gtgacggtat ccgagggtga agccttgatt   12960
agccgctaca agatcgtaaa gagcgaaacc gggcggccgg agtacatcga gatcgagcta   13020
gctgattgga tgtaccgcga gatcacagaa ggcaagaacc cggacgtgct gacggttcac   13080
cccgattact ttttgatcga tcccggcatc ggccgttttc tctaccgcct ggcacgccgc   13140
gccgcaggca aggcagaagc cagatggttg ttcaagacga tctacgaacg cagtggcagc   13200 gccgagagt tcaagaagtt ctgtttcacc gtgcgcaagc tgatcgggtc aaatgacctg   13260
ccggagtacg atttgaagga ggaggcgggg caggctggcc cgatcctagt catgcgctac   13320
cgcaacctga tcgagggcga agcatccgcc ggttcctaat gtacgagca gatgctaggg   13380 caaattgccc tagcagggga aaaggtcga aaggtctct ttcctgtgga tagcacgtac   13440
attgggaacc caaagccgta cattgggaac cggaacccgt acattgggaa cccaaagccg   13500
tacattggga accggtcaca catgtaagtg actgatataa aagagaaaaa aggcgatttt   13560
tccgcctaaa actctttaaa acttattaaa actcttaaaa cccgcctggc ctgtgcataa   13620
ctgtctggcc agcgcacagc cgaagagctg caaaaagcgc ctacccttcg gtcgctgcgc   13680
tccctacgcc ccgccgcttc gcgtcggcct atcgcggccg ctggccgctc aaaaatggct   13740
ggcctacggc caggcaatct accagggcgc ggacaagccg cgccgtcgcc actcgaccgc   13800
cggcgctgag gtctgcctcg tgaagaaggt gttgctgact cataccaggc ctgaatcgcc   13860
ccatcatcca gccagaaagt gagggagcca cggttgatga gagctttgtt gtaggtggac   13920
cagttggtga ttttgaactt ttgctttgcc acggaacggt ctgcgttgtc gggaagatgc   13980
gtgatctgat ccttcaactc agcaaaagtt cgatttattc aacaaagccg ccgtcccgtc   14040
aagtcagcgt aatgctctgc cagtgttaca accaattaac caattctgat tagaaaaact   14100
catcgagcat caaatgaaac tgcaatttat tcatatcagg attatcaata ccatatttt   14160 gaaaaagccg tttctgtaat gaaggagaaa actcaccgag gcagttccat aggatggcaa   14220
gatcctggta tcggtctgcg attccgactc gtccaacatc aatacaacct attaatttcc   14280
cctcgtcaaa ataaggttta tcaagtgaga atcaccatg agtgacgact gaatccggtg   14340
agaatggcaa aagctctgca ttaatgaatc ggccaacgcg cggggagagg cggtttgcgt   14400
attgggcgct cttccgcttc ctcgctcact gactcgctgc gctcggtcgt tcggctgcgg   14460
cgagcggtat cagctcactc aaaggcggta atacggttat ccacagaatc aggggataac   14520
gcaggaaaga acatgtgagc aaaaggccag caaaaggcca ggaaccgtaa aaaggccgcg   14580
ttgctggcgt ttttccatag gctccgcccc cctgacgagc atcacaaaaa tcgacgctca   14640
agtcagaggt ggcgaaaccc gacaggacta taaagatacc aggcgtttcc ccctggaagc   14700
tccctcgtgc gctctcctgt tccgaccctg ccgcttaccg gatacctgtc gcctttctc   14760 ccttcgggaa gcgtggcgct ttctcatagc tcacgctgta ggtatctcag ttcggtgtag   14820
gtcgttcgct ccaagctggg ctgtgtgcac gaaccccccg ttcagcccga ccgctgcgcc   14880
```

-continued

| | |
|---|---|
| ttatccggta actatcgtct tgagtccaac ccggtaagac acgacttatc gccactggca | 14940 |
| gcagccactg gtaacaggat tagcagagcg aggtatgtag gcggtgctac agagttcttg | 15000 |
| aagtggtggc ctaactacgg ctacactaga agaacagtat ttggtatctg cgctctgctg | 15060 |
| aagccagtta ccttcggaaa aagagttggt agctcttgat ccggcaaaca aaccaccgct | 15120 |
| ggtagcggtg gttttttgt ttgcaagcag cagattacgc gcagaaaaaa aggatctcaa | 15180 |
| gaagatcctt tgatcttttc tacggggtct gacgctcagt ggaacgaaaa ctcacgttaa | 15240 |
| gggattttgg tcatgagatt atcaaaaagg atcttcacct agatcctttt gatccggaat | 15300 |
| t | 15301 |

<210> SEQ ID NO 44
<211> LENGTH: 8342
<212> TYPE: DNA
<213> ORGANISM: Artificial sequence
<220> FEATURE:
<223> OTHER INFORMATION: plasmid 15772 ZmABT Assembly

<400> SEQUENCE: 44

| | |
|---|---|
| ccccgaccag cgcgacatgc atggcatggc aaactatata tcgtcatcat cattattatc | 60 |
| atctgaccct cttttttttt cactctcact cccatgtttt tattcccggg cggggccgtg | 120 |
| tgggtgtggg ttgggatggc cggattgggc tcccggggtg gagaaatgac aaatccaggc | 180 |
| ccgcaggcgg ccacccacca aatcggacga cgcagggtgc ccaaatcagg aaggatttta | 240 |
| aggttaaccg gccaccggcg gtgaccgacg ccccacccca ctctccttct cctattctat | 300 |
| ctatatatca cccgcctctt ttttctccct cactccgcca caccttccct cttcttcctc | 360 |
| agctccgtcg cccaccgccg gagcaccgaa aggccccgcg cccgccgcct ttcctgtaaa | 420 |
| aaacccaacc tttagctagc taaccgctcc tcttctcccc ctactcccct tgcccaaatc | 480 |
| agagaagata tttaacggag gaggggaagg agaggatatt tagctgattg ttgattggtg | 540 |
| gtccggggta cggtgttctt gagtcgtgaa gcgaccgtac agtggctagg gccgtctccg | 600 |
| ggttgcgtgc aggatggtcg tcagagatcg ggagtgagga ggcagctcgt ggtcgtggag | 660 |
| gctaaatgta ccgcaagaac gactcggcac tctcctgttt ctacctcttc ctcctctggt | 720 |
| tcttcttctt gaaatagacc agcgccagcc accaggtagc tacctactag ctagcagccc | 780 |
| agttgcgact ggggacgggc tgctgcttgc aagttggaat cttggagcag gagcagagga | 840 |
| gcgggagatg gagctggatc tgaacgtggc cgaggtggcg ccggagaagc catcggcggc | 900 |
| gctggaggcg agcgactcgg ggtcctcggg ctcgtcggtg ctgaacgcgg aggcggcatc | 960 |
| ggcgggcggc gggggccccg cgccggggga ggaggggtca agctcgacgc cggccgtgct | 1020 |
| cgagttcagc atcctcagga gcgacagcga cgcggccggc gcggacgccg acgacggcga | 1080 |
| cgccacgccg tcgccacctc gccaccacca gcagcagctc gtcacccggg agcacttccc | 1140 |
| ggcgccgcag cattgggccg agcacggctt cttccgcgcc ggcccgcagc agcagccgga | 1200 |
| catcagggtc ctgccgcacc cgcacccgta cccgccccg ccgccgcccg cgcagccgca | 1260 |
| gcaggccaag aagagccgcc gcggcccgcg ctcccgcagc tcgcagtacc gcggcgtcac | 1320 |
| cttctaccgc cgcaccggcc gctgggagtc ccacatctgg tcagtagcac tgcaagctca | 1380 |
| ccatgcgccc tttcacctac cgaccaataa tcgcttgtga ttctgacacc caaatgtttc | 1440 |
| gtcttcctgt gctgtcctgt tcctcggaaa tggcagggat tgcgggaagc aggtgtactt | 1500 |
| aggtgagcag caataagcag atcgatctgc agcataaatt tcccgttatt aactagttcg | 1560 |
| tgatctcgat cgaatggcct aattaaccga ttcggtgatc tggccgatgg ccaatctacg | 1620 |

```
caggtggatt cgacactgct catgccgctg caaggtaacg atcaatccat ccatccaccc    1680
ttgtctagct accccaccga ccggccggat taatggaccg ctagctctcg ggacgggctt    1740
gctgcagggc gtacgaccga gcggcgatca agttccgcgg cgtcgacgcc gacataaact    1800
tcaacctcag cgactacgac gacgatatga agcaggtaca tacacgagtg ttcttgcagc    1860
tagcaccgac tgaaacatct gctgaacgta cacgcatggc cctgtgcacc agatgaagag    1920
cctgtccaag gaggagttcg ttcacgccct gcggcggcag agcaccggct tctcccgcgg    1980
cagctccaag tacaggggcg tcaccctgca caagtgcggc cgctgggagg cgcgcaaggg    2040
gcagttcctc ggcaagaagt aagaaacaac acttcgtttg caggcgctgt actttgctgc    2100
agattatttc atttcatcct tgcatgtgcc tttcctttcc atccactcac ttgatggctg    2160
tagtctcgat agagttcgtt cgttcgtact tcgcaccaga tgaactccca cgcacatgat    2220
ttagtactag ttttaccatg cattgttcag taaaagtata tgcttgcttg atcagtggtt    2280
gtttcaatca gaagattaaa aaaacggaat attaatataa aaaaaagggg aagtggctag    2340
ggaattcctc agtcctagct agctagctca ccggtgggaa cgccatgctt ggcttgggtg    2400
caggtacata tatcttgggc tattcgacag cgaagtagag gctgcaaggt tgttcacctc    2460
ggacgattct gccatttgtt catatacacc atgccttttg atttctctct tgcaatttct    2520
cttcttttat catggctttt gattcccaaa gggttgagta ccgactcgat attcgattct    2580
ccctgccgtt tcgtgacccc agggcgtacg acaaggcccc accatggtac gtcctgtaga    2640
aaccccaacc cgtgaaatca aaaaactcga cggcctgtgg gcattcagtc tggatcgcga    2700
aaactgtgga attgatcagc gttggtggga agcgcgttac aagaaagcc gggcaattgc     2760
tgtgccaggc agtttttaacg atcagttcgc cgatgcagat attcgtaatt atgcgggcaa    2820
cgtctggtat cagcgcgaag tctttatacc gaaaggttgg gcaggccagc gtatcgtgct    2880
gcgtttcgat gcggtcactc attacggcaa agtgtgggtc aataatcagg aagtgatgga    2940
gcatcagggc ggctatacgc catttgaagc cgatgtcacg ccgtatgtta ttgccgggaa    3000
aagtgtacgt atcaccgttt gtgtgaacaa cgaactgaac tggcagacta tcccgccggg    3060
aatggtgatt accgacgaaa acggcaagaa aaagcagtct tacttccatg atttctttaa    3120
ctatgccgga atccatcgca gcgtaatgct ctacaccacg ccgaacacct gggtggacga    3180
tatcaccgtg gtgacgcatg tcgcgcaaga ctgtaaccac gcgtctgttg actggcaggt    3240
accaagctgc gaatcttcgt ttttttaagg aattctcgat ctttatggtg tataggctct    3300
gggttttctg tttttttgtat ctcttaggat tttgtaaatt ccagatcttt ctatggccac    3360
ttagtagtat atttcaaaaa ttctccaatc gagttcttca ttcgcatttt cagtcatttt    3420
ctcttcgacg ttgtttttaa gcctgggtat tactcctatt tagttgaact ctgcagcaat    3480
cttagaaaat tagggttttg aggtttcgat ttctctaggt aaccgatcta ttgcattcat    3540
ctgaatttct gcatatatgt cttagatttc tgataagctt acgatacgtt aggtgtaatt    3600
gaagtttatt tttcaagagt gttattttt gtttctgaat ttttcaggtg gtggccaatg     3660
gtgatgtcag cgttgaactg cgtgatgcgg atcaacaggt ggttgcaact ggacaaggca    3720
ctagcgggac tttgcaagtg gtgaatccgc acctctggca accgggtgaa ggttatctct    3780
atgaactgtg cgtcacagcc aaaagccaga cagagtgtga tatctacccg cttcgcgtcg    3840
gcatccggtc agtggcagtg aagggcgaac agttcctgat taaccacaaa ccgttctact    3900
ttactggctt tggtcgtcat gaagatgcgg acttgcgtgg caaaggattc gataacgtgc    3960
```

```
tgatggtgca cgaccacgca ttaatggact ggattggggc caactcctac cgtacctcgc    4020
attacccta  cgctgaagag atgctcgact gggcagatga acatggcatc gtggtgattg    4080
atgaaactgc tgctgtcggc tttaacctct ctttaggcat tggtttcgaa gcgggcaaca    4140
agccgaaaga actgtacagc gaagaggcag tcaacgggaa aactcagcaa gcgcacttac    4200
aggcgattaa agagctgata gcgcgtgaca aaaaccaccc aagcgtggtg atgtggagta    4260
ttgccaacga accggatacc cgtccgcaag gtgcacggga atatttcgcg ccactggcgg    4320
aagcaacgcg taaactcgac ccgacgcgtc cgatcacctg cgtcaatgta atgttctgcg    4380
acgctcacac cgataccatc agcgatctct tgatgtgct  gtgcctgaac cgttattacg    4440
gatggtatgt ccaaagcggc gatttggaaa cggcagagaa ggtactggaa aaagaacttc    4500
tggcctggca ggagaaactg catcagccga ttatcatcac cgaatacggc gtggatacgt    4560
tagccgggct gcactcaatg tacaccgaca tgtggagtga agagtatcag tgtgcatggc    4620
tggatatgta tcaccgcgtc tttgatcgcg tcagcgccgt cgtcggtgaa caggtatgga    4680
atttcgccga ttttgcgacc tcgcaaggca tattgcgcgt tggcggtaac aagaaaggga    4740
tcttcactcg cgaccgcaaa ccgaagtcgg cggcttttct gctgcaaaaa cgctggactg    4800
gcatgaactt cggtgaaaaa ccgcagcagg gaggcaaaca atgagagctc gaatcgaaga    4860
agccacactg taaatctgcc gggaagcggc tggtggcatc cggcccgctc ctccctccgg    4920
gcgccgcaac ttttttcgat cggttttgcg ccgcccggga cggttgtag  ttgatcgatt    4980
ggattcttca taactgtatt tgcgtactgc ttacactacc caagtgaaat cgaaaatggc    5040
gccttctctc gttgaataaa ttgcacgtac gctactcgat ccgctgcggc tcttgctgga    5100
gtggccgccg ccgctataga tagaaggatc aagccaagga atctgtcatg catgggcatg    5160
tgaaggagga gcctcctgca atgtttagtc ttttttggtc gacgcccacc agagatatac    5220
gcactagatt tcatatagct gagctagatc gattccgttg catgcatgct gcatggcgtc    5280
gagattcgag ctagcaccgc ctgttcatca tcgaccgatc cattctgatc gattcccctc    5340
tcgagctttc acgaactgaa cctacctagt gagggtgacg cctaacgcct agtgcgcgcg    5400
cgtgggtctc cgatgtcagt ggccgcacgc gcgcgcgcgt tctcgagatc gcatgtggtc    5460
atagcgcagc aggtttgccc tcagaaccta cagcaactcg accaccggtt tggatttctt    5520
cttttttcaa ggatatgatc ggagagagag agctacctag cgtcgtcct  tgttttcttg    5580
tatcgcatgt ggtgtgggtc tctctcctcc tttcgtacgc acgcatgatt ccattcttac    5640
ccccctcga  gatcgagagg aaatatattg ctattttata cacacacggc gcccccagct    5700
atacgtcact gcttacgtta attcccccac cggatagtag ttgtttaatg gcccaaacaa    5760
accttgttgt tgcatgcatc atggaccaaa caaaatacat agttagttaa atattactgt    5820
tatatataca actaataata attatattat tagttaaaac aaagcaaggc atatgcagca    5880
gctgctggtc ggaccgggcc catcgatgat atcagatctg ttctatagt  gtcacctaaa    5940
tcgtatgtgt atgatacata aggttatgta ttaattgtag ccgcgttcta acgacaatat    6000
gtccatatgg tgcactctca gtacaatctg ctctgatgcc gcatagttaa gccagccccg    6060
acacccgcca acacccgctg acgcgccctg acgggcttgt ctgctcccgg catccgctta    6120
cagacaagct gtgaccgtct ccgggagctg catgtgtcag aggttttcac cgtcatcacc    6180
gaaacgcgcg agacgaaagg gcctcgtgat acgcctattt ttataggtta atgtcatgat    6240
aataatggtt tcttagacgt caggtggcac ttttcgggga aatgtgcgcg gaaccccctat   6300
ttgtttattt ttctaaatac attcaaatat gtatccgctc atgagacaat aaccctgata    6360
```

```
aatgcttcaa taatattgaa aaaggaagag tatgagtatt caacatttcc gtgtcgccct    6420
tattcccttt tttgcggcat tttgccttcc tgttttgct cacccagaaa cgctggtgaa    6480
agtaaaagat gctgaagatc agttgggtgc acgagtgggt tacatcgaac tggatctcaa    6540
cagcggtaag atccttgaga gttttcgccc cgaagaacgt tttccaatga tgagcacttt    6600
taaagttctg ctatgtggcg cggtattatc ccgtattgac gccgggcaag agcaactcgg    6660
tcgccgcata cactattctc agaatgactt ggttgagtac tcaccagtca cagaaaagca    6720
tcttacggat ggcatgacag taagagaatt atgcagtgct gccataacca tgagtgataa    6780
cactgcggcc aacttacttc tgacaacgat cggaggaccg aaggagctaa ccgcttttt    6840 gcacaacatg ggggatcatg taactcgcct tgatcgttgg aaccggagc tgaatgaagc    6900 cataccaaac gacgagcgtg acaccacgat gcctgtagca atggcaacaa cgttgcgcaa    6960
actattaact ggcgaactac ttactctagc ttcccggcaa caattaatag actggatgga    7020
ggcggataaa gttgcaggac cacttctgcg ctcggccctt ccggctggct ggtttattgc    7080
tgataaatct ggagccggtg agcgtgggtc tcgcggtatc attgcagcac tggggccaga    7140
tggtaagccc tcccgtatcg tagttatcta cacgacgggg agtcaggcaa ctatggatga    7200
acgaaataga cagatcgctg agataggtgc ctcactgatt aagcattggt aactgtcaga    7260
ccaagtttac tcatatatac tttagattga tttaaaactt catttttaat ttaaaaggat    7320
ctaggtgaag atcctttttg ataatctcat gaccaaaatc ccttaacgtg agttttcgtt    7380
ccactgagcg tcagaccccg tagaaaagat caaaggatct tcttgagatc ctttttttct    7440
gcgcgtaatc tgctgcttgc aaacaaaaaa accaccgcta ccagcggtgg tttgtttgcc    7500
ggatcaagag ctaccaactc tttttccgaa ggtaactggc ttcagcagag cgcagatacc    7560
aaatactgtt cttctagtgt agccgtagtt aggccaccac ttcaagaact ctgtagcacc    7620
gcctacatac ctcgctctgc taatcctgtt accagtggct gctgccagtg gcgataagtc    7680
gtgtcttacc gggttggact caagacgata gttaccggat aaggcgcagc ggtcgggctg    7740
aacggggggt tcgtgcacac agcccagctt ggagcgaacg acctacaccg aactgagata    7800
cctacagcgt gagctatgag aaagcgccac gcttcccgaa gggagaaagg cggacaggta    7860
tccggtaagc ggcagggtcg gaacaggaga gcgcacgagg gagcttccag ggggaaacgc    7920
ctggtatctt tatagtcctg tcgggtttcg ccacctctga cttgagcgtc gatttttgtg    7980
atgctcgtca gggggggcgga gcctatggaa aaacgccagc aacgcggcct ttttacggtt    8040
cctggccttt tgctggcctt ttgctcacat gttctttcct gcgttatccc ctgattctgt    8100
ggataaccgt attaccgcct ttgagtgagc tgataccgct cgccgcagcc gaacgaccga    8160
gcgcagcgag tcagtgagcg aggaagcgga agagcgccca tacgcaaac cgcctctccc    8220 cgcgcgttgg ccgattcatt aatgcaggtt aacctggctt atcgaaatta atacgactca    8280
ctatagggag accggcctcg agcagctgaa gcttgcatgc ctgcaggtcg actctagagg    8340
ga                                                                   8342
```

<210> SEQ ID NO 45
<211> LENGTH: 15544
<212> TYPE: DNA
<213> ORGANISM: Artificial sequence
<220> FEATURE:
<223> OTHER INFORMATION: plasmid 15773

<400> SEQUENCE: 45

```
attcctgtgg ttggcatgca catacaaatg gacgaacgga taaaccttt  cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga    180
attaagggag tcacgttatg accccgccg atgacgcggg acaagccgtt ttacgtttgg     240
aactgacaga accgcaacgc tgcaggaatt ggccgcagcg gccatttaaa tcaattgggc    300
gcgccagctg cttgtgggga ccagacaaaa aaggaatggt gcagaattgt taggcgcacc    360
taccaaaagc atctttgcct ttattgcaaa gataaagcag attcctctag tacaagtggg    420
gaacaaaata acgtggaaaa gagctgtcct gacagcccac tcactaatgc gtatgacgaa    480
cgcagtgacg accacaaaac tcgagacttt tcaacaaagg gtaatatccg gaaacctcct    540
cggattccat tgcccagcta tctgtcactt tattgtgaag atagtggaaa aggaaggtgg    600
ctcctacaaa tgccatcatt gcgataaagg aaaggctatc gttgaagatg cctctgccga    660
cagtggtccc aaagatggac ccccacccac gaggagcatc gtggaaaaag aagacgttcc    720
aaccacgtct tcaaagcaag tggattgatg tgatatctcc actgacgtaa gggatgacga    780
acaatcccac tatccttcgg taccggaccc cgaccagcgc gacatgcatg gcatggcaaa    840
ctatatatcg tcatcatcat tattatcatc tgaccctctt ttttttcac tctcactccc     900
atgtttttat tcccgggcgg ggccgtgtgg gtgtgggttg ggatggccgg attgggctcc    960
cggggtggag aaatgacaaa tccaggcccg caggcggcca cccaccaaat cggacgacg    1020
agggtgccca aatcaggaag gatttttaagg ttaaccggcc accggcggtg accgacgccc  1080
caccccactc tccttctcct attctatcta tatatcaccc gcctctttt  tctccctcac   1140
tccgccacac cttccctctt cttcctcagc tccgtcgccc accgccggag caccgaaagg   1200
ccccgcgccc gccgcctttc ctgtaaaaaa cccaacctt  agctagctaa ccgctcctct   1260
tctcccccta ctccccttgc ccaaatcaga gaagatattt aacggaggag gggaaggaga   1320
ggatatttag ctgattgttg attggtggtc cggggtacgg tgttcttgag tcgtgaagcg   1380
accgtacagt ggctagggcc gtctccgggt tgcgtgcagg atggtcgtca gagatcggga   1440
gtgaggaggc agctcgtggt cgtggaggct aaatgtaccg caagaacgac tcggcactct   1500
cctgttteta cctcttcctc ctctggttct tcttcttgaa atagaccagc gccagccacc   1560
aggtagctac ctactagcta gcagcccagt tgcgactggg gacgggctgc tgcttgcaag   1620
ttggaatctt ggagcaggag cagaggagcg ggagatggag ctggatctga acgtggccga   1680
ggtggcgccg gagaagccat cggcggcgct ggaggcgagc gactcggggt cctcgggctc   1740
gtcggtgctg aacgcggagg cggcatcggc gggcggcggg gggcccgcgc cggggagga    1800
ggggtcaagc tcgacgccgg ccgtgctcga gttcagcatc ctcaggagcg acagcgacgc   1860
ggccggcgcg gacgccgacg acggcgacgc cacgccgtcg ccacctcgcc accaccagca   1920
gcagctcgtc acccgggagc acttcccggc gccgcagcat tgggccgagc acggcttctt   1980
ccgcgccggc ccgcagcagc agccggacat cagggtcctg ccgcacccgc acccgtaccc   2040
gccccgccg  ccgcccgcgc agccgcagca ggccaagaag agccgccgcg gccccgcgctc  2100
ccgcagctcg cagtaccgcg gcgtcacctt ctaccgccgc accggccgct gggagtccca   2160
catctggtca gtagcactgc aagctcacca tgcgcccttt cacctaccga ccaataatcg   2220
cttgtgattc tgacacccaa atgtttcgtc ttcctgtgct gtcctgttcc tcggaaatgg   2280
cagggattgc gggaagcagg tgtacttagg tgagcagcaa taagcagatc gatctgcagc   2340
ataaatttcc cgttattaac tagttcgtga tctcgatcga atggcctaat taaccgattc   2400
```

```
ggtgatctgg ccgatggcca atctacgcag gtggattcga cactgctcat gccgctgcaa    2460
ggtaacgatc aatccatcca tccacccttg tctagctacc ccaccgaccg gccggattaa    2520
tggaccgcta gctctcggga cgggcttgct gcagggcgta cgaccgagcg gcgatcaagt    2580
tccgcggcgt cgacgccgac ataaacttca acctcagcga ctacgacgac gatatgaagc    2640
aggtacatac acgagtgttc ttgcagctag caccgactga acatctgct gaacgtacac     2700
gcatggccct gtgcaccaga tgaagagcct gtccaaggag gagttcgttc acgccctgcg    2760
gcggcagagc accggcttct cccgcggcag ctccaagtac agggggcgtca ccctgcacaa   2820
gtgcggccgc tgggaggcgc gcaaggggca gttcctcggc aagaagtaag aaacaacact    2880
tcgtttgcag gcgctgtact ttgctgcaga ttatttcatt tcatccttgc atgtgccttt    2940
cctttccatc cactcacttg atggctgtag tctcgataga gttcgttcgt tcgtacttcg    3000
caccagatga actcccacgc acatgattta gtactagttt taccatgcat tgttcagtaa    3060
aagtatatgc ttgcttgatc agtggttgtt tcaatcagaa gattaaaaaa acggaatatt    3120
aatataaaaa aaaggggaag tggctaggga attcctcagt cctagctagc tagctcaccg    3180
gtgggaacgc catgcttggc ttgggtgcag gtacatatat cttgggctat tcgacagcga    3240
agtagaggct gcaaggttgt tcacctcgga cgattctgcc atttgttcat atacaccatg    3300
ccttttgatt tctctcttgc aatttctctt cttttatcat ggcttttgat tcccaaaggg    3360
ttgagtaccg actcgatatt cgattctccc tgccgtttcg tgaccccagg gcgtacgaca    3420
aggccccacc atggtacgtc ctgtagaaac cccaacccgt gaaatcaaaa aactcgacgg    3480
cctgtgggca ttcagtctgg atcgcgaaaa ctgtggaatt gatcagcgtt ggtgggaaag    3540
cgcgttacaa gaaagccggg caattgctgt gccaggcagt tttaacgatc agttcgccga    3600
tgcagatatt cgtaattatg cgggcaacgt ctggtatcag cgcgaagtct ttataccgaa    3660
aggttgggca ggccagcgta tcgtgctgcg tttcgatgcg gtcactcatt acggcaaagt    3720
gtgggtcaat aatcaggaag tgatggagca tcagggcggc tatacgccat tgaagccga    3780
tgtcacgccg tatgttattg ccgggaaaag tgtacgtatc accgtttgtg tgaacaacga    3840
actgaactgg cagactatcc cgccgggaat ggtgattacc gacgaaaacg gcaagaaaaa    3900
gcagtcttac ttccatgatt tctttaacta tgccggaatc catcgcagcg taatgctcta    3960
caccacgccg aacacctggg tggacgtata caccgtggtg acgcatgtcg cgcaagactg    4020
taaccacgcg tctgttgact ggcaggtacc aagctgcgaa tcttcgtttt tttaaggaat    4080
tctcgatctt tatggtgtat aggctctggg ttttctgttt tttgtatctc ttaggatttt    4140
gtaaattcca gatctttcta tggccactta gtagtatatt tcaaaaattc tccaatcgag    4200
ttcttcattc gcattttcag tcattttctc ttcgacgttg tttttaagcc tgggtattac    4260
tcctatttag ttgaactctg cagcaatctt agaaaattag ggttttgagg tttcgatttc    4320
tctaggtaac cgatctattg cattcatctg aatttctgca tatatgtctt agatttctga    4380
taagcttacg atacgttagg tgtaattgaa gtttattttt caagagtgtt attttttgtt    4440
tctgaatttt tcaggtggtg gccaatggtg atgtcagcgt tgaactgcgt gatgcggatc    4500
aacaggtggt tgcaactgga caaggcacta gcgggacttt gcagtggtg aatccgcacc    4560
tctggcaacc gggtgaaggt tatctctatg aactgtgcgt cacagccaaa agccagacag    4620
agtgtgatat ctacccgctt cgcgtcggca tccggtcagt ggcagtgaag gcgaacagt    4680
tcctgattaa ccacaaaccg ttctacttta ctggctttgg tcgtcatgaa gatgcggact    4740
```

```
tgcgtggcaa aggattcgat aacgtgctga tggtgcacga ccacgcatta atggactgga      4800
ttggggccaa ctcctaccgt acctcgcatt acccttacgc tgaagagatg ctcgactggg      4860
cagatgaaca tggcatcgtg gtgattgatg aaactgctgc tgtcggcttt aacctctctt      4920
taggcattgg tttcgaagcg ggcaacaagc cgaaagaact gtacagcgaa gaggcagtca      4980
acggggaaac tcagcaagcg cacttacagg cgattaaaga gctgatagcg cgtgacaaaa      5040
accacccaag cgtggtgatg tggagtattg ccaacgaacc ggatacccgt ccgcaaggtg      5100
cacgggaata tttcgcgcca ctggcggaag caacgcgtaa actcgacccg acgcgtccga      5160
tcacctgcgt caatgtaatg ttctgcgacg ctcacaccga taccatcagc gatctctttg      5220
atgtgctgtg cctgaaccgt tattacggat ggtatgtcca aagcggcgat ttggaaacgg      5280
cagagaaggt actggaaaaa gaacttctgg cctggcagga gaaactgcat cagccgatta      5340
tcatcaccga atacggcgtg gatacgttag ccgggctgca ctcaatgtac accgacatgt      5400
ggagtgaaga gtatcagtgt gcatggctgg atatgtatca ccgcgtcttt gatcgcgtca      5460
gcgccgtcgt cggtgaacag gtatggaatt cgccgatttt gcgacctcg caaggcatat      5520 tgcgcgttgg cggtaacaag aaagggatct tcactcgcga ccgcaaaccg aagtcggcgg      5580
cttttctgct gcaaaaacgc tggactggca tgaacttcgg tgaaaaaccg cagcagggag      5640
gcaaacaatg agagctcgaa tcgaagaagc cacactgtaa atctgccggg aagcggctgg      5700
tggcatccgg cccgctcctc cctccgggcg ccgcaacttt tttcgatcgg ttttgcgccg      5760
cccgggacgg gttgtagttg atcgattgga ttcttcataa ctgtatttgc gtactgctta      5820
cactacccaa gtgaaatcga aaatggcgcc ttctctcgtt gaataaattg cacgtacgct      5880
actcgatccg ctgcggctct tgctggagtg gccgccgccg ctatagatag aaggatcaag      5940
ccaaggaatc tgtcatgcat gggcatgtga aggaggagcc tcctgcaatg tttagtcttt      6000
tttggtcgac gcccaccaga gatatacgca ctagatttca tatagctgag ctagatcgat      6060
tccgttgcat gcatgctgca tggcgtcgag attcgagcta gcaccgcctg ttcatcatcg      6120
accgatccat tctgatcgat tcccctctcg agctttcacg aactgaacct acctagtgag      6180
ggtgacgcct aacgcctagt gcgcgcgcgt gggtctccga tgtcagtggc cgcacgcgcg      6240
cgcgcgttct cgagatcgca tgtggtcata gcgcagcagg tttgccctca gaacctacag      6300
caactcgacc accggtttgg atttcttctt ttttcaagga tatgatcgga gagagagagc      6360
tacctaggcg tcgtccttgt tttcttgtat cgcatgtggt gtgggtctct ctcctccttt      6420
cgtacgcacg catgattcca ttcttacccc ccctcgagat cgagaggaaa tatattgcta      6480
ttttatacac acacggcgcc cccagctata cgtcactgct tacgttaatt cccccaccgg      6540
atagtagttg tttaatggcc caaacaaacc ttgttgttgc atgcatcatg gaccaaacaa      6600
aatacatagt tagttaaata ttactgttat atatacaact aataataatt atattattag      6660
ttaaaacaaa gcaaggcata tgcagcagct gctggtcgga ccgcgatcgc ttaattaagc      6720
ttgcatgcct gcagtgcagc gtgacccggt cgtgcccctc tctagagata atgagcattg      6780
catgtctaag ttataaaaaa ttaccacata ttttttttgt cacacttgtt tgaagtgcag      6840
tttatctatc tttatacata tatttaaact ttactctacg aataatataa tctatagtac      6900
tacaataata tcagtgtttt agagaatcat ataaatgaac agttagacat ggtctaaagg      6960
acaattgagt attttgacaa caggactcta cagttttatc ttttagtgt gcatgtgttc      7020 tccttttttt ttgcaaatag cttcacctat ataatacttc atccatttta ttagtacatc      7080
catttagggt ttagggttaa tggttttat agactaattt ttttagtaca tctattttat      7140
```

```
tctattttag cctctaaatt aagaaaacta aaactctatt ttagtttttt tatttaataa    7200
tttagatata aaatagaata aaataaagtg actaaaaatt aaacaaatac cctttaagaa    7260
attaaaaaaa ctaaggaaac attttttctt gttcgagtag ataatgccag cctgttaaac    7320
gccgtcgacg agtctaacgg acaccaacca gcgaaccagc agcgtcgcgt cgggccaagc    7380
gaagcagacg gcacggcatc tctgtcgctg cctctggacc cctctcgaga gttccgctcc    7440
accgttggac ttgctccgct gtcggcatcc agaaattgcg tggcggagcg gcagacgtga    7500
gccggcacgg caggcggcct cctcctcctc tcacggcacc ggcagctacg ggggattcct    7560
ttcccaccgc tccttcgctt tcccttcctc gcccgccgta ataaatagac ccccctcca    7620 caccctcttt ccccaacctc gtgttgttcg gagcgcacac acacacaacc agatctcccc    7680
caaatccacc cgtcggcacc tccgcttcaa ggtacgccgc tcgtcctccc ccccccccc    7740 tctctacctt ctctagatcg gcgttccggt ccatggttag ggcccggtag ttctacttct    7800
gttcatgttt gtgttagatc cgtgtttgtg ttagatccgt gctgctagcg ttcgtacacg    7860
gatgcgacct gtacgtcaga cacgttctga ttgctaactt gccagtgttt ctctttgggg    7920
aatcctggga tggctctagc cgttccgcag acgggatcga tttcatgatt ttttttgttt    7980
cgttgcatag ggtttggttt gccctttttcc tttatttcaa tatatgccgt gcacttgttt    8040
gtcgggtcat cttttcatgc ttttttttgt cttggttgtg atgatgtggt ctggttgggc    8100
ggtcgttcta gatcggagta gaattctgtt tcaaactacc tggtggattt attaattttg    8160
gatctgtatg tgtgtgccat acatattcat agttacgaat tgaagatgat ggatggaaat    8220
atcgatctag gataggtata catgttgatg cgggttttac tgatgcatat acagagatgc    8280
tttttgttcg cttggttgtg atgatgtggt gtggttgggc ggtcgttcat tcgttctaga    8340
tcggagtaga atactgtttc aaactacctg gtgtatttat taattttgga actgtatgtg    8400
tgtgtcatac atcttcatag ttacgagttt aagatggatg gaaatatcga tctaggatag    8460
gtatacatgt tgatgtgggt tttactgatg catatacatg atggcatatg cagcatctat    8520
tcatatgctc taaccttgag tacctatcta ttataataaa caagtatgtt ttataattat    8580
tttgatcttg atatacttgg atgatggcat atgcagcagc tatatgtgga tttttttagc    8640
cctgccttca tacgctattt atttgcttgg tactgtttct tttgtcgatg ctcaccctgt    8700
tgtttggtgt tacttctgca gggatccccg atcatgcaaa aactcattaa ctcagtgcaa    8760
aactatgcct ggggcagcaa aacggcgttg actgaacttt atggtatgga aaatccgtcc    8820
agccagccga tggccgagct gtggatgggc gcacatccga aaagcagttc acgagtgcag    8880
aatgccgccg gagatatcgt ttcactgcgt gatgtgattg agagtgataa atcgactctg    8940
ctcggagagg ccgttgccaa acgctttggc gaactgcctt tcctgttcaa agtattatgc    9000
gcagcacagc cactctccat tcaggttcat ccaaacaaac acaattctga atcggtttt    9060 gccaaagaaa atgccgcagg tatcccgatg atgccgccg agcgtaacta taaagatcct    9120
aaccacaagc cggagctggt ttttgcgctg acgccttttcc ttgcgatgaa cgcgtttcgt    9180
gaattttccg agattgtctc cctactccag ccggtcgcag gtgcacatcc ggcgattgct    9240 cacttttttac aacagcctga tgccgaacgt ttaagcgaac tgttcgccag cctgttgaat    9300
atgcagggtg aagaaaaatc ccgcgcgctg gcgattttaa aatcggccct cgatagccag    9360
cagggtgaac cgtggcaaac gattcgttta atttctgaat tttacccgga agacagcggt    9420
ctgttctccc cgctattgct gaatgtggtg aaattgaacc ctggcgaagc gatgttcctg    9480
```

-continued

```
ttcgctgaaa caccgcacgc ttacctgcaa ggcgtggcgc tggaagtgat ggcaaactcc   9540
gataacgtgc tgcgtgcggg tctgacgcct aaatacattg atattccgga actggttgcc   9600
aatgtgaaat tcgaagccaa accggctaac cagttgttga cccagccggt gaaacaaggt   9660
gcagaactgg acttcccgat tccagtggat gattttgcct tctcgctgca tgaccttagt   9720
gataaagaaa ccaccattag ccagcagagt gccgccattt tgttctgcgt cgaaggcgat   9780
gcaacgttgt ggaaaggttc tcagcagtta cagcttaaac cgggtgaatc agcgtttatt   9840
gccgccaacg aatcaccggt gactgtcaaa ggccacggcc gtttagcgcg tgtttacaac   9900
aagctgtaag agcttactga aaaaattaac atctcttgct aagctgggag ctcgatccgt   9960
cgacctgcag atcgttcaaa catttggcaa taaagtttct taagattgaa tcctgttgcc  10020
ggtcttgcga tgattatcat ataatttctg ttgaattacg ttaagcatgt aataattaac  10080
atgtaatgca tgacgttatt tatgagatgg gttttatga ttagagtccc gcaattatac  10140
atttaatacg cgatagaaaa caaaatatag cgcgcaaact aggataaatt atcgcgcgcg  10200
gtgtcatcta tgttactaga tctgctagcc ctgcaggaaa tttaccggtg cccggcggg   10260
cagcatggcc gtatccgcaa tgtgttatta agttgtctaa gcgtcaattt gtttacacca  10320
caatatatcc tgccaccagc cagccaacag ctccccgacc ggcagctcgg cacaaaatca  10380
ccactcgata caggcagccc atcagaatta attctcatgt ttgacagctt atcatcgact  10440
gcacggtgca ccaatgcttc tggcgtcagg cagccatcgg aagctgtggt atggctgtgc  10500
aggtcgtaaa tcactgcata attcgtgtcg ctcaaggcgc actcccgttc tggataatgt  10560
tttttgcgcc gacatcataa cggttctggc aaatattctg aaatgagctg ttgacaatta  10620
atcatccggc tcgtataatg tgtggaattg tgagcggata caatttcac acaggaaaca  10680
gaccatgagg gaagcgttga tcgccgaagt atcgactcaa ctatcagagg tagttggcgt  10740
catcgagcgc catctcgaac cgacgttgct ggccgtacat ttgtacggct ccgcagtgga  10800
tggcggcctg aagccacaca gtgatattga tttgctggtt acggtgaccg taaggcttga  10860
tgaaacaacg cggcgagctt tgatcaacga ccttttggaa acttcggctt ccctggaga   10920
gagcgagatt ctccgcgctg tagaagtcac cattgttgtg cacgacgaca tcattccgtg  10980
gcgttatcca gctaagcgcg aactgcaatt tggagaatgg cagcgcaatg acattcttgc  11040
aggtatcttc gagccagcca cgatcgacat tgatctggct atcttgctga caaaagcaag  11100
agaacatagc gttgccttgg taggtccagc ggcggaggaa ctctttgatc cggttcctga  11160
acaggatcta tttgaggcgc taaatgaaac cttaacgcta tggaactcgc cgcccgactg  11220
ggctggcgat gagcgaaatg tagtgcttac gttgtcccgc atttggtaca gcgcagtaac  11280
cggcaaaatc gcgccgaagg atgtcgctgc cgactgggca atggagcgcc tgccggccca  11340
gtatcagccc gtcatacttg aagctaggca ggcttatctt ggacaagaag atcgcttggc  11400
ctcgcgcgca gatcagttgg aagaatttgt tcactacgtg aaaggcgaga tcaccaaagt  11460
agtcggcaaa taaagctcta gtggatctcc gtacccgggg atctggctcg cggcggacgc  11520
acgacgccgg ggcgagacca taggcgatct cctaaatcaa tagtagctgt aacctcgaag  11580
cgtttcactt gtaacaacga ttgagaattt ttgtcataaa attgaaatac ttggttcgca  11640
tttttgtcat ccgcggtcag ccgcaattct gacgaactgc ccatttagct ggagatgatt  11700
gtacatcctt cacgtgaaaa tttctcaagc gctgtgaaca agggttcaga ttttagattg  11760
aaaggtgagc cgttgaaaca cgttcttctt gtcgatgacg acgtcgctat gcggcatctt  11820
attattgaat accttacgat ccacgccttc aaagtgaccg cggtagccga cagcacccag  11880
```

```
ttcacaagag tactctcttc cgcgacggtc gatgtcgtgg ttgttgatct agatttaggt    11940
cgtgaagatg ggctcgagat cgttcgtaat ctggcggcaa agtctgatat tccaatcata    12000
attatcagtg gcgaccgcct tgaggagacg gataaagttg ttgcactcga gctaggagca    12060
agtgatttta tcgctaagcc gttcagtatc agagagtttc tagcacgcat tcgggttgcc    12120
ttgcgcgtgc gccccaacgt tgtccgctcc aaagaccgac ggtcttttttg ttttactgac   12180 tggacactta atctcaggca acgtcgcttg atgtccgaag ctggcggtga ggtgaaactt    12240
acggcaggtg agttcaatct tctcctcgcg tttttagaga accccgcga cgttctatcg     12300 cgcgagcaac ttctcattgc cagtcgagta cgcgacgagg aggtttatga caggagtata    12360
gatgttctca ttttgaggct gcgccgcaaa cttgaggcag atccgtcaag ccctcaactg    12420
ataaaaacag caagaggtgc cggttatttc tttgacgcgg acgtgcaggt ttcgcacggg    12480
gggacgatgg cagcctgagc caattcccag atccccgagg aatcggcgtg agcggtcgca    12540
aaccatccgg cccggtacaa atcggcgcgg cgctgggtga tgacctggtg gagaagttga    12600
aggccgcgca ggccgcccag cggcaacgca tcgaggcaga agcacgcccc ggtgaatcgt    12660
ggcaagcggc cgctgatcga atccgcaaag aatcccggca accgccggca gccggtgcgc    12720
cgtcgattag gaagccgccc aagggcgacg agcaaccaga ttttttcgtt ccgatgctct    12780
atgacgtggg cacccgcgat agtcgcagca tcatggacgt ggccgttttc cgtctgtcga    12840
agcgtgaccg acgagctggc gaggtgatcc gctacgagct tccagacggg cacgtagagg    12900
tttccgcagg gccggccggc atggccagtg tgtgggatta cgacctggta ctgatggcgg    12960
tttcccatct aaccgaatcc atgaaccgat accgggaagg gaagggagac aagcccggcc    13020
gcgtgttccg tccacacgtt gcggacgtac tcaagttctg ccggcgagcc gatggcggaa    13080
agcagaaaga cgacctggta gaaacctgca ttcggttaaa caccacgcac gttgccatgc    13140
agcgtacgaa gaaggccaag aacggccgcc tggtgacggt atccgagggt gaagccttga    13200
ttagccgcta caagatcgta aagagcgaaa ccgggcggcc ggagtacatc gagatcgagc    13260
tagctgattg gatgtaccgc gagatcacag aaggcaagaa cccggacgtg ctgacggttc    13320
accccgatta cttttttgatc gatcccggca tcggccgttt tctctaccgc ctggcacgcc    13380
gcgccgcagg caaggcagaa gccagatggt tgttcaagac gatctacgaa cgcagtggca    13440
gcgccggaga gttcaagaag ttctgtttca ccgtgcgcaa gctgatcggg tcaaatgacc    13500
tgccggagta cgatttgaag gaggaggcgg ggcaggctgg cccgatccta gtcatgcgct    13560
accgcaacct gatcgagggc gaagcatccg ccggttccta atgtacgagg cagatgctag    13620
ggcaaattgc cctagcaggg gaaaaggtc gaaaggtct ctttcctgtg gatagcacgt      13680
acattgggaa cccaaagccg tacattggga accggaaccc gtacattggg aacccaaagc    13740
cgtacattgg gaaccggtca cacatgtaag tgactgatat aaaagagaaa aaaggcgatt    13800
tttccgccta aaactctttta aaacttatta aaactcttaa aacccgcctg gcctgtgcat    13860
aactgtctgg ccagcgcaca gccgaagagc tgcaaaaagc gcctacccttc ggtcgctgc    13920 gctccctacg ccccgccgct tcgcgtcggc ctatcgcggc cgctggccgc tcaaaaatgg    13980
ctggcctacg ccaggcaat ctaccagggc gcggacaagc cgccgtcg ccactcgacc      14040 gccggcgctg aggtctgcct cgtgaagaag gtgttgctga ctcataccag gcctgaatcg    14100
ccccatcatc cagccagaaa gtgagggagc cacggttgat gagagctttg ttgtaggtgg    14160
accagttggt gattttgaac ttttgctttg ccacggaacg gtctgcgttg tcgggaagat    14220
```

```
gcgtgatctg atccttcaac tcagcaaaag ttcgatttat tcaacaaagc cgccgtcccg    14280
tcaagtcagc gtaatgctct gccagtgtta caaccaatta accaattctg attagaaaaa    14340
ctcatcgagc atcaaatgaa actgcaattt attcatatca ggattatcaa taccatattt    14400
ttgaaaaagc cgtttctgta atgaaggaga aaactcaccg aggcagttcc ataggatggc    14460
aagatcctgg tatcggtctg cgattccgac tcgtccaaca tcaatacaac ctattaattt    14520
cccctcgtca aaaataaggt tatcaagtga gaaatcacca tgagtgacga ctgaatccgg    14580
tgagaatggc aaaagctctg cattaatgaa tcggccaacg cgcgggaga ggcggtttgc    14640 gtattgggcg ctcttccgct tcctcgctca ctgactcgct gcgctcggtc gttcggctgc    14700
ggcgagcggt atcagctcac tcaaaggcgg taatacggtt atccacagaa tcaggggata    14760
acgcaggaaa gaacatgtga gcaaaaggcc agcaaaaggc caggaaccgt aaaaaggccg    14820
cgttgctggc gttttccat aggctccgcc cccctgacga gcatcacaaa aatcgacgct    14880
caagtcagag gtggcgaaac ccgacaggac tataaagata ccaggcgttt ccccctggaa    14940
gctccctcgt gcgctctcct gttccgaccc tgccgcttac cggatacctg tccgcctttc    15000
tcccttcggg aagcgtggcg ctttctcata gctcacgctg taggtatctc agttcggtgt    15060
aggtcgttcg ctccaagctg ggctgtgtgc acgaaccccc cgttcagccc gaccgctgcg    15120
ccttatccgg taactatcgt cttgagtcca acccggtaag acacgactta tcgccactgg    15180
cagcagccac tggtaacagg attagcagag cgaggtatgt aggcggtgct acagagttct    15240
tgaagtggtg gcctaactac ggctacacta agaacagt atttggtatc tgcgctctgc    15300
tgaagccagt taccttcgga aaagagttg gtagctcttg atccggcaaa caaaccaccg    15360
ctggtagcgg tggttttttt gtttgcaagc agcagattac gcgcagaaaa aaggatctc    15420 aagaagatcc tttgatcttt tctacggggt ctgacgctca gtggaacgaa aactcacgtt    15480
aagggatttt ggtcatgaga ttatcaaaaa ggatcttcac ctagatcctt ttgatccgga    15540
atta                                                                15544
```

<210> SEQ ID NO 46
<211> LENGTH: 7127
<212> TYPE: DNA
<213> ORGANISM: Zea mays

<400> SEQUENCE: 46

```
agagaggaga tattttcgac cagcgcgaca tgcatggcat ggcaaactat atatcgtcat      60
catcattatt atcatctgac cctctttttt tttcactctc actccatgt ttttattccc      120 gggcggggcc gtgtgggtgt gggttgggat ggccggattg gggtcccggg gtggagaaat     180
gacaaatcca ggcccgcagg cggccaccca ccaaatcgga cgacgcaggg tgcccaaatc     240
aggaaggatt ttaaggttaa ccggccaccg gcggtgaccg acgccccacc ccactctcct    300
tctcctattc tatctatata tcacccgcct cttttttctc cctcactccg ccacaccttc    360
cctcttcttc ctcagctccg tcgcccaccg ccggagctcc gaaaggcccc cgcccgccg    420 cctttcctgt aaaaaaccca acctttagct agctaaccgc tcctcttctc cccctactcc    480
ccttgcccaa atcagagaag atatttaacg gaggagggga aggagaggat atttagctga    540
ttgttgattg gtggtccggg gtacggtgtt cttgagtcgt gaagcgaccg tacagtggct    600
agggccgtct ccggggttgcg tgcaggatgg tcgtcagaga tcgggagtga ggaggcagct    660
cgtggtcgtg gaggctaaat gtaccgcaag aacgactcgg cactctcctg tttctacctc    720
ttcctcctct ggttcttctt cttgaaatag accagcgcca gccaccaggt agctacctac    780
```

```
tagctagcag cccagttgcg actggggacg ggctgctgct tgcaagttgg aatcttggag      840
caggagcaga ggagcgggag atggagctgg atctgaacgt ggccgaggtg gcgccggaga      900
agccatcggc ggcgctggag gcgagcgact cggggtcctc gggctcgtcg gtgctgaacg      960
cggaggcggc atcggcgggc ggcgggggc cgcgccggg ggaggagggg tcaagctcga      1020
cgccggccgt gctcgagttc agcatcctca ggagcgacag cgacgcggcc ggcgcggacg      1080
ccgacgacgg cgacgccacg ccgtcgccac ctcgccacca ccagcagcag ctcgtcaccc      1140
gggagctctt cccggcgccg cagcattggg ccgagctcgg cttcttccgc gccggcccgc      1200
agcagcagcc ggacatcagg gtcctgccgc acccgcaccc gtacccgccc cgccgccgc      1260 ccgcgcagcc gcagcaggcc aagaagagcc gccgcggccc gcgctcccgc agctcgcagt      1320
accgcggcgt caccttctac cgccgcaccg gccgctggga gtcccacatc tggtcagtag      1380
cactgcaagc tcaccatgcg ccctttcacc taccgaccaa taatcgcttg tgattctgac      1440
acccaaatgt ttcgtcttcc tgtgctgtcc tgttcctcgg aaatggcagg gattgcggga      1500
agcaggtgta cttaggtgag cagcaataag cagatcgatc tgcagcataa atttcccgtt      1560
attaactagt tcgtgatctc gatcgaatgg cctaattaac cgattcggtg atctggccga      1620
tggccaatct acgcaggtgg attcgacact gctcatgccg ctgcaaggta acgatcaatc      1680
catccatcca cccttgtcta gctacccac cgaccggccg gattaatgga ccgctagctc      1740
tcgggacggg cttgctgcag ggcgtacgac cgagcggcga tcaagttccg cggcgtcgac      1800
gccgacataa acttcaacct cagcgactac gacgacgata tgaagcaggt acatacacga      1860
gtgttcttgc agctagcacc gactgaaaca tctgctgaac gtacacgcat ggccctgtgc      1920
accagatgaa gagcctgtcc aaggaggagt tcgttcacgc cctgcggcgg cagagcaccg      1980
gcttctcccg cggcagctcc aagtacaggg gcgtcaccct gcacaagtgc ggccgctggg      2040
aggcgcgcat ggggcagttc ctcggcaaga agtaagaaac aacacttcgt ttgcaggcgc      2100
tgtactttgc tgcagattat ttcatttcat ccttgcatgt gcctttcctt tccatccact      2160
cacttgatgg ctgtagtctc gatagagttc gttcgttcgt acttcgcacc agatgaactc      2220
ccacgcacat gatttagtac tagttttacc atgcattgtt cagtaaaagt atatgcttgc      2280
ttgatcagtg gttgtttcaa tcagaagatt aaaaaaacgg aatattaata taaaaaaaag      2340
gggaagtggc tagggaattc ctcagtccta gctagctagc tcaccggtgg gaacgccatg      2400
cttggcttgg gtgcaggtac atatatcttg ggctattcga cagcgaagta gaggctgcaa      2460
ggttgttcac ctcggacgat tctgccattt gttcatatac accatgcctt ttgatttctc      2520
tcttgcaatt tctcttcttt tatcatggct tttgattccc aaagggttga gtaccgactc      2580
gatattcgat tctccctgcc gtttcgtgac cccaggcgc acgacaaggc cgcgatcaaa      2640
tgcaacggta gagaggccgt gacgaacttc gagcccagca cgtacgacgg ggagctgctg      2700
ctgactgctg aagctagcgc agaaggtaat taagtagctg ctcgctgcca tgtaatcttc      2760
agatgacgcc gctgttaatt attagctcat cagctttcgg acgatgccct tgttttcgg      2820 ttgaaccggg gtgaactttc tgaatttgag atttgatttt ttttgtttct gcttctgcag      2880
ttgctgacga cgttgatctg aacttgagca tctcgcaacc ggcatcgtcc cagagcccca      2940
aaagagacaa gaactgcctt ggtccgcagc tccaccacca ccatgggcgg ccgtttgacg      3000
gctccgccgt tctgaagaaa accaaggcaa gcgctaagta ataacgctac gtaccttgac      3060
aagtatcaaa atcagtaaaa ctttcctctt cgtcaaaccc tatctctacc gacggctgtt      3120
```

-continued

```
agttgcccgg ttttgatcat ttgacaatta aacacatacc ctctcgcaag tcgggatcat    3180
ttttagctag gcggactagt ttatcgccaa gcagcgagtt tctctttcgg ggtgggtgat    3240
cgcgacagct gagcagaata cttcttcttc gtctactttt tctccttcct cctaccaaaa    3300
ttgaattgtt taaggaaaat ttatacagag agcggcgtgg acagctttgg atggagctgc    3360
cgataattca actgaaaatc tctcgcttct tcttcttctc atgcagatcg atgctccgtc    3420
tgagctgtcg tcggcgggcc gccctcaccg gtcgttcctc cctcatctcg tggctgccga    3480
gcatctaccg cctcggtctc accccttctt catcacacac catgaggtta gacgacacta    3540
tacagtactg aatcatttgc aaaggtttgt caagctagct agattggcat cataatacac    3600
ggatcaggtg tcagattgtt catgcagtgc agtatgcagc ctgaaggtgt atgcagtttc    3660
agatagcaga tttttagcag ctggttaatt tctctcttgc gtgcggctgt cagtcagtgt    3720
agctctcgtc gtcgcccgct ttatttcctt ggattctagc tagagtccgc ctgtcacccg    3780
tcgatttcag tgaagttaat gggatgcgcg aattttttttt ctcccccgta taggccggct    3840
gttgaatata tgtgtctatc ttgaattggc ctaaatatggg aataatagta ctagcagctt    3900
tatggctaga tcagaatatg tacatgtgtt tgatttttttt tctctctctc ccttagcttc    3960
cttgaaaagg aaaggtccta gacctagcta ccggccagca gcgacacttc aactctaagg    4020
gcatgtacag tggagagacg ccaaaacggt tctccaagca taggagacaa ctaagagact    4080
ctattgtaca atggagtgtc tctaaacgta gtctattaat aaatacagaa ttaaatgtat    4140
ttgtatagca tcagatcgat agaacagacg acaaattcgt acagtgggaa gtgaggcgtc    4200
tgttgttact tggtttacga gccagaggcg tctcttcacg gagagacggc tctaagattt    4260
ttttgcaaat aaccccctaa aacaccttaa gagcccccac attaaacacc actgtacatg    4320
ccctaagccc tgcctggcct gcctaatcaa accctctcgg tcaactatgc tatgcctgcc    4380
tgcctgcttt caacacgtac tgttcctttt tcaaaccttc cctggaaacg aaaacagaag    4440
atgcatggta tttatgcttg gggatttgcc ttcttttcag tgtactaata agcttggggt    4500
ttgtttagtc gttcagcaat caacttggac gagtgttgat aaataaaact cgatctccaa    4560
cctttcgttc ataaatgggt cagctaactt tgaggtcggt ctcactctca caccagtgtc    4620
gctttctgat tgtattgtat tggacgggaa gagctgaggt cgacgctttt ctgcccccag    4680
ctgaactgat gggaaacgct aagctaatta tattggtgga acgagtctcc tgccgtttgc    4740 tctcttttttt gttttgtttc tcttaaaaaa aacatgcttc catgcatcag aaagcgttat    4800
tacttaggat gattaatttg aactgttcat cagttcgttg aattggtcct agggtgaatg    4860
aactttcagt ttatttgttg accatgcatg cagagtgatg catcaagaag agatcccagc    4920
tgggcagcag cagcagcatg gaaggtgacc gcagctgcac ctcctcctcc taccaccacc    4980
ctgttgccgt tgccgctgcc gtcgacgtcg tccgctgcag catcatcagg attctccaat    5040
accgccacga cagctgccgc cgccccatcg gccgcctcct cccgccggtt cgacccgccg    5100
ccaccgtcgt cgtcctcctc ctcgagccat caccaccacc accaccgccg ctgagaatcg    5160
aagaagccac actgtaaatc tgccgggaag cggctggtgg catccggccc gctcctccct    5220
ccgggcgccg caactttttt cgatcggttt tgcgccgccc gggacgggtt gtagttgatc    5280
gattggattc ttcataactg tatttgcgta ctgcttacac tacccaagtg aaatcgaaaa    5340
tggcgccttc tctcgttgaa taaattgcac gtacgctact cgatccgctg cggctcttgc    5400
tggagtggcc gccgccgcta tagatagaag gatcaagcca aggaatctgt catgcatggg    5460
catgtgaagg aggagcctcc tgcaatgttt agtcttttttt ggtcgacgcc caccagagat    5520
```

-continued

```
atacgcacta gatttcatat agctgagcta gatcgattcc gttgcatgca tgctccatgg    5580
cgtcgagatt cgagctagca ccgcctgttc atcatcgacc gatccattct gatcgattcc    5640
cctctcgagc tttcacgaac tgaacctacc tagtgagggt gacgcctaac gcctagtgcg    5700
cgcgcgtggg tctccgatgt cagtggccgc acgcgcgcgc gcgttctcga gatcgcatgt    5760
ggtcatagcg cagcaggttt gccctcagaa cctacagcaa ctcgaccacc ggtttggatt    5820 tcttctttt tcaaggatat gatcggagag agagagctac ctaggcgtcg tccttgtttt     5880
cttgtatcgc atgtggtgtg ggtctctctc ctcctttcgt acgcacgcat gattccattc    5940
ttaccccccc tcgagatcga gaggaaatat attgctattt tatacacaca cggcgccccc    6000
agctatacgt cactgcttac gttaattccc ccaccggata gtagttgttt aatggcccaa    6060
acaaaccttg ttgttgcatg catcatggac caaacaaaat acatagttag ttaaatatta    6120
ctgttatata tacaactaat aataattata ttattagtta aaacaaagca aggcatatgc    6180
agcagctgct ggtactaccc agtacatggc acatgcgttt gtttaatccc ctgttgctgt    6240
gtgtgtgatt gattccttgt attagctaat aattagttag gtcggtcgtc gtctcccctc    6300
taatccctct tcgatttaga attagtagtc ttgtacgttg tttaatatgc ttggacgacg    6360
acgctctttg ttgggtgtgc acttcatctt tccatctaca ctagctagct agacacacat    6420
gtactatagc tagctacttg ttttagtatg ctgctcttct aattaactaa ccaacatgat    6480
tgcactgcta agcaaggcta cctttggtac ggtcttaaac tttgtgtggc ccatatgctg    6540
ctatactata tcatgcatgt agattcttcc tgccaaggtg catggttttt ttatgttaat    6600
aggtacggtt agttgtcgta gtacatacta aggcatcgat cgtccactta tatatatcaa    6660
accctgcagc tcaaacaagc tgcaaataaa aaaaaactg aagctggtat atgagtgtat     6720
attgtatatg aaataataat gcatatgcgg ctgcatgcat cagggagctg agtcagatga    6780
caggtgtagg tttgaagcag cttgctgtac gtgtgcaatt ttttctctc cataatgatg     6840 tctcagattg gtgatctgat gacgctgtga ttattctatt ctattcatct ttggttgtag    6900
acactccttt tcatttgtta atagttttct ggtccagttg atagatagag gttaaataaa    6960
agccagttgt agtctaccct aactagtacg atagtacaac aggattggcc ggcggcgtta    7020
gtaaatttat aatttcgtat acaagctgtt attgttatta catacactag ccggttactc    7080
gtgctttcct atagttgtta tatattatat actcgaggcg tctagag                 7127
```

<210> SEQ ID NO 47
<211> LENGTH: 439
<212> TYPE: DNA
<213> ORGANISM: Zea mays

<400> SEQUENCE: 47

```
tattaaggct gcttctgagg gcccactcaa gggtattatg ggctacgtgg aggaggatct      60
ggtttccacc gacttcaccg gtgacagcag gtcgagcatc ttcgacgcca aggccgggat     120
tgccctgaac gaccacttca tcaagctcgt ctcttggtac gacaacgagt ggggctacag     180
caaccgcgtc gtcgacctga tccgccacat gttcaagacc cagtagagag agatatttct     240
gcctccctat cgagggtcgt ccccgatggc ctttggtcgc agaccatctt tgctgcttgt     300
ctatgctgag aataaatgtg aacggtgccc ctggacgctg gatccatgct ggttttggac     360
acggttgtct ttttgtgttt aacttatctg ctgccgtccg tcctgtaacg aattcgctaa     420
gttttagttc ttttgtgct                                                 439
```

<210> SEQ ID NO 48
<211> LENGTH: 391
<212> TYPE: DNA
<213> ORGANISM: Zea mays

<400> SEQUENCE: 48

```
catgtccttg attattggtg tctacgacga gccaatgact ccagggcaat gcaacatggt    60
ggtggagagg ctcggcgatt acctgatcga gcagggcttc taaaagttcg tcatgttctg   120
ttttggtcat ttgggcacca agtttgcgc ctcatttggt tctgtaatcc gtgagctcgt    180
gcatgtactt ggcgtattgc atgcagtgaa taatttagct tgggtttgtt tgttgggggc   240
agtgttgggg acggatttgg attggggttt atgcttggca tcgcgtcgta tcgaaactca   300
gctgctgttt cgctgagtaa tgtacatttc cctggtaatg gtacttgtgg actctgatgc   360
ttttatggga acgagtgcat tttactgcaa a                                  391
```

<210> SEQ ID NO 49
<211> LENGTH: 136
<212> TYPE: DNA
<213> ORGANISM: Zea mays

<400> SEQUENCE: 49

```
attgggttac aagaattatg gcgtttgtca atatggtcgt aatgtcgtag gatggtggaa    60
tgtggtcaca aactttgcgt atgttgggtc tactggtggt gtctgaatct atgtatggat   120
gtcatgagtt tgtcta                                                   136
```

<210> SEQ ID NO 50
<211> LENGTH: 63
<212> TYPE: DNA
<213> ORGANISM: Zea mays

<400> SEQUENCE: 50

```
ggtgtatccg cgttagaacc ttttgttggt gaacaatatt atcgtggcac gcgttttaag    60
taa                                                                  63
```

<210> SEQ ID NO 51
<211> LENGTH: 632
<212> TYPE: DNA
<213> ORGANISM: Zea mays

<400> SEQUENCE: 51

```
cgctgtgaat gacgagtgca tgctcaagtt cggcgagctg cagtcgaaga ggctgcaccg    60
cttcctaact ttcaagatgg acgacaagtt caaggagatc gttgtggacc aggtcgggga   120
tcgcgctacc agctacgagg acttcacaaa cagcctcccc gagaatgact gccgatacgc   180
gatctatgat ttcgactttg tcactgcaga agatgtccag aagagcagga tcttctatat   240
cctatggtcc ccatcctccg ccaaggtgaa gagcaagatg ctttatgcaa gctcaaacca   300
aaaattcaag agtgggctca atggcattca ggtggaactg caggctactg atgcaagtga   360
aatcagcctt gatgagatca aggatcgggc tcgctaggca tcatgatcat gcatcatgga   420
ctcggcctac tactgtggat ttgtatgcca ttatagactt ggtgctgtga agactgctt    480
gatgatttgc gggtttgttg ctgtgtaaaa aaaggtccca tggctcccag aagaccatga   540
aggttcggat ctatcatgta attccttgtt atctgccaat tatgtatgga ctatggacat   600
tgttgcgct gttcaactta ctactacaaa ta                                  632
```

<210> SEQ ID NO 52
<211> LENGTH: 598
<212> TYPE: DNA
<213> ORGANISM: Zea mays

<400> SEQUENCE: 52

```
gggttgaact atgagcgccg tggcggtttc gtcgtcgctg aacccggacg cgccgctctt      60
catcccggcg gcgctgctgc aggtggagga cttctcgccg cagtggtggg acctcatcac     120
caccactgcc tggttccgcg accactggtc ccgcgagcgc gcccacctgg acgagatggc     180
cgagcagatc gacgcggccg gcctcctccc cgacgacgag gacctcttct acgacgacca     240
gctcgagcag ggccccgtcg ccgccgccct taagacagat tcggtgctca aggcgctgaa     300
catgacctcc ccgaagggcg gcggcgacgc cccgcggggg ttccgggaga aacccaggaa     360
cgccgagaag ccgaccaagt acgccggcag ccccaagagc agcgcccccc gcgtgatcca     420
ccagcctcgc taggttcgct gggggaactc atcaggaagg ctgctgcccc tcttgcagcc     480
ttgctcctgg ctgccgcccg ctgtcgtggt ctgctctttc aagtcgaagt aacggtggtt     540
cgagctagtg gatagtgtgg ctcaactgta gaagttcctt ttgtatagca agcaagta      598
```

<210> SEQ ID NO 53
<211> LENGTH: 516
<212> TYPE: DNA
<213> ORGANISM: Zea mays

<400> SEQUENCE: 53

```
atggctgtcc gcatcatcaa gcatacctg gagatcatcc acctgctcac cgatgccaac      60
cccatccagg tcgtcgtcga cgcgatcatc aacagtggcc ccgtgagga tgccacccgt     120
attggttccg ctggtgttgt gaggaggcag gccgtggata tctcacccct gaggagggtg     180
aaccaggcca tctacctcct caccactggt gccagggaga gtgctttccg gaacatcaaa     240
accattgccg agtgccttgc agatgagctg atcaacgctg ccaagggctc atccaacagt     300
tacgccatca agaagaagga cgagattgag cgtgttgcca aggccaaccg ttgaactgag     360
cttgtatcct ggtgcactct gcgctggaaa ctttttatgtc gctggcagtc gtatcggttc     420
ttgttttacc aatgtttaga gttttttgag acctatatgc ggttttggtt ttcagtgcac     480
aattaaaatt actgagtaat gtagttgatt gggaac                                516
```

<210> SEQ ID NO 54
<211> LENGTH: 64
<212> TYPE: DNA
<213> ORGANISM: Zea mays

<400> SEQUENCE: 54

```
gtgttcggtg aaatcagagt cgtcagtcat ctacatagct tttcttggtt gatagactgt      60
tatt                                                                   64
```

<210> SEQ ID NO 55
<211> LENGTH: 195
<212> TYPE: DNA
<213> ORGANISM: Zea mays

<400> SEQUENCE: 55

```
ataaaatagc atgccgtctc tgtcactggc aatggacggt ggtgcctagc gcaactcagc      60
gcacaactgt gtgtcttgat ttttcttctg tttatcacgg cattagtgcc atgccgtttt     120
atgttacagt gttgtgtgct cgcaagcatc cgaaaatatg cgtctgagtt tagggttggg     180
```
tcaaacttgt cgaat                                                          195

<210> SEQ ID NO 56
<211> LENGTH: 52
<212> TYPE: DNA
<213> ORGANISM: Zea mays

<400> SEQUENCE: 56
gagaaccatc gcctgcattt cgatctgttt caccgcaatt cgcattgtta gt                 52

<210> SEQ ID NO 57
<211> LENGTH: 90
<212> TYPE: DNA
<213> ORGANISM: Zea mays

<400> SEQUENCE: 57
ctatgttgta taaggctagt gcagctgtgc aggttactct atattcttac tctatatcac         60
tatttgtagt ctactcatca attaataaat                                          90

<210> SEQ ID NO 58
<211> LENGTH: 549
<212> TYPE: DNA
<213> ORGANISM: Zea mays

<400> SEQUENCE: 58
tggtcaacgt gcacgcggtc cacagggacc ccgcggtgtg ggacgacccg gacaggttcg         60
tgccggagcg gttcgagggc gccggcggca aggccgaggg gcgcctgctg aagccgttcg        120
ggatggggcg gcgcaagtgc cccggggaga cgctcgcgct gcggaccgtc gggctggtgc        180
tcgccacgct gctccagtgc ttcgactggg acacggttga tggagctcag gttgacatga        240
aggctagcgg cgggctgacc atgccccggg ccgtcccgtt ggaggccatg tgcaggccgc        300
gtacagctat gcgtggtgtt cttaagaggc tctgaaaacc tcatggatcg aattgctggc        360
atcgtctgaa gggtgtatga cgtagcttcc gagttccgag catatatatt cacttgcctt        420
gtactagttg attttcgccg agtgtatgga atggattttc ttttttttc ttgcaatgga         480 tgtgaatttt gttttctcg acgttacaag aagtgaatca acctagcttc tctttgagcg         540
acagcaacg                                                                549

<210> SEQ ID NO 59
<211> LENGTH: 538
<212> TYPE: DNA
<213> ORGANISM: Zea mays

<400> SEQUENCE: 59
cgacttgttt cattgattct tcaagagatc gagcttcttt tgcaccacaa ggtcgaggat         60
gtcttgcagc tgcggatcaa gctgcggctg cggctcaagc tgcaagtgcg gcaagaagta        120
ccctgacctg gaggagacga gcaccgccgc gcagcccacc gtcgtcctcg gggtggcccc        180
ggagaagaag gccgcgcccg agttcgtcga ggccgcggcg gagtccggcg aggcggccca        240
cggctgcagc tgcggtagcg gctgcaagtg cgacccctgc aactgctgat cacatcgatc        300
gacgaccatg gatgattatt atctatctag cttgtggtgg tggttgaaca ataataagcg        360
aggccgagct ggctgccata cataggtatt gtgtggtgtg tgtgtgagag agagagaaac        420
agagttcttc agtttgctat ctctctctgc atgtttggcg tcagtctttg tgctcatgta        480
cgtgtgtcta catgcatgtt ggttgatccg attgcgtctg ctgtaaccat atattaat          538

<210> SEQ ID NO 60
<211> LENGTH: 228
<212> TYPE: DNA
<213> ORGANISM: Zea mays

<400> SEQUENCE: 60

```
tctacccgcc cgagaaggtc tacgacttcg tctgcgggat gaagaagagg ctgggcatcg      60
agtagagcat ccatcggtcg gccggtggct ggccgggagt aataatgacg aaccaataat     120
ctagttttgg ttttagtgtg ctcagcagag cagttcgtgt tcatgagttc gtcgtcgttg     180
tattttctat tgtcagcggt ggcagcgccg tacgtgttgc ctcgtaca                  228
```

<210> SEQ ID NO 61
<211> LENGTH: 737
<212> TYPE: DNA
<213> ORGANISM: Zea mays

<400> SEQUENCE: 61

```
ccgccgagct cgaccgcgtg attggggcac ggccgctggg tcacagagcg cgacctcccg      60
gacctcccct acatcgacgc cgtcgtgaag gagacgatgc ggctgcaccc ggtcggcccg     120
ctcctcgtcc cgcaccacgc ccgcgagcac acggtggtgg ccggctacga cgtccccgcc     180
ggtgcgcgcg tgctggtgaa cgtgtgggcc atcgctcgcg accccgcgtc atggcctgac     240
gcgcctgacg cgttccggcc ggagcggttc ttgaacggca gctccggcgc cagcgtcgac     300
gtgcgcggcg cgcactttga gctgctgccg ttcggggccg ggcggcggat gtgccccgcg     360
cacggcctcg cgatgaagct ggtgaccgct ggcgtggcga acctggtgca cgggttcgcg     420
tggcggctgc cggacggtat ggcgccggag gatgtgagca tggaggagct atttgggctt     480
tccacgcgcc ggaaggttcc gctcgtcgcc gtcgcggagc ccaggctgcc ggcgcacctc     540
tacactaatg tcacgccgcc acagcaggtc gcgggctcca cgattgcgaa cttgtccacc     600
aggccggagt acaagctcgt gttctgaatc attcaccgcc actaaaaata aagcaggaaa     660
aactacactt cctgcgtgct agacgtccgg gcggaacaca acagtgcttg ctcacgttct     720
tctattggtt gtactaa                                                    737
```

<210> SEQ ID NO 62
<211> LENGTH: 141
<212> TYPE: DNA
<213> ORGANISM: Zea mays

<400> SEQUENCE: 62

```
gcgcaatcgt atcgtacgtg catgatacgc atacatctgg aaactactat accaatgcaa      60
acagagatct atacgtacga gtatgtataa cgacgagtga tgtttgtatg gatctacgta     120
tgtaacaagg acctctcgta g                                               141
```

<210> SEQ ID NO 63
<211> LENGTH: 672
<212> TYPE: DNA
<213> ORGANISM: Zea mays

<400> SEQUENCE: 63

```
ctccaagcac ttgttagccg gcgtacagca agaagaacct cggacgcgac cgacatggtc      60
gctctctcag gcgctcacac aatcgggcag gcccagtgct cgagcttcaa cggccacatc     120
tacaacgaca cgaacatcaa cgcggccttc gcgacgtcgc tcaaggccaa ctgccccatg     180
tccggcggca gcagcctggc gccgctggac accatgaccc cgaccgtgtt cgacaacgac     240
```

```
tactacaaga acctgctgtc gcagaagggg ctgctgcact cggaccagga gctgttcaac    300
aacggcagca ccgacagcac ggtcagcaac tttgcgtcca gctcggccgc cttcaccagc    360
gccttcacgg cggccatggt gaagatgggg aacctcggcc cgctcaccgg gaccagtggg    420
cagatcaggc tcacctgctg gaagctcaac tcgtcctaat aattaaggac ggacgtccga    480
tagacgatcc tgcgcaatcg tatcgtacgt gcatgatacg catacatctg gaaactacta    540
taccaatgca aacagagatc tatacgtacg agtatgtata acgacgagtg atgtttgtat    600
ggatctacgt atgtaacaag gacctctcgt agcgcaaagg cgcgcgttgg gagattaatt    660
aggtacacaa gc                                                        672

<210> SEQ ID NO 64
<211> LENGTH: 83
<212> TYPE: DNA
<213> ORGANISM: Zea mays

<400> SEQUENCE: 64
tacgtatact aaagacctta ctaggtacct cgcgtgattg ttgttcaagt gtactagcta     60
ccaagctagt gacaagaatg ttg                                            83

<210> SEQ ID NO 65
<211> LENGTH: 640
<212> TYPE: DNA
<213> ORGANISM: Zea mays

<400> SEQUENCE: 65
tgaggttgcg acagcgtggc taaacaacaa tagcgtcaga tccgctatcc atgccgaacc     60
agtcagttca atcggaccct gggaattatg cacggataaa ctggattttg atcatgatgc    120
cggcagcatg atcatctatc acaagaacct cacgagtcag gctaccgtg ctttcatcta    180 cagcggcgac catgacatgt gtgtaccta caccgggact gaagcatgga ctgcgtcttt    240
aggctacgcc gtcgttgatc cgtggcgaca gtggattgtc gacgaacaag ttgccgggta    300
cacccaagga tatgaaaagg gccttacttt tgccactatt aagggtgctg gcacacagt     360 tcctgagtac aaaccacagg aagcactagc tttctacagc cgttggcttg ccggtgctaa    420
actgtgagga ggcctatttt gtgtgcaaag gtcatgcagt actgaatcaa acagaagttg    480
gataaagcat gcagcaataa ggcagtcgaa ggatcaaagt atccaacgcg ccaactacaa    540
tgttgcattc attttcacat gttataccaa tgcagttgct aattacctgc attgttcatg    600
agttcacagt ccatctaatt ggttgaccac accgtcctat                          640

<210> SEQ ID NO 66
<211> LENGTH: 125
<212> TYPE: DNA
<213> ORGANISM: Zea mays

<400> SEQUENCE: 66
tatcactctc attgtggcta catatctata tctctgaggc caaatgcttg ggtgtccagt     60
actaattaat aataattcag tgcgtatgca agatttgtgg gcaaatattg gtttacgatt    120
tcgga                                                                125

<210> SEQ ID NO 67
<211> LENGTH: 136
<212> TYPE: DNA
<213> ORGANISM: Zea mays

<400> SEQUENCE: 67
```

```
gcaccacctt ggtttgagca aacgcgcggc gccgtgtttt ggcatctgtc accgtaggtg    60 ggcgggata cagtgaagtg ataatgcgct tgtgttaggc gcatgtatat atataataat   120
tagatggata cccgtg                                                  136

<210> SEQ ID NO 68
<211> LENGTH: 142
<212> TYPE: DNA
<213> ORGANISM: Zea mays

<400> SEQUENCE: 68
gcaccacctt ggtttgagca aacgcgcggc gccgtgtttt ggcatctgtc accgtaggtg    60
ggcggggata cagtgaagtg ataatgcgct tgtgttaggc gcatgtatat atataataat   120
tagatggata cccgtgcgtt ac                                           142

<210> SEQ ID NO 69
<211> LENGTH: 154
<212> TYPE: DNA
<213> ORGANISM: Zea mays

<400> SEQUENCE: 69
gagcggccgc ggatctgttc aagaaccacg acctcgcttt cgcctcccgc ccacgcagcg    60
tgggagggga taagctgatg tatgagtgca gcaacgtgtc gttcgcgcct tacggcgaga   120
actggcgccg gggcaagaag atcgctgtgg tcca                              154

<210> SEQ ID NO 70
<211> LENGTH: 289
<212> TYPE: DNA
<213> ORGANISM: Zea mays

<400> SEQUENCE: 70
gagcggccgc ggatctgttc aagaaccacg acctcgcttt cgcctcccgc ccacgcagcg    60
tgggagggga taagctgatg tatgagtgca gcaacgtgtc gttcgcgcct tacggcgaga   120
actggcgccg gggcaagaag atcgctgtgg tccacctcct ctctccacgg cgcgtggaat   180
cgttcgcgcc cgtaagggcc gccgaggtag ccgcgctcgt cgcacggaca cgccgcaccg   240
cggaggctgg ggaggccgtg gagttgaggg agctcctgaa cggctacgc              289

<210> SEQ ID NO 71
<211> LENGTH: 686
<212> TYPE: DNA
<213> ORGANISM: Zea mays

<400> SEQUENCE: 71
gtagccaggc tcttttttgca agatcagact cgaggcatca caaccacat cgttgggaca    60 ttcggctaca tgtctcccga gtatgtgatg cgtggacaat actccataaa atctagatgt   120
atttagtttc ggcatccttg ttatagagat tgtaacagga caaagaaca atgggcatta   180 cttcgacgag caaaacgagg atgttgtgag cattgtatgg aagcactgga gcgagggaac   240
acttgcagag attatagatg attcttagg gagaaactac tcagagactg aggtgctaaa   300
atgtgttaac attggcttgt ggtgccttca acagaatcca atggaccgac ctacaatgtc   360
agatgtcatg gtgatgctca atgatgatga tactagttct ctacctgctg ctgcaaaacc   420 aactttttc ttggatgcaa gctcaggcta ctccttacacc tcgggcacca tttcacatcc   480
ttctgcaagg tagtgtaggc taaggcctaa tgcacacctt tatatgaata tcgacatatt   540
```

```
gttgcttgtt tgtttcttat tgtgtattgg ttgaaagaaa catggaattc accctgaatt    600
gtaatagctt gtgctcatta ttagtttctt ccaaatcctc aaatataaat tttctcttac    660
tagatgtcct acaagctttc agaaag                                         686

<210> SEQ ID NO 72
<211> LENGTH: 337
<212> TYPE: DNA
<213> ORGANISM: Zea mays

<400> SEQUENCE: 72
tcaccaccat cctgcgcaag aagatgggcg acgcgcagct cgtcgaggtc gccgaggaca     60
agaagaagga ggagaagaag cccgaccccg tcgccgaagc tgcggcggcg tactacaacc    120
agtactacta ccactaccca ccgccggccg ccgtcgttta cgaccctac ccacggccgg     180 gcaacacctg ctccataatg tagactcagc ctgtggacat atgcaagtta agttttgtgt    240
gtagcggtgc gtgtgtgggg gaggcgcgca agtgtagttt ctatacggaa ttcttctctt    300
atctcccttt tgaggttaag ggcatgtgca gtcccag                             337

<210> SEQ ID NO 73
<211> LENGTH: 186
<212> TYPE: DNA
<213> ORGANISM: Zea mays

<400> SEQUENCE: 73
ggttccgcgg ccagtagctg ctgcttgggg ctggtgcacg acctgacgcg ctgcttggcc     60
acgctgggca ccgccctcca ctaccgtggt tactacaatg gttgacgttg taacgcggga    120
agcttggaaa ttatgcgtgc atagccatag catcggcact ctggagatgg atctcccagc    180
tctgaa                                                               186

<210> SEQ ID NO 74
<211> LENGTH: 187
<212> TYPE: DNA
<213> ORGANISM: Zea mays

<400> SEQUENCE: 74
accaccgccg ctgagaatcg aagaagccac actgtaaatc tgccgggaag cggctggtgg     60
catccggccc gctcctccct ccgggcgccg caacttttt cgatcggttt tgcgccgccc    120
gggacgggtt gtagttgatc gattggattc ttcataactg tatttgcgta ctgcttacac    180
tacccaa                                                              187

<210> SEQ ID NO 75
<211> LENGTH: 238
<212> TYPE: DNA
<213> ORGANISM: Zea mays
<220> FEATURE:
<221> NAME/KEY: variation
<222> LOCATION: 184
<223> OTHER INFORMATION: nucleotide a at this position can be
      substituted with any nucleotide c, g, or t

<400> SEQUENCE: 75
tggtcgttgg gtccgggtgc cacggcgggg accagaccgt gtacgtgctc cgcgaggagg     60
gcgggagacc tgcgtcctgg tcgcgcgcgc cgccgccgcc gccggagttc gccgggcacg    120
tgcaggcctc ctacttcctt gaactctgaa ctctgaagtg gagggtgtgt acctacacgt    180
accagtggtg gctgtgcata catgacgaaa ctacgctacc gtacttgttg tgccactg     238
```

<210> SEQ ID NO 76
<211> LENGTH: 169
<212> TYPE: DNA
<213> ORGANISM: Zea mays

<400> SEQUENCE: 76
cttgtttcat tgattcttga agagatcgag cttcttttgc accacaaggt cgagatgtct    60
tgcaactgcg gtggcaactg caagtgcgac ccctgcaact gctgatcaca tcgatcgacg   120
accatggata tgattattat ctatctagct tgtggtggtg gttgaacaa               169

<210> SEQ ID NO 77
<211> LENGTH: 114
<212> TYPE: DNA
<213> ORGANISM: Zea mays

<400> SEQUENCE: 77
cgagaacgat ttcgcaggtg tatcagtgta gtatgtatag ccgtatagca agtgcgcatc    60
tcatctcgtg tacgtgaaat tagttggtta ggacgaacag cagcgtgtga tgtt         114

<210> SEQ ID NO 78
<211> LENGTH: 916
<212> TYPE: DNA
<213> ORGANISM: Zea mays

<400> SEQUENCE: 78
gccattcggc gccacgattg cagagccaga gcgagacgcg actgcttttc tgcttcatcc    60
acattggtag ctagctagct tacacgttca cgcatcgctt tccgggccgt ctccggtggt   120
ttagctcagc agagcgggga aggaagaaga tgacctccgt gagcgcgagg cccgttggcg   180
tggggtactg cttcggcggg gcgaggtgcc agccacggtc gcgggtgcgg gtttcggccg   240
cggcctcggc agtggccgcg cccgcgcccg cgatggcggc gacgatgtac gagctgctcg   300
ccgtcgagga cggcggggg cccgacgaga tcaaggcggc gtaccggcgc gccgcgcggc   360
ggtggcaccc ggacgcgtgc cccggcggcg ccgaccgctt catggcggcg cgggaggcct   420
acgaggtgct gtccgacccc gagcgcaggc gcggctacga catccagctc cgctgcggcg   480
cccacttcgg cgacgccggg taccgcgcgg cacgccgcgc cgggttcgcc gactgggagg   540
cgcagctgac cgggctgcag tggcgcgcgg cgggcggcg cgggcgcgcc ggcggggaga   600
cttggggcag caggatgcgc caggcggccg cgcagccgtc cttgtagcgg cgtcgccggt   660
ggctggcctt tgatagttca tacttcgtag tactagtgta ctaccctacc ttcccctttc   720
ctcttcgaca atcgaatggc ccgagaagct gtaattgcgc tgttctgcag cgttttctct   780
tgccaacacg tcatcctcgt cgcactgttc ggagtgcaga cgagcttgaa gtctagaagc   840
agtagacatt ttccccccct ttgaagtgta gtactgtcaa cttttagttc ccactcggtt   900
acatacggtt cgaatc                                                   916

<210> SEQ ID NO 79
<211> LENGTH: 446
<212> TYPE: DNA
<213> ORGANISM: Zea mays

<400> SEQUENCE: 79
tgctccatga agaagtcggt ccacccaatc tcgctgcggc gggcgtctgt agagcctgcg    60
ttacgtgtac ggcgcgtgta cgtatacggc cgtagcgtac atgctcgcct ttgcactcag   120
atgcacaata taacacacag tcacacacac acacacacac acacgacaca cgctgtatac   180

```
actggatcct aggtgttttt ttagcttagc taggaatgca aatttcttga ttcgttggag    240
ggtttttttt ctagcacgcg gcgcggccgg tgcccatctg tctcgcaccg tcgcacgcct    300
cttcatacac tctctcctgt actcggctac tagtgctact gcatgtagac atgtagtgaa    360
tgtgaagtac aaagaataca atacacggag tatagtagtg tagtcttgta tgcatatgta    420
aactactata ctctgtttta cgaaat                                         446

<210> SEQ ID NO 80
<211> LENGTH: 9651
<212> TYPE: DNA
<213> ORGANISM: Artificial sequence
<220> FEATURE:
<223> OTHER INFORMATION: Vector 15289

<400> SEQUENCE: 80
aattaattcc tgtggttggc atgcacatac aaatggacga acggataaac cttttcacgc     60
ccttttaaat atccgattat tctaataaac gctcttttct cttaggttta cccgccaata    120
tatcctgtca aacactgata gtttaaactg aaggcgggaa acgacaatct gatcatgagc    180
ggagaattaa gggagtcacg ttatgacccc cgccgatgac gcgggacaag ccgttttacg    240
tttggaactg acagaaccgc aacgctgcag gaattggccg cagcggccat ttaaatcaat    300
tgggcgcgcc agctgcttgt ggggaccaga caaaaaagga atggtgcaga attgttaggc    360
gcacctacca aaagcatctt tgcctttatt gcaaagataa agcagattcc tctagtacaa    420
gtggggaaca aaataacgtg aaaagagct gtcctgacag cccactcact aatgcgtatg    480
acgaacgcag tgacgaccac aaaactcgag acttttcaac aaagggtaat atccggaaac    540
ctcctcggat ccattgccc agctatctgt cactttattg tgaagatagt ggaaaaggaa    600
ggtggctcct acaaatgcca tcattgcgat aaaggaaagg ctatcgttga agatgcctct    660
gccgacagtg gtcccaaaga tggaccccca cccacgagga gcatcgtgga aaagaagac    720 gttccaacca cgtcttcaaa gcaagtggat tgatgtgata tctccactga cgtaagggat    780
gacgaacaat cccactatcc ttcggtaccg gaccgcgatc gcttaattaa gcttgcatgc    840
ctgcagtgca gcgtgacccg tcgtgcccc tctctagaga taatgagcat tgcatgtcta    900
agttataaaa aattaccaca tattttttt gtcacacttg tttgaagtgc agtttatcta    960
tctttataca tatatttaaa ctttactcta cgaataatat aatctatagt actacaataa   1020
tatcagtgtt ttagagaatc atataaatga acagttagac atggtctaaa ggacaattga   1080
gtattttgac aacaggactc tacagtttta tcttttagt gtgcatgtgt tctccttttt   1140
ttttgcaaat agcttcacct atataatact tcatccattt tattagtaca tccatttagg   1200
gtttagggtt aatggttttt atagactaat ttttttagta catctatttt attctatttt   1260
agcctctaaa ttaagaaaac taaaactcta tttagttttt tttatttaat aatttagata   1320
taaaatagaa taaaataaag tgactaaaaa ttaaacaaat acccttttaag aaattaaaaa   1380 aactaaggaa acatttttct tgtttcgagt agataatgcc agcctgttaa acgccgtcga   1440
cgagtctaac ggacaccaac cagcgaacca gcagcgtcgc gtcgggccaa gcgaagcaga   1500
cggcacggca tctctgtcgc tgcctctgga ccctctcga gagttccgct ccaccgttgg   1560
acttgctccg ctgtcggcat ccagaaattg cgtggcggag cggcagacgt gagccggcac   1620
ggcaggcggc ctcctcctcc tctcacggca ccggcagcta cggggattc ctttcccacc   1680 gctccttcgc tttcccttcc tcgcccgccg taataaatag acacccctc cacaccctct   1740
```

```
ttccccaacc tcgtgttgtt cggagcgcac acacacacaa ccagatctcc cccaaatcca    1800
cccgtcggca cctccgcttc aaggtacgcc gctcgtcctc ccccccccc cctctctacc     1860 ttctctagat cggcgttccg gtccatggtt agggcccggt agttctactt ctgttcatgt    1920
ttgtgttaga tccgtgtttg tgttagatcc gtgctgctag cgttcgtaca cggatgcgac    1980
ctgtacgtca gacacgttct gattgctaac ttgccagtgt ttctctttgg ggaatcctgg    2040
gatggctcta gccgttccgc agacgggatc gatttcatga ttttttttgt ttcgttgcat    2100
agggtttggt ttgcccttt cctttatttc aatatatgcc gtgcacttgt ttgtcgggtc     2160
atcttttcat gcttttttt gtcttggttg tgatgatgtg gtctggttgg gcggtcgttc     2220
tagatcggag tagaattctg tttcaaacta cctggtggat ttattaattt tggatctgta    2280
tgtgtgtgcc atacatattc atagttacga attgaagatg atggatggaa atatcgatct    2340
aggataggta tacatgttga tgcgggtttt actgatgcat atacagagat gcttttgtt    2400 cgcttggttg tgatgatgtg gtgtggttgg gcggtcgttc attcgttcta gatcggagta    2460
gaatactgtt tcaaactacc tggtgtattt attaattttg gaactgtatg tgtgtgtcat    2520
acatcttcat agttacgagt ttaagatgga tggaaatatc gatctaggat aggtatacat    2580
gttgatgtgg gttttactga tgcatataca tgatggcata tgcagcatct attcatatgc    2640
tctaaccttg agtacctatc tattataata aacaagtatg ttttataatt attttgatct    2700
tgatatactt ggatgatggc atatgcagca gctatatgtg gattttttta gccctgcctt    2760
catacgctat ttatttgctt ggtactgttt cttttgtcga tgctcaccct gttgtttggt    2820
gttacttctg cagggatccc cgatcatgca aaaactcatt aactcagtgc aaaactatgc    2880
ctggggcagc aaaacggcgt tgactgaact ttatggtatg gaaaatccgt ccagccagcc    2940
gatggccgag ctgtggatgg gcgcacatcc gaaaagcagt tcacgagtgc agaatgccgc    3000
cggagatatc gtttcactgc gtgatgtgat tgagagtgat aaatcgactc tgctcggaga    3060
ggccgttgcc aaacgctttg gcgaactgcc tttcctgttc aaagtattat gcgcagcaca    3120
gccactctcc attcaggttc atccaaacaa acacaattct gaaatcggtt ttgccaaaga    3180
aaatgccgca ggtatcccga tggatgccgc cgagcgtaac tataaagatc ctaaccacaa    3240
gccggagctg gttttgcgc tgacgccttt ccttgcgatg aacgcgttc gtgaattttc      3300 cgagattgtc tccctactcc agccggtcgc aggtgcacat ccggcgattg ctcactttt    3360 acaacagcct gatgccgaac gtttaagcga actgttcgcc agcctgttga atatgcaggg    3420
tgaagaaaaa tcccgcgcgc tggcgatttt aaaatcggcc ctcgatagcc agcagggtga    3480
accgtggcaa acgattcgtt taatttctga attttacccg gaagacagcg gtctgttctc    3540
cccgctattg ctgaatgtgg tgaaattgaa ccctggcgaa gcgatgttcc tgttcgctga    3600
aacaccgcac gcttacctgc aaggcgtggc gctggaagtg atggcaaact ccgataacgt    3660
gctgcgtgcg ggtctgacgc ctaaatacat tgatattccg gaactggttg ccaatgtgaa    3720
attcgaagcc aaaccggcta accagttgtt gacccagccg gtgaaacaag gtgcagaact    3780
ggacttcccg attccagtgg atgatttttgc cttctcgctg catgaccta gtgataaaga    3840 aaccaccatt agccagcaga gtgccgccat tttgttctgc gtcgaaggcg atgcaacgtt    3900
gtggaaaggt tctcagcagt tacagcttaa accgggtgaa tcagcgttta ttgccgccaa    3960
cgaatcaccg gtgactgtca aaggccacgg ccgtttagcg cgtgtttaca acaagctgta    4020
agagcttact gaaaaaatta acatctcttg ctaagctggg agctcgatcc gtcgacctgc    4080
agatcgttca acatttggc aataaagttt cttaagattg aatcctgttg ccggtcttgc     4140
```

-continued

```
gatgattatc atataatttc tgttgaatta cgttaagcat gtaataatta acatgtaatg    4200
catgacgtta tttatgagat gggtttttat gattagagtc ccgcaattat acatttaata    4260
cgcgatagaa aacaaaatat agcgcgcaaa ctaggataaa ttatcgcgcg cggtgtcatc    4320
tatgttacta gatctgctag ccctgcagga aatttaccgg tgcccgggcg ccagcatgg     4380 ccgtatccgc aatgtgttat taagttgtct aagcgtcaat ttgtttacac cacaatatat    4440
cctgccacca gccagccaac agctccccga ccggcagctc ggcacaaaat caccactcga    4500
tacaggcagc ccatcagaat taattctcat gtttgacagc ttatcatcga ctgcacggtg    4560
caccaatgct tctggcgtca ggcagccatc ggaagctgtg gtatggctgt gcaggtcgta    4620
aatcactgca taattcgtgt cgctcaaggc gcactcccgt tctggataat gttttttgcg    4680
ccgacatcat aacggttctg gcaaatattc tgaaatgagc tgttgacaat taatcatccg    4740
gctcgtataa tgtgtggaat tgtgagcgga taacaatttc acacaggaaa cagaccatga    4800
gggaagcgtt gatcgccgaa gtatcgactc aactatcaga ggtagttggc gtcatcgagc    4860
gccatctcga accgacgttg ctggccgtac atttgtacgg ctccgcagtg gatggcggcc    4920
tgaagccaca cagtgatatt gatttgctgg ttacggtgac cgtaaggctt gatgaaacaa    4980
cgcggcgagc tttgatcaac gaccttttgg aaacttcggc ttcccctgga gagagcgaga    5040
ttctccgcgc tgtagaagtc accattgttg tgcacgacga catcattccg tggcgttatc    5100
cagctaagcg cgaactgcaa tttggagaat ggcagcgcaa tgacattctt gcaggtatct    5160
tcgagccagc cacgatcgac attgatctgg ctatcttgct gacaaaagca agagaacata    5220
gcgttgcctt ggtaggtcca gcggcggagg aactctttga tccggttcct gaacaggatc    5280
tatttgaggc gctaaatgaa accttaacgc tatggaactc gccgcccgac tgggctggcg    5340
atgagcgaaa tgtagtgctt acgttgtccc gcatttggta cagcgcagta accggcaaaa    5400
tcgcgccgaa ggatgtcgct gccgactggg caatggagcg cctgccggcc cagtatcagc    5460
ccgtcatact tgaagctagg caggcttatc ttggacaaga agatcgcttg gcctcgcgcg    5520
cagatcagtt ggaagaattt gttcactacg tgaaaggcga gatcaccaaa gtagtcggca    5580
aataaagctc tagtggatct ccgtacccgg ggatctggct cgcggcggac gcacgacgcc    5640
ggggcgagac cataggcgat ctcctaaatc aatagtagct gtaacctcga agcgtttcac    5700
ttgtaacaac gattgagaat ttttgtcata aaattgaaat acttggttcg catttttgtc    5760
atccgcggtc agccgcaatt ctgacgaact gcccatttag ctggagatga ttgtacatcc    5820
ttcacgtgaa aatttctcaa gcgctgtgaa caagggttca gattttagat tgaaaggtga    5880
gccgttgaaa cacgttcttc ttgtcgatga cgacgtcgct atgcggcatc ttattattga    5940
ataccttacg atccacgcct tcaaagtgac gcgcgtagcc gacagcaccc agttcacaag    6000
agtactctct tccgcgacgg tcgatgtcgt ggttgttgat ctagatttag gtcgtgaaga    6060
tgggctcgag atcgttcgta atctggcggc aaagtctgat attccaatca taattatcag    6120
tggcgaccgc cttgaggaga cggataaagt tgttgcactc gagctaggag caagtgattt    6180
tatcgctaag ccgttcagta tcagagagtt tctagcacgc attcggggttg ccttgcgcgt    6240 gcgccccaac gttgtccgct ccaaagaccg acggtctttt tgttttactg actggacact    6300
taatctcagg caacgtcgct tgatgtccga agctggcggt gaggtgaaac ttacggcagg    6360
tgagttcaat cttctcctcg cgttttaga gaaaccccgc gacgttctat cgcgcgagca     6420
acttctcatt gccagtcgag tacgcgacga ggaggtttat gacaggagta tagatgttct    6480
```

```
cattttgagg ctgcgccgca aacttgaggc agatccgtca agccctcaac tgataaaaac    6540
agcaagaggt gccggttatt tctttgacgc ggacgtgcag gtttcgcacg ggggacgat     6600
ggcagcctga gccaattccc agatccccga ggaatcggcg tgagcggtcg caaaccatcc    6660
ggcccggtac aaatcggcgc ggcgctgggt gatgacctgg tggagaagtt gaaggccgcg    6720
caggccgccc agcggcaacg catcgaggca gaagcacgcc ccggtgaatc gtggcaagcg    6780
gccgctgatc gaatccgcaa agaatccggg caaccgccgg cagccggtgc gccgtcgatt    6840
aggaagccgc ccaagggcga cgagcaacca gattttttcg ttccgatgct ctatgacgtg    6900
ggcacccgcg atagtcgcag catcatggac gtggccgttt ccgtctgtc gaagcgtgac     6960
cgacgagctg gcgaggtgat ccgctacgag cttccagacg ggcacgtaga ggtttccgca    7020
gggccggccg gcatggccag tgtgtgggat tacgacctgg tactgatggc ggtttcccat    7080
ctaaccgaat ccatgaaccg ataccgggaa gggaagggag acaagcccgg ccgcgtgttc    7140
cgtccacacg ttgcggacgt actcaagttc tgccggcgag ccgatggcgg aaagcagaaa    7200
gacgacctgg tagaaacctg cattcggtta acaccacgc acgttgccat gcagcgtacg     7260
aagaaggcca agaacggccg cctggtgacg gtatccgagg gtgaagcctt gattagccgc    7320
tacaagatcg taaagagcga aaccgggcgg ccggagtaca tcgagatcga gctagctgat    7380
tggatgtacc gcgagatcac agaaggcaag aacccggacg tgctgacggt tcaccccgat    7440
tacttttga tcgatcccgg catcggccgt tttctctacc gcctggcacg ccgcgccgca    7500
ggcaaggcag aagccagatg gttgttcaag acgatctacg aacgcagtgg cagcgccgga    7560
gagttcaaga agttctgttt caccgtgcgc aagctgatcg ggtcaaatga cctgccggag    7620
tacgatttga aggaggaggc ggggcaggct ggcccgatcc tagtcatgcg ctaccgcaac    7680
ctgatcgagg gcgaagcatc cgccggttcc taatgtacgg agcagatgct agggcaaatt    7740
gccctagcag gggaaaaagg tcgaaaaggt ctctttcctg tggatagcac gtacattggg    7800
aacccaaagc cgtacattgg gaaccggaac ccgtacattg gaacccaaa gccgtacatt     7860
gggaaccggt cacacatgta agtgactgat ataaagaga aaaaggcga ttttccgcc      7920
taaaactctt taaaacttat taaaactctt aaaacccgcc tggcctgtgc ataactgtct    7980
ggccagcgca cagccgaaga gctgcaaaaa gcgcctaccc ttcggtcgct cgctcccta    8040
cgccccgccg cttcgcgtcg gcctatcgcg gccgctggcc gctcaaaaat ggctggccta    8100
cggccaggca atctaccagg gcgcggacaa gccgcgccgt cgccactcga ccgccggcgc    8160
tgaggtctgc ctcgtgaaga aggtgttgct gactcatacc aggcctgaat cgccccatca    8220
tccagccaga aagtgaggga gccacggttg atgagagctt tgttgtaggt ggaccagttg    8280
gtgattttga acttttgctt tgccacggaa cggtctgcgt tgtcgggaag atgcgtgatc    8340
tgatccttca actcagcaaa agttcgattt attcaacaaa gccgccgtcc cgtcaagtca    8400
gcgtaatgct ctgccagtgt tacaaccaat taaccaattc tgattagaaa aactcatcga    8460
gcatcaaatg aaaactgcaat ttattcatat caggattatc aataccatat ttttgaaaaa   8520
gccgtttctg taatgaagga gaaaactcac cgaggcagtt ccataggatg caagatcct    8580
ggtatcggtc tgcgattccg actcgtccaa catcaataca acctattaat ttcccctcgt    8640
caaaataag gttatcaagt gagaaatcac catgagtgac gactgaatcc ggtgagaatg    8700
gcaaaagctc tgcattaatg aatcggccaa cgcgcgggga gaggcggttt gcgtattggg    8760
cgctcttccg cttcctcgct cactgactcg ctgcgctcgg tcgttcggct gcggcgagcg    8820
gtatcagctc actcaaaggc ggtaatacgg ttatccacag aatcagggga taacgcagga    8880
```

```
aagaacatgt gagcaaaagg ccagcaaaag gccaggaacc gtaaaaaggc cgcgttgctg    8940 gcgttttttcc ataggctccg cccccctgac gagcatcaca aaaatcgacg ctcaagtcag   9000
aggtggcgaa acccgacagg actataaaga taccaggcgt ttcccctgg aagctccctc    9060 gtgcgctctc ctgttccgac cctgccgctt accggatacc tgtccgcctt tctcccttcg   9120
ggaagcgtgg cgctttctca tagctcacgc tgtaggtatc tcagttcggt gtaggtcgtt   9180
cgctccaagc tgggctgtgt gcacgaaccc cccgttcagc ccgaccgctg cgccttatcc   9240
ggtaactatc gtcttgagtc caacccggta agacacgact tatcgccact ggcagcagcc   9300
actggtaaca ggattagcag agcgaggtat gtaggcggtg ctacagagtt cttgaagtgg   9360
tggcctaact acggctacac tagaagaaca gtatttggta tctgcgctct gctgaagcca   9420
gttaccttcg gaaaaagagt tggtagctct tgatccggca acaaaccac cgctggtagc     9480 ggtggttttt tgtttgcaa gcagcagatt acgcgcagaa aaaaggatc tcaagaagat     9540 cctttgatct tttctacggg gtctgacgct cagtggaacg aaaactcacg ttaagggatt   9600
ttggtcatga gattatcaaa aaggatcttc acctagatcc ttttgatccg g            9651
```

<210> SEQ ID NO 81
<211> LENGTH: 21593
<212> TYPE: DNA
<213> ORGANISM: Artificial sequence
<220> FEATURE:
<223> OTHER INFORMATION: ZmABP-948-binary

<400> SEQUENCE: 81

```
ttcctgtggt tggcatgcac atacaaatgg acgaacggat aaaccttttc acgcccttt      60 aaatatccga ttattctaat aaacgctctt ttctcttagg tttacccgcc aatatatcct    120
gtcaaacact gatagtttaa actgaaggcg ggaaacgaca atctgatcat gagcggagaa   180
ttaagggagt cacgttatga ccccccgccga tgacgcggga caagccgttt tacgtttgga  240
actgacagaa ccgcaacgct gcaggaattg gccgcagcgg ccatttaaat caattgggcg   300
cgccagctgc ttgtggggac cagacaaaaa aggaatggtg cagaattgtt aggcgcacct   360
accaaaagca tctttgcctt tattgcaaag ataaagcaga ttcctctagt acaagtgggg    420
aacaaaataa cgtggaaaag agctgtcctg acagcccact cactaatgcg tatgacgaac    480
gcagtgacga ccacaaaact cgagactttt caacaaaggg taatatccgg aaacctcctc    540
ggattccatt gcccagctat ctgtcacttt attgtgaaga tagtggaaaa ggaaggtggc     600
tcctacaaat gccatcattg cgataaagga aaggctatcg ttgaagatgc ctctgccgac    660
agtggtccca agatggaccc ccacccacg aggagcatcg tggaaaaaga agacgttcca     720
accacgtctt caaagcaagt ggattgatgt gatatctcca ctgacgtaag ggatgacgaa    780
caatcccact atccttcggt accggaccct atagaatagc tcactatcct atttattata   840
gtttaagtat atagccaata ttttaaattt actatttatt aaattctagg gaagatagtc    900
tcaattcata actttattat aatacgtttg aaattttaaa tctttaggaa attttcttaa    960
ttcacctaga tacgattctg gagtgttaca agctgcgaat atactggtgc cattgagtat   1020
acataaatgg atttaggtgg tgctcaatag gtgaaaatga gatactaatc acttaaattt   1080
caaaatttct atggtgccac tgtactcgga taggtctatc tagggctgga caaaatgctc   1140
gtggctcgct ggctcgctcg tttcgtggtc agctcggctc ggctcggatc ggctcatttg   1200 aatttttgtca cgagctgagc tgacattcta gctcggttcg ttaacgagcc agctcgcgag  1260
```

```
ctaaacgagc taccatattc tagtaaaacg aaattatatt catatcattt atagaataat    1320
tgatgaacat gttatatata tgtgagatgt ctatggccta tgaattaaac taatgattaa    1380
tgaactatgc ctatgtgtta atttggtcta tgcaaatata attatgggtt aaactgatga    1440
acatgcatgt gaattgtgaa ttaatgagtg atgaattgtg ctaatttggt gttatattga    1500
catggtttgt gaaactatga gtataattac tattttctat tgttaaatta gtttgaaatt    1560
aactaaaaaa taattattat atacatttta tttttttct gctctggctc gcagctaaa      1620 cgagccagct cgacctcgta aacgagccga gccgagctga ctctgtggct cgttacctta    1680
acgagccgag ccgagctggc tcgttagctt aacgagccag ctcgaactcg gacgagccga    1740
gccgagctgg ctcgttatcc accctaggt ctatctagct tctgatgttt gcaaaccta     1800 gagttggagt gttcagccag ctactccttt gctttgctga ataaccatac caaacacgcc    1860
catattaata cccgctcggc ggtggttctg caatcaaacg caggccgcag tcgcgtgcgg    1920
aactagaggt ccttcagaga agtgccgtgc cagtgccacc gccggccgca tcatcgttcc    1980 gccccctgg tacgagcact cgcagagct gcaacctaca tcccttttac ataaatctat      2040
tgtctcgtat tgccgttgac gccggaatag tcttcgcatc ccttttacat aaatccgatg    2100
ttttctttct ccgattcctt tgaggaatca tcacgggtca gggcaggtgt tctgccgttt    2160 gccctttct ttatattctc cttagaagaa atatttagtt ggaggctgga catagccgga     2220
ggagctaact aatcgagcgg tgtactggca aaacaaaagg agcggagcaa gaaaggggag    2280
aaaaaactag ccactgccgg agcgctattg gccgtgttgg gcctggaagc ttgcatcaat    2340
acttccctcg ccccgatttg gttccaaaat catacaagtc ccaaagttgt caagatattg    2400
gaggtatgca agcgacttgg atctcaaaat agaagaaatt tcggatctga gcacaaatct    2460
gagttgaaaa aactgcaact caaaatcatc aaaaaaagaa gaagaaagaa acgaatatat    2520
tcgctcctct tctcagccga acccaaagga attgaatcca aaccctgggt aggcagacag    2580
tgagatatgg aggagagcag gaggcgaaca agagaggctg cggccacgaa tatctcacga    2640
acaagcacat catgggtcca cggagcgggc agggtgacgg gctcccgacg gcgagctaca    2700
tctcggaaga gcaccagggc agcatgtcgt gttgggcagg ttggccgtct ggcggacggc    2760
ggacggtgac tcgtggtcag ggtgcacctg ctcgattaag gcgcctgact actcatgtct    2820
tcgtctcttt gcttgtgttt gctatatgct gctcgtacct catgagcata ctaagttgac    2880
tgctcagtct gctgagtctg tttttctagg gtatagtgct gagcacaagg gatatcattg    2940
ttgggatatg attgctcgtt ggatgagggt ctcttgggat gttgtctttg atgaggctca    3000
ttctttttat tcttgtcctt ctttcgatgc tttgtcaaca tccttggttg atcccatctc    3060
ttttctatat tttctagatg cccgtgttac tattggacct gcctcacgct tggtgcgccc    3120
acgatagtag ccttagctcc ttctgacatg ttcatctctc tttcggtgcc ttcctttgtg    3180
gtgccttcta tagtgttttc tttggagcct gctgctttag cccctgacta cgctatgaac    3240
acttgtctac acccgccggg tcatcaattc ttttggtaca ccatcatcct ctcatgcgtt    3300
gccctcttat gatgtgcgct cttctgcaac tcattcattt tcttgcgatt tacctttgac    3360
tgatgctccc tattcatctc tggatccagc ttcctcagtt gactctttgc tggagccacc    3420
tcttagacgg agtcatcgtt ttcgtcagcc acctaatggg tactctcctt caggtttagt    3480
cgctaccgtt cttttctgagc tgacttctta tcatgatgct attcttcatc tgtaacgaca    3540
acatgcgatt tctgaggaga ttgctactct tgagcgcact agcacgttgg aacttgttcc    3600
ttgtccatca cgtgtttgtc ctatcaccag tatgtgggtc tataaggtca agacccgttc    3660
```

-continued

```
tgatggttct cttgatcgct ataaatctcg tctagttgcc caaggcttcc agtaggaaca    3720
tggttgtggc tatgatgaga tttttgcacc tgttgctcat atgaccactg ttcgcactct    3780
tcttgctatg gcctctgttc gtgcgtggtc catctctcat cttgatgtca agaatacctt    3840
tcttgatggt aagctacttg agttctatat gtagccatcg cctaggtatt ctatttctgc    3900
ttgtatggtt tgttgtcttc gccgttcccc ttatggcctc aagcaggctc cacattcttg    3960
gtttcagctc tttgcttcta tgataactgt tgttggtttt tctaccagta atcatggtcc    4020
tgcactcttt gtgtactacc tcctctcggg gtcggactct tctttatgtt gatgatataa    4080
ttatcactgg agataacctt gagtatgttg actttgttaa ggcacgtctt agttatcatt    4140
ttctcatgtc tgatcttggt cctctgtgtt actttcttgg gacaaaggtt tcttctttgt    4200
ctcagggcct ttatctatct caagaggagt acattcaaga ttttcttcat cgggcttctc    4260
ttaccgatca ctagattgtt gagactccca agcagctcaa tcttcacctt agtgccgatg    4320
atggcgagtc ttttcccgac catactcgtt atcgtcaaca tactgtagga agttttgttt    4380
atctctgtgt cactcgtctt gacatttcat atgttgtgtg tatcctgagt tagtttgctt    4440
cagatcccat ccaggtacac tatagtcact tgctttgtgt cctacaatat ctttgtggaa    4500
ccatatctag atgtatgttc tttccacatt ctagctcgtt gcaactgcaa tcttgttctg    4560
atgctacttg ggctagtgat tttttcgata gttggtctct ttctcaatat tgtgtttttc    4620
ttggtggttc tctcattgct cggaagacta agtagcaggt agcagtttct cgtttgagta    4680
ccgaggctga gttgcgtgct atggcccttg tgactgcaga ggttacttgg ttacgatagt    4740
tgcttgagga ttttcatgtt tctgtttcca tgacgactcc ttttgtctga cagtacaggt    4800
gttatcagta ttgctcgtga tgcggtgaag catgaggtca ccaagcatat tggagttgat    4860
gtttcgtata cacgagctga agtctaggat gatgttatct tgatttggta tgtgccttta    4920
gagcttcagt tggctaattt cttcacgagg gcacaggctc gcgctgagca taaattttc    4980 ctctcaaaac tcagtgttat agatccacct tgagtttgag ggagtattag atagatatgg    5040
gtttatttgt atttttccat tttataaggg tattagatag ataggcaacg actgctatgc    5100
aagtagtcat tctgtgcaag cgtgcaagca aaccatctga tccattatat cgtgatccaa    5160
ccgtgggtca catttaacac ttaaaccctt ccaccaccaa ctcaataatc tttataaaaa    5220 aaccctaac aaacaatggt tatatctgtg gttggatcgt aatctaatag atcagatggt    5280
ttgcttgtac gcttgcacag aatgactgct tgcatagcag ttgttgccta gatagatatg    5340
ggtttatttg tattttctc ttaagggttt ttgtgtatat ttgtactcat gtacctatat    5400
atttgtgcta gttgacccca taatgaatag acctgctatt cataatattt gcaaaccatg    5460
aaaatttgat tattacgaac tatccaaata ctcgaacaca tgggcattat agctcacaaa    5520
aatggaaggt tgagctgctg cttgaagaac ctcaacatct tgaacaaca acctcaacga    5580 aacttgtata tgaaccaact tccaaacaat cccttgtgga aggatagtaa tgacttcagg    5640
gcattgatca cacatatccg acggtggaac tactgtaaca accctctttt ctgtggaata    5700
tagttgaaac tctacaactt gaccaaaacc aagatgacga catatggtgg aactaacaaa    5760
acaagaggac tacactacct cattagctta ttaagcacaa tctcttggca ccacaacaac    5820
gaacaacaaa accatcattt ggatgctctg tgggcgacta aatgcaaatt ctttgcatgg    5880
ttgatcatcc caaattggtg gcacttagct ataggctagc agtgagagga tggccgaaca    5940
acatgcattg tccactatgt tggtgtagcc atgagaccaa ccaccacata aatgccaaac    6000
```

| | |
|---|---|
| gttcattcac caaaaaaatc taggcaacaa tggcttggat tcttacctg cagctccacc | 6060 |
| aagctaactg gagttcaatt aggtcaacgt atgggtggtg gtcgagtata gcagtcacaa | 6120 |
| atgatgttct aaagatgggg ttgtgttaac acatcttgct tgtagcacga gaacactgga | 6180 |
| aggagtgaaa ccaaagaatc tttcaacaca aggacctatc aacgctatcc atgattggga | 6240 |
| aattcaagga cgaaactaga atttgggtga acacatgcac aaggcaccta ggagagcctt | 6300 |
| tcttttgtac tgttaatccc tttttaaact ctctctgtcc ttaggagttc gtttcttccg | 6360 |
| ctctattcaa tgaagttagg cacaatcttg tgtgatttca ttagaaaaac acaagtaaat | 6420 |
| tgcatggtca gtacttgaag tattacagga atctcgtctg cccccaaact attaaacctt | 6480 |
| atatttggct ccctaatgta cttaactgat ctcattctgg tcaaactaaa catggtgatg | 6540 |
| gcaaggagcc gatatggtcg cccatgtgga tgtgatttaa gcaaaaaatc tcatggtcca | 6600 |
| tagctgtgtc aacaagccaa catgccatcg cttccttatg ccgagactgc ccatgtcgct | 6660 |
| cgcttttact gtcatcatca tcaaactgcc tgtcatgtct acggatgcca tgaccgctgt | 6720 |
| cacacatgat gtggagatga acctgtccat caacttccac gtgctgccac tatcgctagc | 6780 |
| tgacaccgtc ttggtcattg ctgtgtaggg ctaggctaag agtcgctgaa tgatcctttc | 6840 |
| gctctccttt acaggaacat gctgtttact ttgtgtcgcc aaggcgtgct agagtacctc | 6900 |
| ttctacacct ccagcaccag tagccttatt gttagcttgc acatcccaca taagcaggcc | 6960 |
| gatgtgaatg ataacttcag ggacgtcgac ggcatgtcac tgccaagagt catttggtgg | 7020 |
| gaagcgttgt catgccatct gtcgtgccat tttgtcctca gttcgaccgc cattaccgtg | 7080 |
| agcacaacct ttgcgcatgg ttggccgctt ccatcaccct tattccgttt cctcgtgttg | 7140 |
| gtcttgcccc aaggctatgg ttagcagacc gtgcatatgg ccggcaaaag actattttgc | 7200 |
| actgtagatt gcactcttta tatagtgaag tttaaaatag gagatgagat gaataaggct | 7260 |
| gctggagata gcctaaaccc ttgcagctcg tgcttgcatc gggggagcca aaaggcgtcc | 7320 |
| acctccacca tcgccgaagc actgagcact actctggctt tgtttcagc accacaccgc | 7380 |
| agagtgctta gggccaccaa cctcctcttg cctctgtgcc cagagcacca tcagctctgc | 7440 |
| tgcctccctc tgttccttgt gcttgctagg caggcaattc cgagctgggg cccaacttgt | 7500 |
| aacgctgatt tcaccatctt gccactgccg ggcaccaagt ggacacattt gacttggcct | 7560 |
| agtgggtttt ctgcataaat cacatacatg tggatgccat atcaggctct ttggtgttgt | 7620 |
| cgtgtctact ttcgacaagg atgagatcac ttaaacatat tagggagcca agtatgtaat | 7680 |
| ttcatagttt agggacctac acaaaaatcg tataatactt tagaacagcc gtgcagttta | 7740 |
| ctcaatcaac acatacaaag tcagatctta agctctgata cttcaaagga atggttgagc | 7800 |
| ccagttgaca aacaatcttg cttcattcat tgaattgttt ataggagtgg ctatgtaact | 7860 |
| actgggtggt tttgtttgac ctgtcatcca aattgtgtag tcaaccataa acatacacgt | 7920 |
| cacacaatac attttggatg tgacagatag gatttaggcg agagaatgta caatgtcact | 7980 |
| gaaaaattac cactgtatgg aaaggacaat ctaagtgaaa agagaaccag ggcctaatgg | 8040 |
| tttcaggact tcaaactccg gccaaatgaa tttacagtgc ttaaattaac tcatgttaat | 8100 |
| catgatagcc aaagcatggg caaaagagaa actatgaata aatcgacaat gtattctata | 8160 |
| tagcagtaat ataccatgtc acgagctttt acactaatgg gctgtatttt tctgcagtta | 8220 |
| ttttaactgg caatattcta tgtcacagta atatttgtta aattttttcc agaaatagcaa | 8280 |
| ctgaactaga agtctagtat ttcttaattg gataacaaaa ggaattagtg tgcatttggc | 8340 |
| ttacgaacaa tcagtcaccc aacattgaat ttgaagttct gtttcctctt tgttcagacg | 8400 |

```
acactctcca aatgaatgcc ttatattttg tgttgctcct cttttctgca gagtgttcag    8460
taacttcttc cgatgtaaac catggtacgt cctgtagaaa ccccaacccg tgaaatcaaa    8520
aaactcgacg gcctgtgggc attcagtctg gatcgcgaaa actgtggaat tgatcagcgt    8580
tggtgggaaa gcgcgttaca agaaagccgg gcaattgctg tgccaggcag ttttaacgat    8640
cagttcgccg atgcagatat tcgtaattat gcgggcaacg tctggtatca gcgcgaagtc    8700
tttataccga aaggttgggc aggccagcgt atcgtgctgc gtttcgatgc ggtcactcat    8760
tacggcaaag tgtgggtcaa taatcaggaa gtgatggagc atcagggcgg ctatacgcca    8820
tttgaagccg atgtcacgcc gtatgttatt gccggaaaa gtgtacgtat caccgtttgt    8880
gtgaacaacg aactgaactg gcagactatc ccgccgggaa tggtgattac cgacgaaaac    8940
ggcaagaaaa agcagtctta cttccatgat ttctttaact atgccggaat ccatcgcagc    9000
gtaatgctct acaccacgcc gaacacctgg gtggacgata tcaccgtggt gacgcatgtc    9060
gcgcaagact gtaaccacgc gtctgttgac tggcaggtac caagctgcga atcttcgttt    9120
ttttaaggaa ttctcgatct ttatggtgta taggctctgg gttttctgtt ttttgtatct    9180
cttaggattt tgtaaattcc agatctttct atggccactt agtagtatat ttcaaaaatt    9240
ctccaatcga gttcttcatt cgcattttca gtcattttct cttcgacgtt gtttttaagc    9300
ctgggtatta ctcctattta gttgaactct gcagcaatct tagaaaatta gggttttgag    9360
gtttcgattt ctctaggtaa ccgatctatt gcattcatct gaatttctgc atatatgtct    9420
tagatttctg ataagcttac gatacgttag gtgtaattga agtttatttt tcaagagtgt    9480 tatttttttgt ttctgaattt ttcaggtggt ggccaatggt gatgtcagcg ttgaactgcg    9540
tgatgcggat caacaggtgg ttgcaactgg acaaggcact agcgggactt tgcaagtggt    9600
gaatccgcac ctctggcaac cgggtgaagg ttatctctat gaactgtgcg tcacagccaa    9660
aagccagaca gagtgtgata tctacccgct tcgcgtcggc atccggtcag tggcagtgaa    9720
gggcgaacag ttcctgatta accacaaacc gttctacttt actggctttg gtcgtcatga    9780
agatgcggac ttgcgtggca aaggattcga taacgtgctg atggtgcacg accacgcatt    9840
aatggactgg attgggccca actcctaccg tacctcgcat taccttacg ctgaagagat    9900 gctcgactgg gcagatgaac atggcatcgt ggtgattgat gaaactgctg ctgtcggctt    9960
taacctctct ttaggcattg gtttcgaagc gggcaacaag ccgaaagaac tgtacagcga    10020
agaggcagtc aacggggaaa ctcagcaagc gcacttacag gcgattaaag agctgatagc    10080
gcgtgacaaa aaccacccaa gcgtggtgat gtggagtatt gccaacgaac cggatacccg    10140
tccgcaaggt gcacgggaat atttcgcgcc actggcggaa gcaacgcgta aactcgaccc    10200
gacgcgtccg atcacctgcg tcaatgtaat gttctgcgac gctcacaccg ataccatcag    10260
cgatctcttt gatgtgctgt gcctgaaccg ttattacgga tggtatgtcc aaagcggcga    10320
tttgaaaacg gcagagaagg tactggaaaa agaacttctg gcctggcagg agaaactgca    10380
tcagccgatt atcatcaccg aatacggcgt ggatacgtta gccgggctgc actcaatgta    10440
caccgacatg tggagtgaag agtatcagtg tgcatggctg gatatgtatc accgcgtctt    10500
tgatcgcgtc agcgccgtcg tcggtgaaca ggtatggaat ttcgccgatt ttgcgacctc    10560
gcaaggcata ttgcgcgttg cggtaacaa gaaagggatc ttcactcgcg accgcaaacc    10620
gaagtcggcg gcttttctgc tgcaaaaacc ctggactggc atgaacttcg gtgaaaaacc    10680
gcagcaggga ggcaaacaat gagagctcga ggtacaaatc tcatctgtgc cttgctctag    10740
```

```
tttcccaaat ggaattaact atgcatgatt tgtttggaaa ctcttattgc atccatccag    10800
ataatgcatc caccataagg taatatcttg atgacatctg tgcctgatgg tgtaccaaat    10860
gtctctatct ctgcattgag ccacgagtag gaggatagcc taggggtgcc ttgactccaa    10920
agttgtattg aaaaagatgg atgaagcagg caaatgctgc ctgaatccat gactcagggc    10980
acagattttc cactcaaagg aagataagat tgcattactt catgatcttt tgaactgcct    11040
ctgcaagacg ggactcggat agtggatgca aagatctaat actggcctca ggcaacgagt    11100
tgtttcactc gaaagtctag aaatgaccgg gctcaaattt gcaccccaa ggaaagtgag     11160 tttgcattac ttcatgacct tttgaactgc ctctgcaaga ctggactcag attacgcttg    11220
attggttgcc ggcctcacct tcgcctggct tgcgcgagcc tgcgtctata gaaatgcgcc    11280
ggactcacgt ctccgtcgat gcaggcattc gactgaaaaa acatttaaac tgcacccatg    11340
cgtgcgggct gagcttatgt catacaagta accaatcaca ggcttaagtt cagtcaacgc    11400
atgcgctaag cttggatgtg gctgaccggg caaccaatca cacagatagt ggatgcacgg    11460
atctaatatt ggctaatttg gttaaacttg tctaacctta gacgtggcaa gtgagtcagc    11520
ggatcaaatc tgctctaaaa ttgtctgcct cctagatgtc cttggtgttc caagatttaa    11580
tcatcactgc actatttctt tgcgttgctt cgctgcagct tcgcgttact tgcattcgct    11640
taatcaggat tactttgatc aactaggttt ctaacttcta ctaccttcac ttgcacaggg    11700
tgcccgtcct gctagccggt gtgcttgctg tgcgatcgtt tggcatgtgc ttgttgaggg    11760
gttgctaggg gattggagag gattgaaggg attaaatctc ctcctattca attttgaata    11820 ggagggatt taatcccctt caatcccct caaaccacta gtaaccgaac gtggcctgag     11880
ggggcgggcg agtcttata ttgaatgaaa ctacataaaa tagcatgccg tctctgtcac     11940
tggcaatgga cggtggtgcc tagcgcaact cagcgcacaa ctgtgtgtct tgattttct    12000 tctgtttatc acggcattag tgccatgccg ttttatgtta cagtgttgtg tgctcgcaag    12060
catccgaaaa tatgcgtctg agtttagggt tgggtcaaac ttgtcgaatt tggggttctg    12120
ttataatatg ttgagcatga ataaagatgg atgctggtga ctctgtcgcc atcgccgtcc    12180
atcatgagtg tcctgtaatt caacttatat ctatcatgta tgtatgtatg tatgtatgta    12240
tgtatgtata tgctgtctac tatgcttctt tgttttaact gaaatgtgtg ttacagtgtt    12300
acttctctgg ggtccattta aaacggcatt tcgtttacga taggaaccag ccattataat    12360
ctttaaccaa taatttcgct aaccaatttc aactattgca atgcgaactt aatattatca    12420
gatttataac cgaatgcgct atcaaataat cataaggttg taatcataat aatataatat    12480
aaaataaatg agtgctcgaa gtgaaatttt agagagcgtt ataagaaaaa ttgatgtgat    12540
ctccaagaat aatagcccct cccggctccc ggtacaaaca tagggcttct ttagaatgca    12600
ggattgtgag aacataggaa taggaaaaat ataggaattc tataggaatg tatatggaaa    12660
acagaggatt gaaaaacaca gaaaaaatgt gaaagcaagt cttggatga agcgtaggaa     12720 acttatagga ataggaattc ataacggacc gcgatcgctt aattaagctt gcatgcctgc    12780
agtgcagcgt gacccggtcg tgcccctctc tagagataat gagcattgca tgtctaagtt    12840
ataaaaaatt accacatatt ttttttgtca cacttgtttg aagtgcagtt tatctatctt    12900
tatacatata tttaaacttt actctacgaa taatataatc tatagtacta caataatatc    12960
agtgttttag agaatcatat aaatgaacag ttagacatgg tctaaaggac aattgagtat    13020
tttgacaaca ggactctaca gttttatctt tttagtgtgc atgtgttctc cttttttttt    13080
gcaaatagct tcacctatat aatacttcat ccatttttatt agtacatcca tttagggttt    13140
```

```
agggttaatg gtttttatag actaattttt ttagtacatc tattttattc tattttagcc    13200
tctaaattaa gaaaactaaa actctatttt agtttttta tttaataatt tagatataaa     13260
atagaataaa ataaagtgac taaaaattaa acaaatacccc tttaagaaat taaaaaaact    13320
aaggaaacat ttttcttgtt tcgagtagat aatgccagcc tgttaaacgc cgtcgacgag    13380
tctaacggac accaaccagc gaaccagcag cgtcgcgtcg ggccaagcga agcagacggc    13440
acggcatctc tgtcgctgcc tctggacccc tctcgagagt tccgctccac cgttggactt    13500
gctccgctgt cggcatccag aaattgcgtg gcggagcggc agacgtgagc cggcacggca    13560
ggcggcctcc tcctcctctc acggcaccgg cagctacggg ggattccttt cccaccgctc    13620
cttcgctttc ccttcctcgc ccgccgtaat aaatagacac cccctccaca ccctctttcc    13680
ccaacctcgt gttgttcgga gcgcacacac acacaaccag atctccccca aatccacccg    13740
tcggcacctc cgcttcaagg tacgccgctc gtcctccccc ccccccctc tctaccttct     13800 ctagatcggc gttccggtcc atggttaggg cccggtagtt ctacttctgt tcatgtttgt    13860
gttagatccg tgtttgtgtt agatccgtgc tgctagcgtt cgtacacgga tgcgacctgt    13920
acgtcagaca cgttctgatt gctaacttgc cagtgtttct cttgggggaa tcctgggatg    13980
gctctagccg ttccgcagac gggatcgatt tcatgatttt ttttgtttcg ttgcataggg    14040
tttggtttgc ccttttcctt tatttcaata tatgccgtgc acttgtttgt cgggtcatct    14100
tttcatgctt ttttttgtct tggttgtgat gatgtggtct ggttgggcgg tcgttctaga    14160
tcggagtaga attctgtttc aaactacctg gtggatttat taattttgga tctgtatgtg    14220
tgtgccatac atattcatag ttacgaattg aagatgatgg atggaaatat cgatctagga    14280
taggtataca tgttgatgcg ggttttactg atgcatatac agagatgctt tttgttcgct    14340
tggttgtgat gatgtggtgt ggttgggcgg tcgttcattc gttctagatc ggagtagaat    14400
actgtttcaa actacctggt gtatttatta attttggaac tgtatgtgtg tgtcatacat    14460
cttcatagtt acgagtttaa gatggatgga aatatcgatc taggataggt atacatgttg    14520
atgtgggttt tactgatgca tatacatgat ggcatatgca gcatctattc atatgctcta    14580
accttgagta cctatctatt ataataaaca agtatgtttt ataattattt tgatcttgat    14640
atacttggat gatggcatat gcagcagcta tatgtggatt tttttagccc tgccttcata    14700 cgctattat ttgcttggta ctgtttcttt tgtcgatgct caccctgttg tttggtgtta     14760
cttctgcagg gatccccgat catgcaaaaa ctcattaact cagtgcaaaa ctatgcctgg    14820
ggcagcaaaa cggcgttgac tgaactttat ggtatgaaaa atccgtccag ccagccgatg    14880
gccgagctgt ggatgggcgc acatccgaaa agcagttcac gagtgcagaa tgccgccgga    14940
gatatcgttt cactgcgtga tgtgattgag agtgataaat cgactctgct cggagaggcc    15000
gttgccaaac gctttggcga actgcctttc ctgttcaaag tattatgcgc agcacagcca    15060
ctctccattc aggttcatcc aaacaaacac aattctgaaa tcggttttgc caagaaaat    15120 gccgcaggta tcccgatgga tgccgccgag cgtaactata aagatcctaa ccacaagccg    15180
gagctggttt ttgcgctgac gcctttcctt gcgatgaacg cgtttcgtga attttccgag    15240
attgtctccc tactccagcc ggtcgcaggt gcacatccgg cgattgctca cttttttacaa   15300 cagcctgatg ccgaacgttt aagcgaactg ttcgccagcc tgttgaatat gcagggtgaa    15360
gaaaaatccc gcgcgctggc gattttaaaa tcggccctcg atagccagca gggtgaaccg    15420
tggcaaacga ttcgtttaat ttctgaattt tacccggaag acagcggtct gttctccccg    15480
```

```
ctattgctga atgtggtgaa attgaaccct ggcgaagcga tgttcctgtt cgctgaaaca   15540
ccgcacgctt acctgcaagg cgtggcgctg aagtgatgg caaactccga taacgtgctg    15600
cgtgcgggtc tgacgcctaa atacattgat attccggaac tggttgccaa tgtgaaattc   15660
gaagccaaac cggctaacca gttgttgacc cagccggtga acaaggtgc agaactggac    15720 ttcccgattc cagtggatga ttttgccttc tcgctgcatg accttagtga taagaaacc    15780 accattagcc agcagagtgc cgccattttg ttctgcgtcg aaggcgatgc aacgttgtgg   15840
aaaggttctc agcagttaca gcttaaaccg ggtgaatcag cgtttattgc cgccaacgaa   15900
tcaccggtga ctgtcaaagg ccacggccgt ttagcgcgtg tttacaacaa gctgtaagag   15960
cttactgaaa aaattaacat ctcttgctaa gctgggagct cgatccgtcg acctgcagat   16020
cgttcaaaca tttggcaata aagtttctta agattgaatc ctgttgccgg tcttgcgatg   16080
attatcatat aatttctgtt gaattacgtt aagcatgtaa taattaacat gtaatgcatg   16140
acgttattta tgagatgggt ttttatgatt agagtcccgc aattatacat ttaatacgcg   16200
atagaaaaca aaatatagcg cgcaaactag gataaaattat cgcgcgcggt gtcatctatg   16260
ttactagatc tgctagccct gcaggaaatt taccggtgcc cgggcggcca gcatggccgt   16320
atccgcaatg tgttattaag ttgtctaagc gtcaatttgt ttacaccaca atatatcctg   16380
ccaccagcca gccaacagct ccccgaccgg cagctcggca caaaatcacc actcgataca   16440
ggcagcccat cagaattaat tctcatgttt gacagcttat catcgactgc acggtgcacc   16500
aatgcttctg gcgtcaggca gccatcggaa gctgtggtat ggctgtgcag gtcgtaaatc   16560
actgcataat tcgtgtcgct caaggcgcac tcccgttctg gataatgttt tttgcgccga   16620
catcataacg gttctggcaa atattctgaa atgagctgtt gacaattaat catccggctc   16680
gtataatgtg tggaattgtg agcggataac aatttcacac aggaaacaga ccatgaggga   16740
agcgttgatc gccgaagtat cgactcaact atcagaggta gttggcgtca tcgagcgcca   16800
tctcgaaccg acgttgctgg ccgtacattt gtacggctcc gcagtggatg gcggcctgaa   16860
gccacacagt gatattgatt tgctggttac ggtgaccgta aggcttgatg aaacaacgcg   16920
gcgagctttg atcaacgacc ttttggaaac ttcggcttcc cctggagaga gcgagattct   16980
ccgcgctgta gaagtcacca ttgttgtgca cgacgacatc attccgtggc gttatccagc   17040
taagcgcgaa ctgcaatttg gagaatggca gcgcaatgac attcttgcag gtatcttcga   17100
gccagccacg atcgacattg atctggctat cttgctgaca aaagcaagag aacatagcgt   17160
tgccttggta ggtccagcgg cggaggaact ctttgatccg gttcctgaac aggatctatt   17220
tgaggcgcta aatgaaacct taacgctatg gaactcgccg cccgactggg ctggcgatga   17280
gcgaaatgta gtgcttacgt tgtcccgcat ttggtacagc gcagtaaccg gcaaaatcgc   17340
gccgaaggat gtcgctgccg actgggcaat ggagcgcctg ccggcccagt atcagcccgt   17400
catacttgaa gctaggcagg cttatcttgg acaagaagat cgcttggcct cgcgcgcaga   17460
tcagttggaa gaatttgttc actacgtgaa aggcgagatc accaaagtag tcggcaaata   17520
aagctctagt ggatctccgt acccggggat ctggctcgcg cggacgcac gacgccgggg    17580 cgagaccata ggcgatctcc taaatcaata gtagctgtaa cctcgaagcg tttcacttgt   17640
aacaacgatt gagaattttt gtcataaaat tgaaatactt ggttcgcatt tttgtcatcc   17700
gcggtcagcc gcaattctga cgaactgccc atttagctgg agatgattgt acatccttca   17760
cgtgaaaatt tctcaagcgc tgtgaacaag ggttcagatt ttagattgaa aggtgagccg   17820
ttgaaacacg ttcttcttgt cgatgacgac gtcgctatgc ggcatcttat tattgaatac   17880
```

```
cttacgatcc acgccttcaa agtgaccgcg gtagccgaca gcacccagtt cacaagagta   17940
ctctcttccg cgacggtcga tgtcgtggtt gttgatctag atttaggtcg tgaagatggg   18000
ctcgagatcg ttcgtaatct ggcggcaaag tctgatattc caatcataat tatcagtggc   18060
gaccgccttg aggagacgga taaagttgtt gcactcgagc taggagcaag tgattttatc   18120
gctaagccgt tcagtatcag agagtttcta gcacgcattc gggttgcctt gcgcgtgcgc   18180
cccaacgttg tccgctccaa agaccgacgg tcttttttgtt ttactgactg gacacttaat   18240
ctcaggcaac gtcgcttgat gtccgaagct ggcggtgagg tgaaacttac ggcaggtgag   18300
ttcaatcttc tcctcgcgtt tttagagaaa ccccgcgacg ttctatcgcg cgagcaactt   18360
ctcattgcca gtcgagtacg cgacgaggag gtttatgaca ggagtataga tgttctcatt   18420
ttgaggctgc gccgcaaact tgaggcagat ccgtcaagcc ctcaactgat aaaaacagca   18480
agaggtgccg gttatttctt tgacgcggac gtgcaggttt cgcacggggg gacgatggca   18540
gcctgagcca attcccagat ccccgaggaa tcggcgtgag cggtcgcaaa ccatccggcc   18600
cggtacaaat cggcgcggcg ctgggtgatg acctggtgga gaagttgaag gccgcgcagg   18660
ccgcccagcg gcaacgcatc gaggcagaag cacgccccgg tgaatcgtgg caagcggccg   18720
ctgatcgaat ccgcaaagaa tcccggcaac cgccggcagc cggtgcgccg tcgattagga   18780
agccgcccaa gggcgacgag caaccagatt ttttcgttcc gatgctctat gacgtgggca   18840
cccgcgatag tcgcagcatc atggacgtgg ccgttttccg tctgtcgaag cgtgaccgac   18900
gagctggcga ggtgatccgc tacgagcttc cagacgggca cgtagaggtt tccgcagggc   18960
cggccggcat ggccagtgtg tgggattacg acctggtact gatggcggtt tcccatctaa   19020
ccgaatccat gaaccgatac cgggaaggga agggagacaa gcccggccgc gtgttccgtc   19080
cacacgttgc ggacgtactc aagttctgcc ggcgagccga tggcggaaag cagaaagacg   19140
acctggtaga aacctgcatt cggttaaaca ccacgcacgt tgccatgcag cgtacgaaga   19200
aggccaagaa cggccgcctg gtgacggtat ccgagggtga agccttgatt agccgctaca   19260
agatcgtaaa gagcgaaacc gggcggccgg agtacatcga gatcgagcta gctgattgga   19320
tgtaccgcga gatcacagaa ggcaagaacc cggacgtgct gacggttcac cccgattact   19380
ttttgatcga tcccggcatc ggccgttttc tctaccgcct ggcacgccgc gccgcaggca   19440
aggcagaagc cagatggttg ttcaagacga tctacgaacg cagtggcagc gccggagagt   19500
tcaagaagtt ctgttttcacc gtgcgcaagc tgatcgggtc aaatgacctg ccggagtacg   19560
atttgaagga ggaggcgggg caggctggcc cgatcctagt catgcgctac cgcaacctga   19620
tcgagggcga agcatccgcc ggttcctaat gtacggagca gatgctaggg caaattgccc   19680
tagcagggga aaaggtcgaa aaggtctct ttcctgtgga tagcacgtac attgggaacc   19740
caaagccgta cattgggaac cggaacccgt acattgggaa cccaaagccg tacattggga   19800
accggtcaca catgtaagtg actgatataa aagagaaaaa aggcgatttt tccgcctaaa   19860
actcttttaaa acttattaaa actcttaaaa cccgcctggc ctgtgcataa ctgtctggcc   19920
agcgcacagc cgaagagctg caaaaagcgc ctacccttcg gtcgctgcgc tccctacgcc   19980
ccgccgcttc gcgtcggcct atcgcggccg ctggccgctc aaaaatggct ggcctacggc   20040
caggcaatct accagggcgc ggacaagccg cgccgtcgcc actcgaccgc cggcgctgag   20100
gtctgcctcg tgaagaaggt gttgctgact cataccaggc ctgaatcgcc ccatcatcca   20160
gccagaaagt gagggagcca cggttgatga gagctttgtt gtaggtggac cagttggtga   20220
```

```
ttttgaacttt ttgctttgcc acggaacggt ctgcgttgtc gggaagatgc gtgatctgat   20280
ccttcaactc agcaaaagtt cgatttattc aacaaagccg ccgtcccgtc aagtcagcgt   20340
aatgctctgc cagtgttaca accaattaac caattctgat tagaaaaact catcgagcat   20400
caaatgaaac tgcaatttat tcatatcagg attatcaata ccatatttt gaaaaagccg    20460 tttctgtaat gaaggagaaa actcaccgag gcagttccat aggatggcaa gatcctggta   20520
tcggtctgcg attccgactc gtccaacatc aatacaacct attaatttcc cctcgtcaaa   20580
aataaggtta tcaagtgaga atcaccatg agtgacgact gaatccggtg agaatggcaa    20640
aagctctgca ttaatgaatc ggccaacgcg cggggagagg cggtttgcgt attgggcgct   20700
cttccgcttc ctcgctcact gactcgctgc gctcggtcgt tcggctgcgg cgagcggtat   20760
cagctcactc aaaggcggta atacggttat ccacagaatc aggggataac gcaggaaaga   20820
acatgtgagc aaaaggccag caaaaggcca ggaaccgtaa aaaggccgcg ttgctggcgt   20880
ttttccatag gctccgcccc cctgacgagc atcacaaaaa tcgacgctca agtcagaggt   20940
ggcgaaaccc gacaggacta taaagatacc aggcgtttcc ccctggaagc tccctcgtgc   21000
gctctcctgt tccgaccctg ccgcttaccg gatacctgtc cgcctttctc ccttcgggaa   21060
gcgtggcgct ttctcatagc tcacgctgta ggtatctcag ttcggtgtag gtcgttcgct   21120
ccaagctggg ctgtgtgcac gaaccccccg ttcagcccga ccgctgcgcc ttatccggta   21180
actatcgtct tgagtccaac ccggtaagac acgacttatc gccactggca gcagccactg   21240
gtaacaggat tagcagagcg aggtatgtag gcggtgctac agagttcttg aagtggtggc   21300
ctaactacgg ctacactaga agaacagtat ttggtatctg cgctctgctg aagccagtta   21360
ccttcggaaa aagagttggt agctcttgat ccggcaaaca aaccaccgct ggtagcggtg   21420
gtttttttgt ttgcaagcag cagattacgc gcagaaaaaa aggatctcaa gaagatcctt   21480
tgatcttttc tacggggtct gacgctcagt ggaacgaaaa ctcacgttaa gggattttgg   21540
tcatgagatt atcaaaaagg atcttcacct agatcctttt gatccggaat taa          21593

<210> SEQ ID NO 82
<211> LENGTH: 15097
<212> TYPE: DNA
<213> ORGANISM: Artificial sequence
<220> FEATURE:
<223> OTHER INFORMATION: ZmABT-990-binary

<400> SEQUENCE: 82
attcctgtgg ttggcatgca catacaaatg gacgaacgga taaacctttt cacgcccttt      60
taaatatccg attattctaa taaacgctct tttctcttag gtttaccgc caatatatcc      120 tgtcaaacac tgatagttta aactgaaggc gggaaacgac aatctgatca tgagcggaga    180
attaagggag tcacgttatg acccccgccg atgacgcggg acaagccgtt ttacgtttgg    240
aactgacaga accgcaacgc tgcaggaatt ggccgcagcg gccatttaaa tcaattgggc    300
gcgccagctg cttgtgggga ccagacaaaa aaggaatggt gcagaattgt taggcgcacc    360
taccaaaagc atctttgcct ttattgcaaa gataaagcag attcctctag tacaagtggg    420
gaacaaaata acgtggaaaa gagctgtcct gacagcccac tcactaatgc gtatgacgaa    480
cgcagtgacg accacaaaac tcgagacttt tcaacaaagg gtaatatccg gaaacctcct   540
cggattccat tgcccagcta tctgtcactt tattgtgaag atagtggaaa aggaaggtgg    600
ctcctacaaa tgccatcatt gcgataaagg aaaggctatc gttgaagatg cctctgccga   660
cagtggtccc aaagatggac ccccacccac gaggagcatc gtggaaaaag aagacgttcc   720
```

```
aaccacgtct tcaaagcaag tggattgatg tgatatctcc actgacgtaa gggatgacga    780
acaatcccac tatccttcgg taccggaccc ggtctgagtt gttaggtgaa ttttactact    840
atccagcgac aactaaaaaa gaaacagagt gagtactaag gaagactata tattttgtat    900
attaacgaga agagatagtt agttacagca catccattgg agcgccggcc aaagcagata    960
tatagtgtcg ttacgtttgt aatcatagtt ctggttttc tactatgtat aattaaacat   1020
aatgcaacct tcttaagacg gatgtatcaa ttcgatgggc tcattccctt ctttttttta   1080
tttatcgcaa tttagtttaa aaagatcta gcggacgata aatatttaag aatgaagata   1140
gtaattatct tcagtcaata caatagtttc tcaacaatat ataatatata tttgcgcgcc   1200
tgtggggtgt gtgttttac aacacaaaca accgacaggg aattctaacg caaatgcttc   1260
cgtttgtact tgattatcaa gacataaaga cgaagatggt tacgttacga tgcttctagt   1320
tggcatctgc acataacatg catgcatgcg ccgggtttaa tgcataatgc tgtgtacata   1380
cattatttgc agcacacacg cgtattgctc atgtgacgtg ccgcctgtct gtctatcctt   1440
gaccggcact tggtaccaac cattatgttc gttgtattgc gagctagcta gctgcctgta   1500
ctatataact gcagaaaggt acactacaga atgcagatgc tgcgccactg gttcgcatac   1560
actattctat tccactggcc acctataaac atatgcatga caattgacaa acaagctagc   1620
gtctctagaa agttggtgcc ggccatagca attattcccg actggagtga agaaaagaaa   1680
ctaccatttc catgtgggtt tcctttgcat atcatagaat caagatgtaa atatctatga   1740
gataccatta tagaattttg ctgacgtggc tgcattgtat gatatagtgt tgcggacagc   1800
ctcagcagcc agctggagct gacaggggag ttcaaaagaa acacacgtac accaaccagc   1860
tagtatctcc tcaacgacat cggctaaatt atcttgtcgg tatgcatact tttcttcgcg   1920 cgcgggggc ctttcattag atgcttgcac ataaaactgc gctagctgat gctgaatctc   1980
agcctaacat atatactcct atatatatat attctcttgt attttatgcc aattaatgta   2040
acgcaattca gatgtgctgg ctggtcaaca cactgtgtgc atatgctggc tttcggagac   2100
taaacctgga ccaagtttgg cgcccgattt ggatggtttc tggtccccta gcggcatgca   2160
ggcatcagtg ggcctataa atatgcatgg agtagagcaa cctctatgca caccacacaa   2220
cacaacacaa taatacagca aaggaggcta gcagaagtgc aggattaata agctaagcta   2280
gtagaaatta agcaaagcat aggcacagcc ttggctacct cctctggttc ttgccttatt   2340
attagcctgt tggtggtggt ggtggcggcg gcgctgtcgg cctcaacggc gtcggcacag   2400
ctgtcgtcga cgttctacga cacgtcgtgc cccagcgcgt tgtccaccat cagcagcggc   2460
gtgaactccg ccgtggcgca gcaggctcgt gtggggcgt cgctgctccg gctccacttc   2520
cacgactgct tcgtccaagc aagtctagct gtctcagatg catctatcta tctacttata   2580
tataagcatg atttcctttc tagctagcta gcatcgtcgt gcattttaat ttgaagataa   2640
aagattagca cgtcgtatat gcatgcgatt aattaaccag gaggcatcaa ggtgaaattt   2700
ctggtggtcc accagggctg cgacgcgtcc attctgctga cgacacgtc cggggagcag   2760 acccagccgc cgaacctaac tctgaacccg agggccttcg acgtcgtcaa cagcatcaag   2820
gcgcaggtgg aggcggcgtg cgcggcgtc gtctcctgcg ccgacatcct cgccgtcgcc   2880
gcccgcgacg gagttgacgc ggtacgtagc tacatcaccg tgcctattaa tttgctggct   2940
agtagcttgt tggtttgcaa actaactaac taattccgat cgtatgcgtg gtgcatatgc   3000
agctcggcgg gccttcgtaa accatggtac gtcctgtaga aaccccaacc cgtgaaatca   3060
```

```
aaaaactcga cggcctgtgg gcattcagtc tggatcgcga aaactgtgga attgatcagc    3120
gttggtggga aagcgcgtta caagaaagcc gggcaattgc tgtgccaggc agttttaacg    3180
atcagttcgc cgatgcagat attcgtaatt atgcgggcaa cgtctggtat cagcgcgaag    3240
tctttatacc gaaaggttgg gcaggccagc gtatcgtgct gcgtttcgat gcggtcactc    3300
attacggcaa agtgtgggtc aataatcagg aagtgatgga gcatcagggc ggctatacgc    3360
catttgaagc cgatgtcacg ccgtatgtta ttgccgggaa aagtgtacgt atcaccgttt    3420
gtgtgaacaa cgaactgaac tggcagacta tcccgccggg aatggtgatt accgacgaaa    3480
acggcaagaa aaagcagtct tacttccatg atttctttaa ctatgccgga atccatcgca    3540
gcgtaatgct ctacaccacg ccgaacacct gggtggacga tatcaccgtg gtgacgcatg    3600
tcgcgcaaga ctgtaaccac gcgtctgttg actggcaggt accaagctgc gaatcttcgt    3660
ttttttaagg aattctcgat ctttatggtg tataggctct gggttttctg ttttttgtat    3720
ctcttaggat tttgtaaatt ccagatcttt ctatggccac ttagtagtat atttcaaaaa    3780
ttctccaatc gagttcttca ttcgcatttt cagtcatttt ctcttcgacg ttgttttttaa   3840
gcctgggtat tactcctatt tagttgaact ctgcagcaat cttagaaaat tagggttttg    3900
aggtttcgat ttctctaggt aaccgatcta ttgcattcat ctgaatttct gcatatatgt    3960
cttagatttc tgataagctt acgatacgtt aggtgtaatt gaagtttatt tttcaagagt    4020
gttatttttt gtttctgaat ttttcaggtg gtggccaatg tgatgtcag cgttgaactg    4080
cgtgatgcgg atcaacaggt ggttgcaact ggacaaggca ctagcgggac tttgcaagtg    4140
gtgaatccgc acctctggca accgggtgaa ggttatctct atgaactgtg cgtcacagcc    4200
aaaagccaga cagagtgtga tatctacccg cttcgcgtcg gcatccggtc agtggcagtg    4260
aagggcgaac agttcctgat taaccacaaa ccgttctact ttactggctt tggtcgtcat    4320
gaagatgcgg acttgcgtgg caaaggattc gataacgtgc tgatggtgca cgaccacgca    4380
ttaatggact ggattggggc caactcctac cgtacctcgc attacccta cgctgaagag    4440
atgctcgact gggcagatga acatggcatc gtggtgattg atgaaactgc tgctgtcggc    4500
tttaacctct ctttaggcat tggtttcgaa gcgggcaaca agccgaaaga actgtacagc    4560
gaagaggcag tcaacgggga aactcagcaa gcgcacttac aggcgattaa agagctgata    4620
gcgcgtgaca aaaaccaccc aagcgtggtg atgtggagta ttgccaacga accggatacc    4680
cgtccgcaag gtgcacggga atatttcgcg ccactggcgg aagcaacgcg taaactcgac    4740
ccgacgcgtc cgatcacctg cgtcaatgta atgttctgcg acgctcacac cgataccatc    4800
agcgatctct ttgatgtgct gtgcctgaac cgttattacg gatggtatgt ccaaagcggc    4860
gatttgaaaa cggcagagaa ggtactgaaa aagaacttc tggcctggca ggagaaactg    4920
catcagccga ttatcatcac cgaatacggc gtggatacgt tagccgggct gcactcaatg    4980
tacaccgaca tgtggagtga agagtatcag tgtgcatggc tggatatgta tcaccgcgtc    5040
tttgatcgcg tcagcgccgt cgtcggtgaa caggtatgga atttcgccga ttttgcgacc    5100
tcgcaaggca tattgcgcgt tggcggtaac aagaaaggga tcttcactcg cgaccgcaaa    5160
ccgaagtcgg cggcttttct gctgcaaaaa cgctggactg gcatgaactt cggtgaaaaa    5220
ccgcagcagg gaggcaaaca atgagagctc ccgcgtacag caagaagaac ctcgacgcga    5280
ccgacatggt cgctctctca ggcgctcaca caatcgggca ggcccagtgc tccagcttca    5340
acggccacat ctacaacgac acgaacatca acgcggcctt cgcgacgtcg ctcaaggcca    5400
actgccccat gtccggcggc agcagcctgg cgccgctgga caccatgacc ccgaccgtgt    5460
```

```
tcgacaacga ctactacaag aacctgctgt cgcagaaggg gctgctgcac tcggaccagg    5520
agctgttcaa caacggcagc accgacagca cggtcagcaa ctttgcgtcc agctcggccg    5580
ccttcaccag cgccttcacg gcggccttgg tgaagatggg gaacctcggc ccgctcaccg    5640
ggaccagtgg gcagatcagg ctcacctgct ggaagctcaa ctcgtcctaa taattaagga    5700
cggacgtccg atagacgatc ctgcgcaatc gtatcgtacg tgcatgatac gcatacatct    5760
ggaaactact ataccaatgc aaacagagat ctatacgtac gagtatgtat aacgacgagt    5820
gatgtttgta tggatctacg tatgtaacaa ggacctctcg tagcgcaaag gcgcgcgttg    5880
ggagattaat taggtacaca agctattacc acattatata tcactctcat tgtggctaca    5940
tatctatatc tctgaggcca aatgcttggg tgtccagtac taattaataa taattcagtg    6000
cgtatgcaag atttgtgggc aaatattggt ttacgatttc ggaaaaaaca aatttcggcc    6060
cccggcgaaa acaagaaat tccgaatttt cggaaattc taggtcaaaa tcaaatagat    6120
tcaatacttt ttaaaacaaa gaatgatata atttatatta aaataccaa ttttggaagc    6180 atatatttt tcggaccca ccaaaatcaa ggcaatttcg gaattttcg tccgaaattg    6240 taaaccctgc ggaccgcgat cgcttaatta agcttgcatg cctgcagtgc agcgtgaccc    6300
ggtcgtgccc ctctctagag ataatgagca ttgcatgtct aagttataaa aaattaccac    6360 atatttttt tgtcacactt gtttgaagtg cagtttatct atcttatac atatatttaa    6420 actttactct acgaataata taatctatag tactacaata atatcagtgt tttagagaat    6480
catataaatg aacagttaga catggtctaa aggacaattg agtattttga caacaggact    6540
ctacagtttt atctttttag tgtgcatgtg ttctccttt tttttgcaaa tagcttcacc    6600
tatataatac ttcatccatt ttattagtac atccatttag ggtttagggt taatggtttt    6660
tatagactaa tttttttagt acatctattt tattctattt tagcctctaa attaagaaaa    6720
ctaaaactct attttagttt ttttatttaa taatttagat ataaaataga ataaaataaa    6780
gtgactaaaa attaaacaaa taccctttaa gaaattaaaa aaactaagga aacattttc    6840 ttgtttcgag tagataatgc cagcctgtta aacgccgtcg acgagtctaa cggacaccaa    6900
ccagcgaacc agcagcgtcg cgtcgggcca agcgaagcag acggcacggc atctctgtcg    6960
ctgcctctgg acccctctcg agagttccgc tccaccgttg gacttgctcc gctgtcggca    7020
tccagaaatt gcgtggcgga gcggcagacg tgagccggca cggcaggcgg cctcctcctc    7080
ctctcacggc accggcagct acggggatt cctttcccac cgctccttcg ctttcccttc    7140
ctcgcccgcc gtaataaata gacacccct ccacaccctc tttccccaac ctcgtgttgt    7200
tcggagcgca cacacacaca accagatctc ccccaaatcc acccgtcggc acctccgctt    7260
caaggtacgc cgctcgtcct cccccccccc ccctctctac cttctctaga tcggcgttcc    7320
ggtccatggt tagggcccgg tagttctact tctgttcatg tttgtgttag atccgtgttt    7380
gtgttagatc cgtgctgcta gcgttcgtac acgatgcga cctgtacgtc agacacgttc    7440
tgattgctaa cttgccagtg tttctctttg gggaatcctg ggatggctct agccgttccg    7500
cagacgggat cgattcatg atttttttg tttcgttgca tagggtttgg tttgcccttt    7560
tcctttattt caatatatgc cgtgcacttg tttgtcgggt catcttttca tgctttttt    7620 tgtcttggtt gtgatgatgt ggtctggttg ggcggtcgtt ctagatcgga gtagaattct    7680
gtttcaaact acctggtgga tttattaatt ttggatctgt atgtgtgtgc catacatatt    7740
catagttacg aattgaagat gatggatgga aatatcgatc taggataggt atacatgttg    7800
```

```
atgcgggttt tactgatgca tatacagaga tgcttttgt tcgcttggtt gtgatgatgt    7860
ggtgtggttg ggcggtcgtt cattcgttct agatcggagt agaatactgt ttcaaactac    7920
ctggtgtatt tattaatttt ggaactgtat gtgtgtgtca tacatcttca tagttacgag    7980
tttaagatgg atggaaatat cgatctagga taggtataca tgttgatgtg ggttttactg    8040
atgcatatac atgatggcat atgcagcatc tattcatatg ctctaacctt gagtacctat    8100
ctattataat aaacaagtat gttttataat tattttgatc ttgatatact tggatgatgg    8160
catatgcagc agctatatgt ggattttttt agccctgcct tcatacgcta tttatttgct    8220
tggtactgtt tcttttgtcg atgctcaccc tgttgtttgg tgttacttct gcagggatcc    8280
ccgatcatgc aaaaactcat taactcagtg caaaactatg cctggggcag caaaacggcg    8340
ttgactgaac tttatggtat ggaaaatccg tccagccagc cgatggccga gctgtggatg    8400
ggcgcacatc cgaaaagcag ttcacgagtg cagaatgccg ccggagatat cgtttcactg    8460
cgtgatgtga ttgagagtga taaatcgact ctgctcggag aggccgttgc caaacgcttt    8520
ggcgaactgc ctttcctgtt caaagtatta tgcgcagcac agccactctc cattcaggtt    8580
catccaaaca aacacaattc tgaaatcggt tttgccaaag aaaatgccgc aggtatcccg    8640
atggatgccg ccgagcgtaa ctataaagat cctaaccaca agccggagct ggttttgcg    8700
ctgacgcctt tccttgcgat gaacgcgttt cgtgaatttt ccgagattgt ctccctactc    8760
cagccggtcg caggtgcaca tccggcgatt gctcactttt tacaacagcc tgatgccgaa    8820
cgtttaagcg aactgttcgc cagcctgttg aatatgcagg gtgaagaaaa atcccgcgcg    8880
ctggcgattt taaaatcggc cctcgatagc cagcagggtg aaccgtggca aacgattcgt    8940
ttaatttctg aattttaccc ggaagacagc ggtctgttct ccccgctatt gctgaatgtg    9000
gtgaaattga ccctggcga agcgatgttc ctgttcgctg aaacaccgca cgcttacctg    9060
caaggcgtgg cgctggaagt gatggcaaac tccgataacg tgctgcgtgc gggtctgacg    9120
cctaaataca ttgatattcc ggaactggtt gccaatgtga aattcgaagc caaaccggct    9180
aaccagttgt tgacccagcc ggtgaaacaa ggtgcagaac tggacttccc gattccagtg    9240
gatgattttg ccttctcgct gcatgacctt agtgataaag aaaccaccat tagccagcag    9300
agtgccgcca ttttgttctg cgtcgaaggc gatgcaacgt tgtggaaagg ttctcagcag    9360
ttacagctta aaccgggtga atcagcgttt attgccgcca acgaatcacc ggtgactgtc    9420
aaaggccacg ccgtttagc gcgtgtttac aacaagctgt aagagcttac tgaaaaaatt    9480
aacatctctt gctaagctgg gagctcgatc cgtcgacctg cagatcgttc aaacatttgg    9540
caataaagtt tcttaagatt gaatcctgtt gccggtcttg cgatgattat catataattt    9600
ctgttgaatt acgttaagca tgtaataatt aacatgtaat gcatgacgtt atttatgaga    9660
tgggttttta tgattagagt cccgcaatta tacatttaat acgcgataga aaacaaaata    9720
tagcgcgcaa actaggataa attatcgcgc gcggtgtcat ctatgttact agatctgcta    9780
gccctgcagg aaatttaccg gtgcccgggc ggccagcatg ccgtatccg caatgtgtta    9840
ttaagttgtc taagcgtcaa tttgtttaca ccacaatata tcctgccacc agccagccaa    9900
cagctccccg accggcagct cggcacaaaa tcaccactcg ataggcag cccatcagaa    9960
ttaattctca tgtttgacag cttatcatcg actgcacggt gcaccaatgc ttctggcgtc   10020
aggcagccat cggaagctgt ggtatggctg tgcaggtcgt aaatcactgc ataattcgtg   10080
tcgctcaagg cgcactcccg ttctggataa tgttttttgc gccgacatca taacggttct   10140
ggcaaatatt ctgaaatgag ctgttgacaa ttaatcatcc ggctcgtata atgtgtggaa   10200
```

```
ttgtgagcgg ataacaattt cacacaggaa acagaccatg agggaagcgt tgatcgccga   10260
agtatcgact caactatcag aggtagttgg cgtcatcgag cgccatctcg aaccgacgtt   10320
gctggccgta catttgtacg gctccgcagt ggatggcggc ctgaagccac acagtgatat   10380
tgatttgctg gttacggtga ccgtaaggct tgatgaaaca acgcggcgag ctttgatcaa   10440
cgaccttttg gaaacttcgg cttcccctgg agagagcgag attctccgcg ctgtagaagt   10500
caccattgtt gtgcacgacg acatcattcc gtggcgttat ccagctaagc gcgaactgca   10560
atttggagaa tggcagcgca atgacattct tgcaggtatc ttcgagccag ccacgatcga   10620
cattgatctg gctatcttgc tgacaaaagc aagagaacat agcgttgcct tggtaggtcc   10680
agcggcggag gaactctttg atccggttcc tgaacaggat ctatttgagg cgctaaatga   10740
aaccttaacg ctatggaact cgccgcccga ctgggctggc gatgagcgaa atgtagtgct   10800
tacgttgtcc cgcatttggt acagcgcagt aaccggcaaa atcgcgccga aggatgtcgc   10860
tgccgactgg gcaatggagc gcctgccggc ccagtatcag cccgtcatac ttgaagctag   10920
gcaggcttat cttggacaag aagatcgctt ggcctcgcgc gcagatcagt tggaagaatt   10980
tgttcactac gtgaaaggcg agatcaccaa agtagtcggc aaataaagct ctagtggatc   11040
tccgtacccg gggatctggc tcgcggcgga cgcacgacgc cggggcgaga ccataggcga   11100
tctcctaaat caatagtagc tgtaacctcg aagcgtttca cttgtaacaa cgattgagaa   11160
ttttttgtcat aaaattgaaa tacttggttc gcattttgt catccgcggt cagccgcaat   11220
tctgacgaac tgcccattta gctggagatg attgtacatc cttcacgtga aaatttctca   11280
agcgctgtga acaagggttc agattttaga ttgaaaggtg agccgttgaa acacgttctt   11340
cttgtcgatg acgacgtcgc tatgcggcat cttattattg aataccttac gatccacgcc   11400
ttcaaagtga ccgcggtagc cgacagcacc cagttcacaa gagtactctc ttccgcgacg   11460
gtcgatgtcg tggttgttga tctagattta ggtcgtgaag atgggctcga gatcgttcgt   11520
aatctggcgg caaagtctga tattccaatc ataattatca gtggcgaccg ccttgaggag   11580
acggataaag ttgttgcact cgagctagga gcaagtgatt ttatcgctaa gccgttcagt   11640
atcagagagt ttctagcacg cattcgggtt gccttgcgcg tgcgcccaa cgttgtccgc   11700
tccaaagacc gacggtcttt ttgttttact gactggacac ttaatctcag gcaacgtcgc   11760
ttgatgtccg aagctggcgg tgaggtgaaa cttacggcag gtgagttcaa tcttctcctc   11820
gcgttttag agaaaccccg cgacgttcta tcgcgcgagc aacttctcat tgccagtcga   11880
gtacgcgacg aggaggttta tgacaggagt atagatgttc tcattttgag gctgcgccgc   11940
aaacttgagg cagatccgtc aagccctcaa ctgataaaaa cagcaagagg tgccggttat   12000
ttctttgacg cggacgtgca ggtttcgcac ggggggacga tggcagcctg agccaattcc   12060
cagatccccg aggaatcggc gtgagcggtc gcaaaccatc cggcccggta caaatcggcg   12120
cggcgctggg tgatgacctg gtggagaagt tgaaggccgc gcaggccgcc cagcggcaac   12180
gcatcgaggc agaagcacgc cccggtgaat cgtggcaagc ggccgctgat cgaatccgca   12240
aagaatcccg gcaaccgccg gcagccggtg cgccgtcgat taggaagccg cccaagggcg   12300
acgagcaacc agatttttc gttccgatgc tctatgacgt gggcacccgc gatagtcgca   12360
gcatcatgga cgtggccgtt ttccgtctgt cgaagcgtga ccgacgagct ggcgaggtga   12420
tccgctacga gcttccagac gggcacgtag aggtttccgc agggccggcc ggcatggcca   12480
gtgtgtggga ttacgacctg gtactgatgg cggtttccca tctaaccgaa tccatgaacc   12540
```

```
gataccggga agggaaggga gacaagcccg gccgcgtgtt ccgtccacac gttgcggacg   12600
tactcaagtt ctgccggcga gccgatggcg gaaagcagaa agacgacctg gtagaaacct   12660
gcattcggtt aaacaccacg cacgttgcca tgcagcgtac gaagaaggcc aagaacggcc   12720
gcctggtgac ggtatccgag ggtgaagcct tgattagccg ctacaagatc gtaaagagcg   12780
aaaccgggcg gccggagtac atcgagatcg agctagctga ttggatgtac cgcgagatca   12840
cagaaggcaa gaacccggac gtgctgacgg ttcaccccga ttacttttg atcgatcccg    12900
gcatcggccg ttttctctac cgcctggcac gccgcgccgc aggcaaggca gaagccagat   12960
ggttgttcaa gacgatctac gaacgcagtg gcagcgccgg agagttcaag aagttctgtt   13020
tcaccgtgcg caagctgatc gggtcaaatg acctgccgga gtacgatttg aaggaggagg   13080
cggggcaggc tggcccgatc ctagtcatgc gctaccgcaa cctgatcgag ggcgaagcat   13140
ccgccggttc ctaatgtacg gagcagatgc tagggcaaat tgccctagca ggggaaaaag   13200
gtcgaaaagg tctctttcct gtggatagca cgtacattgg gaacccaaag ccgtacattg   13260
ggaaccggaa cccgtacatt gggaacccaa agccgtacat tgggaaccgg tcacacatgt   13320
aagtgactga tataaaagag aaaaaaggcg attttccgc ctaaaactct ttaaaactta    13380
ttaaaactct taaaacccgc ctggcctgtg cataactgtc tggccagcgc acagccgaag   13440
agctgcaaaa agcgcctacc cttcggtcgc tgcgctccct acgccccgcc gcttcgcgtc   13500
ggcctatcgc ggccgctggc cgctcaaaaa tggctggcct acggcaggc aatctaccag    13560
ggcgcggaca agccgcgccg tcgccactcg accgccggcg ctgaggtctg cctcgtgaag   13620
aaggtgttgc tgactcatac caggcctgaa tcgccccatc atccagccag aaagtgaggg   13680
agccacggtt gatgagagct tgttgtagg tggaccagtt ggtgattttg aacttttgct    13740
ttgccacgga acggtctgcg ttgtcgggaa gatgcgtgat ctgatccttc aactcagcaa   13800
aagttcgatt tattcaacaa agccgccgtc ccgtcaagtc agcgtaatgc tctgccagtg   13860
ttacaaccaa ttaaccaatt ctgattagaa aaactcatcg agcatcaaat gaaactgcaa   13920
tttattcata tcaggattat caataccata tttttgaaaa agccgtttct gtaatgaagg   13980
agaaaactca ccgaggcagt tccataggat ggcaagatcc tggtatcggt ctgcgattcc   14040
gactcgtcca acatcaatac aacctattaa tttcccctcg tcaaaaataa ggttatcaag   14100
tgagaaatca ccatgagtga cgactgaatc cggtgagaat ggcaaaagct ctgcattaat   14160
gaatcggcca acgcgcgggg agaggcggtt tgcgtattgg gcgctcttcc gcttcctcgc   14220
tcactgactc gctgcgctcg gtcgttcggc tgcggcgagc ggtatcagct cactcaaagg   14280
cggtaatacg gttatccaca gaatcagggg ataacgcagg aaagaacatg tgagcaaaag   14340
gccagcaaaa ggccaggaac cgtaaaaagg ccgcgttgct ggcgtttttc cataggctcc   14400
gcccccctga cgagcatcac aaaaatcgac gctcaagtca gaggtggcga aacccgacag   14460
gactataaag ataccaggcg tttccccctg gaagctccct cgtgcgctct cctgttccga   14520
ccctgccgct taccggatac ctgtccgcct ttctcccttc gggaagcgtg gcgctttctc   14580
atagctcacg ctgtaggtat ctcagttcgg tgtaggtcgt tcgctccaag ctgggctgtg   14640
tgcacgaacc ccccgttcag cccgaccgct gcgccttatc cggtaactat cgtcttgagt   14700
ccaacccggt aagacacgac ttatcgccac tggcagcagc cactggtaac aggattagca   14760
gagcgaggta tgtaggcggt gctacagagt tcttgaagtg gtggcctaac tacggctaca   14820
ctagaagaac agtatttggt atctgcgctc tgctgaagcc agttaccttc ggaaaaagag   14880
ttggtagctc ttgatccggc aaacaaacca ccgctggtag cggtggtttt tttgtttgca   14940
```

-continued agcagcagat tacgcgcaga aaaaaaggat ctcaagaaga tcctttgatc ttttctacgg    15000
ggtctgacgc tcagtggaac gaaaactcac gttaagggat tttggtcatg agattatcaa    15060
aaaggatctt cacctagatc cttttgatcc ggaatta                              15097

<210> SEQ ID NO 83
<211> LENGTH: 35
<212> TYPE: DNA
<213> ORGANISM: Artificial sequence
<220> FEATURE:
<223> OTHER INFORMATION: 5' Bfr1 primer

<400> SEQUENCE: 83
cctggtggag tgcttaagcg acgagttctg cctgg                               35

<210> SEQ ID NO 84
<211> LENGTH: 36
<212> TYPE: DNA
<213> ORGANISM: Artificial sequence
<220> FEATURE:
<223> OTHER INFORMATION: 3'Xba1 primer

<400> SEQUENCE: 84
gggcttctcc tccaggaact ctagattgcc caggcg                              36

<210> SEQ ID NO 85
<211> LENGTH: 37
<212> TYPE: DNA
<213> ORGANISM: Artificial sequence
<220> FEATURE:
<223> OTHER INFORMATION: 5'Gfix primer

<400> SEQUENCE: 85
catcggcaag tgccaccaca gccaccactt cagcctg                             37

<210> SEQ ID NO 86
<211> LENGTH: 30
<212> TYPE: DNA
<213> ORGANISM: Artificial sequence
<220> FEATURE:
<223> OTHER INFORMATION: 3'Gfix primer

<400> SEQUENCE: 86
gctgtggtgg cacttgccga tggggctggg                                     30

<210> SEQ ID NO 87
<211> LENGTH: 33
<212> TYPE: DNA
<213> ORGANISM: Artificial sequence
<220> FEATURE:
<223> OTHER INFORMATION: 5'1Ab5XbaI primer

<400> SEQUENCE: 87
gcccgcctgg gcaatctaga gttcctggag gag                                 33

<210> SEQ ID NO 88
<211> LENGTH: 37
<212> TYPE: DNA
<213> ORGANISM: Artificial sequence
<220> FEATURE:
<223> OTHER INFORMATION: 3'1Ab3d6 primer

<400> SEQUENCE: 88
gcgagctcct agatgcggcc ctcgagttcc tcgaaga                             37

```
<210> SEQ ID NO 89
<211> LENGTH: 29
<212> TYPE: DNA
<213> ORGANISM: Artificial sequence
<220> FEATURE:
<223> OTHER INFORMATION: oligonucleotide cy2'

<400> SEQUENCE: 89
ccctgtacgg cacgatgggc aacgctgca                                    29

<210> SEQ ID NO 90
<211> LENGTH: 30
<212> TYPE: DNA
<213> ORGANISM: Artificial sequence
<220> FEATURE:
<223> OTHER INFORMATION: oligonucleotide cy1

<400> SEQUENCE: 90
atatatccac catggacaac aaccccaaca                                   30

<210> SEQ ID NO 91
<211> LENGTH: 31
<212> TYPE: DNA
<213> ORGANISM: Artificial sequence
<220> FEATURE:
<223> OTHER INFORMATION: oligonucleotide cy2

<400> SEQUENCE: 91
tatatagagc tcctagatgc ggccctcgag t                                 31
```